United States Patent
Nicolaou et al.

(10) Patent No.: US 10,889,590 B2
(45) Date of Patent: *Jan. 12, 2021

(54) DERIVATIVES OF UNCIALAMYCIN, METHODS OF SYNTHESIS AND THEIR USE AS ANTITUMOR AGENTS

(71) Applicants: WILLIAM MARSH RICE UNIVERSITY, Houston, TX (US); BRISTOL-MYERS SQUIBB COMPANY, Princeton, NJ (US); THE SCRIPPS RESEARCH INSTITUTE, La Jolla, CA (US)

(72) Inventors: Kyriacos C. Nicolaou, Houston, TX (US); Min Lu, Houston, TX (US); Debashis Mandal, Houston, TX (US); Sanjeev Gangwar, Foster City, CA (US); Naidu S. Chowdari, Dublin, CA (US); Yam B. Poudel, Fremont, CA (US)

(73) Assignees: William Marsh Rice University, Houston, TX (US); The Scripps Research Institute, La Jolla, CA (US); Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/357,109

(22) Filed: Mar. 18, 2019

(65) Prior Publication Data
US 2019/0382412 A1    Dec. 19, 2019

Related U.S. Application Data

(62) Division of application No. 15/677,959, filed on Aug. 15, 2017, now Pat. No. 10,233,192, which is a division of application No. 14/911,881, filed as application No. PCT/US2014/051127 on Aug. 14, 2014, now Pat. No. 9,777,013.

(60) Provisional application No. 61/865,896, filed on Aug. 14, 2013, provisional application No. 61/868,783, filed on Aug. 22, 2013, provisional application No. 61/937,003, filed on Feb. 7, 2014.

(51) Int. Cl.
C07D 491/08    (2006.01)
A61K 47/68    (2017.01)

(52) U.S. Cl.
CPC ........ *C07D 491/08* (2013.01); *A61K 47/6803* (2017.08); *A61K 47/6851* (2017.08)

(58) Field of Classification Search
CPC ............ A61K 47/6803; A61K 47/6851; C07D 491/08
See application file for complete search history.

(56) References Cited

U.S. PATENT DOCUMENTS

| 7,517,903 B2 | 4/2009 | Chen et al. |
| 8,394,607 B2 | 3/2013 | Ebens et al. |
| 8,709,431 B2 | 4/2014 | Chowdari et al. |
| 9,156,850 B2 | 10/2015 | Chowdari et al. |
| 9,777,013 B2* | 10/2017 | Nicolaou ........... A61K 47/6803 |
| 2013/0209494 A1 | 8/2013 | Chowdari et al. |

FOREIGN PATENT DOCUMENTS

| EP | 0 484 855 A2 | 5/1992 |
| JP | Hei 5-508634 | 2/1993 |
| WO | WO 92-00762 | 1/1992 |
| WO | WO 93/23046 | 11/1993 |
| WO | WO 96/03124 | 2/1996 |
| WO | WO 2007/038868 A2 | 4/2007 |
| WO | WO 2013/122823 A1 | 8/2013 |

OTHER PUBLICATIONS

Davies, Julian et al., "Uncialamycin, A New Enediyne Antibiotic." *Organic Letters*, 7(23):5233-5236, 2005.
International Preliminary Report on Patentability issued in International Application No. PCT/US2014/051127 dated Feb. 25, 2016.
Nicolaou, K.C. et al., "Asymmetric synthesis and biological properties of Uncialamycin and 26-epi-Uncialamycin." *Angewandte Chemie International Edition*, 47(1):185-189, 2008.
Nicolaou, K.C., et al., "Total Synthesis and Stereochemistry of Uncialamycin," et al., *Angew. Chem. Int. Ed.*, 46(25):4704-4707, 2007.
Non-Final Office Action issued in U.S. Pat. No. 10,233,192 dated Jul. 6, 2018.
Office Action issued in European Application No. 14758223.3 dated Jan. 10, 2017.
Office Action issued in Eurasian Application No. 201690388 dated Jan. 18, 2017.
PCT International Search Report and Written Opinion issued in International Application No. PCT/US2014/051127 dated Nov. 28, 2014.
Restriction Action issued in U.S. Pat. No. 9,777,013 dated Oct. 28, 2016.
Restriction Action issued in U.S. Pat. No. 10,233,192 dated Jan. 16, 2018.
Office Action issued in Indian Application No. 201617006642, dated Apr. 21, 2020.

* cited by examiner

*Primary Examiner* — Erich A Leeser
(74) *Attorney, Agent, or Firm* — Parker Highlander PLLC

(57) ABSTRACT

In one aspect, the present disclosure provides new analogs of uncialamycin. The present disclosure also provides novel synthetic pathways to obtaining uncialamycin and analogs thereof. Additionally, the present disclosure also describes methods of use of uncialamycin and analogs thereof. In another aspect, the present disclosure provides antibody-drug conjugates which may be used to treat cancer or another disease or disorder.

20 Claims, 2 Drawing Sheets

DERIVATIVES OF UNCIALAMYCIN, METHODS OF SYNTHESIS AND THEIR USE AS ANTITUMOR AGENTS

This application is a divisional application of U.S. application Ser. No. 15/677,959 filed Aug. 15, 2017, which is a divisional application of U.S. application Ser. No. 14/911,881 filed Feb. 12, 2016, which is a national phase application under 35 U.S.C. § 371 of International Application No. PCT/US2014/051127, filed Aug. 14, 2014, and claims the benefit of U.S. Provisional Application No. 61/865,896, filed on Aug. 14, 2013, U.S. Provisional Application No. 61/868,783, filed on Aug. 22, 2013, and U.S. Provisional Application No. 61/937,003, filed on Feb. 7, 2014, the entirety of each is incorporated herein by reference.

This invention was made with government support under AI055475 awarded by the National Institutes of Health. The government has certain rights in the invention.

BACKGROUND

1. Field of the Invention

This disclosure relates to the fields of medicine, pharmacology, chemistry and oncology. In particular, compounds, drug conjugates, methods of treatment, and methods of synthesis relating to uncialamycin and analogs thereof are disclosed.

2. Related Art

Uncialamycin is an antibiotic which has shown great promise as a potential anticancer reagent. The use of uncialamycin as an anticancer agent has been described in Nicolaou, et al., 2007 and Nicolaou, et al., 2008, both of which are incorporated herein by reference. The compound has been shown to be a potent antitumor cancer agent with an $IC_{50}$ in the picomolar. Furthermore, the compound has been envisioned as a potential antibody payload. Unfortunately, the current synthetic methods lack the flexibility to produce numerous analogs and generate sufficient quantities of the desired compounds. Given the widespread and world wide impact of cancer, new therapeutic agents are of the commercial importance.

SUMMARY

Thus, in accordance with the present disclosure, there is provided a compound of the formula:

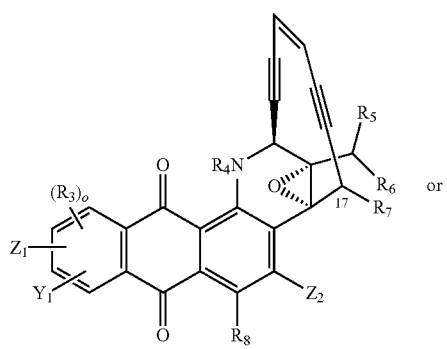

(I)

or

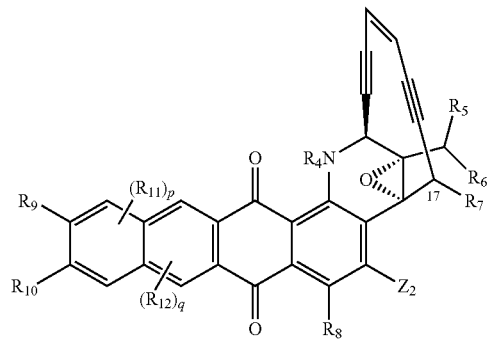

(II)

wherein: $Y_1$ is $-O(CH_2)_mY'$, $-NH(CH_2)_mY'$, $-S(CH_2)_mY'$, or $-(CH_2)_mNR_1R_2$, or is taken together with $Z_1$ as defined below; wherein: Y' is hydroxy, halo, mercapto, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, acyl$_{(C\leq12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; and $R_1$ and $R_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, $-C(O)O(CH_2)_nS-A_1$, $-C(O)O(CH_2)_nS(O)-A_1$, or $-C(O)O(CH_2)_nS(O)_2-A_1$, wherein: $A_1$ is aryl$_{(C6-12)}$, substituted aryl$_{(C6-12)}$, or

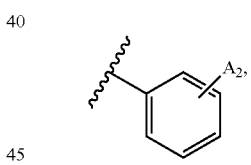

wherein: $A_2$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$; wherein $A_2$ is not $-CO_2H$, $-CO_2CH_3$, $-OCH_3$, $-OCH_2CH_3$, $-C(O)CH_3$, $-NHCH_3$, $-NHCH_2CH_3$, $-N(CH_3)_2$, $-C(O)NH_2$, and $-OC(O)CH_3$; n is 1, 2, 3, 4, or 5; or $R_1$ and $R_2$ are taken together and are divalent amine protecting group, alkanediyl$_{(C1-12)}$, alkylaminodiyl$_{(C2-8)}$; alkoxydiyl$_{(C2-8)}$; or a substituted version of either of these groups; or $Y_1$ is taken with $Z_1$ and is alkylaminodiyl$_{(C2-8)}$ substituted alkylaminodiyl$_{(C2-8)}$; -alkanediyl$_{(C1-6)}$-$NZ_2$-alkanediyl$_{(C1-6)}$, or -substituted alkanediyl$_{(C1-6)}$-$NZ_2$-substituted alkanediyl$_{(C1-6)}$, wherein: $Z_2$ is hydrogen, an amine protecting group, acyl$_{(C6-12)}$, substituted acyl$_{(C6-12)}$, $-C(O)O(CH_2)_nS-A_3$, or $-C(O)O(CH_2)_nS(O)_2-A_3$, wherein: $A_3$ is aryl$_{(C6-12)}$, substituted aryl$_{(C6-12)}$, or

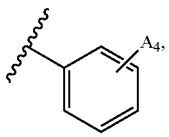

wherein: $A_4$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein $A_4$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; $Z_1$ is absent, hydrogen or taken together with $Y_1$ as defined above; $R_3$ and $Z_2$ are each independently selected from hydrogen, hydroxy, halo, amino, cyano, nitro, phosphate, or mercapto, or alkyl$_{(C1-12)}$, alkenyl$_{(C2-12)}$, alkynyl$_{(C1-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; o is 1, 2, or 3; $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —OX$_1$, —NX$_2$X$_3$, or —SX$_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and $R_9$, $R_{10}$, $R_{11}$, and $R_{12}$ are each independently selected from hydrogen, hydroxy, amino, mercapto, —OX$_1$, —NX$_2$X$_3$, or —SX$_4$, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or $Y_2$—$R_{13}$; wherein: $X_1$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(2-12)}$, substituted heterocycloalkyl$_{(C2-12)}$, acyl$_{(C1-12)}$, substituted acyl$_{(C1-12)}$, or a hydroxy protecting group; $X_2$ and $X_3$ are independently selected from hydrogen, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, a monovalent amine protecting group, or when $X_2$ and $X_3$ are taken together form a divalent amine protecting group; $X_4$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a thiol protecting group; $Y_2$ is alkanediyl$_{(C1-12)}$ or substituted alkanediyl$_{(C1-12)}$; and $R_{13}$ is hydroxy, amino, mercapto, —OX$_1$, —NX$_2$X$_3$, or —SX$_4$, or heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and p and q are each independently 1 or 2; $Z_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; provided that $Y_1$ is not —NHMe or —NHCH$_2$CH$_2$NH$_2$; or a pharmaceutically acceptable salt thereof. In some embodiments, the compound is further defined as:

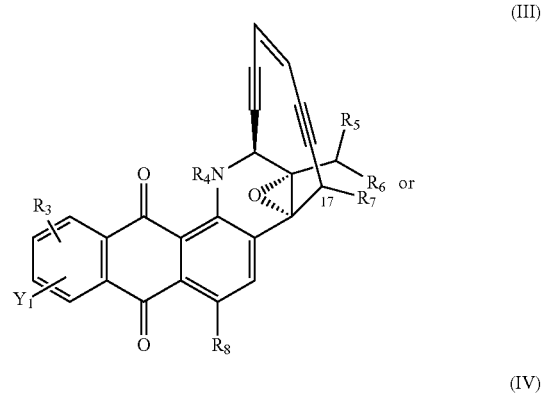

(III)

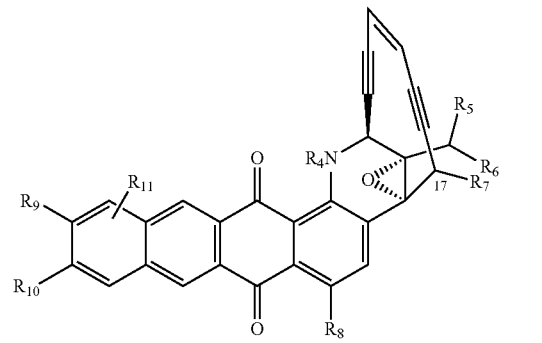

(IV)

wherein: $Y_1$ is —O(CH$_2$)$_m$Y', —NH(CH$_2$)$_m$Y', —S(CH$_2$)$_m$Y' or —CH$_2$NR$_1$R$_2$, wherein: Y' is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, acyl$_{(C≤12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; $R_1$ and $R_2$ are each independently selected from hydrogen, hydroxy, alkyl$_{(C1-12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, or a substituted version of any of these groups; $R_1$ and $R_2$ are taken together and are a divalent protecting group, alkanediyl$_{(C1-12)}$, alkoxydiyl$_{(C1-8)}$; or a substituted version of either of these groups; or —C(O)O(CH$_2$)$_n$S-A$_1$, or —C(O)O(CH$_2$)$_n$S(O)$_2$-A$_1$, wherein: A$_1$ is aryl$_{(C6-12)}$, substituted aryl$_{(C6-12)}$, or

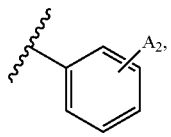

wherein: $A_2$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$; wherein $A_2$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; n is 1, 2, 3, 4, or 5; $R_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —OX$_1$, —NX$_2$X$_3$, or —SX$_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; $R_9$, $R_{10}$, and $R_{11}$ are each independently selected from hydrogen, hydroxy, amino, mercapto, —OX$_1$, —NX$_2$X$_3$, or —SX$_4$, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or $Y_2$—$R_{12}$; wherein: $X_1$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(2-12)}$, substituted heterocycloalkyl$_{(C2-12)}$, acyl$_{(C1-12)}$, substituted acyl$_{(C1-12)}$, or a hydroxy protecting group; $X_2$ and $X_3$ are independently selected from hydrogen, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, a monovalent amine protecting group, or when $X_2$ and $X_3$ are taken together form a divalent amine protecting group; $X_4$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a thiol protecting group; $Y_2$ is alkanediyl$_{(C1-12)}$ or substituted alkanediyl$_{(C1-12)}$; or $R_{12}$ is hydroxy, amino, mercapto, —OX$_1$, —NX$_2$X$_3$, or —SX$_4$, or heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or provided that $Y_1$ is not —NHMe, —NHC(O)C$_6$H$_4$NH$_2$, —NHC(O)CH$_2$NH$_2$, —NHC(O)CH(CH$_2$OH)NH$_2$, —NHC(O)CH(NH$_2$)CH$_2$CH$_2$CH$_2$CH$_2$NH$_2$, or —NHCH$_2$CH$_2$NH$_2$; or a pharmaceutically acceptable salt thereof. In some embodiments, the formula is further defined as:

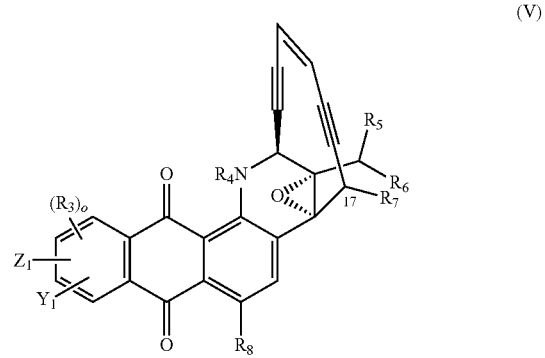

(V)

wherein: $Y_1$ is —O(CH$_2$)$_m$Y', —NH(CH$_2$)$_m$Y', —S(CH$_2$)$_m$Y', or —(CH$_2$)$_m$NR$_1$R$_2$, or taken together with $Z_1$ as described below; wherein: Y' is hydroxy, halo, mercapto, alkenyl$_{(C2-12)}$, substituted alkenyl$_{(C2-12)}$, alkynyl$_{(C2-12)}$, substituted alkynyl$_{(C2-12)}$, acyl$_{(C≤12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; and $R_1$ and $R_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, —C(O)O(CH$_2$)$_n$S-A$_1$, —C(O)O(CH$_2$)$_n$S(O)-A$_1$, or —C(O)O(CH$_2$)$_n$S(O)$_2$-A$_1$, wherein: A$_1$ is aryl$_{(C6-12)}$ or substituted aryl$_{(C6-12)}$; n is 1, 2, 3, 4, or 5; $R_1$ and $R_2$ are taken together and are a divalent protecting group, alkanediyl$_{(C≤12)}$, alkylaminodiyl$_{(C≤8)}$; alkoxydiyl$_{(C≤8)}$; or a substituted version of either of these groups; or $Y_1$ is taken with $Z_1$ and is alkylaminodiyl$_{(C1-8)}$ substituted alkylaminodiyl$_{(C1-8)}$; or -alkanediyl$_{(C1-6)}$-NZ$_2$-alkanediyl$_{(C1-6)}$, wherein: $Z_2$ is hydrogen, an amine protecting group, acyl$_{(C6-12)}$, substituted acyl$_{(C6-12)}$, —C(O)O(CH$_2$)$_n$S-A$_3$, or —C(O)O(CH$_2$)$_n$S(O)$_2$-A$_3$, wherein: A$_3$ is aryl$_{(C6-12)}$ or substituted aryl$_{(C6-12)}$; $Z_1$ is absent, hydrogen or taken together with $Y_1$ as defined above; $R_3$ is hydrogen, hydroxy, halo, amino, cyano, nitro, phosphate, or mercapto, or alkyl$_{(C1-12)}$, alkenyl$_{(C2-12)}$, alkynyl$_{(C1-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; o is 1, 2, or 3; $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —$OX_1$, —$NX_2X_3$, or —$SX_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or a pharmaceutically acceptable salt thereof. In some embodiments, the formula is further defined as:

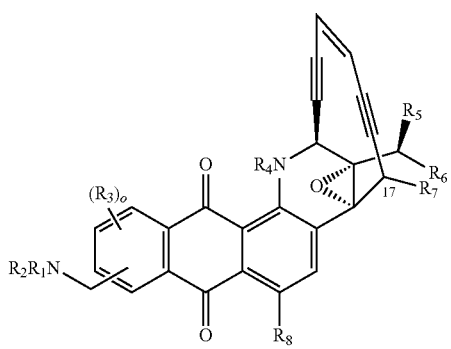

(VI)

wherein: $R_1$ and $R_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, —C(O)O(CH$_2$)$_n$S-A$_1$, —C(O)O(CH$_2$)$_n$S(O)-A$_1$, or —C(O)O(CH$_2$)$_n$S(O)$_2$-A$_1$, wherein: A$_1$ is aryl$_{(C6-12)}$ or substituted aryl$_{(C6-12)}$; and n is 1, 2, 3, 4, or 5; $R_3$ is hydrogen, hydroxy, halo, or alkoxy$_{(C1-12)}$ or substituted alkoxy$_{(C1-12)}$; o is 1, 2, or 3; $R_4$ is hydrogen, a monovalent amine protecting group, alkyl$_{(C1-12)}$, or substituted alkyl$_{(C1-12)}$; $R_5$, $R_6$, and $R_7$ are each independently hydrogen, hydroxy, amino, mercapto, —$OX_1$, —$NX_2X_3$, or —$SX_4$; or alkyl$_{(C1-12)}$ or substituted alkyl$_{(C1-12)}$; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; and $X_4$ is a thiol protecting group; and $R_8$ is hydroxy, amino, or mercapto; or a pharmaceutically acceptable salt thereof. In some embodiments, the formula is further defined as:

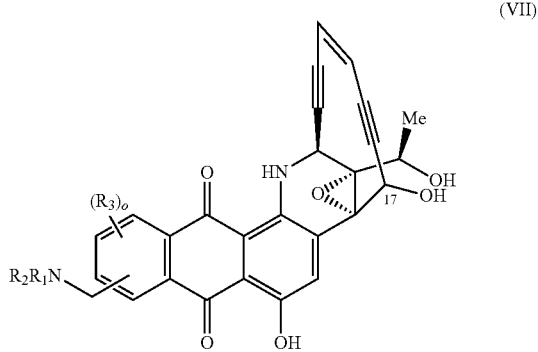

(VII)

wherein: $R_1$ and $R_2$ are each independently selected from hydrogen, hydroxy, alkyl$_{(C1-12)}$, substituted alkyl$_{(C1-12)}$, aryl$_{(6-12)}$, substituted aryl$_{(C6-12)}$, aralkyl$_{(C7-12)}$, substituted aralkyl$_{(C7-12)}$, acyl$_{(C1-12)}$, substituted acyl$_{(C1-12)}$, a monovalent amine protecting group, —C(O)O(CH$_2$)$_n$S—C$_6$H$_5$, —C(O)O(CH$_2$)$_n$S(O)—C$_6$H$_5$, or —C(O)O(CH$_2$)$_n$S(O)$_2$—C$_6$H$_5$, a monovalent amine protecting group, or $R_1$ and $R_2$ are taken together and form a divalent amine protecting group, or alkyl$_{(C1-12)}$, aryl$_{(C6-12)}$, aralkyl$_{(C7-12)}$, acyl$_{(C1-12)}$, or a substituted version of any of these groups; $R_3$ is hydrogen, hydroxy, halo, or alkoxy$_{(C1-12)}$ or substituted alkoxy$_{(C1-12)}$; and o is 1, 2, or 3; or a pharmaceutically acceptable salt thereof. In some embodiments, the formula is further defined as:

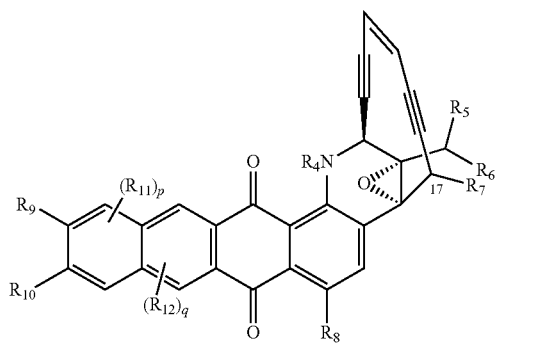

(VIII)

wherein: $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —$OX_1$, —$NX_2X_3$, or —$SX_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; $R_9$, $R_{10}$, $R_{11}$, and $R_{12}$ are each independently selected from hydrogen, hydroxy, amino, —$NX_2X_3$, or heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C2-12)}$, or a substituted version of any of these groups;

or $Y_2$—$R_{13}$; wherein: $X_2$ and $X_3$ are independently selected from hydrogen, a monovalent amine protecting group, or when $X_2$ and $X_3$ are taken together form a divalent amine protecting group; $Y_2$ is alkanediyl$_{(C1-12)}$ or substituted alkanediyl$_{(C1-12)}$; or $R_{13}$ is hydroxy, amino, or —$NX_2X_3$, or alkylamino$_{(C1-12)}$, dialkylamino$_{(C2-12)}$, amido$_{(C1-12)}$, or a substituted version of any of these groups; or p and q are each independently 1 or 2; a pharmaceutically acceptable salt thereof. In some embodiments, the formula is further defined as:

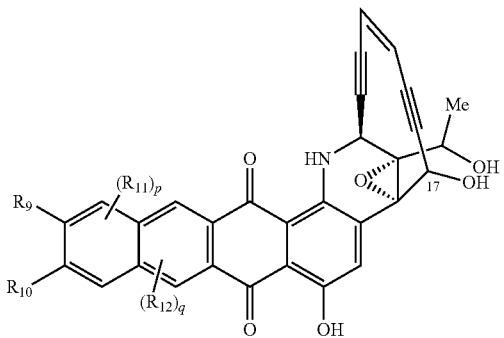

(IX)

wherein: $R_9$, $R_{10}$, $R_{11}$, and $R_{12}$ are each independently selected from hydrogen, hydroxy, amino, —$NX_2X_3$, or alkoxy$_{(C1-12)}$, alkylamino$_{(C1-12)}$, dialkylamino$_{(C2-12)}$, amido$_{(C1-12)}$, or a substituted version of any of these groups; or $Y_2$—$R_{13}$; wherein: $X_2$ and $X_3$ are independently selected from hydrogen, a monovalent amine protecting group, or when $X_2$ and $X_3$ are taken together form a divalent amine protecting group; $Y_2$ is alkanediyl$_{(C1-12)}$ or substituted alkanediyl$_{(C1-12)}$; or $R_{13}$ is hydroxy, amino, or —$NX_2X_3$, or alkylamino$_{(C1-12)}$, dialkylamino$_{(C2-12)}$, amido$_{(C1-12)}$, or a substituted version of any of these groups; and p and q are each independently 1 or 2; or a pharmaceutically acceptable salt thereof. In some embodiments, the compound is further defined as:

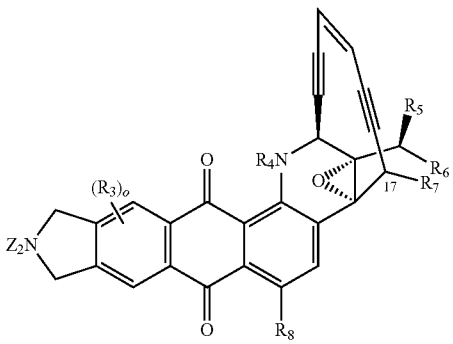

(X)

wherein: $Z_2$ is hydrogen, an amine protecting group, acyl$_{(C1-12)}$, substituted acyl$_{(C1-12)}$, —C(O)O(CH$_2$)$_n$S-A$_3$, —C(O)O(CH$_2$)$_n$S(O)-A$_3$, or —C(O)O(CH$_2$)$_n$S(O)$_2$-A$_3$, wherein: A$_3$ is aryl$_{(C6-12)}$ or substituted aryl$_{(C6-12)}$; $R_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; o is 1 or 2; $R_4$ is hydrogen, a monovalent amine protecting group, alkyl$_{(C1-12)}$, or substituted alkyl$_{(C1-12)}$; $R_5$, $R_6$, and $R_7$ are each independently hydrogen, hydroxy, amino, mercapto, —$OX_1$, —$NX_2X_3$, or —$SX_4$; or alkyl$_{(C1-12)}$ or substituted alkyl$_{(C1-12)}$; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or a pharmaceutically acceptable salt thereof. In some embodiments, the compound is further defined as:

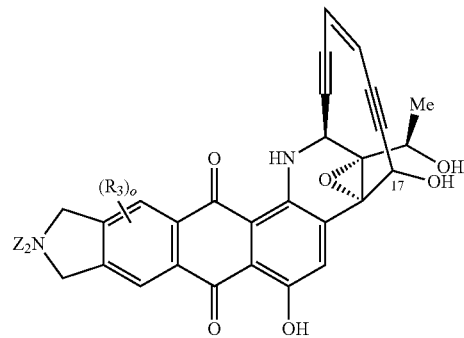

(XI)

wherein: $Z_2$ is hydrogen, an amine protecting group, acyl$_{(C6-12)}$, substituted acyl$_{(C6-12)}$, —C(O)O(CH$_2$)$_n$S-A$_3$, —C(O)O(CH$_2$)$_n$S(O)-A$_3$, or —C(O)O(CH$_2$)$_n$S(O)$_2$-A$_3$, wherein: A$_3$ is aryl$_{(C6-12)}$ or substituted aryl$_{(C6-12)}$; $R_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; o is 1 or 2; or a pharmaceutically acceptable salt thereof. In some embodiments, the formula is further defined as:

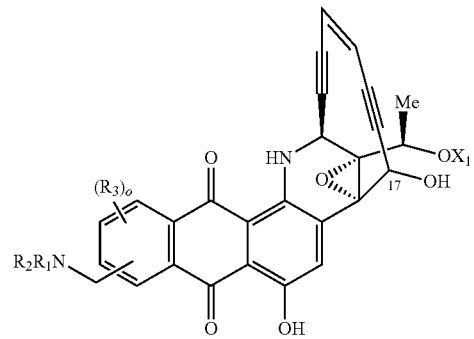

(VII)

wherein: $X_1$ is a hydroxy protecting group; $R_1$ and $R_2$ are each independently selected from hydrogen, alkyl$_{(C1-12)}$, or substituted alkyl$_{(C1-12)}$; and $R_3$ is hydrogen, alkoxy$_{(C1-12)}$, or substituted alkoxy$_{(C1-12)}$; and o is 2; or a pharmaceutically acceptable salt thereof. In some embodiments, the formula is formula I. In some embodiments, the formula is formula II. In some embodiments, $Y_1$ is taken together with $Z_1$ and is -alkanediyl$_{(C≤6)}$-$NZ_2$-alkanediyl$_{(C≤6)}$. In some embodiments, $Y_1$ is taken together with $Z_1$ and is —$CH_2CH_2$—$NZ_2$—$CH_2CH_2$—. In some embodiments, $Z_2$ is hydrogen. In other embodiments, $Z_2$ is an amine protecting group. In some embodiments, the amine protecting group is 2-(trimethylsilyl)ethoxycarbonyl or t-butoxycarbonyl. In some embodiments, $Z_2$ is —$C(O)O(CH_2)_nS$—$C_6H_5$. In some embodiments, $Z_2$ is —$C(O)O(CH_2)_nS(O)_2$—$C_6H_5$. In some embodiments, $Z_1$ is hydrogen. In some embodiments, $Y_1$ is —$O(CH_2)_mY'$, —$S(CH_2)_mY'$, or —$(CH_2)_mNR_1R_2$. In some embodiments, $Y_1$ is —$(CH_2)_mNR_1R_2$. In some embodiments, m is 1, 2, or 3. In some embodiments, m is 1 or 2. In some embodiments, $R_1$ is —$C(O)O(CH_2)_nS$-$A_1$ or —$C(O)O(CH_2)_nS(O)_2$-$A_1$, wherein: $A_1$ is aryl$_{(C \leq 12)}$, substituted aryl$_{(C \leq 12)}$, or

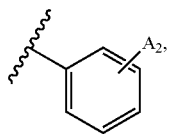

wherein: $A_2$ is acyloxy$_{(C \leq 12)}$, substituted acyloxy$_{(C \leq 12)}$, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, or substituted dialkylamino$_{(C \leq 12)}$, wherein $A_2$ is not —$CO_2H$, —$CO_2CH_3$, —$OCH_3$, —$OCH_2CH_3$, —$C(O)CH_3$, —$NHCH_3$, —$NHCH_2CH_3$, —$N(CH_3)_2$, —$C(O)NH_2$, and —$OC(O)CH_3$; and n is 1, 2, 3, 4, or 5. In some embodiments, $R_1$ is hydrogen. In other embodiments, $R_1$ is alkyl$_{(C \leq 12)}$ or substituted alkyl$_{(C \leq 12)}$. In some embodiments, $R_1$ is alkyl$_{(C \leq 12)}$. In some embodiments, $R_1$ is methyl. In other embodiments, $R_1$ is a monovalent amine protecting group. In some embodiments, $R_1$ is 2-(trimethylsilyl)ethoxycarbonyl or t-butoxycarbonyl. In other embodiments, $R_1$ is —$C(O)O(CH_2)_2SC_6H_5$. In other embodiments, $R_1$ is —$C(O)O(CH_2)_2S(O)_2C_6H_5$. In other embodiments, $R_1$ is taken together with $R_2$ and is a divalent protecting group. In some embodiments, $R_1$ and $R_2$ is phthalimide or substituted phthalimide. In some embodiments, $R_2$ is hydrogen. In other embodiments, $R_2$ is alkyl$_{(C \leq 12)}$ or substituted alkyl$_{(C \leq 12)}$. In other embodiments, $R_2$ is alkyl$_{(C \leq 12)}$. In some embodiments, $R_2$ is methyl. In other embodiments, $R_2$ is a monovalent amine protecting group. In some embodiments, $R_2$ is 2-(trimethylsilyl)ethoxycarbonyl or t-butoxycarbonyl. In other embodiments, $R_2$ is —$C(O)O(CH_2)_nS$-$A_1$ or —$C(O)O(CH_2)_nS(O)_2$-$A_1$, wherein: $A_1$ is aryl$_{(C \leq 12)}$, substituted aryl$_{(C \leq 12)}$, or

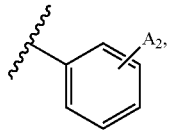

wherein: $A_2$ is acyloxy$_{(C \leq 12)}$, substituted acyloxy$_{(C \leq 12)}$, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, or substituted dialkylamino$_{(C \leq 12)}$, wherein $A_2$ is not —$CO_2H$, —$CO_2CH_3$, —$OCH_3$, —$OCH_2CH_3$, —$C(O)CH_3$, —$NHCH_3$, —$NHCH_2CH_3$, —$N(CH_3)_2$, —$C(O)NH_2$, and —$OC(O)CH_3$; and n is 1, 2, 3, 4, or 5. In other embodiments, $R_2$ is —$C(O)O(CH_2)_2SC_6H_5$. In other embodiments, $R_2$ is —$C(O)O(CH_2)_2S(O)_2C_6H_5$. In other embodiments, $R_2$ is taken together with $R_1$ and is a divalent protecting group. In some embodiments, $R_1$ and $R_2$ are phthalimide or substituted phthalimide. In some embodiments, $R_3$ is hydrogen. In other embodiments, $R_3$ is alkoxy$_{(C \leq 12)}$. In some embodiments, $R_3$ is methoxy. In some embodiments, $R_4$ is hydrogen. In other embodiments, $R_4$ is a monovalent amine protecting group. In some embodiments, $R_4$ is —$C(O)CH_2CH=CH_2$. In some embodiments, $R_5$ is alkyl$_{(C \leq 12)}$. In some embodiments, $R_5$ is methyl. In some embodiments, $R_6$ is hydroxy. In some embodiments, $R_7$ is hydroxy. In some embodiments, $R_8$ is hydroxy. In some embodiments, $R_9$ is amino. In other embodiments, $R_9$ is alkyl$_{(C \leq 12)}$. In some embodiments, $R_9$ is methyl. In other embodiments, $R_9$ is $Y_2$—$R_{12}$. In some embodiments, $Y_2$ is alkanediyl$_{(C \leq 12)}$. In some embodiments, $Y_2$ is —$CH_2$—. In some embodiments, $R_{12}$ is amino. In other embodiments, $R_{12}$ is —$NX_2X_3$. In some embodiments, $X_2$ and $X_3$ are taken together and form a phthalimide. In other embodiments, $X_2$ and $X_3$ are taken together and form a substituted phthalimide. In other embodiments, $X_2$ is hydrogen. In some embodiments, $X_3$ is t-butoxycarbonyl. In some embodiments, $R_{10}$ is amino. In other embodiments, $R_{10}$ is alkyl$_{(C \leq 12)}$. In some embodiments, $R_{10}$ is methyl. In other embodiments, $R_{10}$ is $Y_2$—$R_{12}$. In some embodiments, $Y_2$ is alkanediyl$_{(C \leq 12)}$. In some embodiments, $Y_2$ is —$CH_2$—. In some embodiments, $R_{12}$ is amino. In other embodiments, $R_{12}$ is —$NX_2X_3$. In some embodiments, $X_2$ and $X_3$ are taken together and form a phthalimide. In other embodiments, $X_2$ and $X_3$ are taken together and form a substituted phthalimide. In other embodiments, $X_2$ is hydrogen. In some embodiments, $X_3$ is t-butoxycarbonyl. In some embodiments, $R_{11}$ is hydrogen. In some embodiments, carbon atom 17 is in the R configuration. In some embodiments, carbon atom 17 is in the S configuration. In some embodiments, the compound is further defined as:

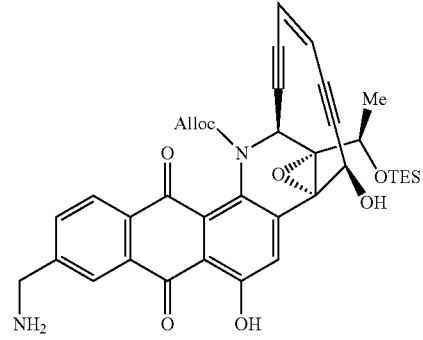

or a pharmaceutically acceptable salt thereof. In some embodiments, the compound is further defined as:

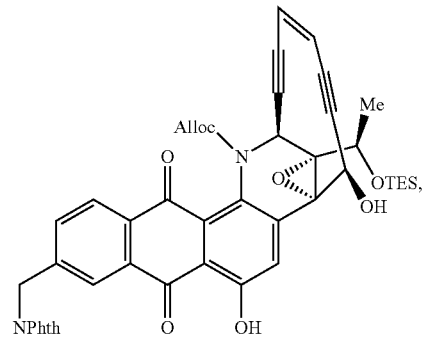

-continued
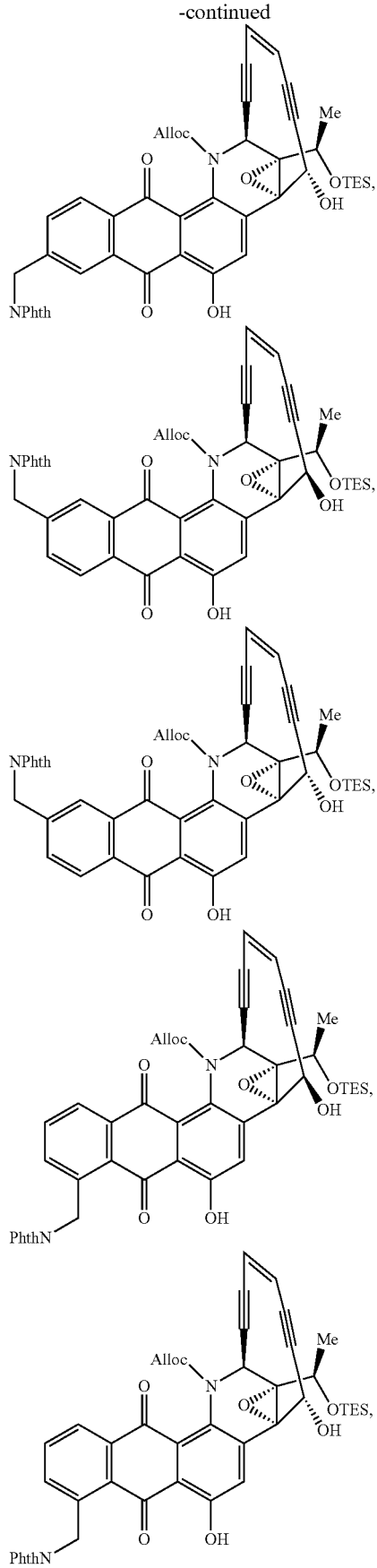
-continued
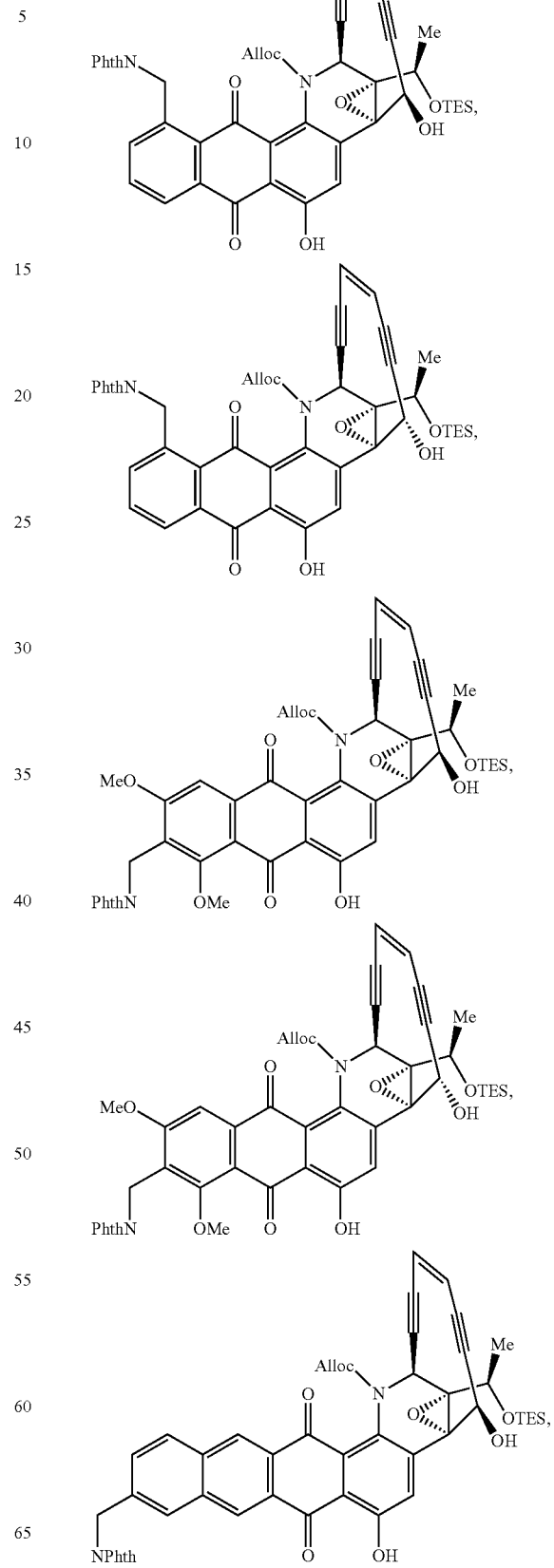

-continued
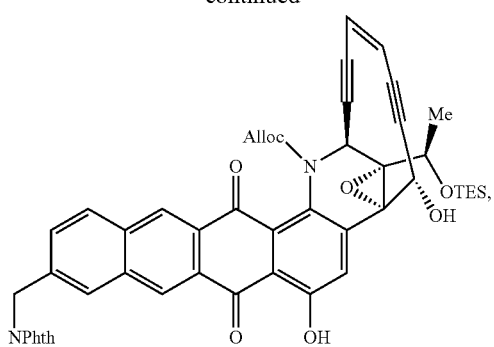
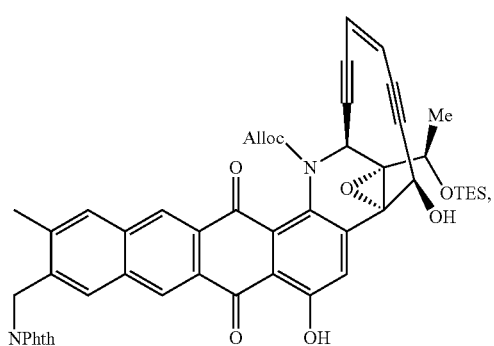
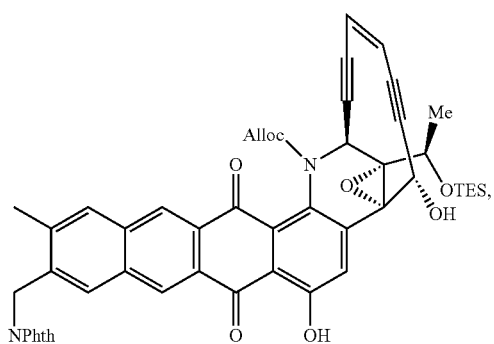
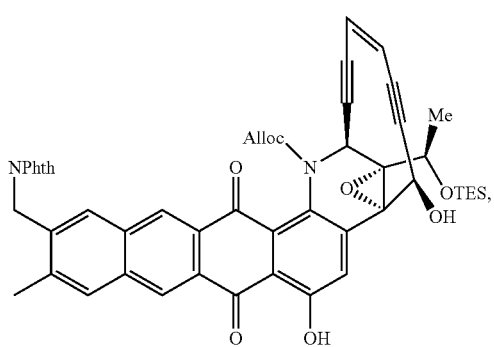
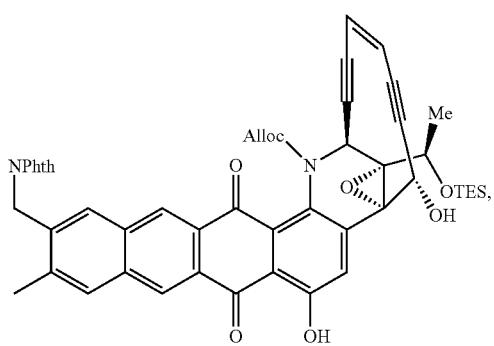
-continued
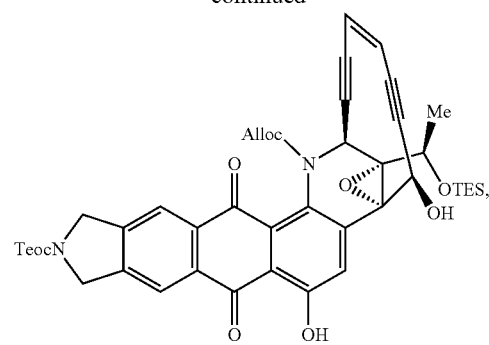
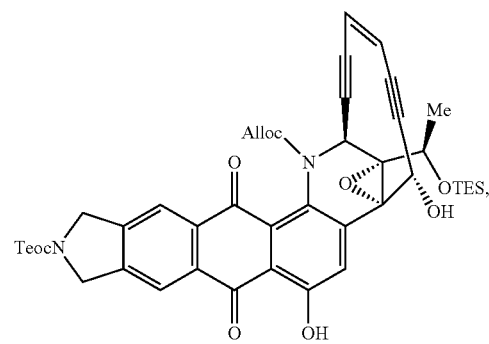
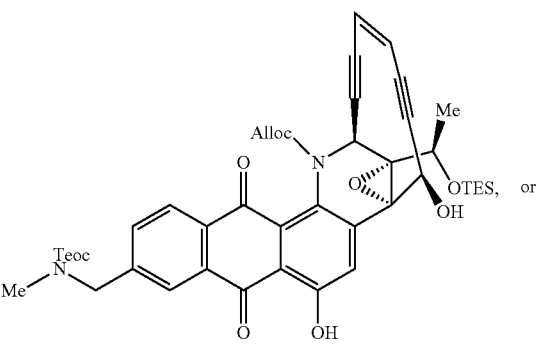
or
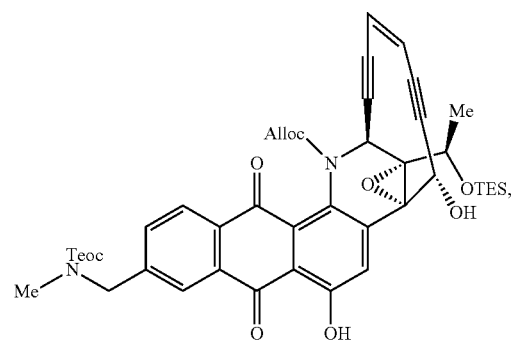
or a pharmaceutically acceptable salt thereof. In some embodiments, the compound is further defined as:

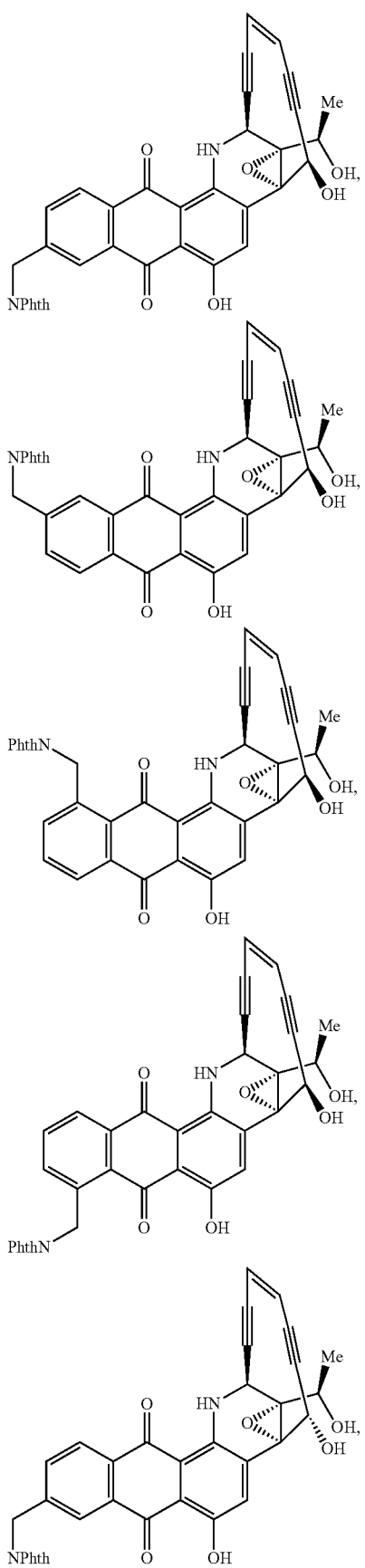
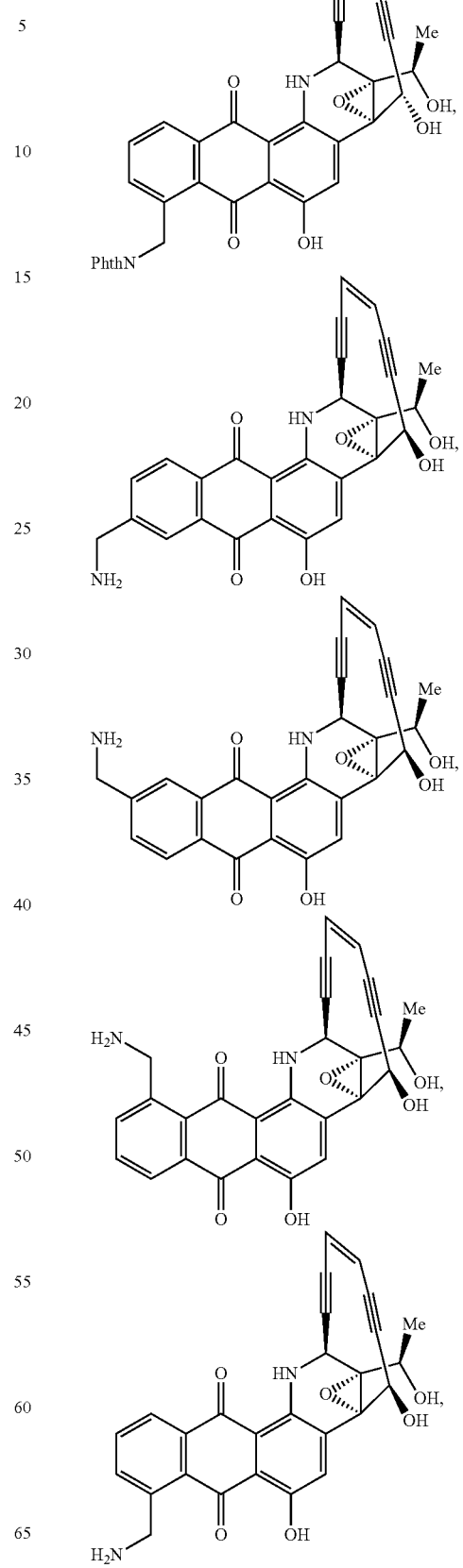

-continued
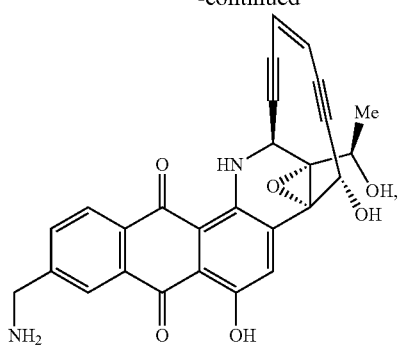
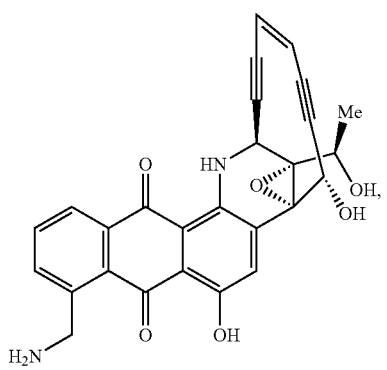
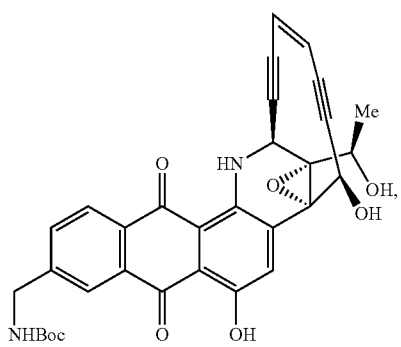
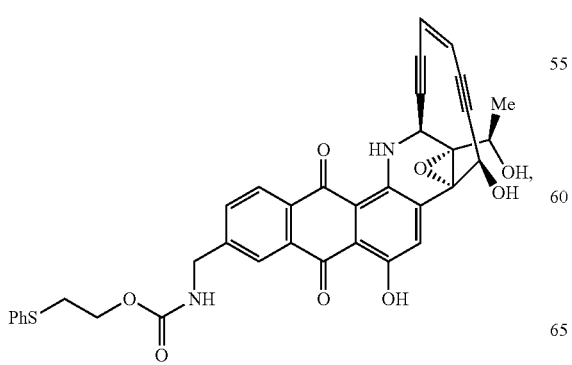
-continued
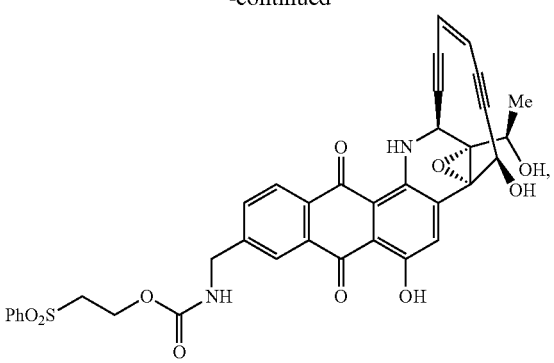
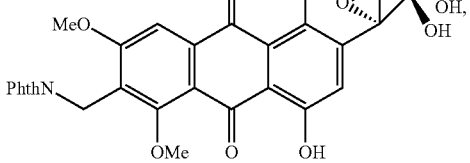
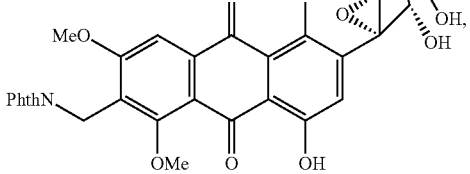
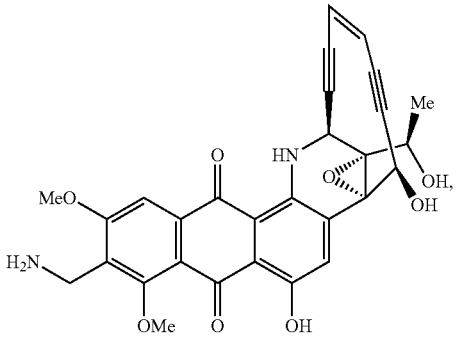
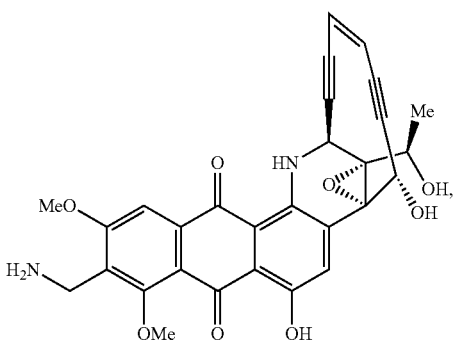

21
-continued
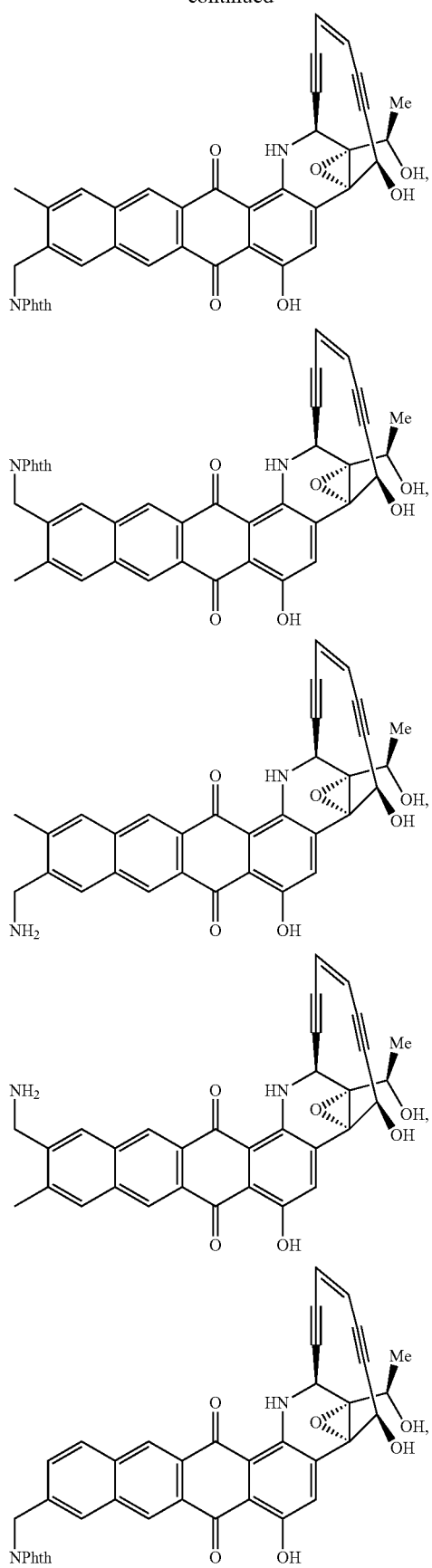
22
-continued
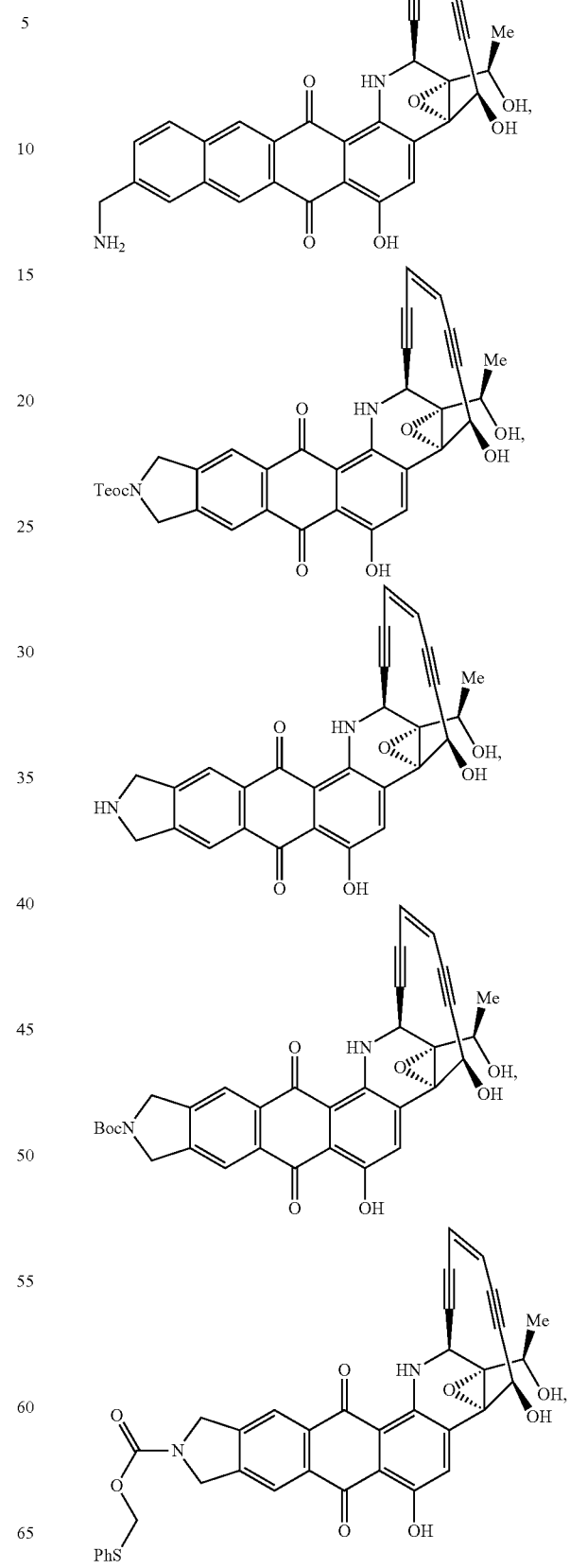

-continued

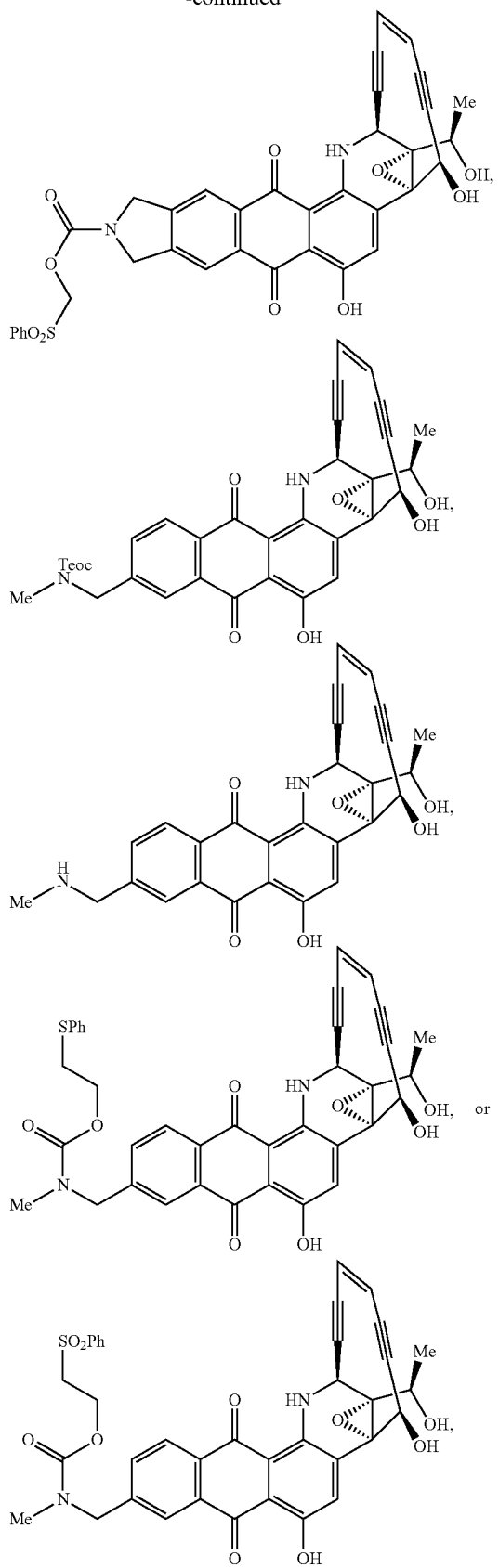

or a pharmaceutically acceptable salt thereof.

In another aspect, the present disclosure provides a pharmaceutical composition comprising a compound and an excipient. In some embodiments, the composition is formulated for oral, intraadiposal, intraarterial, intraarticular, intracranial, intradermal, intralesional, intramuscular, intranasal, intraocular, intrapericardial, intraperitoneal, intrapleural, intraprostatical, intrarectal, intrathecal, intratracheal, intratumoral, intraumbilical, intravaginal, intravenous, intravesicular, intravitreal, liposomal, local, mucosal, parenteral, rectal, subconjunctival, subcutaneous, sublingual, topical, transbuccal, transdermal, vaginal, via a catheter, via a lavage, via continuous infusion, via infusion, via inhalation, via injection, via local delivery, or via localized perfusion administration.

In yet another aspect, the present disclosure provides a method of preparing a compound of the formula:

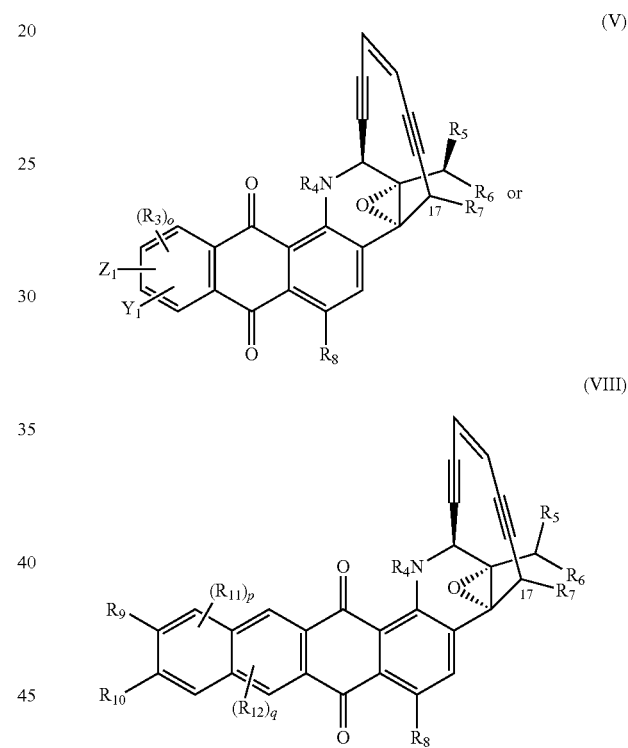

wherein: $Y_1$ is $-O(CH_2)_m Y'$, $-NH(CH_2)_m Y'$, $-S(CH_2)_m Y'$, or $-(CH_2)_m NR_1 R_2$, or is taken together with $Z_1$ as described below; wherein: Y' is hydroxy, halo, mercapto, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; and $R_1$ and $R_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, $-C(O)O(CH_2)_n S-A_1$, $-C(O)O$ $(CH_2)_nS(O)$-$A_1$, or —$C(O)O(CH_2)_nS(O)_2$-$A_1$, wherein: $A_1$ is aryl$_{(C6-12)}$, substituted aryl$_{(C6-12)}$, or

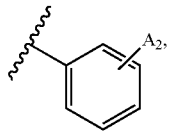

wherein: $A_2$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein $A_2$ is not —$CO_2H$, —$CO_2CH_3$, —$OCH_3$, —$OCH_2CH_3$, —$C(O)CH_3$, —$NHCH_3$, —$NHCH_2CH_3$, —$N(CH_3)_2$, —$C(O)NH_2$, and —$OC(O)CH_3$; n is 1, 2, 3, 4, or 5; or $R_1$ and $R_2$ are taken together and are divalent amine protecting group, alkanediyl$_{(C1-12)}$, alkylaminodiyl$_{(C1-8)}$; alkoxydiyl$_{(C1-8)}$; or a substituted version of either of these groups; or $Y_1$ is taken with $Z_1$ and is alkylaminodiyl$_{(C1-8)}$ substituted alkylaminodiyl$_{(C2-8)}$; -alkanediyl$_{(C1-6)}$-$NZ_2$-alkanediyl$_{(C1-6)}$, or -substituted alkanediyl$_{(C1-6)}$-$NZ_2$-substituted alkanediyl$_{(C1-6)}$, wherein: $Z_2$ is hydrogen, an amine protecting group, acyl$_{(C6-12)}$, substituted acyl$_{(C6-12)}$, —$C(O)O(CH_2)_nS$-$A_3$, or —$C(O)O(CH_2)_nS(O)_2$-$A_3$, wherein: $A_3$ is aryl$_{(C6-12)}$, substituted aryl$_{(C6-12)}$, or

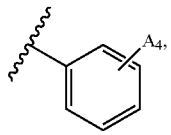

wherein: $A_4$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein $A_4$ is not —$CO_2H$, —$CO_2CH_3$, —$OCH_3$, —$OCH_2CH_3$, —$C(O)CH_3$, —$NHCH_3$, —$NHCH_2CH_3$, —$N(CH_3)_2$, —$C(O)NH_2$, and —$OC(O)CH_3$; $Z_1$ is absent, hydrogen or taken together with $Y_1$ as defined above; $R_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C1-12)}$, amido$_{(C1-12)}$, or a substituted version of any of these groups; o is 1, 2, or 3; $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —$OX_1$, —$NX_2X_3$, or —$SX_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and $R_9$, $R_{10}$, and $R_{11}$ are each independently selected from hydrogen, hydroxy, amino, mercapto, —$OX_1$, —$NX_2X_3$, or —$SX_4$, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or $Y_2$—$R_{13}$; wherein: $X_1$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a hydroxy protecting group; $X_2$ and $X_3$ are independently selected from hydrogen, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, a monovalent amine protecting group, or when $X_2$ and $X_3$ are taken together form a divalent amine protecting group; $X_4$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a thiol protecting group; $Y_2$ is alkanediyl$_{(C1-12)}$ or substituted alkanediyl$_{(C1-12)}$; and $R_{13}$ is hydroxy, amino, mercapto, —$OX_1$, —$NX_2X_3$, or —$SX_4$, or heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and p and q are each independently 1 or 2; by carrying out a reaction comprising admixing a compound of the formula:

(XII)

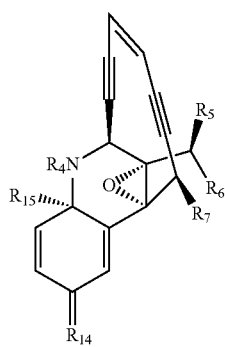

wherein: $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —$OX_1$, —$NX_2X_3$, or —$SX_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: $X_1$ is a hydroxy protecting group; $X_2$ and $X_3$ are independently selected from hydrogen, a monovalent amine protecting group, or when $X_2$ and $X_3$ are taken together form a divalent amine protecting group; $X_4$ is a thiol protecting group; and $R_{14}$ is —O—, —S—, or —$NR_{15}$—; wherein: $R_{15}$ is hydrogen, alkyl$_{(C1-6)}$, or substituted alkyl$_{(C1-6)}$; R$_{15}$ is cyano, alkoxy$_{(C1-12)}$, substituted alkoxy$_{(C1-12)}$, acyloxy$_{(C1-12)}$, substituted acyloxy$_{(C1-12)}$, alkylthio$_{(C1-12)}$, substituted alkylthio$_{(C1-12)}$, alkylsulfonyl$_{(C1-12)}$, substituted allylsulfonyl$_{(C1-12)}$, arylsulfonyl$_{(C1-12)}$, substituted arylsulfonyl$_{(C1-12)}$ alkylsulfonyloxy$_{(C1-12)}$, substituted alkylsulfonyloxy$_{(C1-12)}$, arylsulfonyloxy$_{(C1-12)}$, or substituted arylsulfonyloxy$_{(C1-12)}$; with a compound of the formula:

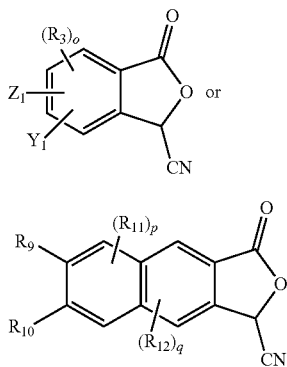

wherein: Y$_1$ is —O(CH$_2$)$_m$Y', —NH(CH$_2$)$_m$Y', —S(CH$_2$)$_m$Y', or —(CH$_2$)$_m$NR$_1$R$_2$, or is taken with Z$_1$ as described below; wherein: Y' is hydroxy, halo, mercapto, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; and R$_1$ and R$_2$ are each independently selected from hydrogen, hydroxy, alkyl$_{(C1-12)}$, substituted alkyl$_{(1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, —C(O)O(CH$_2$)$_n$S-A$_1$, —C(O)O (CH$_2$)$_n$S(O)-A$_1$, or —C(O)O(CH$_2$)$_n$S(O)$_2$-A$_1$, wherein: A$_1$ is aryl$_{(C6-12)}$, substituted aryl$_{(C6-12)}$, or

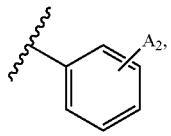

wherein: A$_2$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein A$_2$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; n is 1, 2, 3, 4, or 5; or R$_1$ and R$_2$ are taken together and are divalent amine protecting group, alkanediyl$_{(C1-12)}$, alkylaminodiyl$_{(C2-8)}$; alkoxydiyl$_{(C1-8)}$; or a substituted version of either of these groups; or Y$_1$ is taken with Z$_1$ and is alkylaminodiyl$_{(C1-8)}$ substituted alkylaminodiyl$_{(C2-8)}$; -alkanediyl$_{(C1-6)}$-NZ$_2$-alkanediyl$_{(C1-6)}$, or -substituted alkanediyl$_{(C1-6)}$-NZ$_2$-substituted alkanediyl$_{(C1-6)}$, wherein: Z$_2$ is hydrogen, an amine protecting group, acyl$_{(C1-12)}$, substituted acyl$_{(C1-12)}$, —C(O)O(CH$_2$)$_n$S-A$_3$, or —C(O)O(CH$_2$)$_n$S(O)$_2$-A$_3$, wherein: A$_3$ is aryl$_{(C6-12)}$, substituted aryl$_{(C6-12)}$, or

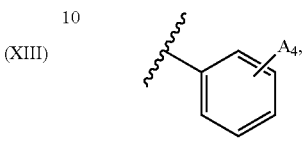

wherein: A$_4$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein A$_4$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; Z$_1$ is absent, hydrogen or taken together with Y$_1$ as defined above; R$_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; and o is 1 or 2; or R$_9$, R$_{10}$, R$_{11}$, and R$_{12}$ are each independently selected from hydrogen, hydroxy, amino, mercapto, —OX$_1$, —NX$_2$X$_3$, or —SX$_4$, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or Y$_2$—R$_{13}$; wherein: X$_1$ is a hydroxy protecting group; X$_2$ and X$_3$ are independently selected from hydrogen, a monovalent amine protecting group, or when X$_2$ and X$_3$ are taken together form a divalent amine protecting group; X$_4$ is a thiol protecting group; Y$_2$ is alkanediyl$_{(C1-12)}$ or substituted alkanediyl$_{(C1-12)}$; or R$_{13}$ is hydroxy, amino, mercapto, —OX$_1$, —NX$_2$X$_3$, or —SX$_4$, or heteroaryl$_{(C6-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and p and q are each independently 1 or 2; in the presence of a strong non-nucleophilic base in a solvent under conditions sufficient to cause a reaction. In some embodiments, Y$_1$ is not —NH$_2$, —NHMe, or —NHCH$_2$CH$_2$NH$_2$. In some embodiment, the base is lithium bis(trimethylsilyl)amide, sodium bis(trimethylsilyl)amide, potassium bis(trimethylsilyl)amide, lithium diisopropyl amide, sodium diisopropyl amide, potassium diisopropyl amide, lithium tetramethylpiperidide, lithium t-butoxide, sodium t-butoxide, or potassium t-butoxide, lithium hydride, sodium hydride, or potassium hydride. In some embodiments, the base is lithium bis(trimethylsilyl)amide. In some embodiments, the solvent is tetrahydrofuran. In some embodiments, the method further comprises admixing the compound of formula IV or formula V with the base before contacting the compound of formula III with the compound of formula IV or formula V. In some embodiments, the compound of formula III is dissolved in THF and added via cannula. In some embodiments, the method further comprising dissolving the compound of formula I or formula II in an organic solvent and reacting the compound of the formula:

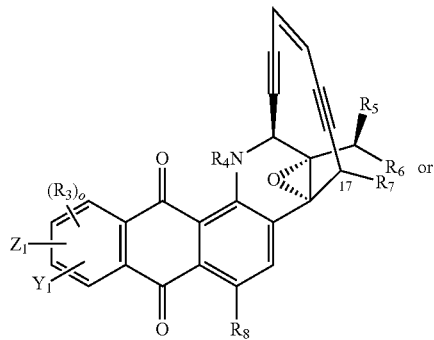

(V)

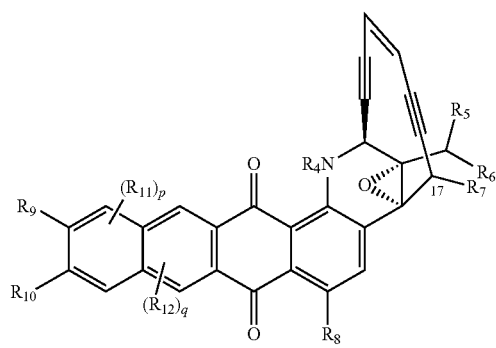

(VIII)

wherein: $Y_1$ is —O(CH$_2$)$_m$Y', —NH(CH$_2$)$_m$Y', —S(CH$_2$)$_m$Y', or —(CH$_2$)$_m$NR$_1$R$_2$, or is taken together with $Z_1$ as described below; wherein: Y' is hydroxy, halo, mercapto, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; and $R_1$ and $R_2$ are each independently selected from hydrogen, hydroxy, alkyl$_{(C1-12)}$, substituted alkyl$_{(1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, —C(O)O(CH$_2$)$_n$S-A$_1$, —C(O)O(CH$_2$)$_n$S(O)-A$_1$, or —C(O)O(CH$_2$)$_n$S(O)$_2$-A$_1$, wherein: A$_1$ is aryl$_{(C6-12)}$, substituted aryl$_{(C6-12)}$, or

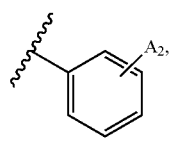

wherein: A$_2$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein A$_2$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; n is 1, 2, 3, 4, or 5; or $R_1$ and $R_2$ are taken together and are divalent amine protecting group, alkanediyl$_{(C1-12)}$, alkylaminodiyl$_{(C1-8)}$; alkoxydiyl$_{(C1-8)}$; or a substituted version of either of these groups; or $Y_1$ is taken with $Z_1$ and is alkylaminodiyl$_{(C1-8)}$ substituted alkylaminodiyl$_{(C1-8)}$; -alkanediyl$_{(C1-6)}$-NZ$_2$-alkanediyl$_{(C1-6)}$, or -substituted alkanediyl$_{(C1-6)}$-NZ$_2$-substituted alkanediyl$_{(C1-6)}$, wherein: $Z_2$ is hydrogen, an amine protecting group, acyl$_{(C1-12)}$, substituted acyl$_{(C1-12)}$, —C(O)O(CH$_2$)$_n$S-A$_3$, or —C(O)O(CH$_2$)$_n$S(O)$_2$-A$_3$, wherein: A$_3$ is aryl$_{(C6-12)}$, substituted aryl$_{(C6-12)}$, or

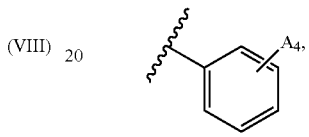

wherein: A$_4$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein A$_2$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; $Z_1$ is absent, hydrogen or taken together with $Y_1$ as defined above; $R_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; o is 1 or 2; $R_4$ is hydrogen, alkyl$_{(C1-12)}$, a monovalent amine protecting group, or substituted alkyl$_{(C1-12)}$; $R_5$, $R_6$, and $R_7$ are each independently hydrogen, hydroxy, amino, mercapto, —OX$_1$, —NX$_2$X$_3$, or —SX$_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: X$_1$ is a hydroxy protecting group; X$_2$ and X$_3$ are independently selected from hydrogen, a monovalent amine protecting group, or when X$_2$ and X$_3$ are taken together form a divalent amine protecting group; X$_4$ is a thiol protecting group; R$_5$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and $R_9$, $R_{10}$, $R_{11}$, and $R_{12}$ are each independently selected from hydrogen, hydroxy, amino, mercapto, —OX$_1$, —NX$_2$X$_3$, or —SX$_4$, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or Y$_2$—R$_{13}$; wherein: X$_1$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a hydroxy protecting group; X$_2$ and X$_3$ are independently selected from hydrogen, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, a monovalent amine protecting group, or when X$_2$ and X$_3$ are taken together form a divalent amine protecting group; X$_4$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a thiol protecting group; Y$_2$ is alkanediyl$_{(C1-12)}$ or substituted alkanediyl$_{(C1-12)}$; and R$_{13}$ is hydroxy, amino, mercapto, —OX$_1$, —NX$_2$X$_3$, or —SX$_4$, or heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and p and q are each independently 1 or 2; with a palladium salt in the presence of a base under conditions sufficient to cause a reaction to form a compound of the formula:

(XV)

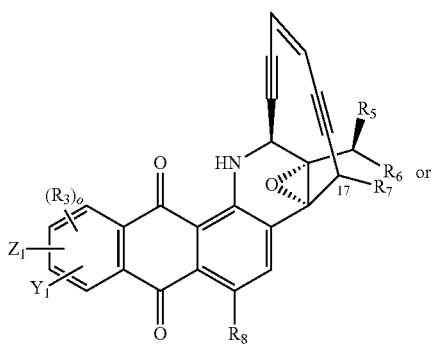

(XVI)

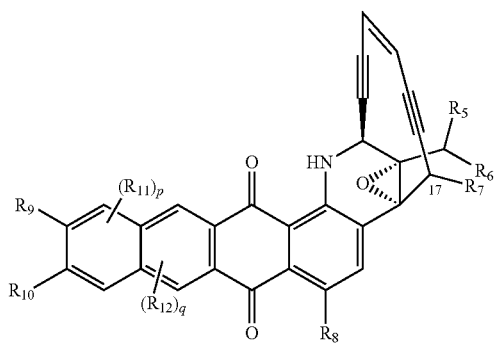

wherein: Y$_1$ is —O(CH$_2$)$_m$Y', —NH(CH$_2$)$_m$Y', —S(CH$_2$)$_m$Y', or —(CH$_2$)$_m$NR$_1$R$_2$, or is taken together with Z$_1$ as described below; wherein: Y' is hydroxy, halo, mercapto, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, or substituted alkylamino$_{(C1-12)}$; m is 1, 2, 3, 4, 5, or 6; and R$_1$ and R$_2$ are each independently selected from hydrogen, hydroxy, alkyl$_{(C1-12)}$, substituted alkyl$_{(1-12)}$, alkenyl$_{(C1-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group, —C(O)O(CH$_2$)$_n$S-A$_1$, —C(O)O(CH$_2$)$_n$S(O)-A$_1$, or —C(O)O(CH$_2$)$_n$S(O)$_2$-A$_1$, wherein: A$_1$ is aryl$_{(C6-12)}$, substituted aryl$_{(C6-12)}$, or

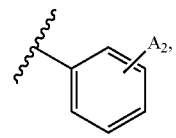

wherein: A$_2$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein A$_2$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; n is 1, 2, 3, 4, or 5; or R$_1$ and R$_2$ are taken together and are divalent amine protecting group, alkanediyl$_{(C1-12)}$, alkylaminodiyl$_{(C1-8)}$; alkoxydiyl$_{(C2-8)}$; or a substituted version of either of these groups; or Y$_1$ is taken with Z$_1$ and is alkylaminodiyl$_{(C1-8)}$ substituted alkylaminodiyl$_{(C1-6)}$; -alkanediyl$_{(C1-6)}$-NZ$_2$-alkanediyl$_{(C1-6)}$, or -substituted alkanediyl$_{(C1-6)}$-NZ$_2$-substituted alkanediyl$_{(C1-6)}$, wherein: Z$_2$ is hydrogen, an amine protecting group, acyl$_{(C1-12)}$, substituted acyl$_{(C1-12)}$, —C(O)O(CH$_2$)$_n$S-A$_3$, or —C(O)O(CH$_2$)$_n$S(O)$_2$-A$_3$, wherein: A$_3$ is aryl$_{(C6-12)}$, substituted aryl$_{(C6-12)}$, or

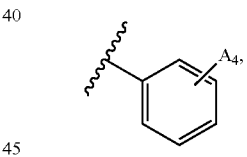

wherein: A$_4$ is alkenyl$_{(C2-12)}$, substituted alkenyl$_{(C2-12)}$, alkynyl$_{(C2-12)}$, substituted alkynyl$_{(C2-12)}$, acyl$_{(C1-12)}$, substituted acyl$_{(C1-12)}$, acyloxy$_{(C1-12)}$, substituted acyloxy$_{(C1-12)}$, alkoxy$_{(C1-12)}$, substituted alkoxy$_{(C1-12)}$, alkylamino$_{(C1-12)}$, substituted alkylamino$_{(C1-12)}$, dialkylamino$_{(C2-12)}$, or substituted dialkylamino$_{(C2-12)}$, wherein A$_2$ is not —CO$_2$H, —CO$_2$CH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, and —OC(O)CH$_3$; Z$_1$ is absent, hydrogen or taken together with Y$_1$ as defined above; R$_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups; o is 1 or 2; R$_5$, R$_6$, and R$_7$ are each independently hydrogen, hydroxy, amino, mercapto, —OX$_1$, —NX$_2$X$_3$, or —SX$_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; wherein: X$_1$ is a hydroxy protecting group;

$X_2$ and $X_3$ are independently selected from hydrogen, a monovalent amine protecting group, or when $X_2$ and $X_3$ are taken together form a divalent amine protecting group; $X_4$ is a thiol protecting group; $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and $R_9$, $R_{10}$, $R_{11}$, and $R_{12}$ are each independently selected from hydrogen, hydroxy, amino, mercapto, —$OX_1$, —$NX_2X_3$, or —$SX_4$, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or $Y_2$—$R_{13}$; wherein: $X_1$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a hydroxy protecting group; $X_2$ and $X_3$ are independently selected from hydrogen, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, a monovalent amine protecting group, or when $X_2$ and $X_3$ are taken together form a divalent amine protecting group; $X_4$ is alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, or a thiol protecting group; $Y_2$ is alkanediyl$_{(C1-12)}$ or substituted alkanediyl$_{(C1-12)}$; and $R_{13}$ is hydroxy, amino, mercapto, —$OX_1$, —$NX_2X_3$, or —$SX_4$, or heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; and p and q are each independently 1 or 2. In some embodiments, the palladium salt further comprises a palladium phosphine complex or a palladium salt in the presence of a ligand or other metal complexes or salts. In some embodiments, the palladium salt is Pd(PPh$_3$)$_4$. In some embodiments, the base is triethylamine, diisopropylethylamine, ethylenediamine, 1,8-diazabicyclo[5.4.0]undec-7-ene, or morpholine. In some embodiments, the base is morpholine. In some embodiments, the solvent is tetrahydrofuran. In some embodiments, the method further comprises removing one or more protecting groups.

In yet another aspect, the present disclosure provides a conjugate of the formula:

wherein: $A_5$ is a compound of claim 1; L is a linker; r is 1, 2, 3, 4, 5, 6, 7, 8, 9, 10, 11, or 12; and $A_6$ is a cell targeting moiety. In some embodiments, L comprises a polypeptide cleavable by an intracellular enzyme. In some embodiments, the enzyme is cathepsin B. In some embodiments, L comprises a self-immolating group. In some embodiments, L is:

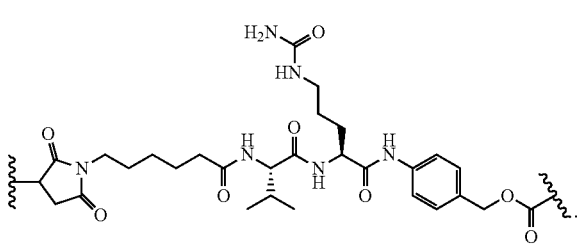 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

In some embodiments, $A_6$ is an antibody whose antigen is a tumor associated antigen. In some embodiments, the antigen is mesothelin, glypican-3, or CD70. In some embodiments, $A_5$ is a compound according to formula (I). In some embodiments, the conjugate further comprising a structure of the formula:

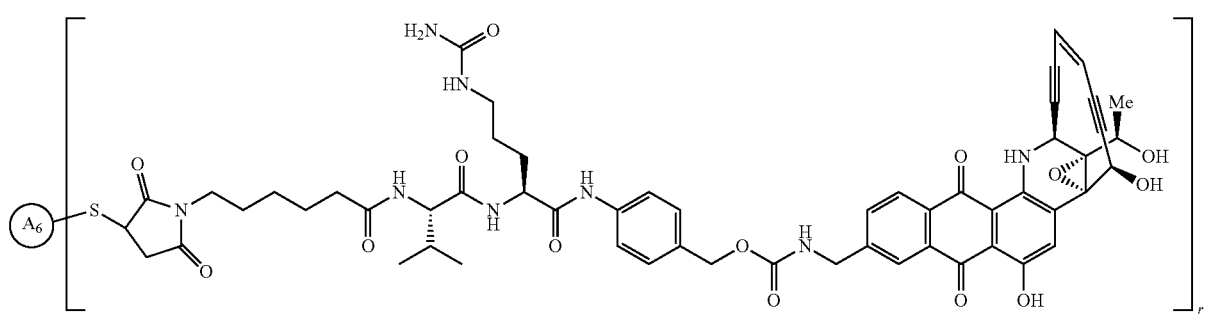

wherein: $A_6$ is an antibody and r is 1, 2, 3, or 4. In some embodiments, the antibody is an anti-mesothelin, anti-glypican-3, or anti-CD70 antibody.

In still another aspect, the present disclosure provides a pharmaceutical composition comprising a conjugate of the present disclosure and an excipient. In some embodiments, the compound is formulated for oral, intraadiposal, intraarterial, intraarticular, intracranial, intradermal, intralesional, intramuscular, intranasal, intraocular, intrapericardial, intraperitoneal, intrapleural, intraprostatical, intrarectal, intrathecal, intratracheal, intratumoral, intraumbilical, intravaginal, intravenous, intravesicularl, intravitreal, liposomal, local, mucosal, parenteral, rectal, subconjunctival, subcutaneous, sublingual, topical, transbuccal, transdermal, vaginal, via a catheter, via a lavage, via continuous infusion, via infusion, via inhalation, via injection, via local delivery, or via localized perfusion administration.

In another aspect, the present disclosure provides a method of treating a disease or disorder comprising administering to a patient in need thereof a pharmaceutically effective amount of a compound, conjugate, or composition of the present disclosure. In some embodiments, the disease or disorder is cancer. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, leukemia, melanoma, mesothelioma, multiple myeloma, or seminoma. In some embodiments, the cancer is lung cancer, gastric cancer, ovarian cancer, liver cancer, renal cancer, or breast cancer. In some embodiments, the cancer is H226 lung cancer, N87 gastric cancer, OVCAR3 ovarian cancer, Hep3B liver cancer, HepG2 liver cancer, 786-O renal cancer, or ADR multidrug resistant breast cancer. In some embodiments, the cancer exhibit one or more tumor markers. In some embodiments, the tumor marker is mesothelin, prostate specific membrane antigen, CD19, CD22, CD30, CD70, B7H$_4$, protein tyrosine kinase 7, glypican-3, RG1, CTLA-4, or CD44. In some embodiments, the tumor marker is mesothelin, glypican-3, or CD70. In some embodiments, the method comprises administering a compound or a composition of a compound of the present disclosure. In some embodiments, the method comprises administering a conjugate or a composition of the present disclosure. In some embodiments, the compound comprises an antibody. In some embodiments, the antibody binds to an antigen on the surface of the cancer cell. In some embodiments, the binding of the antibody to the antigen on the cell surface triggers the internalization of the compound. In some embodiments, the internalization of the compound triggers cleavage of a therapeutic compound from the antibody. In some embodiments, the method further comprises administering a second therapeutic agent. In some embodiments, the second therapeutic agent is a second chemotherapeutic agent, surgery, a radiotherapy, a genetic therapy, or an immunotherapy. In some embodiments, the method comprises administering the compound once. In other embodiments, the method comprises administering the compound two or more times. In some embodiments, the disease or disorder is a bacterial infection. In some embodiments, the bacterial infection is an infection of *Staphylococcus aureus*, *Escherichia coli*, or *Burkholderia cepacia*. In some embodiments, the bacterial infection is an infection of *Burkholderia cepacia*.

In still another aspect, the present disclosure provides a method of preparing a compound of the formula:

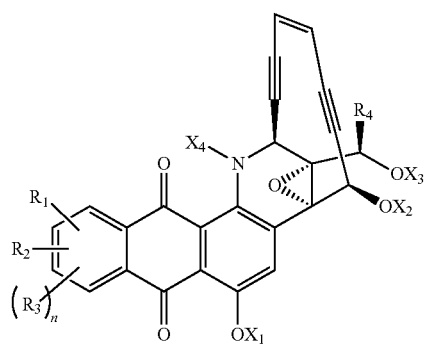

(XVIII)

wherein: $X_1$, $X_2$, $X_3$ are hydrogen or a hydroxy protecting group; $X_4$ is hydrogen or an amino protecting group; $R_1$ and $R_2$ are each independently absent, hydrogen, or $R_1$ and $R_2$ are taken together and are alkylaminodiyl$_{(C1-12)}$, substituted alkylaminodiyl$_{(C1-12)}$, alkenediyl$_{(C2-12)}$, or substituted alkenediyl$_{(C2-12)}$; $R_3$ is hydrogen, amino, carboxy, cyano, halo, hydroxy, or alkyl$_{(C1-12)}$, acyl$_{(C1-12)}$, amido$_{(C1-12)}$, alkoxy$_{(C1-12)}$, alkylamino$_{(C1-12)}$, dialkylamino$_{(C2-12)}$, or a substituted version of any of these groups; or —$Y_1$-$A_1$; wherein: $Y_1$ is alkanediyl$_{(C1-8)}$ or substituted alkanediyl$_{(C1-8)}$; $A_1$ is a linker wherein the linker has the formula:

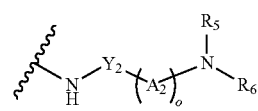

wherein: $R_5$ is hydrogen, alkyl$_{(C1-6)}$, or substituted alkyl$_{(C1-6)}$; $R_6$ is —C(O)—$Y_3$-$A_3$, wherein: $Y_3$ is alkanediyl$_{(C1-12)}$ or substituted alkanediyl$_{(C1-12)}$; and $A_3$ is a thiol reactive group; $Y_2$ is —C(O)—, —C(O)-alkanediyl$_{(C1-12)}$; substituted —C(O)-alkanediyl$_{(C1-12)}$, or a self immolating group; $A_2$ is a covalent bond, an amino acid residue, or a polypeptide; and o is 1, 2, 3, 4, 5, 6, 7, or 8; n is 1, 2, 3, or 4; and $R_4$ is alkyl$_{(C1-12)}$ or substituted alkyl$_{(C1-12)}$; comprising a) reacting a compound of the formula:

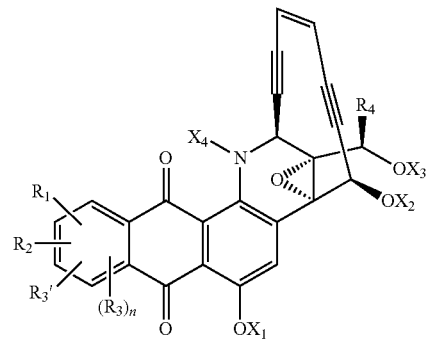

(XIX)

wherein: $R_1$, $R_2$, $R_3$, $R_4$, $X_1$, $X_2$, $X_3$, and $X_4$ are as defined above; n is 0, 1, 2, or 3; $R_3'$ is —$Y_1$-$A_1$; wherein: $Y_1$ is alkanediyl$_{(C1-8)}$ or substituted alkanediyl$_{(C1-8)}$; and $A_1$ is —NPhth; with an alkylamine$_{(C1-12)}$, dialkylamine$_{(C1-18)}$, or a substituted version of either of these groups with water in a solvent under conditions sufficient to cause a reaction to form a compound of the formula:

(XX)

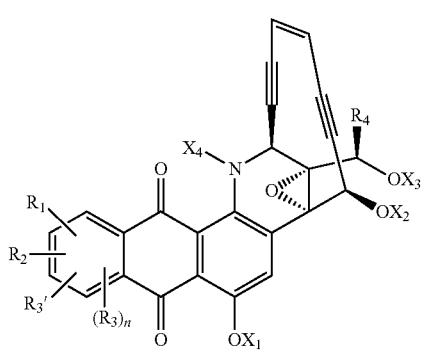

wherein: $R_1$, $R_2$, $R_3$, $R_4$, n, $X_1$, $X_2$, $X_3$, and $X_4$ are as defined above; $R_3{}'$ is —$Y_1$—$NH_2$; wherein: $Y_1$ is alkanediyl$_{(C1-8)}$ or substituted alkanediyl$_{(C1-8)}$; b) reacting the compound of formula XX with a linker of the formula:

(XXI)

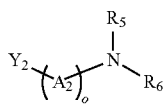

wherein: $R_5$ and $R_6$ is hydrogen, alkyl$_{(C1-6)}$, substituted alkyl$_{(C1-6)}$, or an amine protecting group; $Y_2$ is —C(O)OH, HOC(O)-alkanediyl$_{(C1-12)}$; substituted HOC(O)-alkanediyl$_{(C1-12)}$, a self immolating group, or an activated self immolating group; $A_2$ is a covalent bond, an amino acid residue, or a polypeptide; and o is 0, 1, 2, 3, 4, 5, 6, 7, or 8; and a base in a solvent under conditions sufficient to cause a reaction to form a compound of the formula:

(XXII)

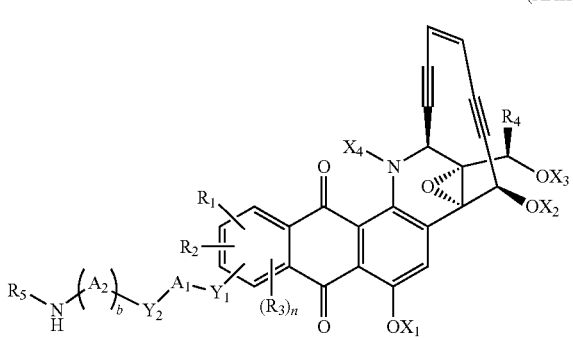

wherein: $R_1$, $R_2$, $R_3$, $R_4$, $X_1$, $X_2$, $X_3$, $X_4$, n, o, $Y_1$, $Y_2$, $A_1$, $A_2$, and $R_5$ are as defined above; c) deprotecting one or more functional groups on the compound of formula XXII comprising reacting the compound with a reagent which removes the protecting group under conditions sufficient to cause a reaction to form a compound of the formula:

(XXIII)

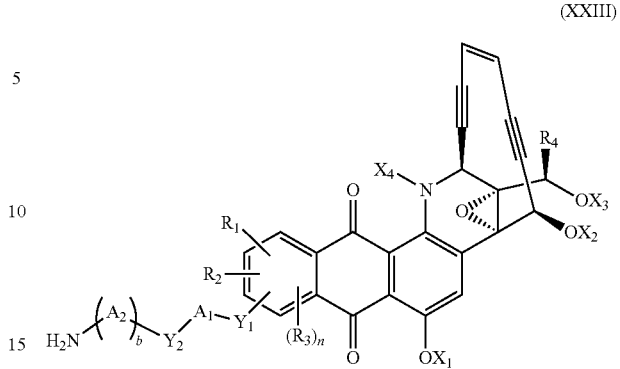

wherein: $R_1$, $R_2$, $R_3$, $R_4$, $X_1$, $X_2$, $X_3$, $X_4$, n, o, $Y_1$, $Y_2$, $A_1$, and $A_2$ are as defined above; d) reacting the compound of formula XXIII with a compound of the formula:

(XXIV)

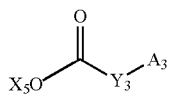

wherein: $X_5$ is hydrogen or an activating agent; $Y_3$ is alkanediyl$_{(C1-12)}$ or substituted alkanediyl$_{(C1-12)}$; and $A_3$ is a thiol reactive group; in the presence of a base in solvent under conditions sufficient to cause a reaction to form a compound of formula XVIII. In some embodiments, the compound of the formula is further defined as:

(XXV)

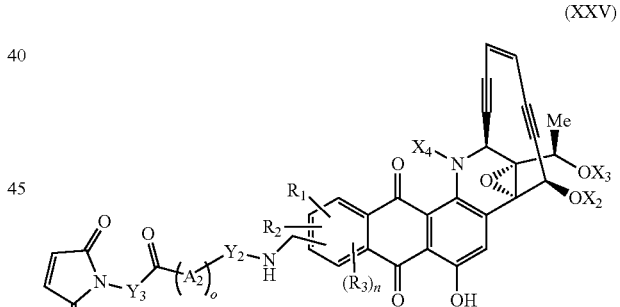

wherein: $X_2$ and $X_3$ are hydrogen or a hydroxy protecting group; $X_4$ is hydrogen or an amino protecting group; $R_1$ and $R_2$ are each independently absent, hydrogen, or $R_1$ and $R_2$ are taken together and are alkylaminodiyl$_{(C1-8)}$; substituted alkylaminodiyl$_{(C2-8)}$; alkenediyl$_{(C2-8)}$, or substituted alkenediyl$_{(C2-8)}$; $R_3$ is hydrogen, amino, carboxy, cyano, halo, hydroxy, or alkoxy$_{(C1-12)}$ or substituted alkoxy$_{(C1-12)}$; or $Y_2$ is —C(O)—, —C(O)-alkanediyl$_{(C1-12)}$, substituted —C(O)-alkanediyl$_{(C\leq 12)}$, or a self immolating group; $A_2$ is a covalent bond, an amino acid residue, or a polypeptide; and o is 1, 2, 3, 4, 5, 6, 7, or 8; n is 1, 2, or 3; and $Y_3$ is a covalent bond, alkanediyl$_{(C1-12)}$, or substituted alkanediyl$_{(C1-12)}$. In some embodiments, the compound of formula XXV is further defined as:

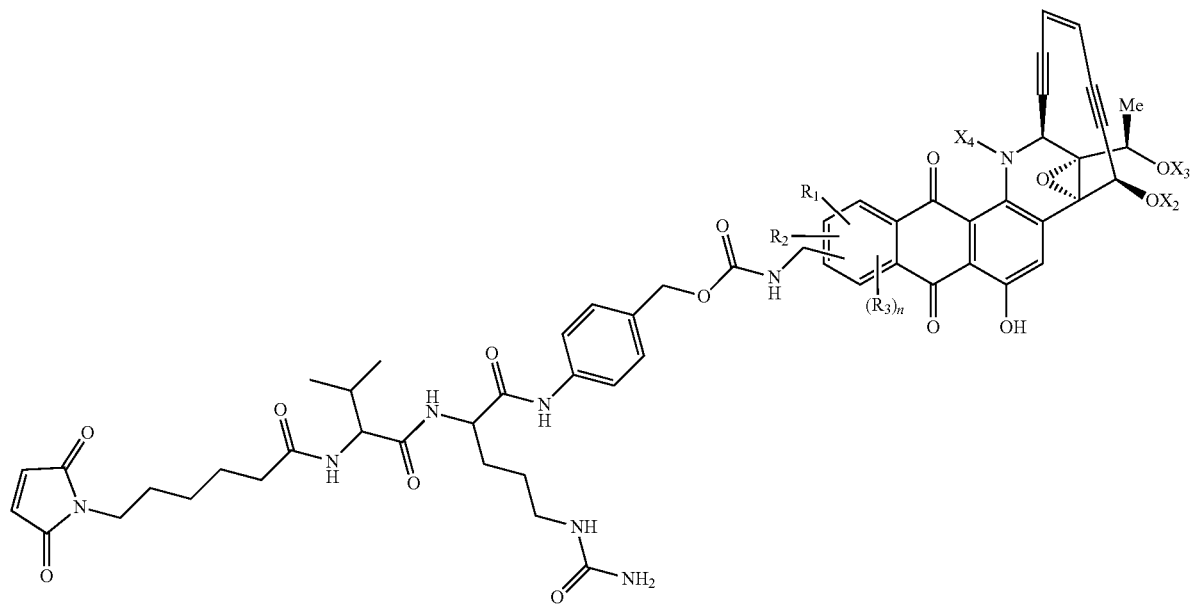

(XXVI)

wherein: $X_2$ and $X_3$ are hydrogen or a hydroxy protecting group; $X_4$ is hydrogen or an amino protecting group; $R_1$ and $R_2$ are each independently absent, hydrogen, or $R_1$ and $R_2$ are taken together and are alkylaminodiyl$_{(C1-8)}$; substituted alkylaminodiyl$_{(C1-8)}$; alkenediyl$_{(C2-8)}$, or substituted alkenediyl$_{(C2-8)}$; $R_3$ is hydrogen, amino, carboxy, cyano, halo, hydroxy, or alkoxy$_{(C1-12)}$ or substituted alkoxy$_{(C1-12)}$; and n is 1, 2, or 3. In some embodiments, the compound of formula XIX is further defined as:

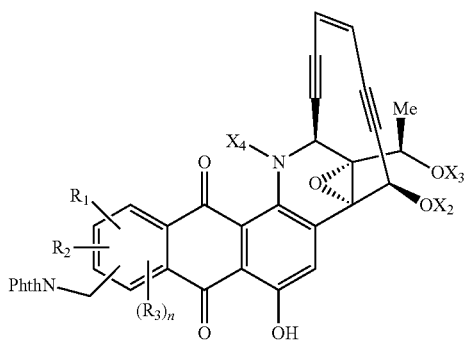

(XXVII)

wherein: $R_1$, $R_2$, $R_3$, n, $X_2$, $X_3$, and $X_4$ are as defined above. In some embodiments, the compound of formula XXI is further defined as:

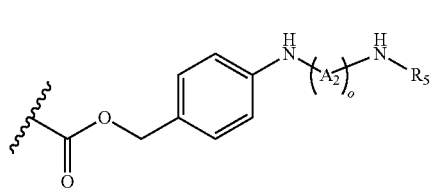

(XXVIII)

wherein: $R_5$ is an amine protecting group; $A_2$ is a covalent bond, an amino acid residue, or a polypeptide; and o is 1, 2, 3, 4, 5, 6, 7, or 8. In some embodiments, the compound of formula XXIV is further defined as:

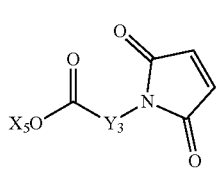

(XXIX)

wherein: $X_5$ is hydrogen or an activating agent; and $Y_3$ is alkanediyl$_{(C1-12)}$ or substituted alkanediyl$_{(C1-12)}$. In some embodiments, the compound of formula XXIV is further defined as:

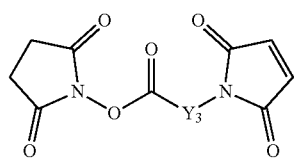

(XXX)

wherein: $Y_3$ is alkanediyl$_{(C1-12)}$ or substituted alkanediyl$_{(C1-12)}$. In some embodiments, $R_1$ is hydrogen. In other embodiments, $R_1$ is alkoxy$_{(C1-12)}$. In some embodiments, $R_1$ is methoxy. In other embodiments, $R_1$ and $R_2$ are taken together and are alkenediyl$_{(C2-12)}$ or substituted alkenediyl$_{(C2-12)}$. In some embodiments, the formula is further defined as:

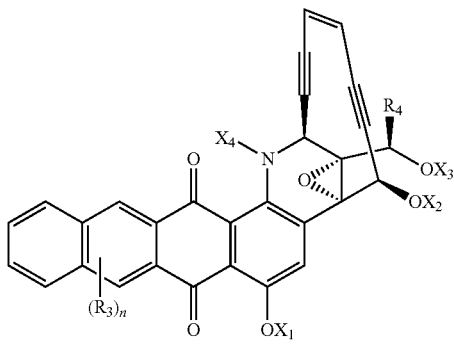

(XXXI)

wherein: $R_3$, $R_4$, n, $X_1$, $X_2$, $X_3$, and $X_4$ are as defined above. In other embodiments, $R_1$ and $R_2$ are taken together and are alkylaminodiyl$_{(C1-12)}$ or substituted alkylaminodiyl$_{(C1-12)}$. In some embodiments, the formula is further defined as:

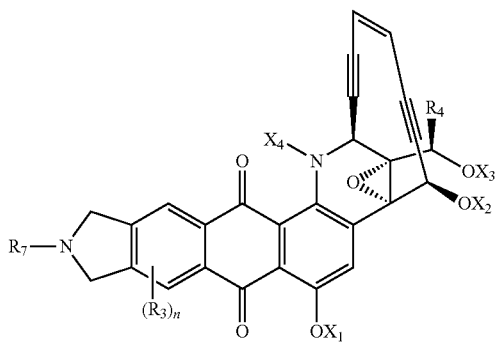

(XXXII)

wherein: $R_3$, $R_4$, n, $X_1$, $X_2$, $X_3$, and $X_4$ are as defined above; and $R_7$ is hydrogen or an amino protecting group. In some embodiments, $R_3$ is —$Y_1$-$A_1$; wherein: $Y_1$ is alkanediyl$_{(C1-8)}$ or substituted alkanediyl$_{(C1-8)}$; $A_1$ is a linker wherein the linker has the formula:

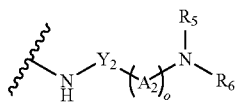

wherein: $R_5$ is hydrogen, alkyl$_{(C1-6)}$, or substituted alkyl$_{(C1-6)}$; $R_6$ is —C(O)—$Y_3$-$A_3$, wherein: $Y_3$ is alkanediyl$_{(C1-12)}$ or substituted alkanediyl$_{(C1-12)}$; and $A_3$ is a thiol reactive group; $Y_2$ is —C(O)—, —C(O)-alkanediyl$_{(C1-12)}$, substituted —C(O)-alkanediyl$_{(C1-12)}$, or a self immolating group; $A_2$ is a covalent bond, an amino acid residue, or a polypeptide; and o is 1, 2, 3, 4, 5, 6, 7, or 8. In some embodiments, $R_3$ is

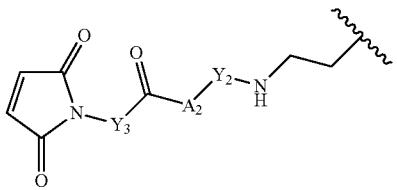

(XXXIII)

wherein $Y_2$, $A_2$, and $Y_3$ are as defined above. In some embodiments, $A_2$ is —HN-Val-Cit-C(O)O—. In some embodiments, $Y_2$ is a self-immolating group. In some embodiments, $Y_2$ is

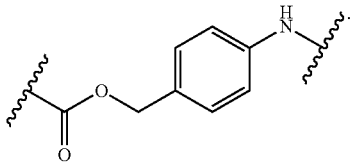 [SMILES: *Nc1ccc(COC(*)=O)cc1]

In some embodiments, $R_4$ is methyl. In some embodiments, $X_1$, $X_2$, or $X_3$ are hydrogen. In some embodiments, $X_3$ is a hydroxy protecting group. In some embodiments, $X_4$ is hydrogen. In some embodiments, $X_4$ is an amine protecting group. In some embodiments, the alkylamine$_{(C1-12)}$ or substituted alkylamine$_{(C1-12)}$ of step a) is methylamine. In some embodiments, the base of step b) is a nitrogenous base and the base is diisopropylethylamine. In some embodiments, the reagent which removes the protecting group of step c) is a base and the base is piperidine. In some embodiments, the base of step d) is a nitrogenous base and the base is diisopropylethylamine. In some embodiments, the method further comprises one or more deprotection steps. In other embodiments, these compounds of the present disclosure are envisioned to be joined to an antibody or other cell targeting moiety as disclosed in U.S. Pat. No. 8,798,431, US Patent Application No. 2013/0209494 and PCT Patent Application WO 2013/122823, all of which are incorporated herein by reference.

In the embodiments of this disclosure, it is contemplated that the conditions sufficient to cause a reaction to occur can encompass a variety of factors which effective the efficacy of the reaction. Modification of such is envisioned within the embodiments of any of the present methods. Such conditions include the number of equivalents of a compound, the choice of solvent, the choice of temperature, or the reaction time. In some aspects of the present disclosure, the reactions of the present disclosure can be run in any organic solvents. In some embodiments, the solvent is an amide$_{(C1-12)}$, an ester$_{(C1-12)}$, an alcohol$_{(C1-12)}$, an arene$_{(C1-12)}$, a substituted arene$_{(C1-12)}$, an alkane$_{(C1-12)}$, a substituted alkane$_{(C1-12)}$, a heterocycloalkane$_{(C1-12)}$, or an ether$_{(C1-12)}$. In some embodiments, the solvent of the present disclosure is diethyl ether, acetonitrile, dimethylformamide, tetrahydrofuran, dimethylsulfoxide, chloroform, dichloromethane, hexanes, methanol, ethanol, pentanes, benzene, toluene, ethyl acetate, or N-methyl-2-pyrrolidone. Furthermore, the conditions can affect the temperature of the reaction. In some embodiments, the temperature is at room temperature. In some embodiments, the room temperature or 25° C. can also be performed at a temperature from about 10° C. to about 40° C. or more preferably from about 20° C. to about 30° C. In some embodiments, the temperature can be reduced to improve the efficacy of the reaction. In some embodiments, the reduced temperature is a temperature less than room temperature. In some embodiments, the temperature is either 0° C. or −78° C. In some embodiments, the temperature is within 20° C. of the stated temperature and more preferably 10° C. of the stated temperature. In some embodiments, the temperature can be raised to speed the reaction. In some embodiments, the reaction temperature is a temperature is from about 50° C. to about 100° C. In some embodiments, the temperature is within 20° C. of the stated temperature and more preferably 10° C. of the stated temperature. Additionally, the reaction time may be varied to increase the efficacy of the reaction. In some embodiments, the reaction is from about half the exemplified time and to about twice the exemplified time. By way of a non-limiting example, a reaction which has exemplified as reacting for 1 hour, the reaction time is from about 30 minutes to 2 hours. Finally, the amount of equivalents added can also modify the efficacy of the reaction. In some embodiments, the addition of a reagent is envisioned from about half the exemplified amount to about 3 times the exemplified amount. By way of a non-limiting example, the addition of the reagent is measured based upon one of the starting material containing a carbon atom which appears in the final product. Additionally, the equivalents of a reagent which is consumed (i.e. not catalytic) is envisioned to not be less than 1 equivalent.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed.

DESCRIPTION OF ILLUSTRATIVE EMBODIMENTS

Figure 1:
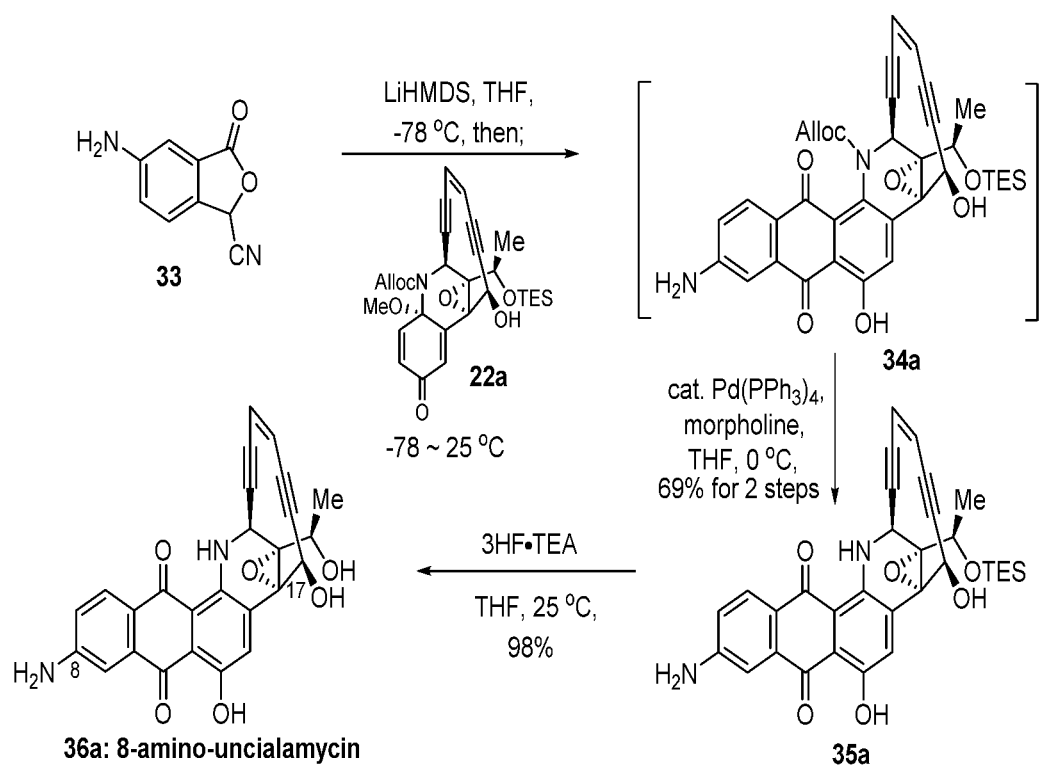
FIG. 1—Synthesis of uncialamycin analogs
Figure 2:
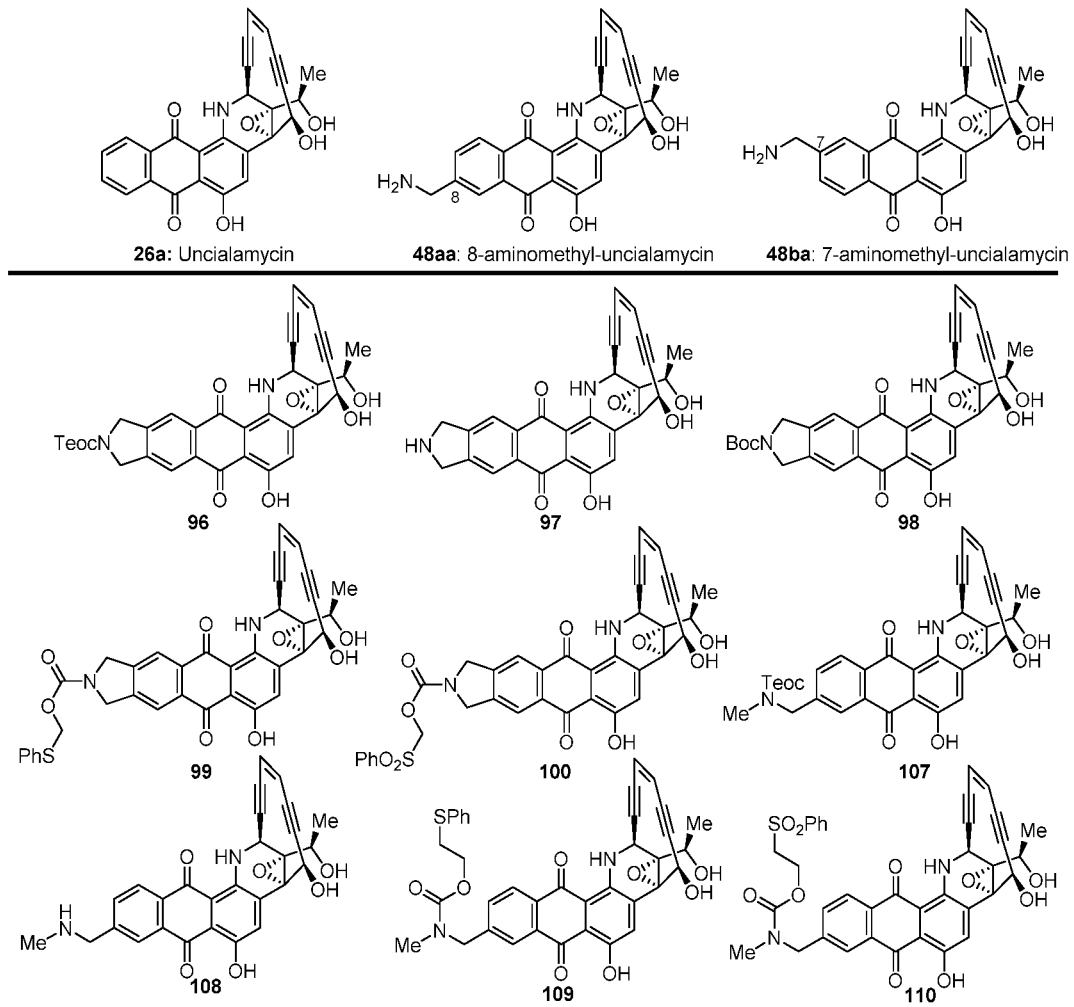
FIG. 2—Uncialamycin and some examples of aminomethyl uncialamycin and other amine containing uncialamycin analogs.

The present disclosure provides new analogs of uncialamycin and provides improved methods of synthesizing uncialamycin and analogs. These compounds have been shown to have picomolar $IC_{50}$ in cancer cells. Furthermore, these analogs are functionalized with an amine group which can be used to modify cell targeting moieties to generate novel therapeutics such as but not limited to an antibody-drug conjugate.

I. UNCIALAMYCIN AND FORMULATIONS THEREOF

The compounds provided by the present disclosure are shown, for example, above in the Summary section and in the claims below. They may be made using the methods outlined in the Examples section. Uncialamycin and its analogs can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The uncialamycin and its analogs of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of uncialamycin and its analogs can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up uncialamycin and its analogs are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

II. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example is the cell targeting agents described in U.S. Patent Publication No. 2004/005647 and in Winthrop et al., 2003 that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL2 may also be used as a cell-specific targeting moiety in a chimeric protein to target IL2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL4 receptor and may be targeted by moieties that bind these receptors, such as CD40 ligand, IL4, IL5, IL6 and CD28. The elimination of immune cells such as T cells and B cells is particularly useful in the treatment of lymphoid tumors.

Other cytokines that may be used to target specific cell subsets include the interleukins (IL1 through IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that bind to the Fn14 receptor, such as TWEAK (see, e.g., Winkles, 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-$\beta$2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-$\gamma$, IFN-$\alpha$, and IFN-$\beta$); immunoglobin superfamily (such as B7.1 (CD80), and B7.2 (B70, CD86)); TNF family (such as TNF-$\alpha$ (cachectin), TNF-$\beta$ (lymphotoxin, LT, LT-$\alpha$), LT-$\beta$, CD40 ligand (CD40L), Fas ligand (FasL), CD27 ligand (CD27L), CD30 ligand (CD30L), and 4-1BBL)); and those unassigned to a particular family (such as TGF-$\beta$, IL 1$\alpha$, IL-1$\beta$, IL-1 RA, IL-10 (cytokine synthesis inhibitor F), IL-12 (NK cell stimulatory factor), MIF, IL-16, IL-17 (mCTLA-8), and/or IL-18 (IGIF, interferon-$\gamma$ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated to virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

A. Antibodies and Antibody-Like Targeting Moieties

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular Immuno-Pharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. In some aspects, the antibody can be a VHH (i.e., an antigen-specific VHH) antibody that comprises only a heavy chain. For example, such antibody molecules can be derived from a llama or other camelid antibody (e.g., a camelid IgG2 or IgG3, or a CDR-displaying frame from such camelid Ig) or from a shark antibody. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting.

As used herein, an "antibody fragment" includes a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

"Mini-antibodies" or "minibodies" are also contemplated for use with the present embodiments. Minibodies are sFv polypeptide chains which include oligomerization domains at their C-termini, separated from the sFv by a hinge region (Pack et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

In some cases antibody-like molecules are protein scaffolds that can be used to display antibody CDR domains. The origin of such protein scaffolds can be, but is not limited to, the structures selected among: fibronectin (see, e.g., U.S. Patent Publication No. 2009/0253899, incorporated herein by reference) including fibronectin type III domain 10, protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat." The techniques for preparing and using various antibody-based constructs and fragments are well known in the art. Additional antibody-like molecules, such as anti-calins are described in detail in US Patent Publication Nos. 2010/0285564, 2006/0058510, 2006/0088908, 2005/0106660, PCT Publication No. WO 2006/056464 and (Skerra, 2001), incorporated herein by reference.

Antibody-like binding peptidomimetics are also contemplated in the present embodiments. Liu et al. (2003) describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using such peptides are provided in U.S. Patent Publication No. 2010/0317547, incorporated herein by reference.

Monoclonal antibodies (MAbs) are recognized to have certain advantages, e.g., reproducibility and large-scale production. Embodiments of the disclosure provide monoclonal antibodies of the human, murine, monkey, rat, hamster, rabbit and chicken origin. In some embodiments, human monoclonal antibodies or fragments thereof are utilized.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. Methods for humanizing antibodies are well known in the art, see, e.g., Harvey et al., 2004, incorporated herein by reference.

B. Formulations

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Formulations for oral use include tablets containing the active ingredient(s) (e.g., uncialamycin and its analogs) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

III. THERAPIES

A. Indications i. Cancer and Other Hyperproliferative Disease

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the uncialamycin analogs may be used to lead to decreased cell counts and as such can potentially be used to treat a variety of types of cancer lines. In various aspects, it is anticipated that the uncialamycin analogs of the present disclosure may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

ii. Bacterial Infections

In some aspects of the present disclosure, the compounds disclosed herein may be used to treat a bacterial infection. While humans contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy.

Additionally, different bacteria have a wide range of interactions with body and those interactions can modulate ability of the bacteria to cause an infection. For example, bacteria can be conditionally pathogenic such that they only cause an infection under specific conditions. For example, *Staphylococcus* and *Streptococcus* bacteria exist in the normal human bacterial biome, but these bacteria when they are allowed to colonize other parts of the body causing a skin infection, pneumonia, or sepsis. Other bacteria are known as opportunistic pathogens and only cause diseases in a patient with a weakened immune system or another disease or disorder.

Bacteria can also be intracellular pathogens which can grow and reproduce within the cells of the host organism. Such bacteria can be divided into two major categories as either obligate intracellular parasites or facultative intracellular parasites. Obligate intracellular parasites require the host cell in order to reproduce and include such bacteria as but are not limited to *Chlamydophila, Rickettsia*, and *Ehrlichia* which are known to cause pneumonia, urinary tract infections, typhus, and Rocky Mountain spotted fever. Facultative intracellular parasites can reproduce either intracellular or extracellular. Some non-limiting examples of facultative intracellular parasites include *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis.

Finally, bacterial infections could be targeted to a specific location in or on the body. For example, bacteria could be harmless if only exposed to the specific organs, but when it comes in contact with a specific organ or tissue, the bacteria can begin replicating and cause a bacterial infection.

In particular, the inventors contemplate treatment of bacterial infections, including those caused by *Staphyloccoccus aureus. S. aureus* is a major human pathogen, causing a wide variety of illnesses ranging from mild skin and soft tissue infections and food poisoning to life-threatening illnesses such as deep post-surgical infections, septicaemia, endocarditis, necrotizing pneumonia, and toxic shock syndrome. These organisms have a remarkable ability to accumulate additional antibiotic resistance determinants, resulting in the formation of multiply-drug-resistant strains.

Additionally, the compounds provided by the present disclosure may be used to treat an infection of *Burkholderia cepacia. B. cepacia* is a major human pathogen, which causes pneumonia particular in immunocompromised patients. This particular pathogen is known to be resistant to a number of antibiotics and thus new antibiotics are therapeutically important.

B. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the uncialamycin derivatives of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

C. Methods of Treatment

Cancer, known medically as a malignant neoplasm, is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. Not all tumors are cancerous; benign tumors do not invade neighboring tissues and do not spread throughout the body. There are over 200 different known cancers that affect humans.

The causes of cancer are diverse, complex, and only partially understood. Many things are known to increase the risk of cancer, including tobacco use, dietary factors, certain infections, exposure to radiation, lack of physical activity, obesity, and environmental pollutants. These factors can directly damage genes or combine with existing genetic faults within cells to cause cancerous mutations. Approximately 5-10% of cancers can be traced directly to inherited genetic defects. Many cancers could be prevented by not smoking, eating more vegetables, fruits and whole grains, eating less meat and refined carbohydrates, maintaining a healthy weight, exercising, minimizing sunlight exposure, and being vaccinated against some infectious diseases.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In some aspects of the present disclosure, the present disclosure provides compounds which are administered without modification or administered as pro-drugs. In some embodiments, the compounds are administered in combination with another therapeutically agent wherein each agent is administered independently or wherein the drugs are combined through chemical modifications and a linker group. In some embodiments, the drugs are administered as a conjugate with a cell targeting moiety. In some embodiments, the compounds of the present disclosure are administered as a conjugate with an antibody.

i. Antibody-Drug Conjugates (ADCs)

In some embodiments, the compounds of the present disclosure are potent cytotoxins and are used therapeutically in antibody-drug conjugates (ADCs). Without being bound by theory, the conjugation of the compound of the present disclosure to an antibody enables the targeted delivery of the compound to the site of intended action such as a cancer cell and reduces the risk of systemic toxicity.

The conjugation of an antibody to the compound may be used with a linker such that the antibody is enzymatically cleaved from the compound of the present disclosure. In some embodiments, the ADCs of the present disclosure contain a cathepsin cleavable linker. Without being bound by theory, the cathepsin cleavable linker has the following mechanism of action:

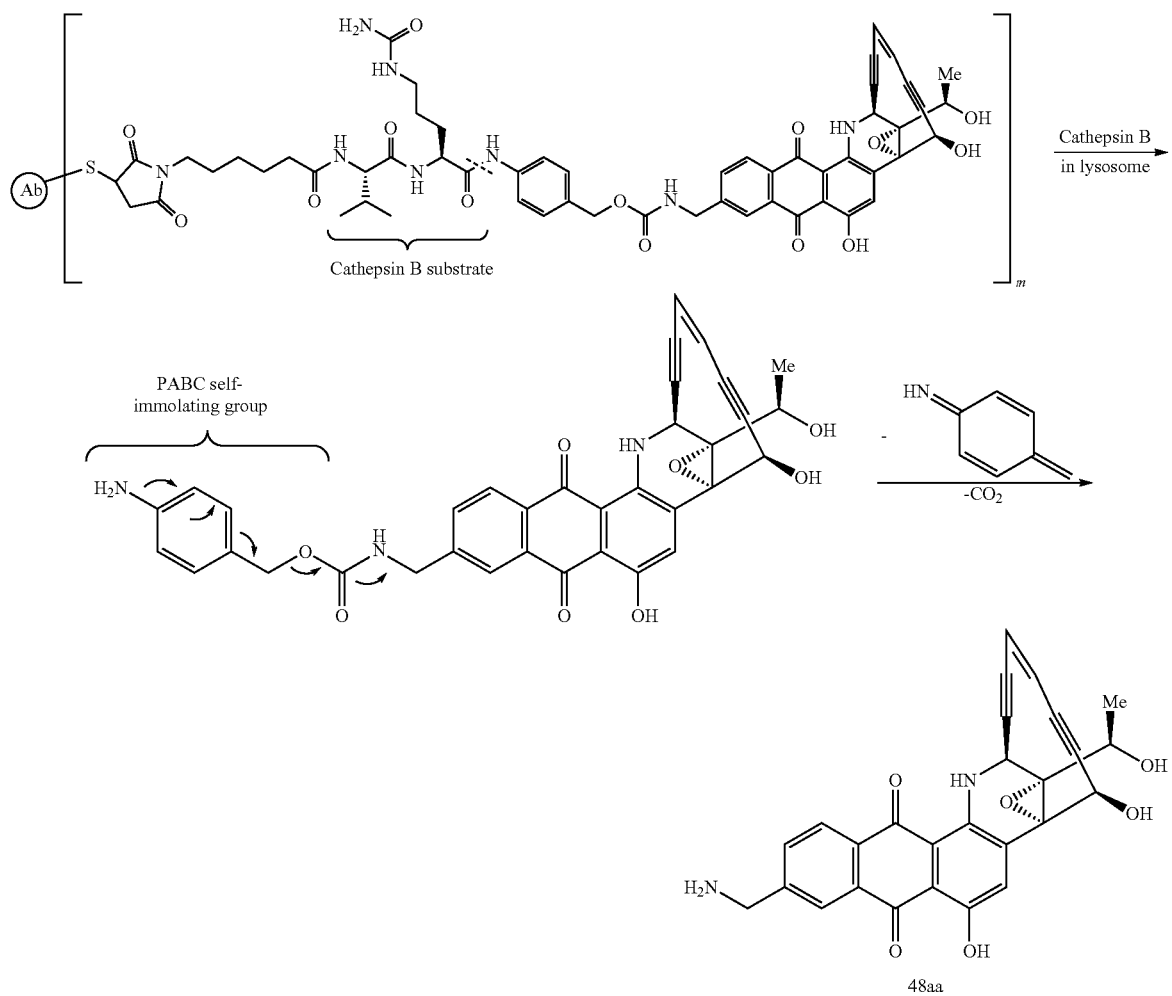

After binding of the antibody to its antigen on a target cancerous cell, the ADC is internalized into the cancerous cell and eventually it makes its way into a lysosome, where the enzyme cathepsin B is present. The citrulline-valine (Cit-Val) dipeptide is a substrate motif for cathepsin B (other substrate motifs are known and can be used instead) and is cleaved by cathepsin B at the location indicated by the dotted line. The molecule resulting from the cleavage contains a p-aminobenzyloxycarbonyl (PABC) group, which is unstable and undergoes 1,6-elimination (self-immolation) and decarboxylation to release 48aa. Without being bound by theory, in the linker, the PABC group serves as a spacer between the 48aa moiety and the Cit-Val dipeptide, to prevent the 48aa from sterically interfering with the action of cathepsin B. The 48aa damages DNA via a mechanism characteristic of the enediyne cytotoxins and causes cell death. In this manner, the 48aa is released only inside a target cell but not while the ADC is in general circulation, avoiding systemic toxicity.

Those skilled in the art will understand that the above-described conditions and methodology are exemplary and non-limiting and that other approaches for conjugation are known in the art and usable ADCs of the cytotoxins of the present disclosure may be prepared using those approaches.

An alternative conjugation technique that may be used includes copper-free "click chemistry," in which an azide group adds across the strained alkyne bond of a cyclooctyne to form an 1,2,3-triazole ring. See, e.g., Agard et al., $J.$ $Amer.$ $Chem.$ $Soc.$ 2004, 126, 15046-15047; Best, $Biochemistry$ 2009, 48, 6571-6584. In some embodiments, the azide is located on the antibody and the cyclooctyne on the drug moiety, or vice-versa. In some embodiments, the cyclooctyne group is provided by a DIBO reagent (available from Invitrogen/Molecular Probes, Eugene, Oreg.).

Yet another conjugation technique that may be used involves introducing a non-natural amino acid into an antibody, with the non-natural amino acid providing functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site by the formation of an oxime with a hydroxylamino group on the drug moiety. Alternatively, the non-natural amino acid p-azidophenylalanine can be incorporated into an antibody to provide an azide functional group for conjugation via click chemistry. Non-natural amino acids can also be incorporated into an antibody or other polypeptide using cell-free methods, as taught in Goerke et al., US 2010/0093024 A1 (2010) and Goerke et al., Biotechnol. Bioeng. 2009, 102 (2), 400-416.

Still another conjugation technique that may be used relies on an amine ($NH_2$) group that can be used for conjugation using the enzyme transglutaminase, as taught in Jeger et al., *Angew. Chem. Int. Ed.* 2010, 49, 9995-9997.

Further, another conjugation technique that may be used utilizes the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be attached to the antibody and the nucleophilic acceptor motif (typically GGG) is located on the drug moiety, or vice-versa.

Additional conjugation techniques are taught, for example, by US 2013/0209494, which is incorporated herein by reference.

Those skilled in the art will appreciate that, as multiple thiol groups may be introduced via the thiolation reaction, more than one drug moiety (i.e., 116) may be attached to an antibody. This ratio is referred to as the substitution ratio (SR) or, alternatively, the drug-antibody ratio (DAR). In some embodiments, the DAR is between about 1 and about 4. In other embodiments, the DAR is between about 1.2 and about 1.9. Those skilled in the art will also appreciate that, while each individual antibody is conjugated to an integer number of drug moieties, as a whole, a particular composition of an ADC can have a non-integer DAR as the DAR reflects a statistical average of the individual molecules within the composition.

In some aspects, the ADCs contain an antibody developed to specifically bind any cancer antigens. In some embodiments, the antibodies that can be used in ADCs of this disclosure include those specifically binding the following antigens: mesothelin, prostate specific membrane antigen (PSMA), CD19, CD22, CD30, CD70, B7H4 (also known as O8E), protein tyrosine kinase 7 (PTK7), glypican-3, RG1, CTLA-4, and CD44. The antibody can be animal (e.g., murine), chimeric, humanized, or human. In some embodiments, the antibody is a human antibody. In some aspects, the antibody is monoclonal. In some embodiments, the antibody is a monoclonal human antibody. The preparation of human monoclonal antibodies against some of the aforementioned antigens is disclosed in Korman et al., US 2009/0074660 A1 (B7H$_4$); Rao-Naik et al., U.S. Pat. No. 8,097,703 B2 (CD19); King et al., US 2010/0143368 A1 (CD22); Keler et al., U.S. Pat. No. 7,387,776 B2 (2008) (CD30); Terrett et al., U.S. Pat. No. 8,124,738 B2 and Coccia et al., US 2010/0150950 (2010) (CD70); Korman et al., U.S. Pat. No. 6,984,720 B1 (2006) (CTLA-4); Korman et al., U.S. Pat. No. 8,008,449 B2 (2011) (PD-1); Huang et al., US 2009/0297438 A1 and Cardarelli et al., U.S. Pat. No. 7,875,278 B2 (PSMA); Terrett et al., US 2010/0034826 A1 (PTK7); Terrett et al., US 2010/0209432 (A1) and Terrett et al., U.S. Pat. No. 8,680,247 (2014) (glypican-3); Harkins et al., U.S. Pat. No. 7,335,748 B2(2008) (RG1); Terrett et al., U.S. Pat. No. 8,268,970 B2 (2012) and Terrett et al., U.S. Pat. No. 8,268,970 B2 (2012) (mesothelin); and Xu et al., US 2010/0092484 A1 (CD44); each of which is incorporated herein by reference.

D. Combination Therapies

It is very common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with an uncialamycin analog or an antibody drug conjugate of uncialamycin analog and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the uncialamycin analog or the antibody drug conjugate of uncialamycin analog and the other includes the other agent.

Alternatively, the uncialamycin analog or the antibody drug conjugate of uncialamycin analog may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the peptide or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. The following is a general discussion of cancer therapies that may be used in combination with the peptides of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1f, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

6. Antibiotics

The term "antibiotics" are drugs which may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

In some embodiments, the present compounds are administered in combination with one or more additional antibiotic. In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug which acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim.

IV. SYNTHETIC METHODS

In some aspects, the compounds of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry*: Reactions, Mechanisms, and Structure (2007), which is incorporated by reference herein 1. Process Scale-Up The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein could be used to produce preparative scale quantities of uncialamycin and derivatives thereof.

2. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol '====' represents a single bond or a double bond. Thus, for example, the formula

includes

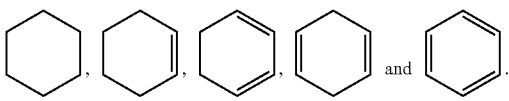

And it is understood that no one such ring atom forms part of more than one double bond. Furthermore, it is noted that the covalent bond symbol "-", when connecting one or two stereogenic atoms, does not indicate any preferred stereochemistry. Instead, it cover all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "▦" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

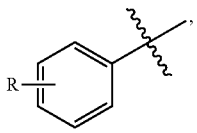

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

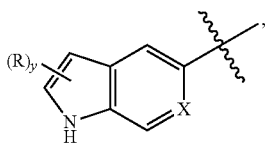

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms. Furthermore, carbon limits can also be expressed as ranges before the variable. For example, C6-C12 aryl denotes an aryl group having a minimum of 6 carbon atoms and a maximum of twelve carbon atoms. A person of skill in the art would appreciate that all of these expressions of carbon limitations are the same and can be used interchangeably.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$(i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

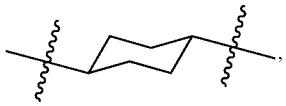 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

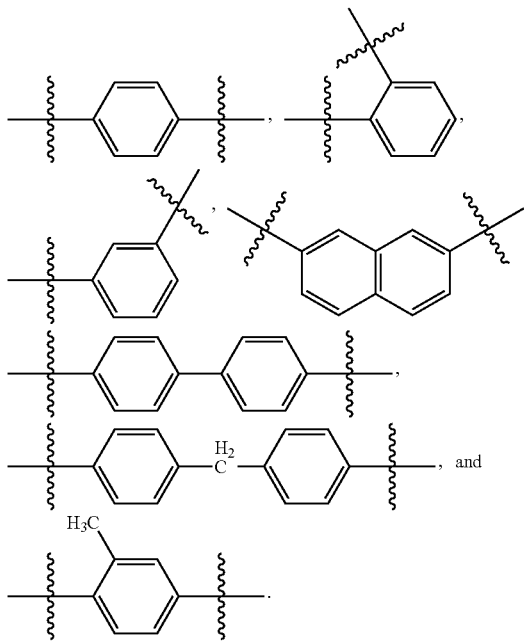

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

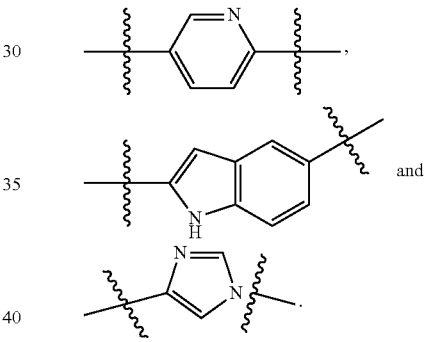

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. When these terms are used with the "substituted" modifier one or more hydrogen atom on the heteroatom has been replaced with an appropriate protecting group, for example a hydrogen atom bound to an amine may be replace with an amine protecting group as that group is defined.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

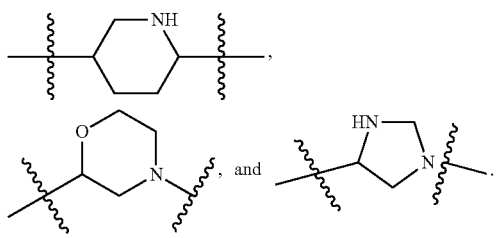

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC). When these terms are used with the "substituted" modifier one or more hydrogen atom on the heteroatom has been replaced with an appropriate protecting group, for example a hydrogen atom bound to an amine may be replace with an amine protecting group as that group is defined.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂ or one or more of the hydrogen atoms directly attached to the nitrogen atom is an amine protecting group. The groups —NHC(O)OCH₃ and —NHC(O)NHCH₃ are non-limiting examples of substituted amido groups. The term alkylamine, dialkylamino or trialkylamine represent a compound wherein the group is NH₂R, NHRR', or NRR'R", respectively wherein R, R', and R" are alkyl as that term is defined above.

The terms "alkylsulfonyl" and "alkylsulfinyl" when used without the "substituted" modifier refers to the groups —S(O)₂R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner as those terms are defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "alkylsilyl" when used without the "substituted" modifier refers to a monovalent group, defined as —SiH₂R, —SiHRR', or —SiRR'R", in which R, R' and R" can be the same or different alkyl groups, or any combination of two of R, R' and R" can be taken together to represent an alkanediyl. The groups, —SiH₂CH₃, —SiH(CH₃)₂, —Si(CH₃)₃ and —Si(CH₃)₂C(CH₃)₃, are non-limiting examples of unsubstituted alkylsilyl groups. The term "substituted alkylsilyl" refers —SiH₂R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same or different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom. The term "arylsilyl" or "aralkylsilyl" refers to the group as defined above where at least one of R, R', or R" is an aryl or aralkyl group as those groups are defined above.

An "amino acid" is a functional group which contains a —CO₂H and a —NH₂ group on the same linear carbon skeleton. In its preferred embodiment, the term "amino acid" refers to one of the naturally occurring or commercially available amino acids as well as their enantiomers and diastereomers. As used herein, the term "amino acid residue" refers to a divalent amino acid which is linked through both the amine group and carboxylate group which are connected by an alkanediyl$_{(C≤6)}$ which has been optionally substituted by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —NHC(O)NH₂, —NHC(NH)NH₂, or —S(O)₂NH₂ or an alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, or a substituted version of any of these groups wherein one or more hydrogen atoms on the chemical group has been substituted with —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —NHC(O)NH₂, —NHC(NH)NH₂, or —S(O)₂NH₂, e.g.,

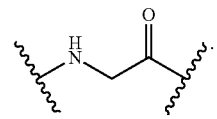 [SMILES: *NCC(*)=O]

In some embodiments, the amino acid residue is an α-amino acid wherein the alkanediyl is a methylene such that the carbonyl and the amine are joined by a single carbon. Furthermore, the A "linker" is a bifunctional chemical group which allows the reaction of each end of the molecule independently of the other either through different relativities or through the use of protecting groups so that two molecules might be joined together. Some non-limiting examples of linkers include polypeptides, polymers, oligonucleotides, amino acids, polyethylene glycol, ethylenediamine, or ethanolamine.

A "base" in the context of this application is a compound which has a lone pair of electron. Non-limiting examples of a base can include triethylamine, a metal hydroxide, metal hydride, or an metal alkane.

An alkyllithium is a compound of the formula alkyl$_{(C≤12)}$-Li. A nitrogenous base is an alkylamine, dialkylamine, trialkylamine, nitrogen containing heterocycloalkane, or heteroarene wherein the base can accept a proton to form a positively charged species. Some non-limiting examples include a nitrogenous base could be 4,4-dimethylpyridine, pyridine, piperidine, 1,8-diazabicyclo[5.4.0]undec-7-ene, diisopropylethylamine, or triethylamine.

A "fluoride source" in the context of this application is a reagent which generates or contains a fluoride ion. Some non-limiting examples include hydrofluoric acid, metal fluoride, triethylamine trihydrofluoride, or tetrabutylammonium fluoride.

An "activating agent" as used in the context of this application is a compound which reacts with a carboxylic acid group to enhance its ability to react with a nucleophile. Such reagents are widely known in the art. The reagents are commonly employed in the production of an amide bond from an amine group and a carboxylic acid. Some commonly groups include N-hydroxysuccinimide, 4-nitrophenol, carbodiimide reagents, and triazole reagents. Such reagents are taught, for example, by Montalbetti and Falque, 2005, which is incorporate herein by reference.

A "metal" in the context of this application is a transition metal or a metal of groups I or II.

A "self immolating group" is a group which undergoes decomposition at physiological conditions. Such groups are well understood in the art. Such groups are taught by Kratz et al., 2011 in "Chapter 19: Site-Specific Prodrug Activation and the Concept of Self-Immolation" in *Drug Delivery in Oncology: From Basic Research to Cancer Therapy*, which is incorporated herein by reference.

A "thiol reactive group" is a chemical functional group which undergoes a reaction with a —SH group such as on a side chain of an amino acid to form a covalent bond linking the sulfur atom to the group. Such groups are well known in the art and include but are not limited to agents which can undergo conjugate addition. Some non-limiting examples include a maleimide or a haloacetamide such as iodoacetamide.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth).

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

All reactions were carried out under an argon atmosphere with dry solvents under anhydrous conditions, unless otherwise noted. Dry tetrahydrofuran (THF), toluene, benzene, methanol (MeOH), diethyl ether (Et$_2$O), N,N-dimethylformamide (DMF), and methylene chloride (CH$_2$Cl$_2$) were obtained by passing commercially available pre-dried, oxygen-free formulations through activated alumina columns. Yields refer to chromatographically and spectroscopically ($^1$H NMR) homogeneous materials, unless otherwise stated. Reagents were purchased at the highest commercial quality and used without further purification, unless otherwise stated. Reactions were monitored by thin-layer chromatography (TLC) carried out on 0.25 mm E. Merck silica gel plates (60F-254) using UV light as visualizing agent and an ethanolic solution of phosphomolybdic acid and cerium sulfate, and heat as developing agents. E. Merck silica gel (60, particle size 0.040-0.063 mm) was used for flash column chromatography, and was deactivated by suspending in eluent with 5% added H$_2$O 12 hours prior to chromatography. NMR spectra were recorded on Bruker DRX-500 or DRX-600 instruments and calibrated using residual undeuterated solvent (CDCl$_3$: $\delta_H$=7.26 ppm, $\delta_C$=77.0 ppm; or CD$_3$CN: $\delta_H$=1.94 ppm, $\delta_C$=118.26 ppm) as an internal reference. The following abbreviations were used to designate multiplicities: s=singlet, d=doublet, t=triplet, q=quartet, m=multiplet, br=broad. Infrared (IR) spectra were recorded on a Perkin-Elmer 100 FT-IR spectrometer. High-resolution mass spectra (HRMS) were recorded on an Agilent ESI-TOF (time of flight) mass spectrometer using MALDI (matrix-assisted laser desorption ionisation) or ESI (electrospray ionization). Optical rotations were recorded on a Perkin-Elmer Model 343 polarimeter at 589 nm, and are reported in units of 10$^{-1}$ (deg cm$^2$ g$^{-1}$).

Example 2—Description of Synthetic Methods for Preparation of Uncialamycin and Analogs Thereof The synthetic strategy for the synthesis of uncialamycin and analogs thereof is highlighted in the above detailed experimental section and the synthetic schemes (Schemes 1-21) highlighted and discussed below. Dichloroethene was reacted with catalytic palladium and copper under Sonogashira conditions with triisopropylsilylacetylene to form 27. Compound 27 was reacted with trimethylsilylacetylene under Sonogashira conditions to produce 28. The trimethylsilyl group of 28 was cleaved under potassium carbonate to give 11. The preparation of 11 is shown in Scheme 1.

Scheme 1. Synthesis of enediyne building block 11.

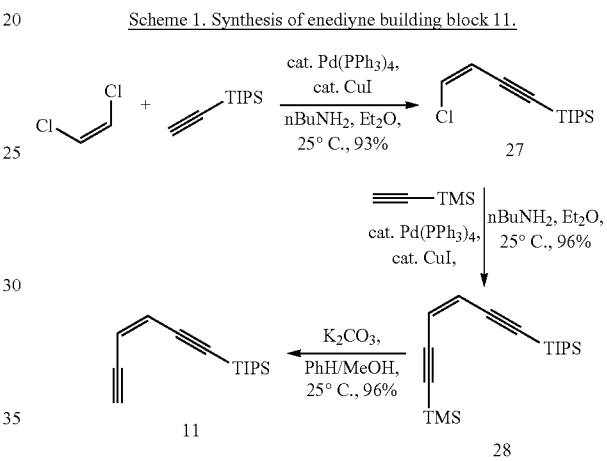

As shown in Scheme 2, starting material 1 was reacted with boron tribromide to give the deprotected isatin 2. Isatin 2 was reacted with trans-4-methoxy-3-buten-2-one in the presence of base followed by acidification. The resultant mixture was treated with potassium carbonate and heat and then acidified to give 4. Ketoacid 4 was protected with dimethoxybenzyl bromide to give intermediate 6 which was reacted with the Noyori catalyst to give lactone 8. Lactone 8 was reduced to give hemiacetal intermediate which was then protected with TES chloride to give 10. TES lactol 10 was reacted with 11 to give the enediyne 12. The TES group of 12 was cleaved using acetic acid to give 13. Lactol 13 was treated with a reducing agent and then epoxidized with mCPBA to give epoxide 14.

Scheme 2. Improved synthesis of uncialamycin (26a). Construction of key intermediate 14.

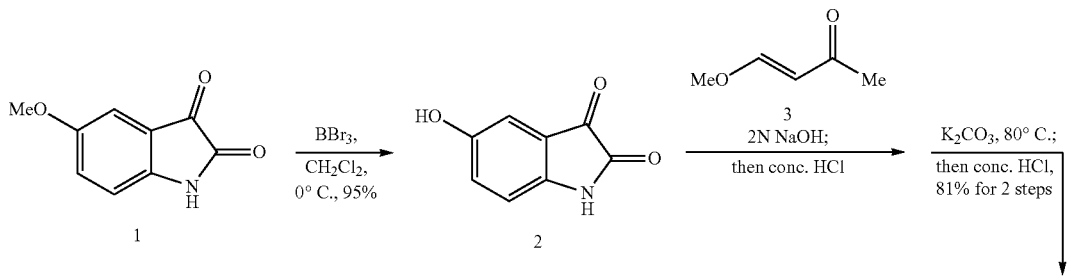

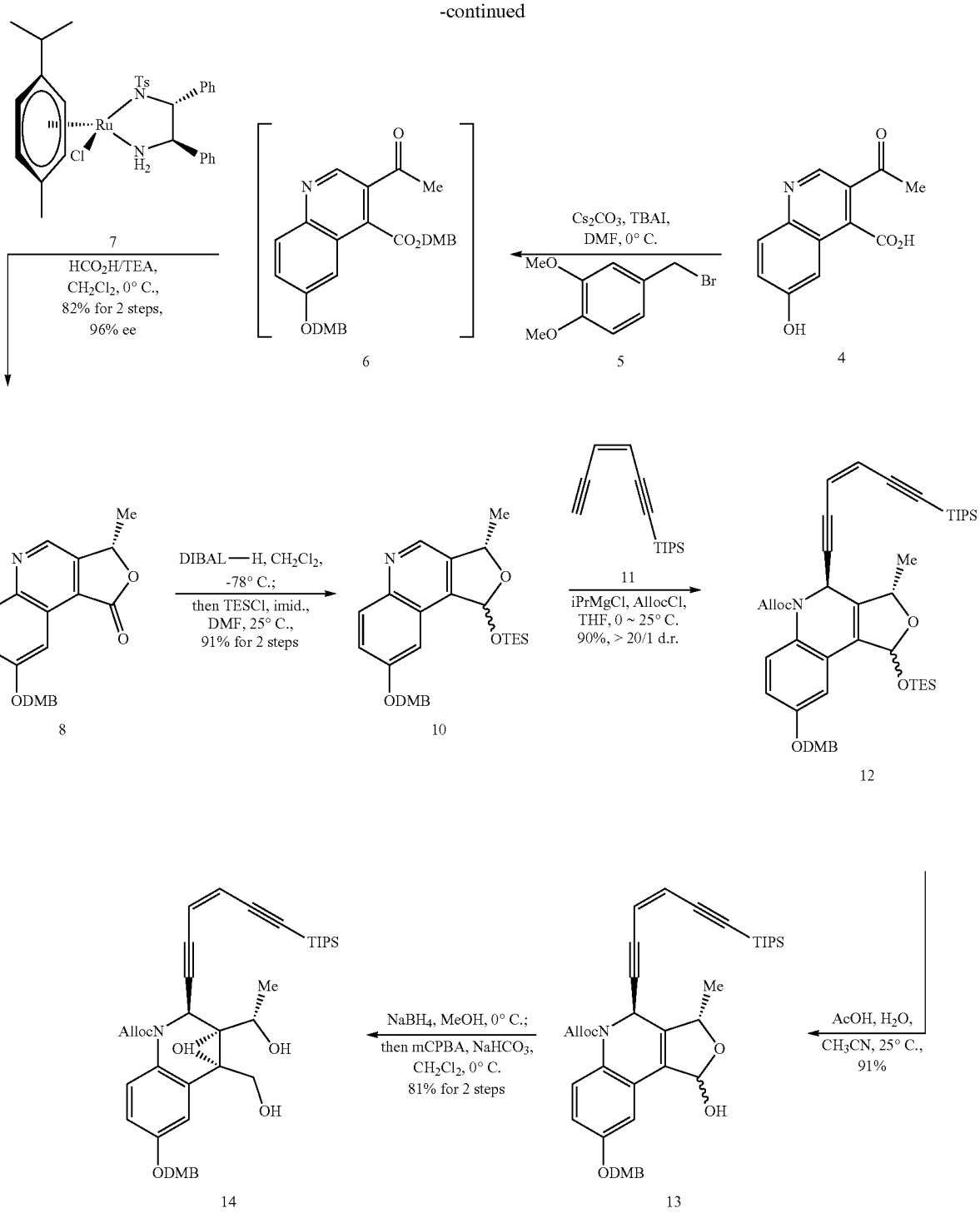

After the preparation of 14, the primary alcohol was acylated to give 15. Acetate 15 was oxidized with Dess-Martin periodinane to give ketone 16. Using TBAF, the enediyne was deprotected and the ketone reduced to give secondary alcohol 17. The secondary alcohol 17 was protected with TES chloride and then the acetate was deprotected with potassium carbonate to give primary alcohol 18. The primary alcohol 18 was oxidized to give aldehyde 19 using Dess-Martin periodinane. Using DDQ, the dimethoxybenzyl group was removed to give free phenol 20. In the presence of the strong nucleophilic base, KHMDS, and CeCl$_3$, 20 cyclizes to give cyclic enediyne 21a. Cyclic enediyne 21a was methoxylated with methanol and PhI(OAc)$_2$ to give quinone aminal 22a. Starting material 23 was reacted with 22a under Hauser condensation conditions to give protected uncialamycin derivative 24a which was deprotected with Pd(PPh$_3$)$_4$ and morpholine to give 25a. TES protected uncialamycin analog 25a was reacted with HF to give uncialamycin 26a.

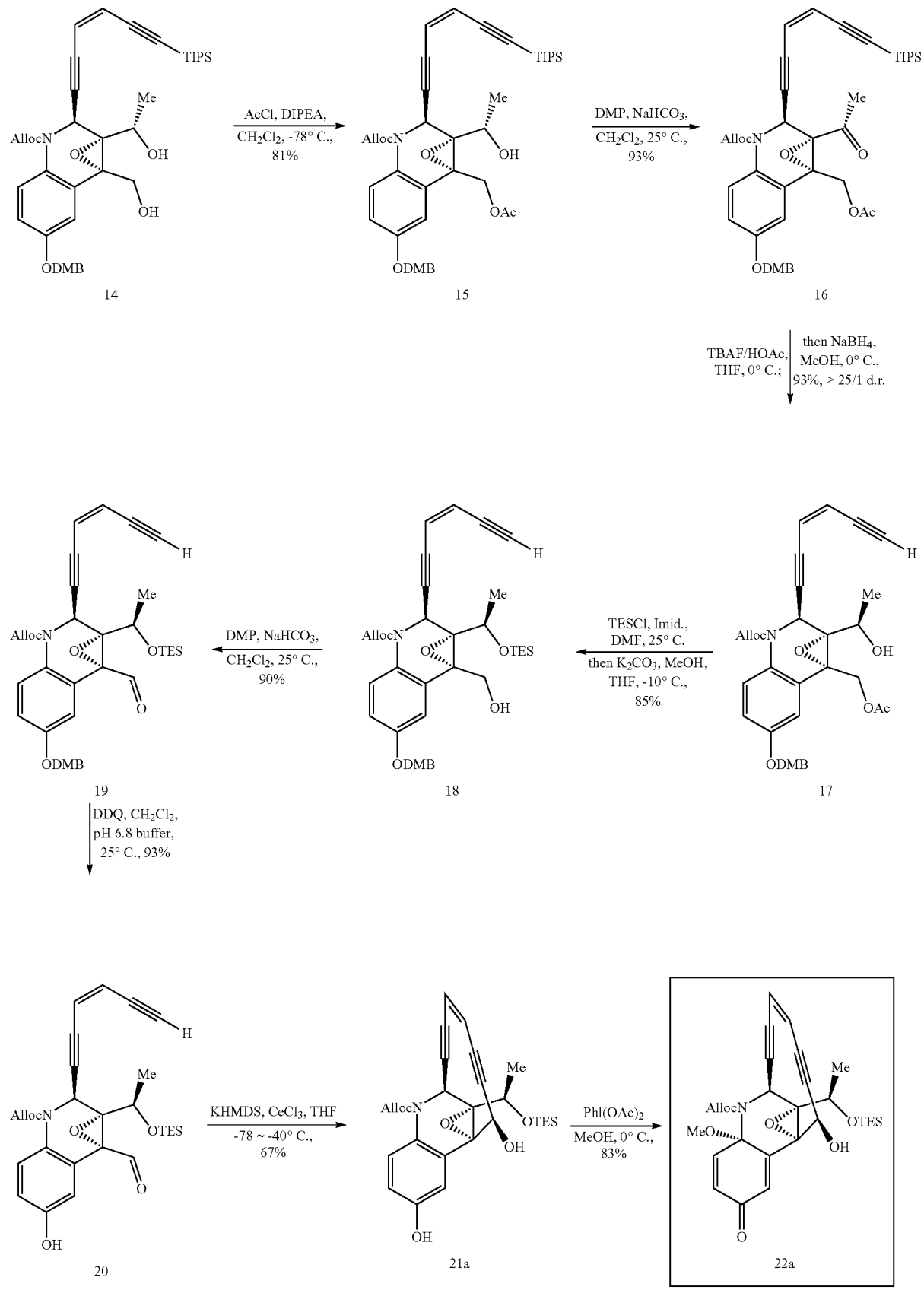
Scheme 3. Improved synthesis of uncialamycin (26a). Construction of key intermediate 22a and completion of the synthesis.

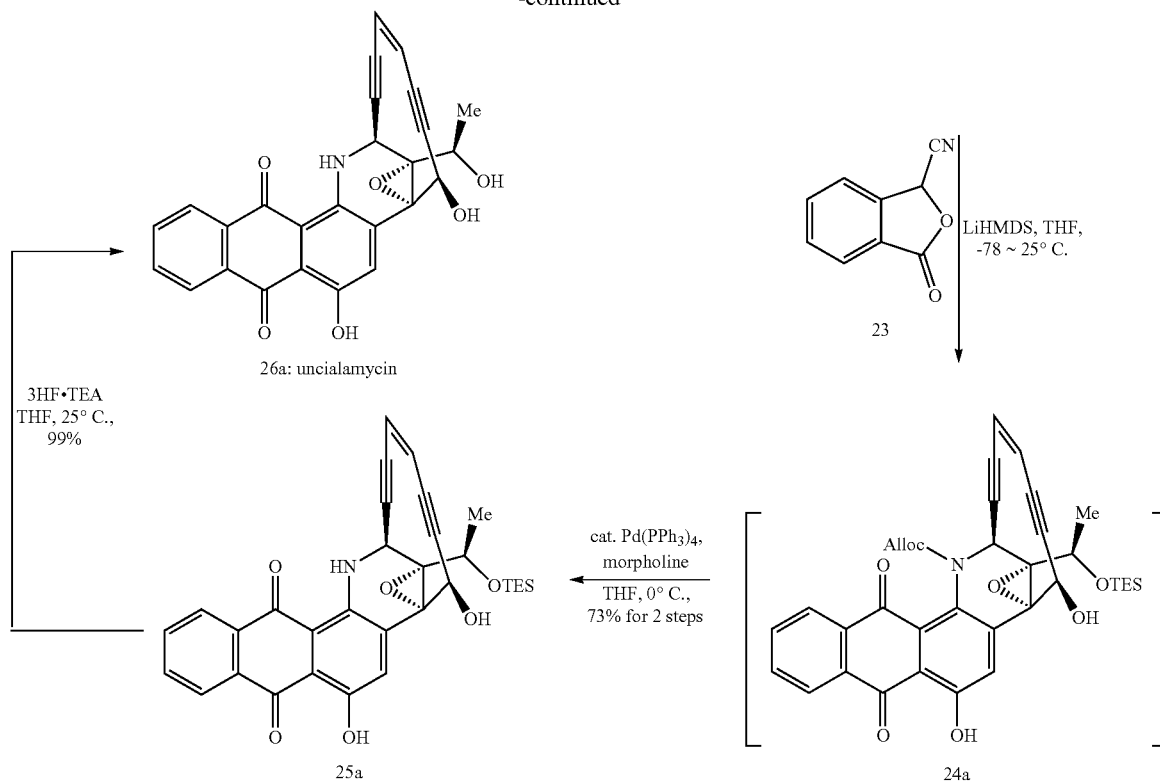

In Scheme 4, an analog of 23 is prepared to allow access to 8-aminouncialamycin analogs. 6-aminophthalide was reacted with Boc anhydride to give Boc protected phthalide 29. The protect phthalide 29 was reacted with NBS and AIBN to give bromated derivative 30 which was hydrated to give hydroxy compound 31 which undergoes nucleophilic substitution with diethylamine after activation with SOCl₂ to give formylbenzamide 32. A cyano group was introduced to 32 with TMSCN and KCN followed by cyclization under acidic conditions to give cyanophthalide 33. As described previously in Scheme 3 for uncialamycin, cyanophthalide 33 was reacted with cyclic enediyne 22a to give uncialamycin analog 34a. As shown in Scheme 5, the uncialamycin analog 34a was deprotected with morpholine and Pd(PPh₃)₄ to give TES protected 8-aminouncialamycin 35a. With HF, the TES group was removed to give 8-aminouncialamycin 36a.

Scheme. 4. Synthesis of cyanophthalide 33.

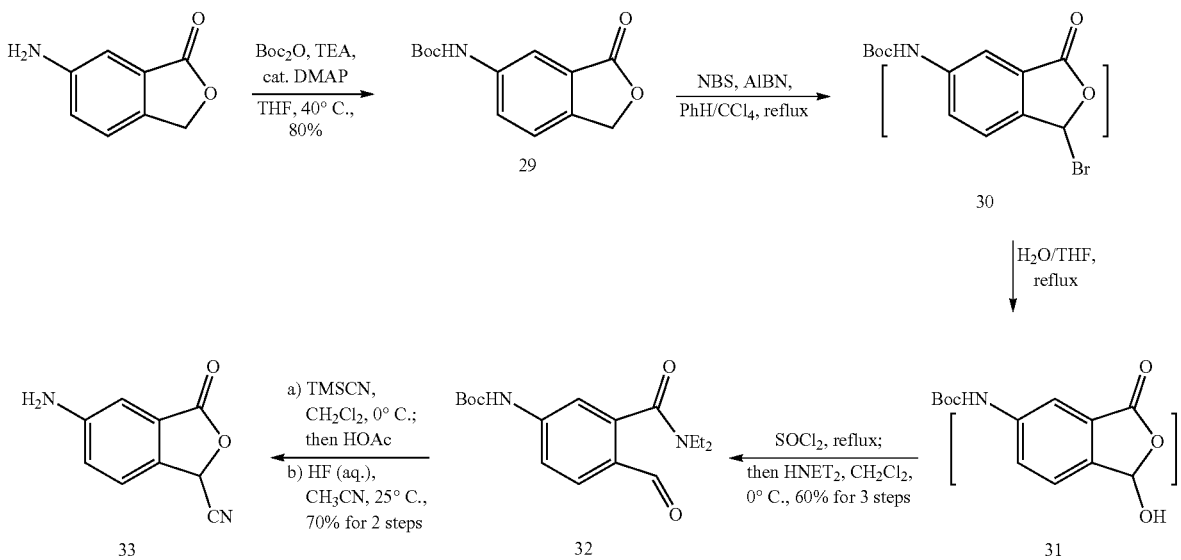

Scheme 5. Synthesis of 8-amino-uncialamycin (36a).

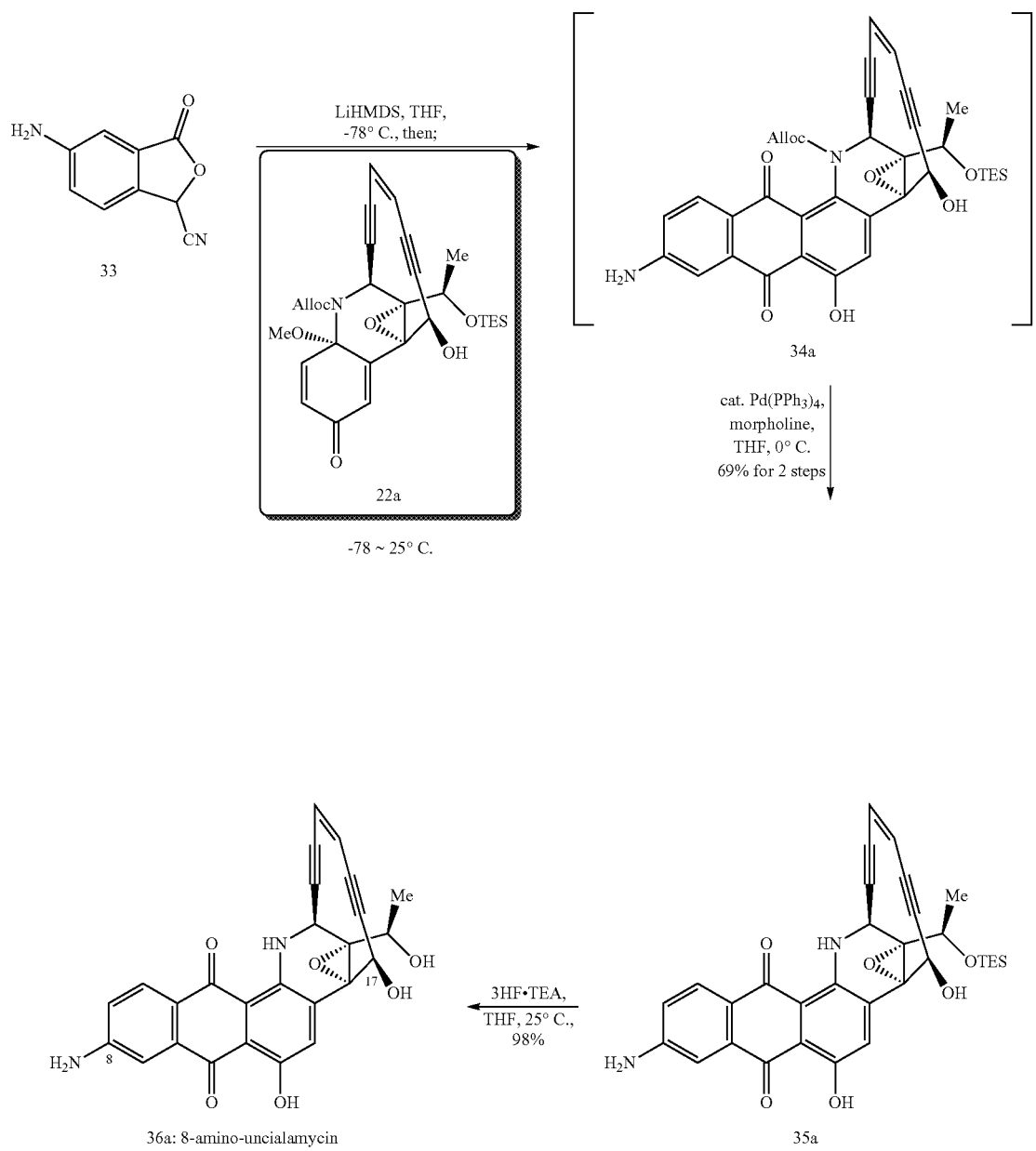

Similar to the reactions shown in Schemes 4 and 5, aminomethyl derivatives of uncialamycin were prepared. 2,5-dimethylbenzoic acid was converted to methyl ester 37a using MeI followed by bromination, cyclization and then reaction with phthalimide in basic condition to give phthalide 40a. The phthalide was brominated with NBS and AIBN followed by hydroxylation, activation and nucleophilic addition of diethylamine to give 43a. Formylbenzamide 43a was then reacted with TMSCN and KCN followed by acetic acid to give cyanophthalide 44a. Similarly, isomers 44b, 44c, and 44d were prepared. As depicted in Scheme 7, the cyanophthalide 44a or one of its isomers was reacted with either 22a or its diastereomer 22b with a strong non-nucleophilic base under Hauser condensation conditions to give protected aminomethyluncialamycin analog 45aa which was deprotected with Pd(PPh$_3$)$_4$ and morpholine to give 46aa and then HF to give 47aa. The phthalimide group was removed with methylamine to give aminomethyluncialamycin 48aa which was then Boc protected using Boc anhydride to give 49aa. Using similar methods and with comparable yields, other aminomethyluncialamycin analogs were prepared including 48ba, 48ca, 48da, and 48ba.

Scheme 6: Synthesis of cyanophthalides 44a, 44b, 44c, and 44d.
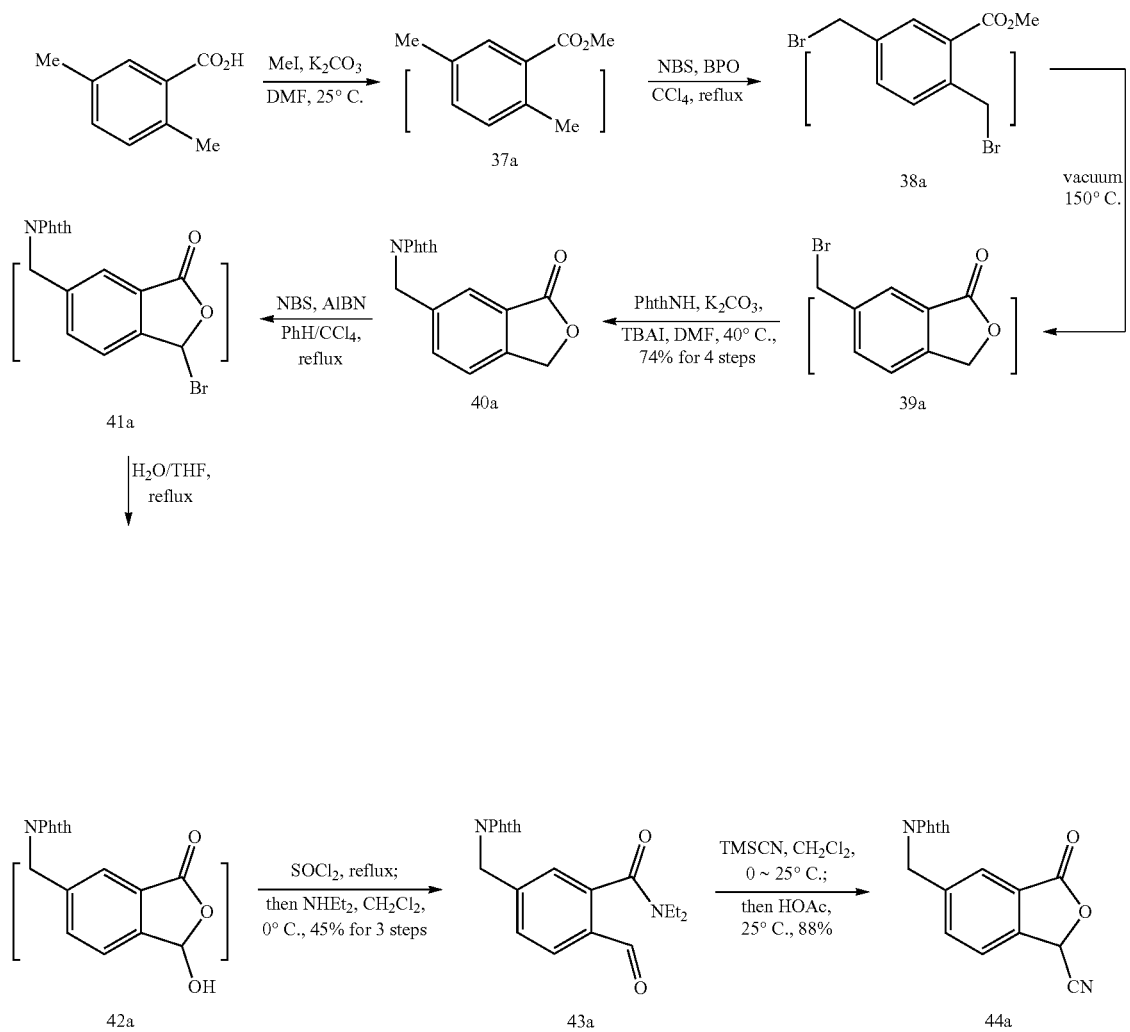
44b, 44c, and 44d are prepared according to the above route with comparable yields:
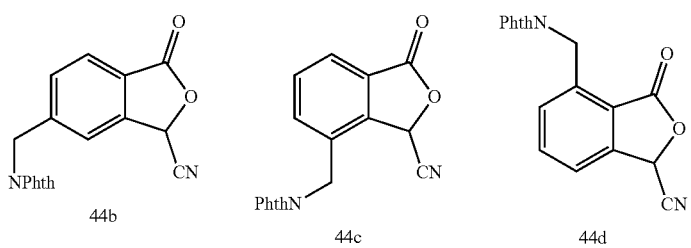

Scheme 7. Synthesis of aminomethyl-uncialamycins (48aa, 48ba, 48ca, and 48da).
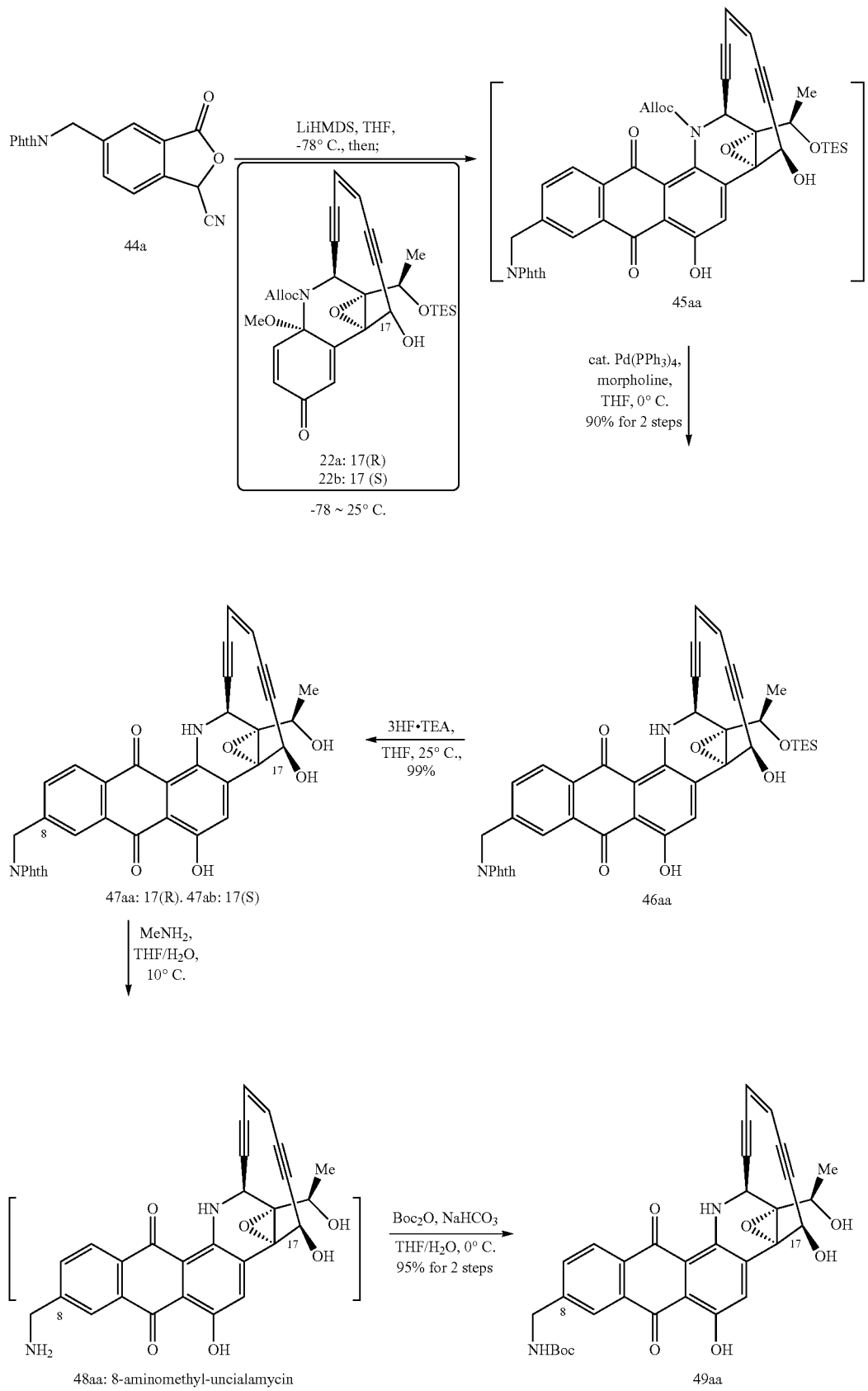

47ba, 47ca, 47da, 47db, 48ba, 48ca, and 48da prepared according to the above route with comparable yields:

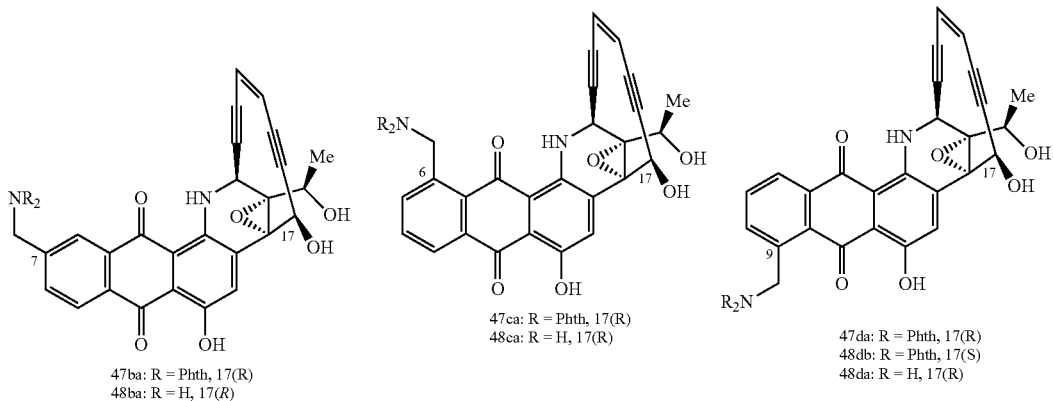

47ba: R = Phth, 17(R)
48ba: R = H, 17(R)

47ca: R = Phth, 17(R)
48ca: R = H, 17(R)

47da: R = Phth, 17(R)
48db: R = Phth, 17(S)
48da: R = H, 17(R)

As was described in Scheme 3 and Scheme 5, a similar method was employed to obtain cyanophthalide 55 starting from methyl 2,4-dihydroxy-3-methylbenzoate and is shown in Scheme 9. After preparation of the cyanophthalide 55, the compound under went Hauser condensation to give an analog of uncialamycin 58b which is described in Scheme 10.

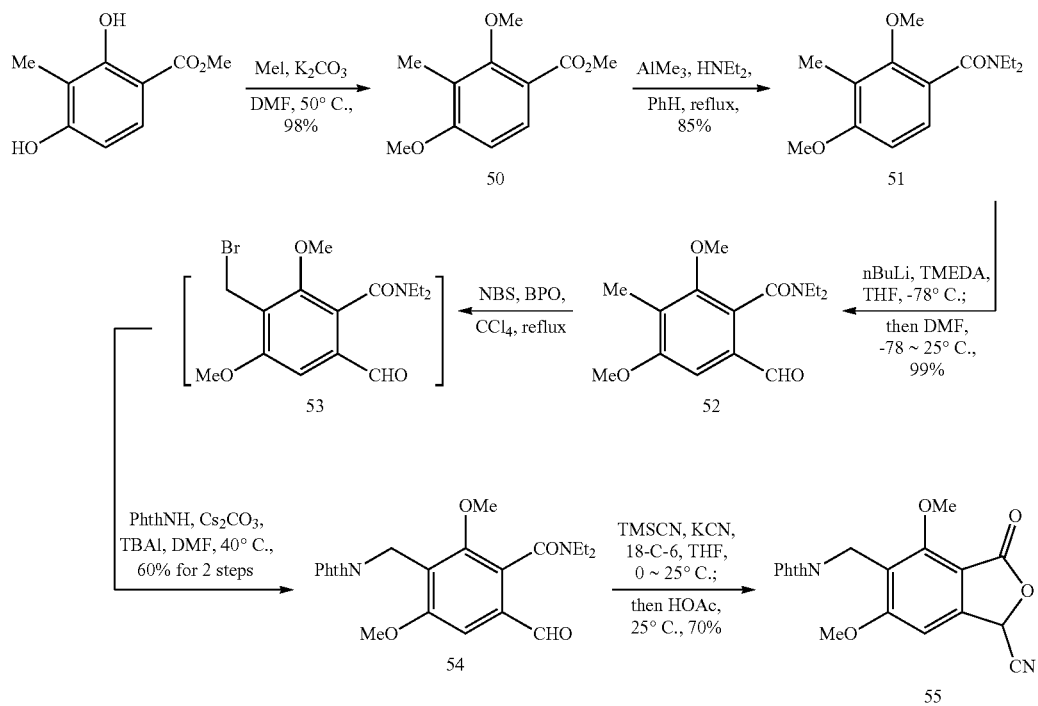

Scheme 9. Synthesis of cyanophthalides 55.

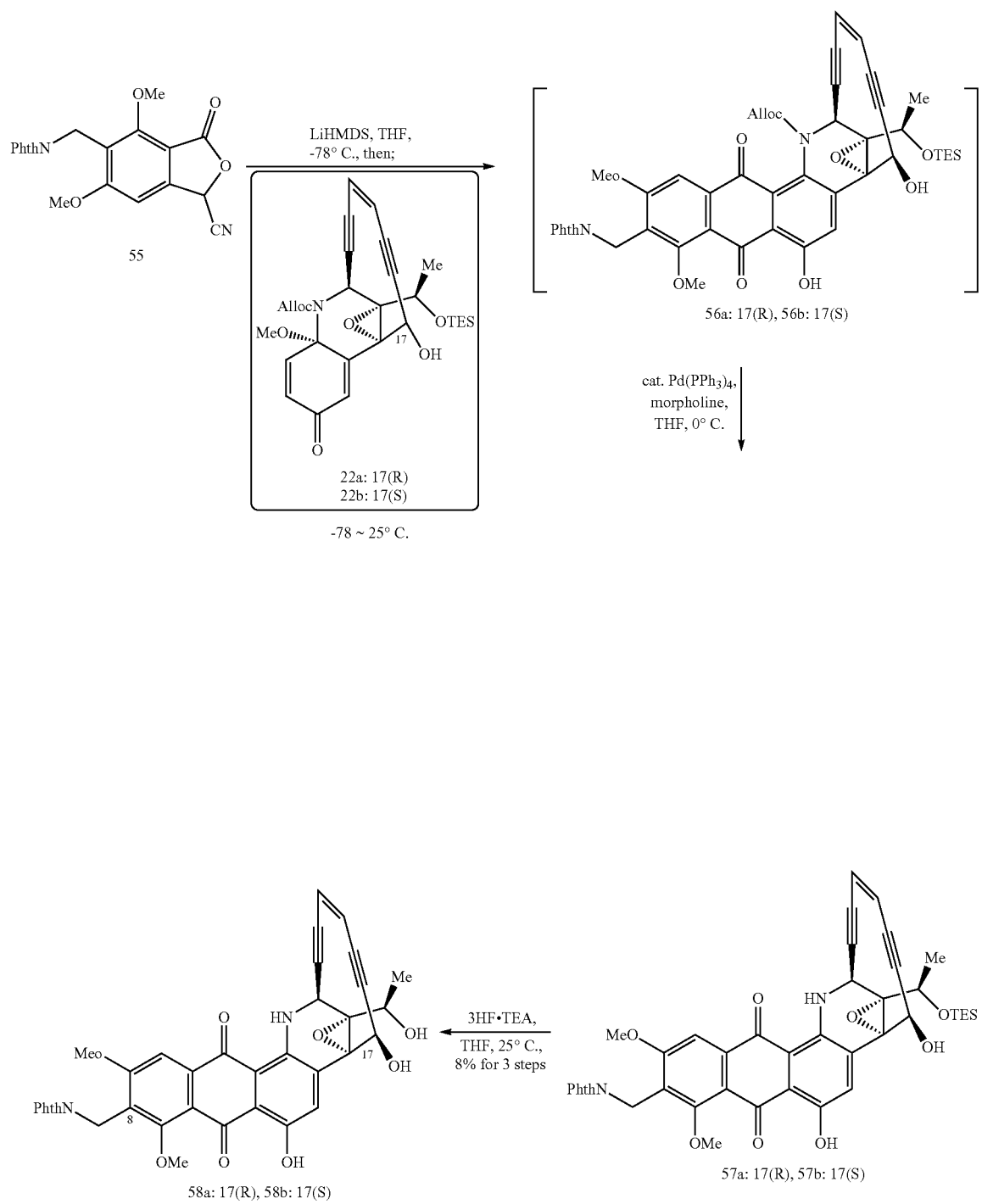
Scheme 10. Synthesis of 8-phthalimidomethyl-uncialamycin 58a, and 58b.
Similarly to the other uncialamycin derivatives described above, an expanded uncialamycin was prepared using naphthalene core cyanophthalides 63a and 63b. The preparation is shown in Scheme 11. Similarly, the condensation to form the appropriate uncialamycin analog is described in Scheme 12.

Scheme 11. Synthesis of cyanophthalides 63a, and 63b.
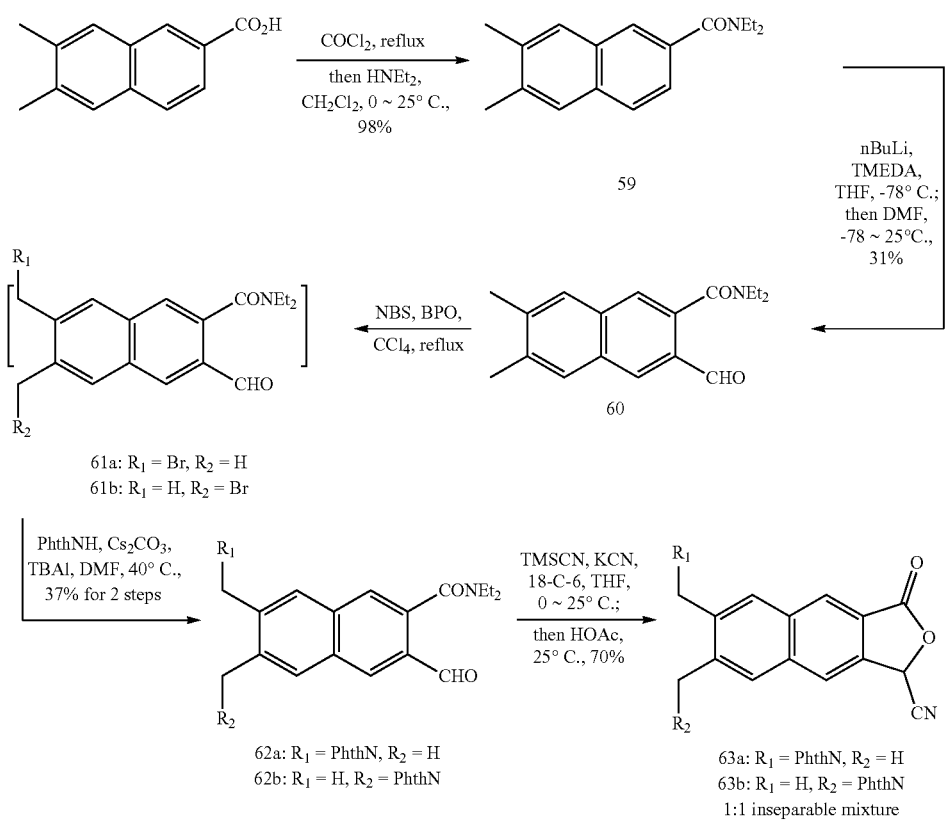
Scheme 12. Synthesis of 8-phthalimidomethyl-uncialamycins 66a/66b.
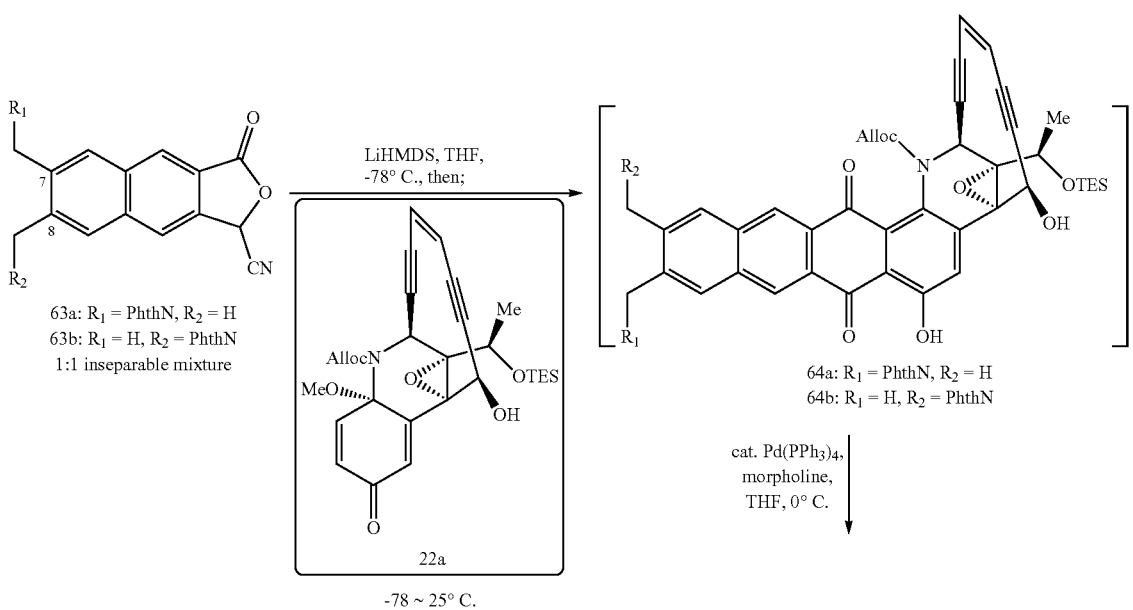

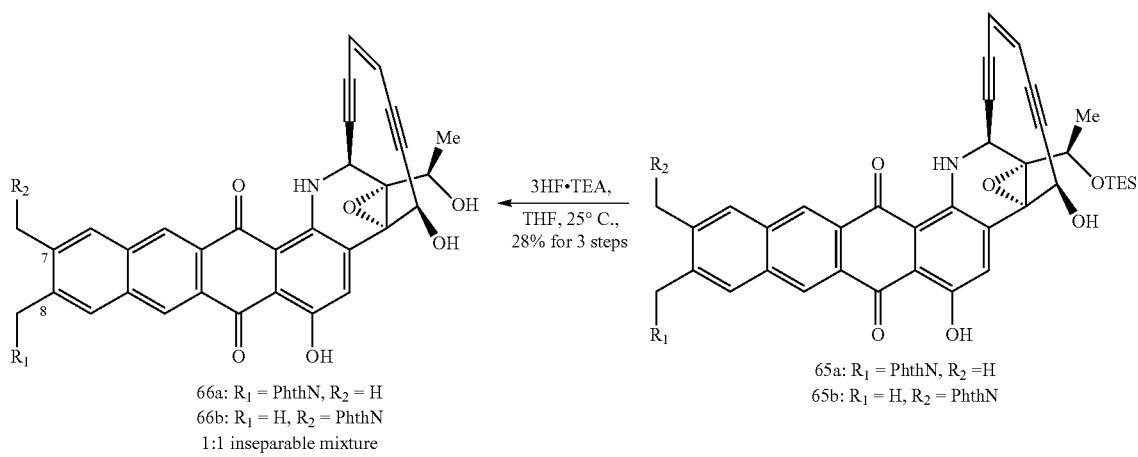
Additionally, the schemes 13-16 are also envisioned as potential synthetic pathways which can allow the production of uncialamycin and its analogs. These schemes shown additional synthetic methods which can be employed to access the analogs of uncialamycin described herein.
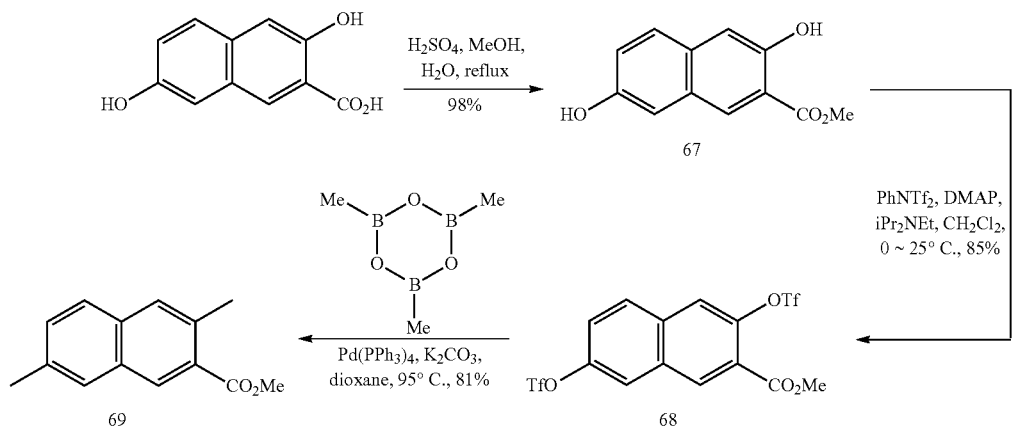

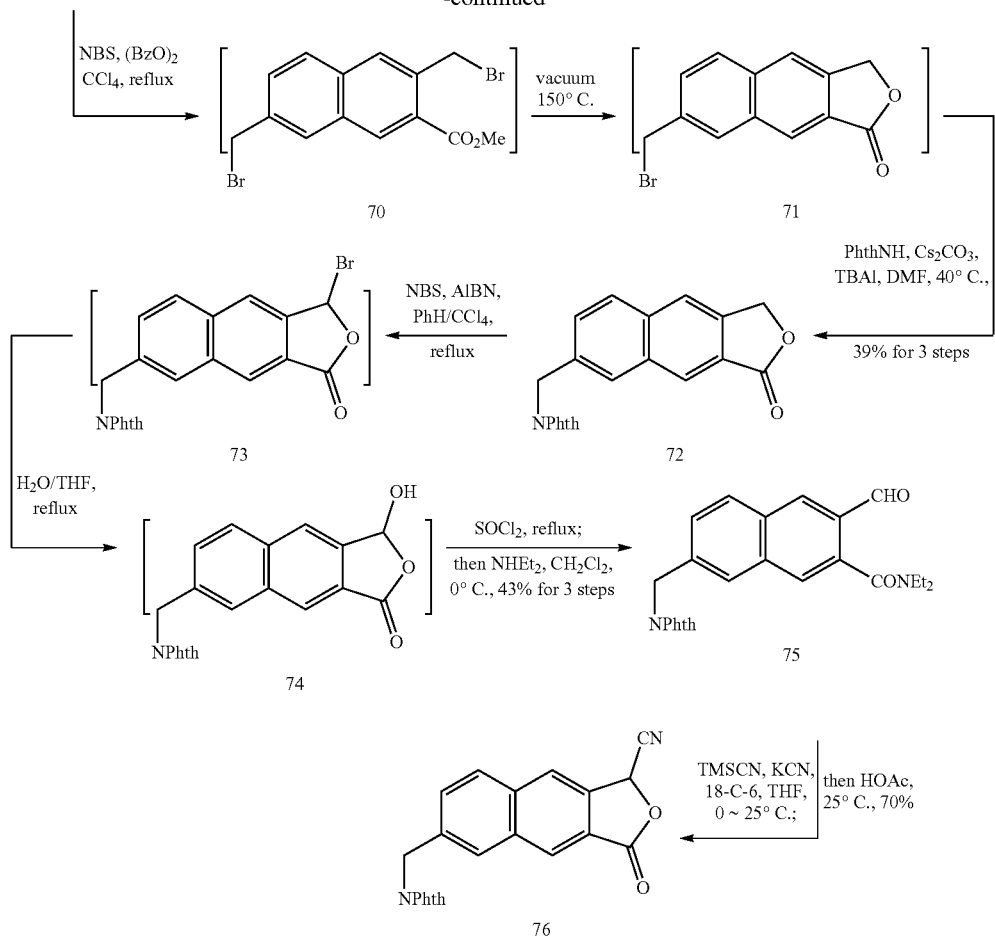
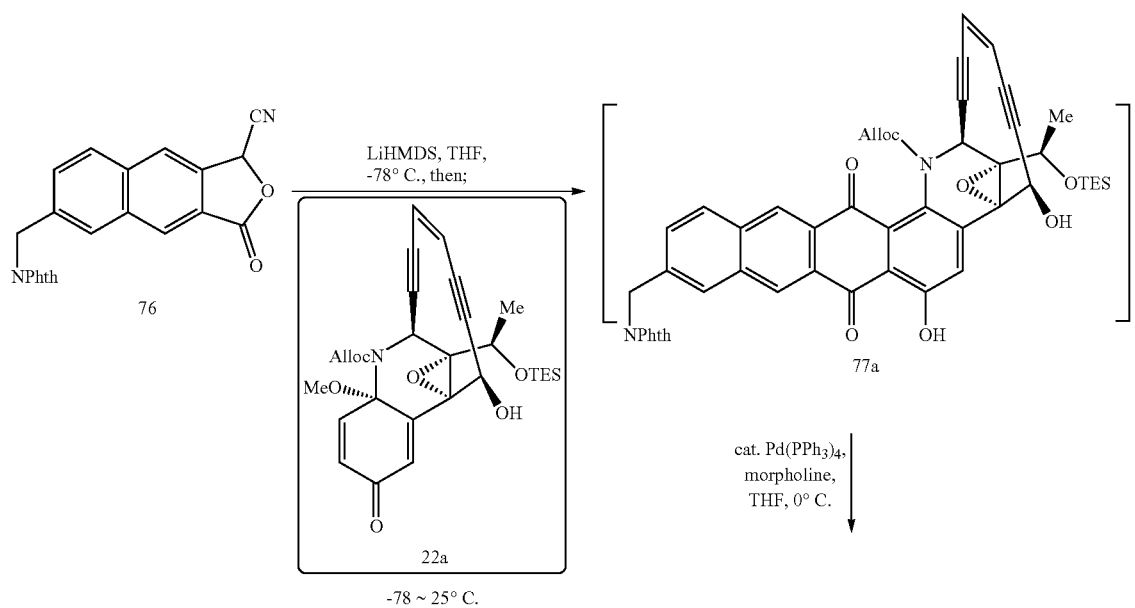
Scheme 14. Synthesis of phthalimidomethyl-benzo-uncialamycins 79a.

-continued
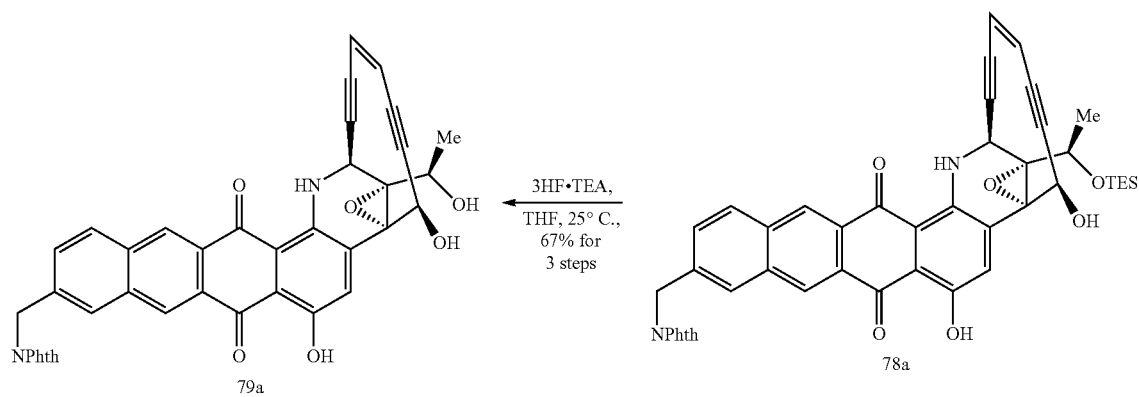
Scheme 15. Synthesis of cyanophthalides 84.
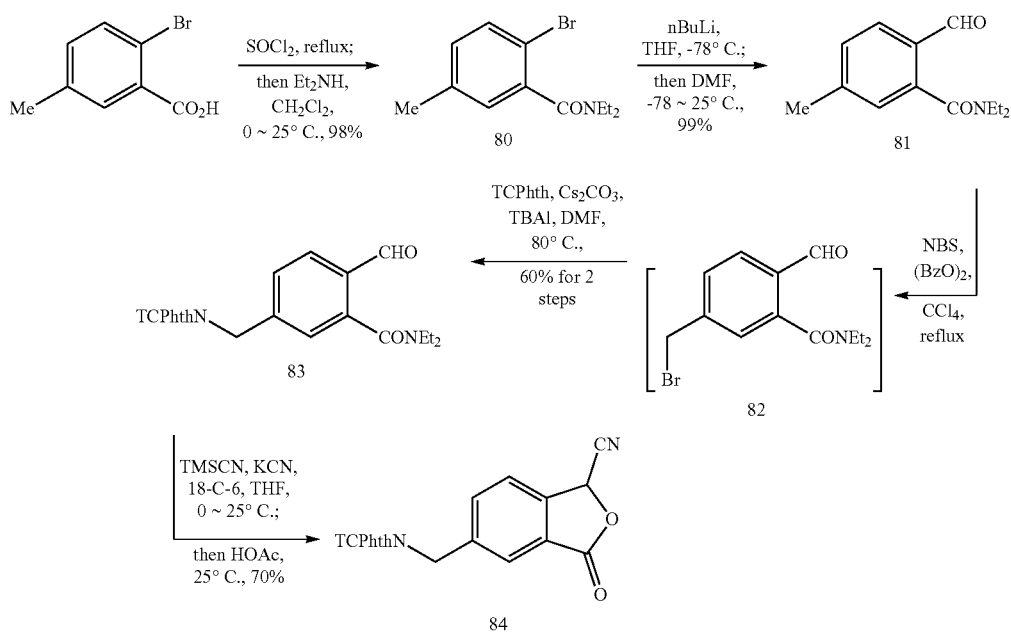
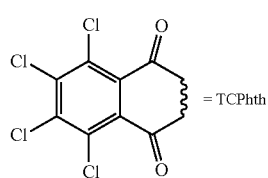

Scheme 16. Synthesis of 8-aminomethyl-uncialamycin 48aa and 49aa.

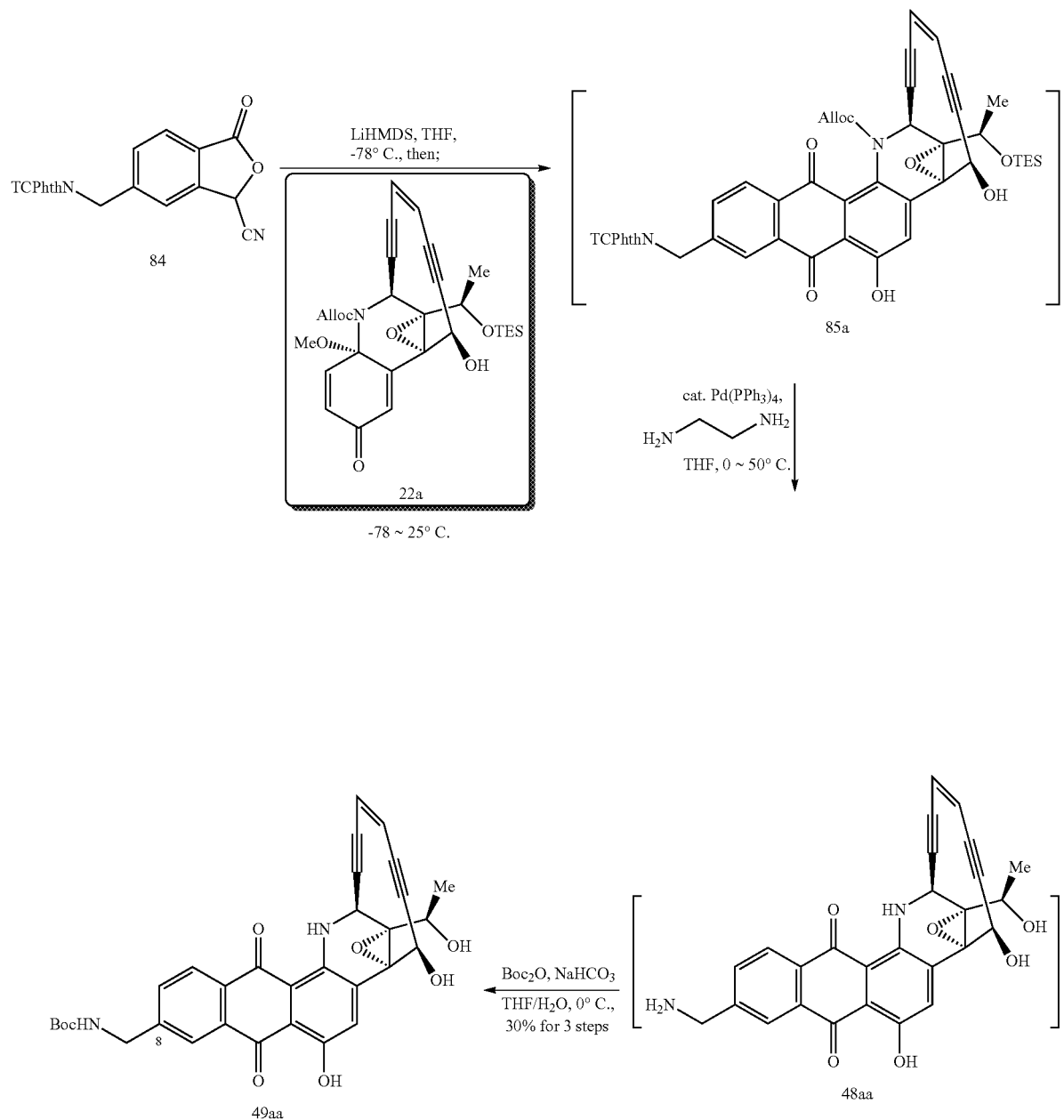

Analogs of uncialamycin with an isoindoline ring system were prepared starting from 2,4,5-trimethylbenzoic acid which was protected as the methyl ester and then brominated and cyclized to give 88. 88 was then reacted with tritylamine in the presence of Hunig's base to give 89. The trityl group was removed with acid and the amine protected with a Teoc group to give 90. The lactone 90 was opened with hydroxide and then oxidized with PCC to give hydroxylated compound 92. Hydroxylated compound 92 is converted to cyanophthalide 93 as shown in Scheme 17. As described previously and shown specifically in Scheme 18 and 19, the cyanophthalide 93 was reacted with 22a to give the desired analog of uncialamycin or a derivatized version thereof.

Scheme 17. Synethesis of cyanophthalide 93.
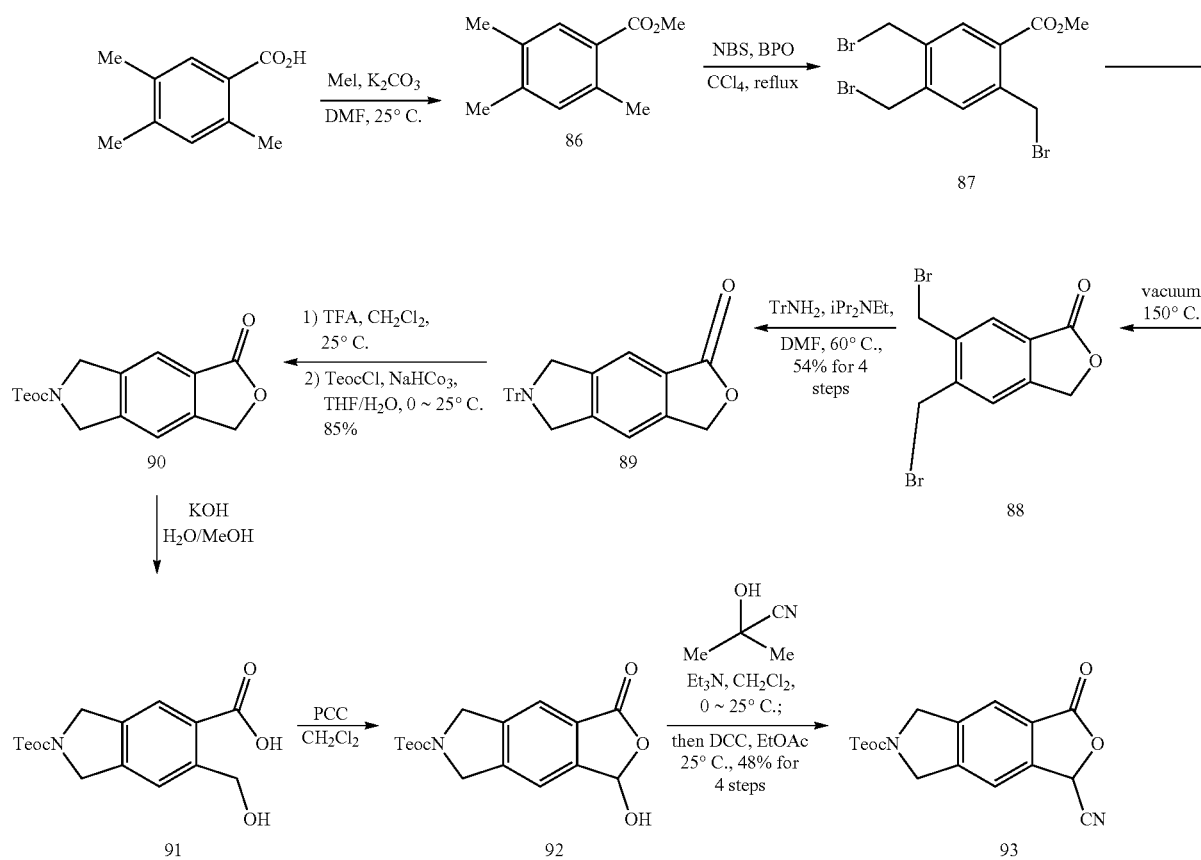
Scheme 18. Synthesis of isoindoline-uncialamycins (96, 97, and 98).
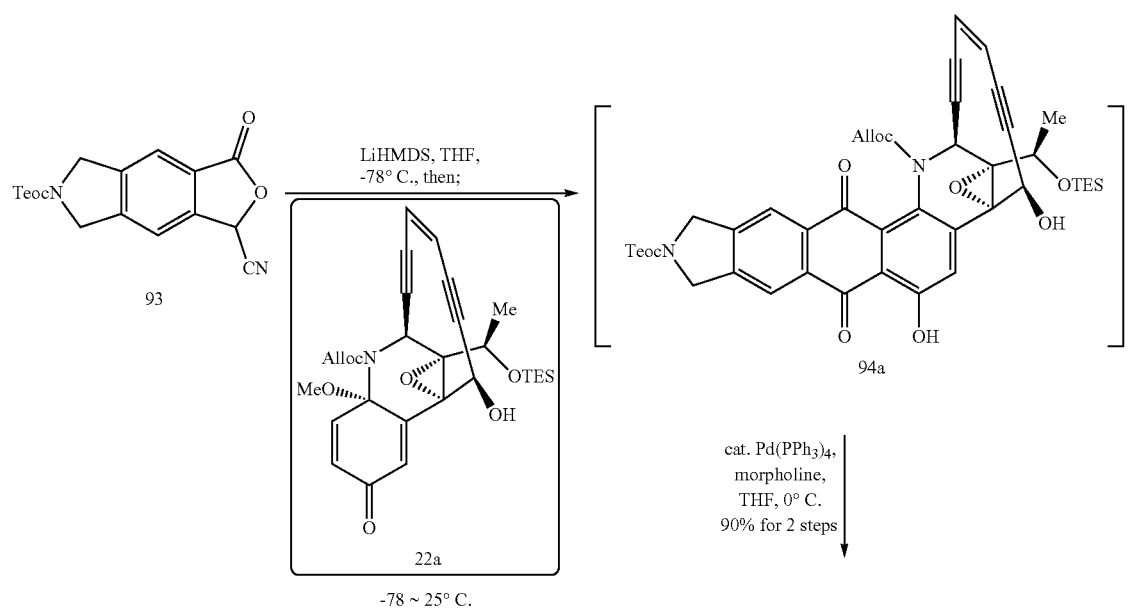

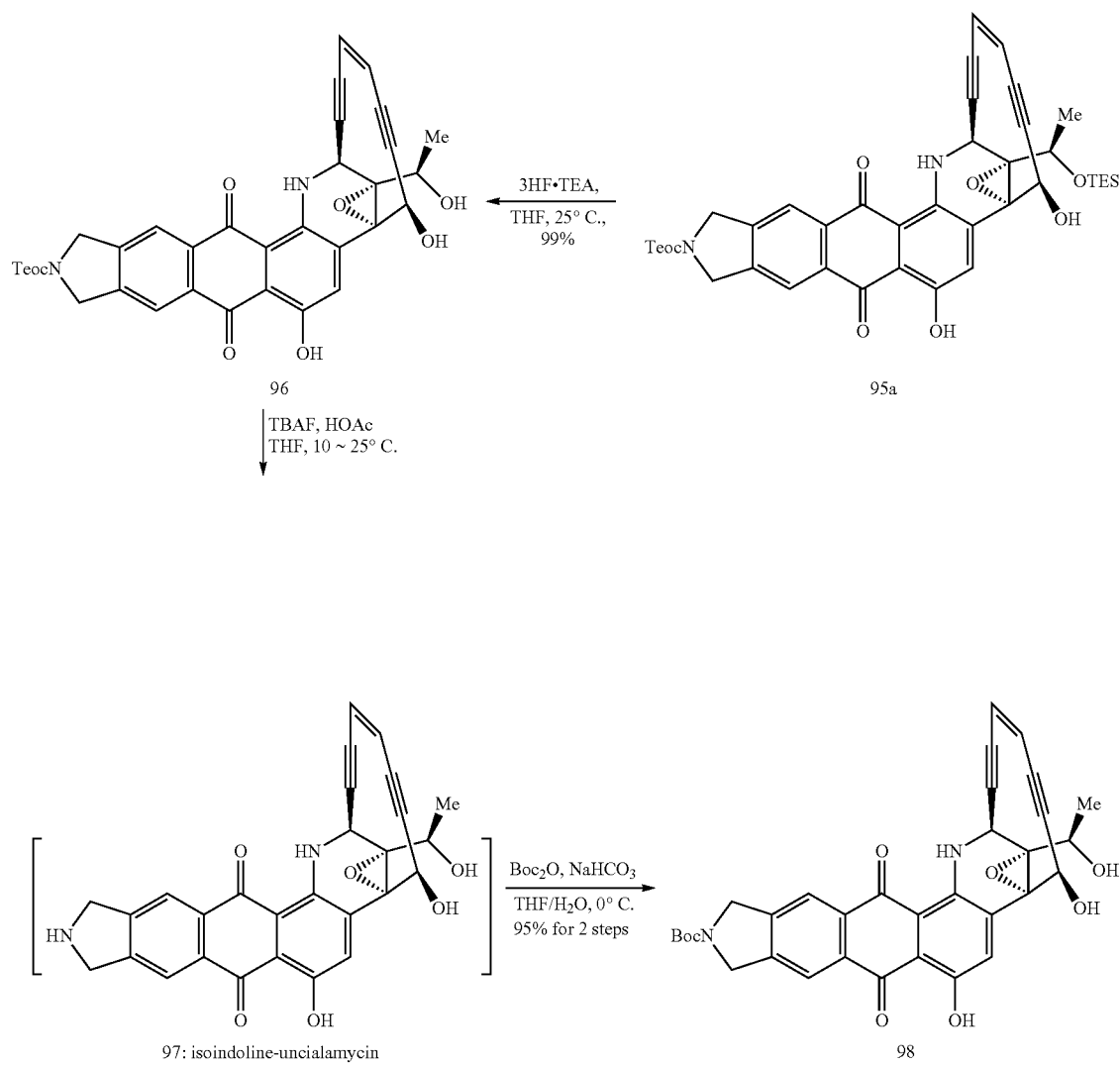
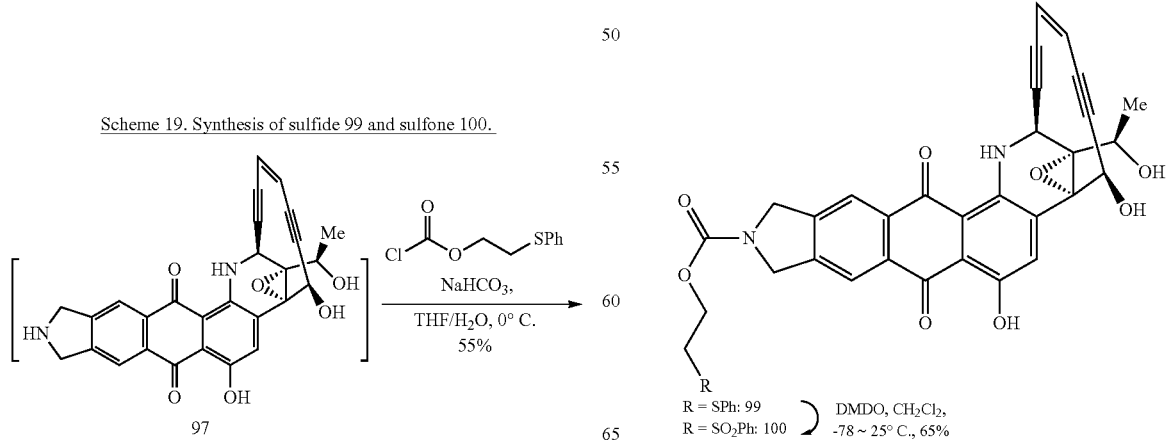
Scheme 19. Synthesis of sulfide 99 and sulfone 100.

Using a similar method to that employed in scheme 17, a methylamine version of 8-aminomethyluncialamycin is prepared. As shown in Scheme 20, the cyanophthalide was prepared starting with bromomethylphthalide which was reacted with TeocNHMe in basic conditions to give the phthalide 101. After opening of the cyclic ester to give 102, the compound was oxidized to give 103 and a cyano group was introduced to give cyanophthalide 104. The cyanophthalide was then reacted under strongly basic conditions with 22a to give the methylaminomethyluncialamycin analog and derivatives thereof which is described in Scheme 21.

Scheme 20. Synthesis of cyanophthalide 104.

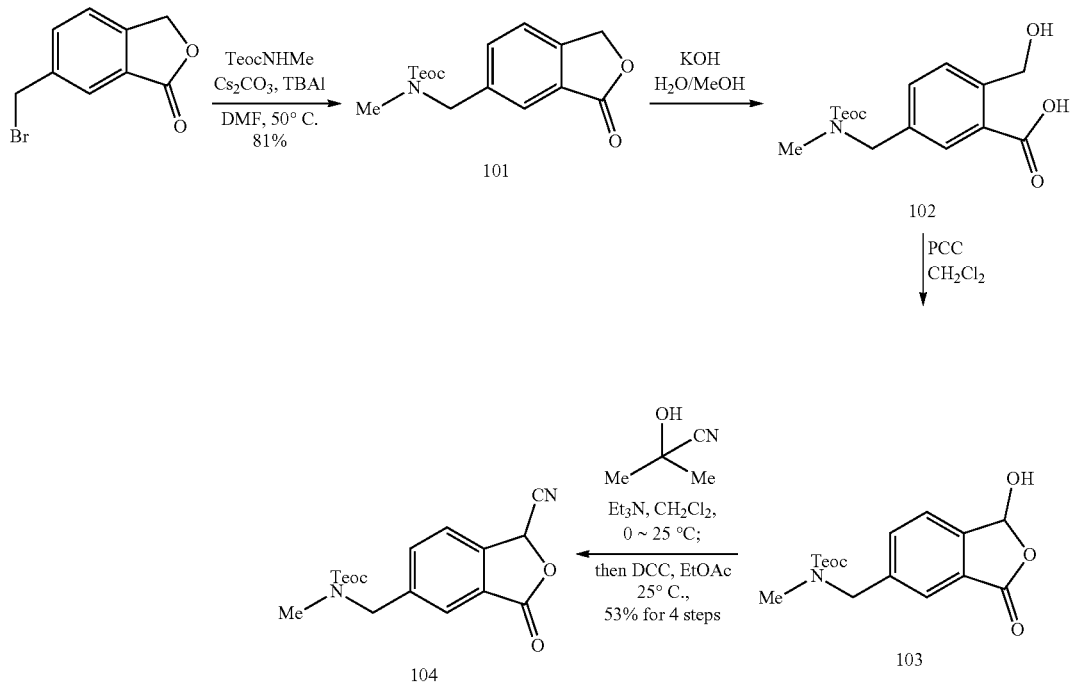

Scheme 21. Synthesis of 8-N-methylaminomethyl-uncialamycins (107, 108, 109, and 110).

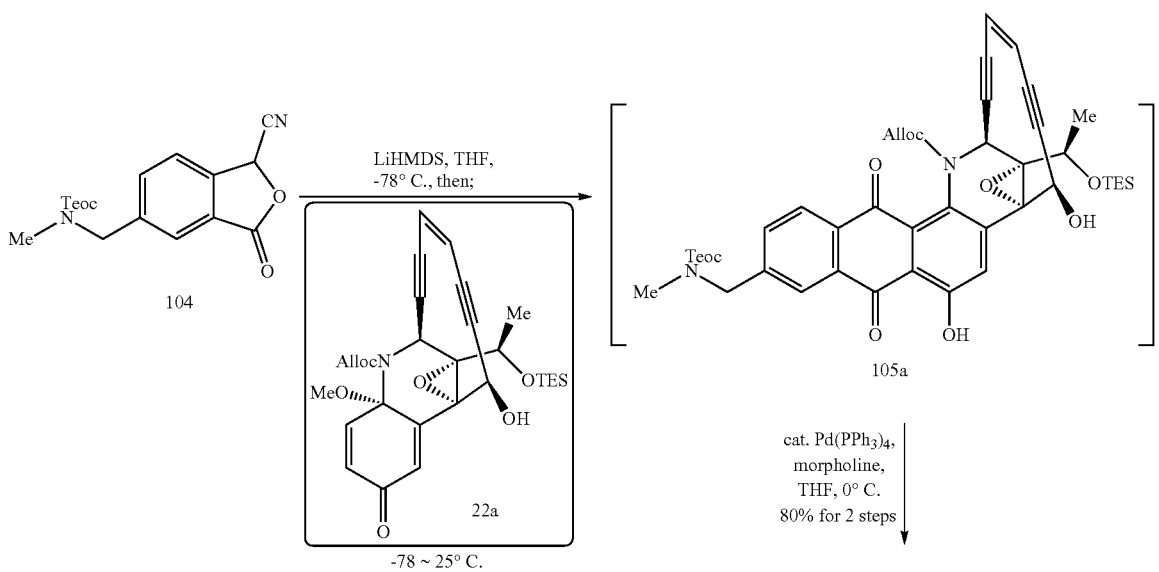

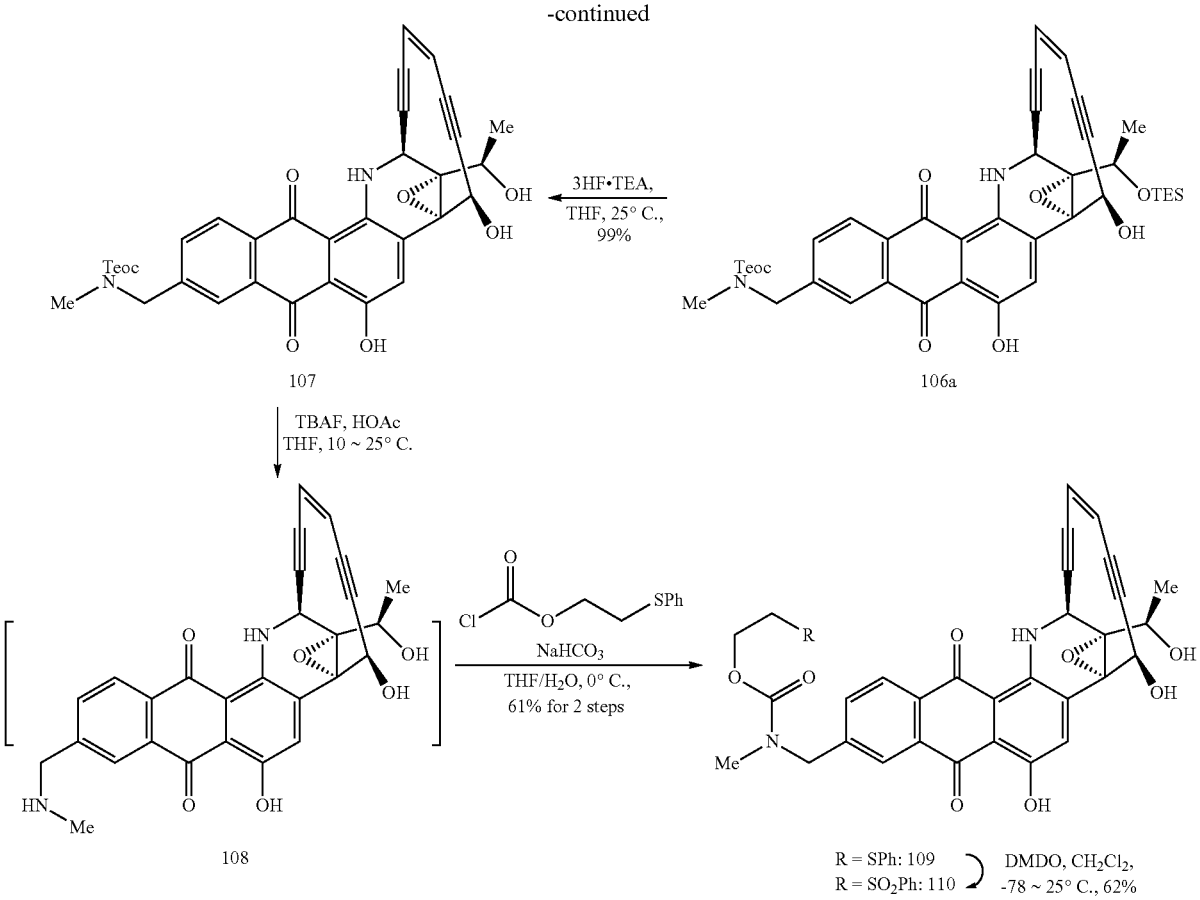

Example 3—Synthetic Methods and Characterization

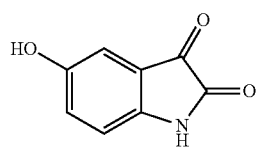

5-Hydroxy isatin (2)

To a stirred solution of 5-methoxy isatin (1) (10.0 g, 56.5 mmol, 1.0 equiv) in $CH_2Cl_2$ (40 mL) at 0° C., $BBr_3$ (36.8 g, 147 mmol, 2.6 equiv) was added dropwise over 2 h under vigorous stirring at 0° C. Upon completion of addition, the ice bath was removed and the reaction mixture was stirred for another 1 h at room temperature and was diluted with $CH_2Cl_2$ (500 mL), cooled to 0° C., quenched by careful sequential addition of solid $NaHCO_3$ (37 g), and cold (0-5° C.) $H_2O$ (60 mL) (CAUTION, HBr gas). The resulting mixture was washed with brine (50 mL), and the combined aqueous phases were extracted with $CH_2Cl_2$ (50 mL). The combined organic phases were concentrated and the residue was recrystallized from glacial acetic acid to yield isatin 2 as a dark red solid (8.8 g, 54 mmol, 95% yield). $R_f$=0.31 (silica gel, $CH_2Cl_2$:EtOAc 1:1); IR (film) $\nu_{max}$=3278, 1720, 1614, 1477, 1291, 1194, 881, 822, 800 $cm^{-1}$; $^1$H NMR (500 MHz, DMSO): δ=10.73 (s, 1H), 9.52 (br, 1H), 7.00 (dd, J=8.5, 2.6 Hz, 1H), 6.83 (d, J=2.6 Hz, 1H), 6.74 (d, J=8.3 Hz, 1H) ppm; $^{13}$C NMR (125 MHz, $CDCl_3$): δ=184.9, 159.5, 153.2, 143.1, 125.1, 118.2, 113.1, 110.5, 105.1 ppm; HRMS (ESI-TOF): calcd for $C_8H_6NO_3^+$ [M+H$^+$]: 164.0342, found 164.0344.

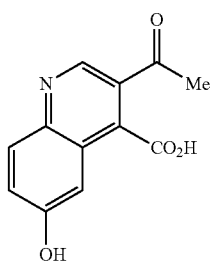

Ketoacid 4

Isatin 2 (6.7 g, 47 mmol, 1.0 equiv) was dissolved in aqueous 2N NaOH (47 mL, 94 mmol, 2.0 equiv) at room temperature, and trans-4-methoxy-3-buten-2-one (90% purity, 9.1 g, 94 mmol, 2.0 equiv) was added in one portion under vigorous stirring. The reaction mixture was stirred for 15 min, cooled to 0° C., and acidified with conc. HCl to pH 1. The resulting green solid was collected by filtration and washed with ice water (pH of filtrate after each wash was tested, and keep washing until pH 5-6). The wet solid was dissolved in saturated aq. NaHCO$_3$ (60 mL) and after filtering off a trace of dark insoluble material, saturated aq. K$_2$CO$_3$ (20 mL) was added. The resulting mixture was stirred at 80° C. for 30 min and then, at the same temperature, carefully acidified with conc. HCl to pH 1 (CAUTION, CO$_2$ gas). The resulting suspension was stirred for another 10 min at 80° C., then allowed to cool to ambient temperature, and stored at 0° C. for 12 h. The resulting solid was collected by filtration, washed with ice water (pH of filtrate after each wash was tested, and keep washing with small amount of ice water until pH 5-6), and dried under vacuum to yield ketoacid 2 as a brown solid (7.7 g, 33 mmol, 81% yield). The crude material was used directly for the next step without further purification.

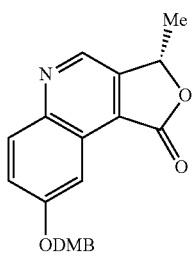

Lactone 8

To a stirred solution of ketoacid 4 (7.7 g, 33 mmol, 1.0 equiv) in DMF (50 mL) at room temperature, was sequentially added solid Cs$_2$CO$_3$ (10.8 g, 167 mmol, 5.0 equiv), n-Bu$_4$NI (1.8 g, 5.0 mmol, 0.15 equiv), followed by a solution of 3,4-dimethoxybenzyl bromide (5) [DMBBr, 30.7 g, 133 mmol, 4.0 equiv in DMF (15 mL)]. The reaction mixture was stirred at the same temperature for 5 h, and then partitioned between EtOAc (300 mL) and H$_2$O (300 mL). The aqueous layer was extracted with EtOAc (3×150 mL), and the combined organic layers were washed with H$_2$O (3×150 mL) and brine (150 mL), dried over MgSO$_4$ and concentrated. The residue was passed through a short pad of Celite® and eluted with hexanes/EtOAc (v/v=1/2), concentrated and coevaporated with toluene (3×25) to yield crude bis-DMB ketoester 6 as a dark oil, which was dissolved in CH$_2$Cl$_2$ (150 mL) and cooled to 0° C. To this solution were sequentially added (S,S)-Noyori catalyst 7 (1.0 g, 1.7 mmol, 0.05 equiv) and a premixed cold (0-5° C.) Et$_3$N/HCO$_2$H mixture (Et$_3$N: 8.4 g, 83 mmol, 2.5 equiv; HCO$_2$H: 6.6 g, 143 mmol, 4.3 equiv). The resulting mixture was stirred at 0° C. for 24 h, then quenched with saturated aq. NaHCO$_3$ (150 mL), the aqueous layer was separated and extracted with CH$_2$Cl$_2$ (3×150 mL), and the combined organic layers were washed with saturated aq. NaHCO$_3$ (150 mL) and brine (150 mL), dried over MgSO$_4$, and concentrated. Flash column chromatography (silica gel, CH$_2$Cl$_2$:EtOAc 15:1 to 10:1) gave a dark brown solid, which was recrystallized from EtOAc to yield lactone (+)-8 as an off-white solid (6.1 g, 17 mmol, 82% yield, >99% ee by HPLC analysis of bis-TES ether derivative 9 derived from DIBAL-H reduction and TES protection; chiral OD-H 5μ column, 4.6×250 mm, hexanes:i-PrOH 98:2, 1 mL min$^{-1}$; major enantiomer retention time=14.37 min, minor enantiomer retention time=16.88 min). 8: [α]$_D^{25}$=+19 (c=1.00, CH$_2$Cl$_2$), R$_f$=0.21 (silica gel, hexanes:EtOAc 7:3); IR (film) ν$_{max}$=2935, 2836, 2254, 1756, 1605, 1509, 1460, 1263, 1213 cm$^{-1}$; $^1$H NMR (600 MHz, CDCl$_3$): δ=8.88 (s, 1H), 8.20 (d, J=2.8 Hz, 1H), 8.08 (d, J=9.2 Hz, 1H), 7.49 (dd, J=9.2, 2.8 Hz, 1H), 7.05 (d, J=8.2 Hz, 1H), 7.04 (s, 1H), 6.87 (d, J=8.1 Hz, 1H), 5.70 (q, J=6.8 Hz, 1H), 5.16 (s, 2H), 3.91 (s, 3H), 3.86 (s, 3H), 1.73 (d, J=6.8 Hz, 3H) ppm; $^{13}$C NMR (150 MHz, CDCl$_3$): δ=169.5, 159.2, 149.0, 145.0, 144.4, 140.8, 131.1, 128.2, 126.4, 124.2, 123.9, 120.7, 111.3, 111.0, 101.8, 76.4, 70.5, 55.8, 20.0 ppm; HRMS (ESI-TOF): calcd for C$_{21}$H$_{20}$NO$_5^+$ [M+H$^+$]: 366.1336, found 366.1338.

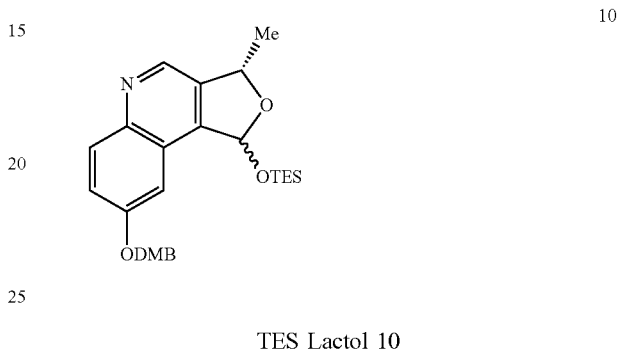

TES Lactol 10

To a stirred solution of lactone 8 (3.80 g, 10.4 mmol, 1.0 equiv) in CH$_2$Cl$_2$ (75 mL) at −78° C. was slowly added DIBAL-H (1.0 M in CH$_2$Cl$_2$, 25 mL, 25 mmol, 2.4 equiv) over 2 h. The reaction mixture was stirred at −78° C. for another 1 h, until TLC showed full consumption of 8 (hexanes:EtOAc 1:1). The reaction mixture was diluted with CH$_2$Cl$_2$ (400 mL), and then slowly poured into saturated aq. sodium potassium tartrate (200 mL). The resulting mixture was vigorously stirred at ambient temperature for 6 h until two layers were formed, the organic layer was separated, and the aqueous layer was extracted with CH$_2$Cl$_2$ (5×150 mL), then EtOAc (3×50 mL). The combined organic extracts were dried over MgSO$_4$ and concentrated. The resultant pale yellow residue was taken up in DMF (120 mL). To this mixture was added imidazole (1.84 g, 27.0 mmol, 2.6 equiv), then TESCl (2.26 mL, 2.04 g, 13.5 mmol, 1.3 equiv) at 0° C. The reaction mixture was stirred at ambient temperature for 20 min, then partitioned between Et$_2$O (150 mL) and saturated aq. NaHCO$_3$ (150 mL). The aqueous layer was extracted with Et$_2$O (2×150 mL), and the combined organic layers were washed with H$_2$O (3×150 mL) and brine (150 mL), dried over MgSO$_4$, and concentrated. Flash column chromatography (silica gel, hexanes:EtOAc 2:1 to 3:2) yielded TES lactol 10 (4.55 g, 9.46 mmol, 91% yield over 2 steps, ca. 1:1 inconsequential mixture of diastereoisomers) as a pale yellow oil. 10: R$_f$=0.31 (syn isomer) and 0.25 (anti isomer) (silica gel, hexanes:EtOAc 3:2); IR (film) ν$_{max}$=2953, 2875, 1625, 1604, 1515, 1461, 1211 cm$^{-1}$; $^1$H NMR (600 MHz, CDCl$_3$) of syn isomer: δ=8.69 (s, 1H), 8.10 (d, J=9.2 Hz, 1H), 7.44 (dd, J=9.2, 2.7 Hz, 1H), 7.27 (d, J=2.8 Hz, 1H), 7.02 (d, J=6.9 Hz, 1H), 7.01 (s, 1H), 6.90 (d, J=6.8 Hz, 1H), 6.90 (s, 1H), 5.68 (dq, J=6.5, 2.3 Hz, 1H), 5.09 (dd, J=17.1, 10.9 Hz, 1H), 3.92 (s, 3H), 3.91 (s, 3H), 1.59 (d, J=6.5 Hz, 3H), 1.02 (t, J=7.9 Hz, 9H), 0.74 (q, J=7.8 Hz, 6H) ppm; anti isomer: δ=8.69 (s, 1H), 8.11 (d, J=9.2 Hz, 1H), 7.43 (dd, J=9.2, 2.6 Hz, 1H), 7.32 (d, J=2.4 Hz, 1H), 7.01 (d, J=6.1 Hz, 1H), 7.00 (s, 1H), 6.91 (d, J=8.6 Hz, 1H), 6.84 (s, 1H), 5.46 (q, J=6.5 Hz, 1H), 5.09 (dd, J=18.3, 10.8 Hz, 1H), 3.92 (s, 3H), 3.91 (s, 3H), 1.67 (d, J=6.5 Hz, 3H), 1.06 (t, J=8.0 Hz, 9H), 0.79 (q, J=7.7 Hz, 6H) ppm; $^{13}$C NMR (150 MHz, CDCl$_3$) of syn isomer: δ=157.6, 149.2, 149.1, 144.0, 143.6, 141.5, 136.7, 131.1, 128.6, 124.1, 122.5, 120.4, 111.0, 111.0, 102.6, 100.0, 78.5, 70.3, 55.9, 55.9, 21.4, 6.8, 5.1 ppm; anti isomer: δ=157.6, 149.2, 149.1, 143.9, 143.1, 141.5, 136.8, 131.0, 128.6, 124.3, 122.6, 120.4, 111.1, 111.0, 102.5, 100.5, 79.5, 70.3, 56.0, 55.9, 23.6, 6.9, 5.1 ppm; HRMS (ESI-TOF): calcd for C$_{27}$H$_{36}$NO$_5$Si$^+$ [M+H$^+$]: 482.2357, found 482.2367.

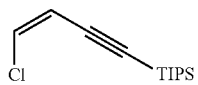

27

Eneyne 27

To a stirred suspension of Pd(PPh$_3$)$_4$ (380 mg, 0.3 mmol, 3 mol %) and CuI (60 mg, 0.3 mmol, 3 mol %) in 50 mL of Et$_2$O at room temperature was added sequentially n-BuNH$_2$ (1.61 g, 2.20 mL, 22.0 mmol, 2.0 equiv), (Z)-1,2-dichloroethylene (2.03 g, 1.74 mL, 21.0 mmol, 1.9 equiv), and triisopropylsilylacetylene (2.00 g, 2.55 mL, 11.0 mmol, 1.0 equiv), and the reaction mixture was stirred at ambient temperature for 10 h (volatile materials, leave as little gas phase as possible in a sealed flask). After evaporation of the solvent, the residue was taken up with hexanes and filtered through a short pad of Celite®, eluted with hexanes, and the filtrate was concentrated. Flash column chromatography (silica gel, hexanes) yielded a colourless oil (2.48 g, 10.2 mmol, 93% yield). R$_f$ (hexanes)=0.77; IR (film) ν$_{max}$=2945, 2154, 1463, 882, 671 cm$^{-1}$; $^1$H NMR (500 MHz, CDCl$_3$): δ=6.39 (d, J=7.5 Hz, 1H), 5.89 (d, J=7.5 Hz, 1H), 1.09 (s, 18H), 1.07 (s, 3H); $^{13}$C NMR (125 MHz, CDCl$_3$): δ=129.2, 112.4, 100.5, 100.1, 18.6, 11.3 ppm; HRMS (EI): calcd for C$_{13}$H$_{23}$SiCl: 242.1257, found 242.1285.

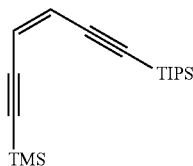

28

Enediyne 28

To a stirred suspension of Pd(PPh$_3$)$_4$ (140 mg, 0.12 mmol, 2.5 mol %) and CuI (25 mg, 0.13 mmol, 2.5 mol %) in 25 mL of Et$_2$O at room temperature was added sequentially n-BuNH$_2$ (731 mg, 1.0 mL, 10.0 mmol, 2.0 equiv), eneyne 27 (1.19 g, 4.9 mmol, 1.0 equiv), and trimethylsilylacetylene (972 mg, 1.40 mL, 9.9 mmol, 2.0 equiv), and the reaction mixture was stirred at ambient temperature for 12 h (volatile materials, leave as little gas phase as possible in a sealed flask). After evaporation of the solvent, the residue was taken up with hexanes and filtered through a short pad of Celite®, eluted with hexanes, and the filtrate was concentrated. Flash column chromatography (silica gel, hexanes) yielded a colourless oil (1.44 g, 4.7 mmol, 96% yield). R$_f$ (hexanes)=0.48; IR (film) ν$_{max}$=2948, 2153, 2121, 1250, 1069, 848 cm$^{-1}$; $^1$H NMR (500 MHz, CDCl$_3$): δ=5.84 (d, J=11.3 Hz, 1H), 5.82 (d, J=11.3 Hz, 1H), 1.09 (s, 18H), 1.07 (s, 3H), 0.18 (s, 9H); $^{13}$C NMR (125 MHz, CDCl$_3$): δ=120.5, 120.0, 103.7, 103.0, 102.0, 100.0, 18.7, 11.2, −0.3 ppm; HRMS (EI): calcd for C$_{18}$H$_{32}$Si$_2$: 304.2042, found 304.2032.

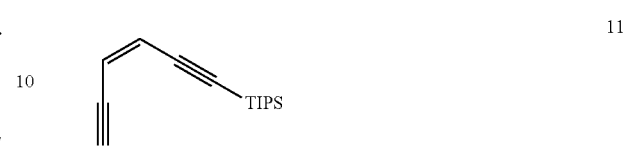

11

Enediyne 11

To a stirred solution of enediyne 28 (1.38 g, 4.5 mmol, 1.0 equiv) in 70 mL of benzene/methanol (1:1) at room temperature was added K$_2$CO$_3$ (0.69 g, 5.0 mmol, 1.1 equiv), and the reaction mixture was stirred at ambient temperature for 2 h. Water (50 mL) was added and the aqueous phase was extracted with hexanes (3×50 mL). The organic phases were washed with brine (50 mL), dried over anhydrous MgSO$_4$ and evaporated to leave a yellowish oil (1.01 g, 4.3 mmol, 96%) (CAUTION: 11 slowly turned black during storage, which led to diminished yields for following steps, use fresh for best yields). R$_f$ (hexanes)=0.66; IR (film) ν$_{max}$=3303, 2945, 2149, 1463, 1049, 882 cm$^{-1}$; $^1$H NMR (500 MHz, CDCl$_3$): δ=5.91 (dd, J=11.0, 0.7 Hz, 1H), 5.81 (dd, J=11.0, 1.2 Hz, 1H), 3.30 (dd, J=1.2, 0.7 Hz, 1H), 1.08 (s, 18H), 1.07 (s, 3H); $^{13}$C NMR (125 MHz, CDCl$_3$): δ=119.3, 103.4, 100.3, 84.8, 80.9, 18.7, 11.2 ppm; HRMS (EI): calcd for C$_{15}$H$_{24}$Si: 189.1099, found 189.1100.

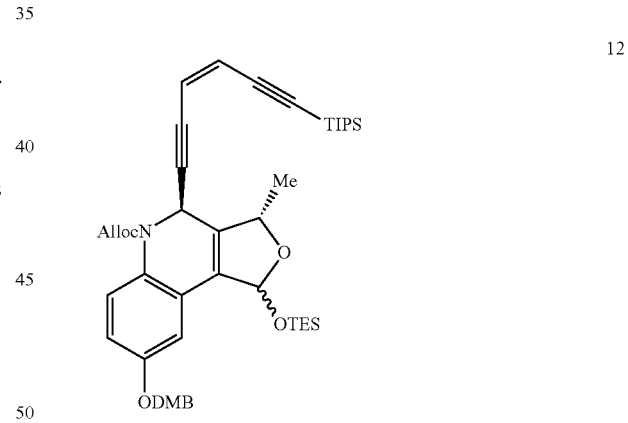

12

Enediyne 12

To a stirred solution of freshly prepared enediyne 11 (11.56 g, 49.76 mmol, 2.0 equiv) in THF (116 mL) at 0° C. was added isopropylmagnesium chloride (2.0 M in THF, 24.9 mL, 49.76 mmol, 2.0 equiv) dropwise. The reaction mixture was stirred at 25° C. for 1 h, then briefly heated with a heat gun to reflux. Again, the reaction mixture was stirred at 25° C. for 1 h, then briefly heated with a heat gun to reflux. Finally, the reaction mixture was stirred at 25° C. for 45 min then cooled to 0° C., followed by the addition of a solution of TES lactol 10 (12.0 g, 24.88 mmol, 1.0 equiv) in THF (54 mL) via cannula. The resulting mixture was stirred at 0° C. for 1 h, followed by dropwise addition of allyl chloroformate (5.29 mL, 49.76 mmol, 2.0 equiv) over 30 min at 0° C. The reaction mixture was stirred at 25° C. for 30 min, until TLC showed full consumption of 10 (hexanes:EtOAc 3:2). The reaction mixture was then partitioned between EtOAc (150 mL) and H$_2$O (150 mL). The aqueous layer was extracted with EtOAc (3×150 mL), and the combined organic layers were washed with saturated aq. NH$_4$Cl (150 mL), saturated aq. NaHCO$_3$ (150 mL), and brine (150 mL), then dried over MgSO$_4$ and concentrated. Flash column chromatography (silica gel, hexanes:EtOAc 10:1 to 4:1) yielded enediyne 12 (17.87 g, 22.38 mmol, 90% yield) as a pale yellow solid., 12: R$_f$=0.43 (silica gel, hexanes:EtOAc 4:1); IR (film) $v_{max}$=2957, 2877, 2261, 1705, 1517, 1498, 1381, 1261, 1238 cm$^{-1}$; $^1$H NMR (600 MHz, CD$_3$CN): δ=7.58 (br, 1H), 7.1-6.8 (m, 5H), 6.45-6.40 (m, 1H), 6.3-6.2 (m, 1H), 5.99 (m, 1H), 6.9-6.8 (m, 2H), 5.35-4.95 (m, 5H), 4.70 (m, 2H), 3.80 (s, 3H), 3.79 (s, 3H), [1.46 (d, J=6.5 Hz, 3H) and 1.37 (d, J=6.5 Hz, 3H) diastereotopic pair], 1.11 (m, 21H), 0.99 (m, 9H), 0.70 (m, 6H) ppm; HRMS (ESI-TOF): calcd for C$_{46}$H$_{64}$NO$_7$Si$_2^+$ [M+H$^+$]: 798.4216, found 798.4217.

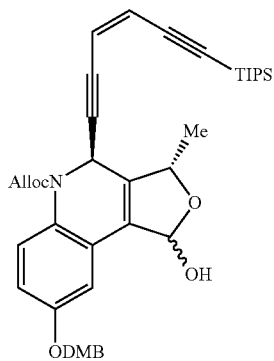

Lactol 13

To a stirred solution of enediyne 12 (16.68 g, 20.89 mmol) in CH$_3$CN (84 mL) and H$_2$O (21 mL) at ambient temperature was added AcOH (42 mL). The reaction mixture was stirred at 25° C. for 2 h, diluted with EtOAc (100 mL) and quenched with saturated aq. NaHCO$_3$ (100 mL). The organic layer was separated, and the aqueous layer was extracted with EtOAc (2×150 mL). The combined organic layers were washed with saturated aq. NaHCO$_3$ (150 mL) and brine (150 mL), dried over MgSO$_4$, and concentrated. Flash column chromatography (silica gel, hexanes:EtOAc 4:1 to 2:1) yielded lactol 13 (12.86 g, 18.79 mmol, 91% yield) as a yellow solid. 13: R$_f$=0.28 (silica gel, hexanes:EtOAc 3:2); IR (film) $v_{max}$=3443, 2960, 2261, 2144, 1702, 1516, 1498, 1380, 1260 cm$^{-1}$; $^1$H NMR (600 MHz, CD$_3$CN): δ=7.56 (br, 1H), 7.1-6.9 (m, 5H), 6.3-6.2 (m, 2H), 6.00 (m, 1H), 5.9-5.8 (m, 2H), 5.4-5.3 (m, 1H), 5.25 (m, 1H), 5.25-4.9 (m, 3H), 4.8-4.5 (m, 3H), 3.80 (s, 3H), 3.79 (s, 3H), [1.44 (d, J=6.5 Hz, 3H) and 1.35 (d, J=6.5 Hz, 3H) diastereotopic pair], 1.11 (m, 21H), [0.19 (s, 9H) diastereotopic pair] ppm; HRMS (ESI-TOF): calcd for C$_{40}$H$_{50}$NO$_7$Si$^+$ [M+H$^+$]: 684.3351, found 684.3348.

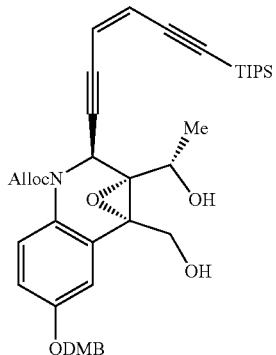

Epoxide 14

To a stirred solution of lactol 13 (12.00 g, 17.5 mmol, 1.0 equiv) in MeOH (117 mL) at 0° C. was added portionwise NaBH$_4$ (863 mg, 22.8 mmol, 1.3 equiv) (CAUTION: gas evolution). The reaction mixture was stirred at 0° C. for 20 min, until TLC showed full consumption of 13 (hexanes: EtOAc 1:1), then diluted with brine (200 mL), and extracted with CH$_2$Cl$_2$ (3×200 mL). The combined organic extracts were dried over MgSO$_4$, concentrated, and taken up in CH$_2$Cl$_2$ (100 mL). To this solution at 0° C. was added powdered NaHCO$_3$ (2.94 g, 35.0 mmol, 2.0 equiv), followed by dropwise addition of a cold (0° C.) solution of m-CPBA (90% purity, 3.47 g, 24.5 mmol, 1.4 equiv) in CH$_2$Cl$_2$ (17 mL) via cannula. The reaction mixture was stirred at 0° C. for 4 h (CAUTION: if reaction temperature exceeded 0° C., allyl carbamate will be epoxidized), then quenched with saturated aq. NaHCO$_3$ (50 mL) and saturated aq. Na$_2$S$_2$O$_3$ (50 mL). The organic layer was separated, and the aqueous layer was extracted with CH$_2$Cl$_2$ (2×200 mL). The combined organic layers were dried over MgSO$_4$ and concentrated. Flash column chromatography (silica gel, hexanes:EtOAc 3:2 to 1:1) yielded epoxide 14 (10.01 g, 14.23 mmol, 81% yield over two steps) as a yellow solid. 14: R$_f$=0.47 (silica gel, hexanes:EtOAc 3:7); [α]$_D^{25}$=+200.00 (c=1.00, CH$_2$Cl$_2$); IR (film) $v_{max}$=3475, 2940, 1703, 1505, 1261 cm$^{-1}$; $^1$H NMR (600 MHz, CD$_3$CN): δ=7.37 (d, J=2.5 Hz, 1H), 7.25 (br, 1H), 7.06 (d, J=1.9 Hz, 1H), 7.00 (dd, J=8.2, 1.9 Hz, 1H), 6.96 (dd, J=8.7, 2.6 Hz, 1H), 6.93 (d, J=8.2 Hz, 1H), 6.03 (br, 1H), 5.89 (br, 1H), 5.88 (d, J=11.0 Hz, 1H), 5.73 (dd, J=11.0, 1.3 Hz, 1H), 5.45-5.10 (br, 2H), 5.02 (AB system, 2H), 4.75-4.45 (br, 2H), 4.22 (qd, J=6.8, 4.5 Hz, 1H), 4.19 (dd, J=13.0, 4.9 Hz, 1H), 4.04 (dd, J=11.9, 5.1 Hz, 1H), 3.80 (s, 3H), 3.80 (s, 3H), 3.64 (d, J=3.5 Hz, 1H), 3.35 (t, J=5.1 Hz, 1H), 1.43 (d, J=6.9 Hz, 3H), 1.10 (s, 21H) ppm; $^{13}$C NMR (150 MHz, CD$_3$CN): δ=157.1, 155.4, 149.9, 149.9, 133.4, 130.2, 130.0, 129.6, 129.1, 121.5, 121.4, 120.2, 117.8, 115.7, 114.9, 112.6, 112.2, 104.4, 100.6, 94.1, 82.8, 77.8, 70.8, 68.1, 67.4, 62.2, 60.3, 56.1, 45.0, 21.3, 18.9, 11.8 ppm; HRMS (ESI-TOF): calcd for C$_{40}$H$_{52}$NO$_8$Si$^+$ [M+H$^+$]: 702.3457, found 702.3460.

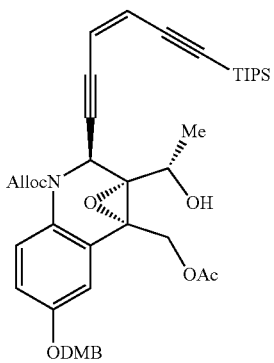

Acetate 15

To a stirred solution of epoxide 14 (11.0 g, 15.67 mmol, 1.0 equiv) in CH$_2$C$_2$ (261 mL) at −78° C. was added N,N-diisopropylethylamine (5.45 mL, 31.32 mmol, 2.0 equiv) and AcCl (1.12 mL, 15.67 mmol, 1.0 equiv). The resulting mixture was stirred at −78° C. for 16 h. The reaction was quenched with saturated aq. NaHCO$_3$ (150 mL) and extracted with CH$_2$Cl$_2$ (2×200 mL). The combined organic layers were dried over MgSO$_4$ and concentrated. Flash column chromatography (silica gel, hexanes:EtOAc 3:2 to 1:1) yielded acetate 15 (9.45 g, 13.45 mmol, 81% yield) as a yellow foam. 15: R$_f$=0.17 (silica gel, hexanes: EtOAc 3:2); [α]$_D^{25}$=−60.4° (c=1.00, CH$_2$Cl$_2$); IR (film) $v_{max}$=3485, 2941, 2136, 1708, 1504, 1382, 1236 cm$^{-1}$; $^1$H NMR (600 MHz, CD$_3$CN): δ=7.23 (br, 1H), 7.10 (d, J=2.8 Hz, 1H), 7.04 (d, J=1.9 Hz, 1H), 7.00 (dd, J=8.8, 2.7 Hz, 1H), 6.98 (dd, J=8.2, 1.9 Hz, 1H), 6.92 (d, J=8.2 Hz, 1H), 6.09 (s, 1H), 5.90 (br, 1H), 5.88 (d, J=11.0 Hz, 1H), 5.73 (dd, J=11.3, 1.9 Hz, 1H), 5.3-5.1 (br, 2H), 5.02 (s, 2H), 4.7-4.5 (br, 4H), 4.18 (qd, J=6.8, 4.4 Hz, 1H), 3.80 (s, 3H), 3.80 (s, 3H), 3.65 (d, J=3.5 Hz, 1H), 2.04 (s, 3H), 1.43 (d, J=7.0 Hz, 3H), 1.11 (s, 21H) ppm; $^{13}$C NMR (150 MHz, CD$_3$CN): δ=171.1, 158.2, 157.4, 155.4, 150.2, 150.0, 133.5, 130.3, 130.0, 129.6, 128.7, 121.4, 120.2, 115.8, 115.0, 112.6, 112.5, 104.5, 100.8, 93.7, 83.3, 78.4, 71.0, 68.1, 67.6, 62.2, 60.7, 56.3, 56.3, 44.8, 21.4, 20.9, 19.0, 11.9 ppm; HRMS (ESI-TOF): calcd for C$_{42}$H$_{54}$NO$_9$Si$^+$ [M+H$^+$]: 744.3562, found 744.3556.

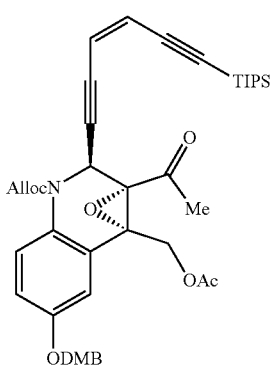

Ketone 16

To a stirred solution of acetate 15 (9.0 g, 12.09 mmol, 1.0 equiv) in CH$_2$Cl$_2$ (128 mL) was added powdered NaHCO$_3$ (4.06 g, 48.36 mmol, 4.0 equiv), and Dess-Martin periodinane (10.26 g, 24.18 mmol, 2.0 equiv) at 0° C. The resulting mixture was stirred at 25° C. for 2 h, then quenched with saturated aq. Na$_2$S$_2$O$_3$ (150 mL). The organic layer was separated, and the aqueous layer was extracted with CH$_2$Cl$_2$ (2×200 mL). The combined organic extracts were washed with saturated aq. NaHCO$_3$ (150 mL) and brine (150 mL), dried over MgSO$_4$, and filtered through a short plug of Celite® (washed with EtOAc prior to use). The solids were rinsed with EtOAc, and the combined filtrates were concentrated to ca. 5 mL in volume. Flash column chromatography (silica gel, hexanes:EtOAc 2:1) yielded ketone 16 (8.35 g, 11.25 mmol, 93% yield) as a yellow oil. 16: R$_f$=0.30 (silica gel, hexanes:EtOAc 3:2); [α]$_D^{25}$=+41.8° (c=1.00, CH$_2$Cl$_2$); IR (film) $v_{max}$=2958, 2142, 1747, 1712, 1505, 1384, 1308, 1222 cm$^{-1}$; $^1$H NMR (600 MHz, CD$_3$CN): δ=7.33 (br d, J=7.3 Hz, 1H), 7.16 (d, J=2.7 Hz, 1H), 7.07 (dd, J=8.8, 2.8 Hz, 1H), 7.05 (d, J=1.9 Hz, 1H), 6.99 (dd, J=8.1, 1.9 Hz, 1H), 6.93 (d, J=8.2 Hz, 1H), 6.05 (br s, 1H), 5.89 (br, 1H), 5.89 (d, J=11.3 Hz, 1H), 5.76 (dd, J=11.2, 1.9 Hz, 1H), 5.25-5.15 (br, 2H), 5.04 (s, 2H), 4.73 (d, J=12.8 Hz, 1H), 4.7-4.5 (br, 2H), 4.55 (d, J=12.8 Hz, 1H), 3.80 (s, 3H), 3.80 (s, 3H), 2.49 (s, 3H), 2.01 (s, 3H), 1.11 (s, 21H) ppm; $^{13}$C NMR (150 MHz, CD$_3$CN): δ=200.1, 170.6, 157.6, 155.6, 150.1, 150.0, 133.2, 130.1, 129.9, 129.4, 126.7, 121.9, 121.4, 119.8, 116.6, 114.8, 112.6, 112.4, 104.5, 102.3, 91.5, 83.9, 76.6, 71.0, 67.8, 61.3, 61.1, 56.3, 46.2, 29.9, 20.7, 19.0, 11.9 ppm; HRMS (ESI-TOF): calcd for C$_{42}$H$_{52}$NO$_9$Si$^+$ [M+H$^+$]: 742.3406, found 742.3400.

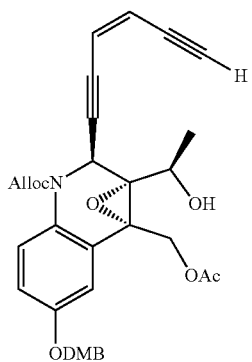

Secondary Alcohol 17

To a stirred solution of ketone 16 (1.94 g, 2.62 mmol, 1.0 equiv) in THF (20 mL) was added a premixed solution of HOAc/TBAF in THF (HOAc: 394 mg, 6.55 mmol, 2.5 equiv; TBAF: 6.55 mL, 1.0 M in THF, 6.55 mmol, 2.5 equiv) at 0° C., the reaction mixture was stirred at 15° C. for 1 h, and then MeOH (25 mL) was added at 0° C. followed by portionwise addition of NaBH$_4$ (200 mg, 5.25 mmol, 2.0 equiv) (CAUTION: gas evolution, if added too fast, the d.r. will be diminished). The resulting mixture was stirred at 0° C. for 30 min, then quenched with H$_2$O (10 mL). The reaction mixture was carefully evaporated to ca. 20 mL in volume, then partitioned between EtOAc (100 mL) and H$_2$O (60 mL). The aqueous layer was extracted with EtOAc (3×100 mL), and the combined organic layers were dried over MgSO$_4$ and concentrated to yield secondary alcohol 17 (1.43 g, 2.44 mmol, 93% yield, >25:1 dr) as a yellow solid (CAUTION: 17 slowly turned black during storage, which led to diminished yields for following steps, use fresh for best yields). 17: $R_f$=0.19 (silica gel, hexanes:EtOAc 3:2); $[\alpha]_D^{25}$=+158.9° (c=1.00, $CH_2Cl_2$); IR (film) $\nu_{max}$=3508, 3283, 2931, 1740, 1706, 1507, 1263, 1239, 1027 $cm^{-1}$; $^1H$ NMR (600 MHz, $CD_3CN$): δ=7.27 (br d, J=8.6 Hz, 1H), 7.14 (d, J=2.8 Hz, 1H), 7.05 (d, J=1.6 Hz, 1H), 7.01 (dd, J=8.8, 2.8 Hz, 1H), 6.99 (dd, J=8.1, 1.6 Hz, 1H), 6.93 (d, J=8.2 Hz, 1H), 6.05-5.83 (br, 2H), 5.81 (AB system, 2H), 5.40-5.12 (br, 2H), 5.03 (AB system, 2H), 4.76 (dd, J=18.1, 13.0 Hz, 2H), 4.70-4.50 (br, 2H), 4.23 (qd, J=6.2, 4.6 Hz, 1H), 3.80 (s, 3H), 3.80 (s, 3H), 3.47 (s, 1H), 3.15 (d, J=4.7 Hz, 1H), 2.04 (s, 3H), 1.43 (d, J=6.4 Hz, 3H) ppm; $^{13}C$ NMR (150 MHz, $CD_3CN$): δ=171.2, 157.4, 155.7, 150.2, 150.0, 133.4, 130.4, 129.8, 128.8, 121.3, 121.3, 120.7, 118.0, 115.9, 115.1, 112.6, 112.5, 93.3, 86.9, 82.7, 81.0, 77.2, 71.0, 67.6, 67.1, 62.0, 61.2, 60.9, 56.3, 45.8, 21.0, 20.1 ppm; HRMS (ESI-TOF): calcd for $C_{33}H_{34}NO_9^+$ [M+H]$^+$: 588.2228, found 588.2224.

3286, 2955, 2876, 1701, 1504, 1387, 1261, 1237 $cm^{-1}$; $^1H$ NMR (600 MHz, $CD_3CN$): δ=7.39 (d, J=2.8 Hz, 1H), 7.22 (br d, J=8.8 Hz, 1H), 7.06 (d, J=1.6 Hz, 1H), 7.01 (dd, J=8.2, 1.9 Hz, 1H), 6.96 (dd, J=8.8, 2.8 Hz, 1H), 6.93 (d, J=8.2 Hz, 1H), 6.20-5.80 (br, 2H), 5.76 (AB system, 2H), 5.47-5.05 (br, 2H), 5.03 (AB system, 2H), 4.80-4.45 (br, 2H), 4.38 (q, J=6.3 Hz, 1H), 4.24 (dd, J=12.5, 5.7 Hz, 1H), 4.17 (dd, J=12.5, 5.0 Hz, 1H), 3.81 (s, 3H), 3.80 (s, 3H), 3.40 (d, J=1.3 Hz, 1H), 3.15 (t, J=5.5 Hz, 1H), 1.43 (d, J=6.3 Hz, 3H), 0.95 (t, J=7.9 Hz, 9H), 0.63 (q, J=7.9 Hz, 6H) ppm; $^{13}C$ NMR (150 MHz, $CD_3CN$): δ=157.2, 155.8, 150.1, 150.0, 133.7, 133.5, 130.5, 130.3, 129.8, 129.5, 129.0, 121.6, 121.6, 120.3, 117.9, 116.0, 115.1, 112.8, 112.5, 94.4, 86.6, 81.6, 81.0, 76.8, 70.9, 67.9, 67.5, 63.4, 60.1, 56.3, 45.9, 21.5, 7.2, 5.5 ppm; HRMS (ESI-TOF): calcd for $C_{37}H_{46}NO_8Si^+$ [M+H]$^+$: 660.2987, found 660.2989.

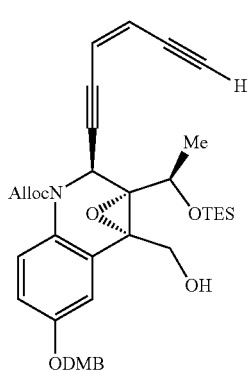

18

Primary Alcohol 18

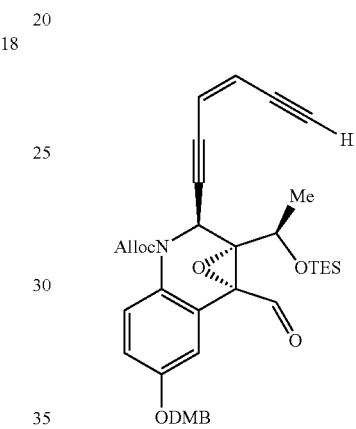

19

Aldehyde 19

To a stirred solution of acetate 17 (1.43 g, 2.44 mmol, 1.0 equiv) in DMF (15 mL) at 0° C. was added imidazole (332 mg, 4.88 mmol, 2.0 equiv) and TESCl (551 mg, 3.66 mmol, 1.5 equiv). The reaction mixture was stirred at 0° C. for 15 min, and at 25° C. for 5 min, then quenched with saturated aq. $NaHCO_3$ (50 mL), and extracted with $Et_2O$ (3×50 mL). The combined organic extracts were washed with $H_2O$ (3×50 mL) and brine (50 mL), dried over $MgSO_4$, and concentrated. The resulting residue was taken up in THF (20 mL) and cooled to 0° C. To this solution was added a cold (0-5° C.) saturated solution of $K_2CO_3$ in MeOH (2.5 mL), and the reaction mixture was stirred at −10 OC for 20 min (CAUTION: 18 slowly underwent deprotection of TES at this temperature thus the reaction should be carefully monitored at 2 min intervals). The resulting mixture was then partitioned between EtOAc (50 mL) and pH 6.8 buffer (50 mL). The aqueous layer was extracted with EtOAc (2×50 mL), then the combined organic layers were washed with brine (50 mL), dried over $MgSO_4$, and concentrated to ca. 5 mL in volume. Flash column chromatography (silica gel, hexanes:EtOAc 3:1 to 2:1) yielded primary alcohol 18 (1.36 g, 2.07 mmol, 85% yield over two steps) as a yellow solid (CAUTION: 18 slowly turned black during storage, which led to diminished yields for following steps, use fresh for best yields). 18: $R_f$=0.42 (silica gel, hexanes:EtOAc 3:2); $[\alpha]_D^{25}$=+47.2° (c=1.00, $CH_2Cl_2$); IR (film) $\nu_{max}$=3493, To a stirred solution of primary alcohol 18 (1.25 g, 1.90 mmol, 1.0 equiv) in $CH_2Cl_2$ (20 mL) at 0° C. was added powdered $NaHCO_3$ (639 mg, 7.60 mmol, 4.0 equiv), and Dess-Martin periodinane (3.22 g, 3.80 mmol, 2.0 equiv). The reaction mixture was stirred at 25° C. for 1.5 h, then partitioned between $CH_2Cl_2$ (30 mL) and saturated aq. $Na_2S_2O_3$ (30 mL). The aqueous layer was extracted with $CH_2Cl_2$ (2×30 mL), and the combined organic layers were washed with brine (30 mL), dried over $MgSO_4$, and filtered through a short plug of Celite® (washed with EtOAc prior to use). The solids were rinsed with EtOAc, and the combined filtrates were concentrated to ca. 5 mL in volume. Flash column chromatography (silica gel, hexanes:EtOAc 4:1) yielded aldehyde 19 (1.12 g, 1.71 mmol, 90% yield) as a yellow oil (CAUTION: 19 slowly turned black during storage, which led to diminished yields for following steps, use fresh for best yields). 19: $R_f$=0.47 (silica gel, hexanes:EtOAc 3:2); $[\alpha]_D^{25}$=+86.9° (c=1.00, $CH_2Cl_2$); IR (film) $\nu_{max}$=3282, 2956, 2877, 2261, 1708, 1502, 1385, 1263, 1239 $cm^{-1}$; $^1H$ NMR (600 MHz, $CD_3CN$): δ=9.83 (s, 1H), 7.31 (br d, J=7.4 Hz, 1H), 7.21 (d, J=2.8 Hz, 1H), 7.04 (d, J=1.9 Hz, 1H), 7.02 (dd, J=8.8, 2.8 Hz, 1H), 6.98 (dd, J=8.2, 1.9 Hz, 1H), 6.92 (d, J=8.2 Hz, 1H), 6.0-5.8 (br, 2H), 5.80 (m, 2H), 5.3-5.1 (br, 2H), 5.00 (AB doublet, 2H), 4.7-4.5 (br, 2H), 4.38 (q, J=6.3 Hz, 1H), 3.80 (s, 3H), 3.80 (s, 3H), 3.44

(d, J=1.8 Hz, 1H), 1.43 (d, J=6.4 Hz, 3H), 0.96 (t, J=8.0 Hz, 9H), 0.63 (q, J=8.0 Hz, 6H) ppm; $^{13}$C NMR (150 MHz, CD$_3$CN): δ=196.3, 157.0, 155.6, 150.1, 150.0, 133.3, 130.2, 129.9, 125.2, 121.5, 121.1, 121.0, 118.0, 116.2, 115.0, 112.7, 112.4, 92.7, 87.0, 83.1, 80.9, 80.5, 70.9, 67.7, 67.5, 64.6, 56.2, 46.2, 22.2, 7.0, 5.4 ppm; HRMS (ESI-TOF): calcd for C$_{37}$H$_{44}$NO$_8$Si$^+$ [M+H$^+$]: 658.2831, found 658.2846.

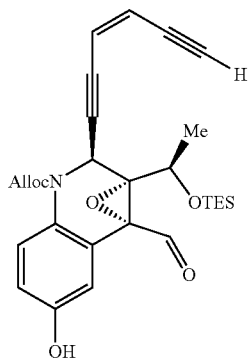

Phenol 20

To a stirred solution of aldehyde 19 (1.12 g, 1.71 mmol, 1.0 equiv) in CH$_2$Cl$_2$ (50 mL) at ambient temperature was added pH 6.8 buffer (5.0 mL) and DDQ (1.16 g, 5.13 mmol, 3.0 equiv). The reaction flask was wrapped with aluminium foil and the resulting mixture was stirred at ambient temperature for 12 h, until TLC showed full consumption of 19 (4% EtOAc in CH$_2$Cl$_2$). The reaction mixture was then partitioned between CH$_2$Cl$_2$ (100 mL) and pH 6.8 buffer (100 mL). The aqueous layer was extracted with CH$_2$Cl$_2$ (2×100 mL), and the combined organic layers were washed with pH 6.8 buffer (50 mL), H$_2$O (50 mL), and brine (50 mL), dried over MgSO$_4$, and filtered through a short plug of Celite® (washed with EtOAc prior to use). The solids were rinsed with 5% EtOAc in CH$_2$Cl$_2$, and the combined filtrates were concentrated to ca. 5 mL in volume. Flash column chromatography (CH$_2$Cl$_2$:EtOAc 1:0 to 30:1, then hexanes:EtOAc 4:1 after 3,4-dimethoxy-benzaldehyde was fully eluted) yielded phenol 20 (CAUTION: 20 was sensitive to trace HCl in CH$_2$Cl$_2$, concentration of fractions to ca. 20 mL, then diluted with 20 mL toluene; repeat the same operations 3 times and then concentrate to dryness) (810 mg, 1.59 mmol, 93% yield) as a yellow oil (CAUTION: 20 slowly turned black during storage, which led to diminished yields for following steps, use fresh for best yields). 20: R$_f$=0.44 (silica gel, hexanes:EtOAc 3:2); [α]$_D^{25}$=+121.2° (c=1.00, CH$_2$Cl$_2$); IR (film) ν$_{max}$=3296, 2956, 1680, 1505, 1392, 1315 cm$^{-1}$; $^1$H NMR (500 MHz, CD$_3$CN): δ=9.79 (s, 1H), 7.22 (br d, J=8.4 Hz, 1H), 7.15 (br s, 1H), 7.06 (d, J=2.8 Hz, 1H), 6.84 (dd, J=8.6, 2.6 Hz, 1H), 5.90 (br s, 1H), 5.81 (s, 2H), 5.3-5.1 (br, 2H), 4.7-4.5 (br, 2H), 4.38 (q, J=6.4 Hz, 1H), 3.49 (s, 1H), 1.42 (d, J=6.4 Hz, 3H), 0.96 (t, J=8.0 Hz, 9H), 0.63 (q, J=8.0 Hz, 6H) ppm; $^{13}$C NMR (125 MHz, CD$_3$CN): δ=196.4, 155.3, 133.4, 130.1, 125.2, 121.1, 121.0, 117.9, 116.7, 115.1, 92.8, 86.9, 83.1, 68.2, 67.6, 67.5, 64.6, 46.3, 22.2, 7.0, 5.4 ppm; HRMS (ESI-TOF): calcd for C$_{28}$H$_{34}$NO$_6$Si$^+$ [M+H$^+$]: 508.2150, found 508.2140.

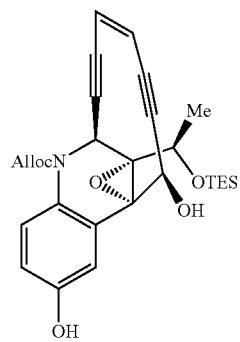

Cyclic Enediyne 21a

A 250 mL round bottom flask containing commercially available anhydrous CeCl$_3$ (beads, −10 mesh, 1.57 g, 6.36 mmol, 4.0 equiv) was heated to 110° C. (oil bath temperature) under high vacuum with vigorous stirring for 16 h to afford a white powder. The flask was flushed with Ar, and THF (50 mL) was added to form a cloudy suspension, which was sonicated for 2 h to afford a milky suspension. A solution of phenol 20 (810 mg, 1.59 mmol, 1.0 equiv) in THF (50 mL) was added to the preformed CeCl$_3$ suspension via cannula under sonication over 20 min at ambient temperature. The resulting mixture was stirred at ambient temperature for 30 min, and then cooled to −78° C., followed by dropwise addition of KHMDS (1.0 M in THF, 9.60 mL, 9.60 mmol, 6.0 equiv), during which time the color of reaction mixture turned from light yellow to brown, then dark brown. The reaction mixture was stirred at −78° C. for 1 h, then slowly warmed up to −40° C. over 2 h, and was quenched by the addition of AcOH (1.0 M in THF, 19.1 mL, 19.1 mmol, 12.0 equiv) at the same temperature. Upon completion of addition, the reaction mixture was allowed to warm to ambient temperature, carefully concentrated to ca. 40 mL in volume and then partitioned between EtOAc (100 mL) and pH 6.8 buffer (100 mL). The aqueous layer was extracted with EtOAc (2×100 mL), and the combined organic layers were washed with H$_2$O (50 mL) and brine (50 mL), dried over MgSO$_4$, and filtered through a short plug of Celite® (washed with EtOAc prior to use). The solids were rinsed with EtOAc, and the combined filtrates were concentrated to ca. 5 mL in volume. Flash column chromatography (silica gel, hexanes:EtOAc 4:1 to 3:1) yielded cyclic enediyne 21a (601 mg, 1.18 mmol, 74% yield) as an off-white solid and a mixture of 21a and its C17-epimer 21b (154 mg, 21a:21b 1:3, 19% yield) as an yellowish solid. 21a: R$_f$=0.36 (silica gel, hexanes:EtOAc 3:2); [α]$_D^{25}$=+477.80 (c=0.50, CH$_2$Cl$_2$); IR (film) ν$_{max}$=3395, 2955, 2877, 1682, 1504, 1395, 1281 cm$^{-1}$; $^1$H NMR (600 MHz, CD$_3$CN): δ=7.94 (d, J=2.8 Hz, 1H), 7.14 (br, 1H), 6.95 (s, 1H), 6.73 (dd, J=8.7, 2.8 Hz, 1H), 5.91 (br, 1H), 5.90 (d, J=10.0 Hz, 1H), 5.83 (s, 1H), 5.75 (d, J=9.9 Hz, 1H), 5.35-5.15 (br, 2H), 5.05 (d, J=4.7 Hz, 1H), 4.75-4.55 (br, 2H), 4.54 (q, J=6.3 Hz, 1H), 4.24 (d, J=4.7 Hz), 1.38 (d, J=6.2 Hz, 3H), 0.98 (t, J=8.0 Hz, 9H), 0.65 (m, 6H) ppm; $^{13}$C NMR (150 MHz, CD$_3$CN): δ=154.3, 133.5, 130.2, 128.3, 124.5, 123.9, 118.3, 117.7, 115.4, 100.3, 97.1, 91.3, 77.2, 67.3, 66.8, 66.0, 64.9, 60.9, 47.4, 22.3, 7.2, 5.6 ppm; HRMS (ESI-TOF): calcd for C$_2$H$_{34}$NO$_6$Si$^+$[M+H$^+$]: 508.2150, found 508.2140.

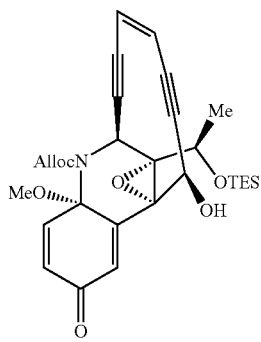

Quinone Aminal 22a

To a stirred solution of cyclic enediyne 21a (601 mg, 1.18 mmol, 1.0 equiv) in MeOH (40 mL) at 0° C. was added a solution of PhI(OAc)$_2$ (420 mg, 1.30 mmol, 1.1 equiv) in MeOH (20 mL) via cannula. The resulting mixture was stirred at 0° C. for 10 min and at 25° C. for 5 min, then partitioned between EtOAc (100 mL) and half saturated aq. NaHCO$_3$ (100 mL). The aqueous layer was extracted with EtOAc (2×50 mL), and the combined organic layers were washed with brine (50 mL), dried over MgSO$_4$, and filtered through a short plug of Celite® (washed with EtOAc prior to use). The solids were rinsed with EtOAc, and the combined filtrates were concentrated to ca. 3 mL in volume. Flash column chromatography (silica gel, hexanes:EtOAc 4:1 to 3:1) yielded quinone aminal 22a (529 mg, 0.983 mmol, 83% yield) as a white solid. 22a: R$_f$=0.30 (silica gel, hexanes:EtOAc 3:2); [α]$_D^{25}$=+592.2° (c=0.50, CH$_2$Cl$_2$); IR (film) ν$_{max}$=3448, 2954, 2877, 1707, 1666, 1390, 1282 cm$^{-1}$; $^1$H NMR (600 MHz, CD$_3$CN): δ=7.54 (br, 1H), 7.04 (d, J=1.9 Hz, 1H), 6.27 (dd, J=10.4, 2.0 Hz, 1H), 6.05-5.95 (m, 3H), 5.86 (d, J=9.9 Hz, 1H), 5.36 (d, J=17.0 Hz, 1H), 5.25 (d, J=10.5 Hz, 1H), 4.83 (d, J=4.8 Hz, 1H), 4.8-4.6 (br, 2H), 4.54 (q, J=6.3 Hz, 1H), 4.25 (d, J=5.0 Hz, 1H), 3.03 (s, 3H), 1.34 (d, J=6.3 Hz, 3H), 0.96 (t, J=8.0 Hz, 9H), 0.63 (m, 6H) ppm; $^{13}$C NMR (150 MHz, CD$_3$CN): δ=184.8, 138.6, 133.4, 128.7, 124.8, 124.6, 99.7, 98.1, 92.3, 89.0, 70.0, 66.5, 63.8, 51.3, 46.8, 22.4, 7.2, 5.6 ppm; HRMS (ESI-TOF): calcd for C$_{29}$H$_{36}$NO$_7$Si$^+$ [M+H$^+$]: 538.2255, found 538.2247.

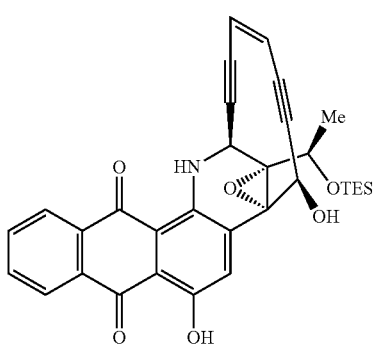

Anthraquinone 25a

To a solution of 3-cyano-1(3H)-isobenzofuranone (23, 34 mg, 0.22 mmol, 3.0 equiv) in THF (1.0 mL) at −78° C. was added LiHMDS (1.0 M in THF, 0.29 mL, 0.29 mmol, 4.0 equiv). The resulting mixture was stirred at −78° C. for 20 min, and a pre-cooled solution of quinone aminal 22a (39 mg, 72 μmol, 1.0 equiv) in THF (1.0 mL) at −78° C. was added via cannula. After stirring for 5 min at −78° C., the reaction mixture was warmed to ambient temperature and stirred for another 50 min during which time the reaction mixture turned dark red and TLC showed full consumption of 22a (8% EtOAc in CH$_2$Cl$_2$). The reaction mixture was then quenched by the addition of pH 6.8 buffer (20 mL) and extracted with EtOAc (3×20 mL). The combined organic extracts were washed with brine (20 mL), dried over MgSO$_4$, and filtered through a short plug of Celite® (washed with EtOAc prior to use). The solids were rinsed with EtOAc, and the combined filtrates were concentrated to yield crude alloc-anthraquinone 24 as a dark red solid, which was dissolved in degassed THF (1.5 mL) under Ar and cooled to 0° C. To this solution was added Pd(PPh$_3$)$_4$(6 mg, 5.2 μmol, 0.08 equiv), followed by dropwise addition of morpholine (16 mg, 0.17 mmol, 2.4 equiv), the reaction flask was wrapped with aluminium foil, and the resulting mixture was allowed to stir at 0° C. for 2 h during which time the reaction mixture turned dark purple. The cooling bath was removed and the reaction mixture was stirred at ambient temperature for 20 min, and then quenched by the addition of pH 6.8 buffer (20 mL) and extracted with EtOAc (3×20 mL). The combined organic extracts were washed with saturated aq. NaHCO$_3$ (20 mL) and brine (20 mL), dried over MgSO$_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes:EtOAc 2:1 to 1:1] yielded anthraquinone 25a (29 mg, 52 μmol, 73% yield) as a purple solid. 25: R$_f$=0.58 (silica gel, hexanes: EtOAc 3:2); [α]$_D^{25}$=+2600° (c=0.002, EtOAc); IR (film) ν$_{max}$=3429, 2955, 2876, 1788, 1620, 1587, 1487, 1277, 1234 cm$^{-1}$; $^1$H NMR (600 MHz, CD$_3$CN): δ=13.17 (s, 1H), 9.98 (d, J=4.0 Hz, 1H), 8.48 (s, 1H), 8.29 (d, J=7.9 Hz, 1H), 8.27 (d, J=8.0 Hz, 1H), 7.86 (t, J=7.7 Hz, 1H), 7.81 (t, J=7.0 Hz, 1H), 5.95 (d, J=9.9 Hz, 1H), 5.88 (d, J=10.1 Hz, 1H), 5.12 (d, J=5.0 Hz, 1H), 4.99 (d, J=4.4 Hz, 1H), 4.56 (q, J=6.3 Hz, 1H), 4.43 (d, J=5.0 Hz, 1H), 1.39 (d, J=6.4 Hz, 3H), 0.99 (t, J=8.0 Hz, 9H), 0.67 (q, J=7.7 Hz, 6H) ppm; $^{13}$C NMR (150 MHz, CD$_3$CN): δ=188.5, 184.2, 156.6, 144.7, 136.2, 135.8, 135.5, 134.3, 133.6, 130.9, 127.7, 127.0, 124.8, 123.8, 114.2, 112.3, 100.2, 99.8, 91.3, 88.4, 77.3, 66.8, 64.8, 44.3, 22.6, 7.2, 5.6 ppm; HRMS (ESI-TOF): calcd for C$_{32}$H$_{32}$NO$_6$Si$^+$ [M+H$^+$]: 554.1993, found 554.1992.

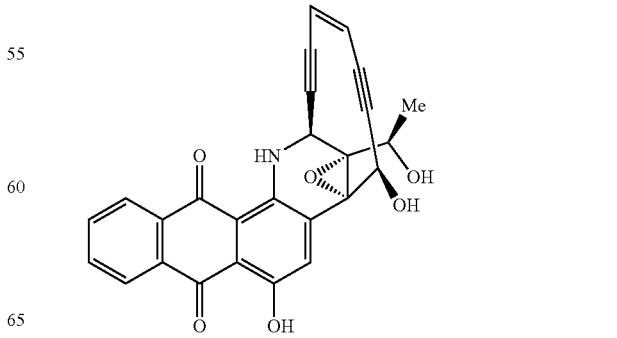

Uncialamycin (26a)

To a solution of anthraquinone 25a (29 mg, 52 μmol, 1.0 equiv) in degassed THF (9.0 mL) at room temperature was added a solution of 1:1 3HF.Et$_3$N:THF (3.0 mL). The sealed reaction flask was wrapped with aluminium foil, and the reaction mixture was stirred at room temperature for 1.5 h, then partitioned between EtOAc (30 mL) and saturated aq. NaHCO$_3$ (30 mL). The organic layer was washed with brine (30 mL), dried over Na$_2$SO$_4$, and concentrated to ca. 1 mL in volume. Flash column chromatography [deactivated silica gel (see General Methods), hexanes:EtOAc 1:1 to 1:2] yielded uncialamycin (26a) (23 mg, 52 μmol, 99% yield) as a purple solid. 26: m.p.=175° C. (decomp., EtOAc); R$_f$=0.14 (silica gel, hexanes:EtOAc 3:2); [α]$_D^{25}$=+2300° (c=0.002, EtOAc); IR (film) ν$_{max}$=3429, 2926, 1715, 1620, 1587, 1484, 1355, 1234 cm$^{-1}$; $^1$H NMR (600 MHz, DMSO-d$_6$): δ=13.19 (s, 1H), 10.01 (d, J=4.5 Hz, 1H), 8.53 (s, 1H), 8.24 (overlapping doublets, 2H), 7.94 (td, J=7.4, 1.1 Hz, 1H), 7.89 (td, J=7.4, 1.1 Hz, 1H), 6.68 (d, J=5.1 Hz, 1H), 6.06 (d, J=9.8 Hz, 1H), 5.98 (d, J=10.0 Hz, 1H), 5.39 (d, J=5.7 Hz, 1H), 5.16 (d, J=5.1 Hz, 1H), 5.07 (d, J=4.6 Hz, 1H), 4.33 (quint, J=6.2 Hz, 1H), 1.31 (d, J=6.5 Hz, 3H) ppm; $^{13}$C NMR (150 MHz, DMSO-d$_6$): δ=186.8, 182.1, 154.7, 143.5, 135.5, 134.8, 134.3, 133.5, 132.1, 129.8, 126.5, 126.0, 123.9, 123.2, 112.6, 110.3, 100.3, 98.8, 89.6, 87.3, 75.9, 63.5, 62.9, 59.7, 43.1, 21.9 ppm; HRMS (ESI-TOF): calcd for C$_{26}$H$_{18}$NO$_6^+$ [M+H$^+$]: 440.1129, found 440.1123.

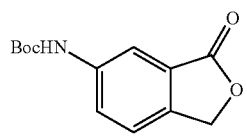

Phthalide 29

To a stirred solution of 6-aminophthalide (10.0 g, 67.0 mmol, 1.0 equiv), DMAP (164 mg, 1.34 mmol, 0.02 equiv), and Et$_3$N (13.6 g, 18.7 mL, 134 mmol, 2.0 equiv) in THF (40 mL) at 0° C., Boc$_2$O (17.6 g, 80.4 mmol, 1.2 equiv) was added portionwise over 10 min under vigorous stirring at 0° C. (CAUTION: gas evolution). Upon completion of addition, the ice bath was removed and the reaction mixture was stirred for 3 h at 40° C. and was diluted with EtOAc (50 mL), cooled to 0° C., quenched by careful addition of saturated aq. NH$_4$Cl (40 mL). The resulting mixture was extracted with EtOAc (3×50 mL), and the combined organic layers were washed with water (50 mL) and brine (50 mL), dried over MgSO$_4$ and concentrated. Flash column chromatography (silica gel, hexanes:EtOAc 2:1 to 1:1) gave phthalide 29 as a yellowish solid (13.4 g, 53.6 mmol, 80% yield). 29: R$_f$=0.31 (silica gel, hexanes:EtOAc 2:1); IR (film) ν$_{max}$=3341, 2979, 2931, 2851, 1741, 1719, 1604, 1538, 1497, 1450, 1423, 1390, 1365, 1316, 1299, 1234, 1126, 1063, 1002 cm$^{-1}$; $^1$H NMR (500 MHz, CDCl$_3$): δ=7.83 (d, J=2.0, 1H), 7.76 (d, J=7.8, 1H), 7.36 (d, J=8.3, 1H), 6.92 (br, 1H), 5.23 (s, 2H), 1.47 (s, 9H) ppm; $^{13}$C NMR (125 MHz, CDCl$_3$): δ=170.9, 152.5, 140.5, 139.6, 126.4, 124.8, 122.5, 114.6, 81.1, 69.5, 28.2 ppm; HRMS (ESI-TOF): calcd for C$_{13}$H$_{16}$NO$_4^+$ [M+H$^+$]: 250.1074, found 250.1076.

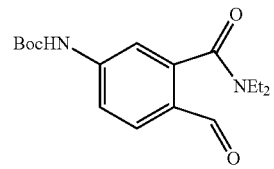

Formylbenzamide 32

To a stirred suspension of phthalide 29 (13.4 g, 53.6 mmol, 1.0 equiv) in CCl$_4$/benzene (200 mL, 1:1) at room temperature, was added N-bromosuccinimide (11.4 g, 64.3 mmol, 1.2 equiv) in one portion. The reaction mixture was heated to reflux, and azobisisobutyronitrile (1.76 g, 10.7 mmol, 0.2 equiv) was then added in one portion. The reaction mixture was vigorously stirred at reflux for another 2 h, then cooled to ambient temperature, and stored at 0° C. for 8 h. The reaction mixture was filtered and the precipitates were washed with CCl$_4$ (0-5° C.). The combined filtrates were concentrated to yield crude 30 as a yellow foam, which was suspended in H$_2$O/THF (200 mL, 1:1). The suspension was stirred at 85° C. for 5 h and cooled to ambient temperature. The reaction mixture was extracted with EtOAc (5×50 mL), and the combined organic layers were dried over MgSO$_4$ and concentrated to yield crude 31 as a yellow hygroscopic solid, which was dried over P$_2$O$_5$ for a further 8 h. The crude acid 31 was suspended in SOCl$_2$ (60 mL) and the reaction mixture was heated to reflux for 2 h. The reaction mixture was then cooled to ambient temperature and concentrated under N$_2$ and the residue was coevaporated with toluene (2×25 mL) to remove all traces of SOCl$_2$. The crude product was dissolved in CH$_2$Cl$_2$ (50 mL) and the reaction mixture was cooled to 0° C. A solution of diethylamine (7.1 g, 10 mL, 96.7 mmol, 1.8 equiv) in CH$_2$Cl$_2$ (10 mL) was added dropwise. Upon completion of addition, the ice bath was removed and the reaction mixture was stirred at ambient temperature for 2 h. The reaction was quenched with 1N HCl (100 mL), and the aqueous layer was extracted with CH$_2$Cl$_2$ (2×50 mL). The combined organic layers were washed with brine (50 mL), dried over MgSO$_4$ and concentrated. Flash column chromatography (silica gel, hexanes:EtOAc 3:1 to 2:1) gave formylbenzamide 32 as a yellowish solid (10.3 g, 32.2 mmol, 60% yield). 32: R$_f$=0.31 (silica gel, hexanes:EtOAc 2:1); $^1$H NMR (600 MHz, CDCl$_3$): δ=9.89 (s, 1H), 7.82 (d, J=8.5 Hz, 1H), 7.52 (dd, J=8.4, 1.4 Hz, 1H), 7.33 (d, J=1.6 Hz, 1H), 7.33 (br, 1H), 3.60 (br, 2H), 3.12 (q, J=7.1 Hz, 2H), 1.51 (s, 9H), 1.30 (t, J=7.1 Hz, 3H), 1.04 (t, J=7.1 Hz, 3H) ppm; $^{13}$C NMR (150 MHz, CDCl$_3$): δ=189.1, 168.5, 151.9, 144.1, 140.6, 131.6, 126.9, 117.8, 115.7, 81.5, 60.4, 43.0, 39.2, 28.2, 13.8, 12.6 ppm; HRMS (ESI-TOF): calcd for C$_{17}$H$_{25}$N$_2$O$_4^+$ [M+H$^+$]: 321.1809, found 321.1810.

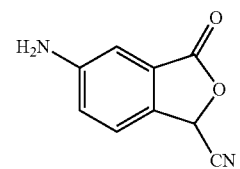

Cyanophthalide 33

To a stirred solution of formylbenzamide 32 (1.03 g, 3.22 mmol, 1.0 equiv) in CH$_2$Cl$_2$ (6 mL) at 0° C., was added TMSCN (640 mg, 0.81 mL, 6.44 mmol, 2.0 equiv), and a solution of KCN (5.2 mg, 0.08 mmol, 0.025 equiv) and 18-crown-6 (16 mg, 0.06 mmol, 0.02 equiv) in THF (0.6 mL). The reaction mixture was stirred at the same temperature for 1.5 h in a sealed flask, and for 30 min at ambient temperature. The reaction mixture was then concentrated under N$_2$ and the residue was coevaporated with toluene (2×25 mL) to remove all traces of TMSCN. The resulting brown oil was dissolved in AcOH (3 mL) and stirred for 36 h at room temperature. The reaction was quenched by careful addition of 1N NaOH (10 mL), and the resulting mixture was partitioned between EtOAc (20 mL) and 1N NaOH (10 mL). The aqueous layer was extracted with EtOAc (3×20 mL), and the combined organic layers were washed with H$_2$O (20 mL) and brine (20 mL), dried over MgSO$_4$ and concentrated to give the crude product as a crystalline solid. The crude product was dissolved in CH$_3$CN (20 mL) and aq. HF (48% to 51%, 4 mL) was added in one portion at room temperature. After stirred for 16 h at room temperature, the reaction mixture was cautiously poured into saturated aq. NaHCO$_3$ (150 mL). The aqueous layer was extracted with EtOAc (3×50 mL), and the combined organic layers were washed with H$_2$O (25 mL) and brine (25 mL), dried over MgSO$_4$ and concentrated. Flash column chromatography (silica gel, CH$_2$Cl$_2$:EtOAc 4:1) gave cyanophthalide 33 as a white solid (393 mg, 2.25 mmol, 70% yield). 33: R$_f$=0.31 (silica gel, CH$_2$Cl$_2$:EtOAc 4:1); $^1$H NMR (400 MHz, CD$_3$CN): δ=7.46 (d, J=8.3, 1H), 7.09 (dd, J=8.3, 1.7 Hz, 1H), 7.02 (d, J=1.7 Hz, 1H), 6.15 (s, 1H), 4.76 (br, 2H) ppm; $^{13}$C NMR (150 MHz, CD$_3$CN): δ=169.5, 151.9, 131.2, 126.4, 124.5, 122.9, 116.3, 109.2, 67.1 ppm; HRMS (ESI-TOF): calcd for C$_9$H$_7$N$_2$O$_2$$^+$ [M+H$^+$]: 175.0502, found 175.0503.

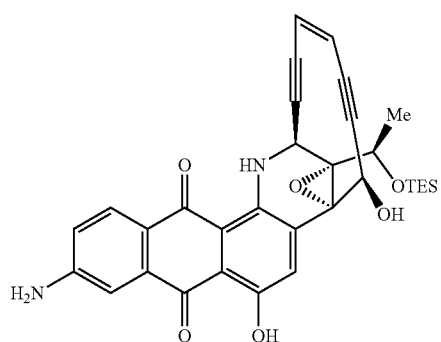

Anthraquinone 35a

To a solution of cyanophthalide 33 (38 mg, 0.22 mmol, 3.0 equiv) in THF (1.0 mL) at −78° C. was added LiHMDS (1.0 M in THF, 0.29 mL, 0.29 mmol, 4.0 equiv). The resulting mixture was stirred at −78° C. for 20 min, and a pre-cooled solution of quinone aminal 22a (39 mg, 73 µmol, 1.0 equiv) in THF (1.0 mL) at −78° C. was added via cannula. After stirring for 5 min at −78° C., the reaction mixture was warmed to ambient temperature and stirred for another 1 h during which time the reaction mixture turned dark red and TLC showed full consumption of 22a (8% EtOAc in CH$_2$Cl$_2$). The reaction mixture was then quenched by the addition of pH 6.8 buffer (20 mL) and extracted with EtOAc (3×20 mL). The combined organic extracts were washed with brine (20 mL), dried over MgSO$_4$, and filtered through a short plug of Celite® (washed with EtOAc prior to use). The solids were rinsed with EtOAc, and the combined filtrates were concentrated to yield crude alloc-anthraquinone 34a as a dark red solid, which was dissolved in degassed THF (1.5 mL) under Ar and cooled to 0° C. To this solution was added Pd(PPh$_3$)$_4$ (8 mg, 3.5 µmol, 0.1 equiv), followed by dropwise addition of morpholine (16 mg, 16 µL, 0.17 mmol, 2.4 equiv), the reaction flask was wrapped with aluminium foil, and the resulting mixture was allowed to stir at 0° C. for 2 h during which time the reaction mixture turned dark purple. The cooling bath was removed and the reaction mixture was stirred at ambient temperature for 20 min, and then quenched by the addition of pH 6.8 buffer (20 mL) and extracted with EtOAc (3×20 mL). The combined organic extracts were washed with saturated aq. NaHCO$_3$ (20 mL) and brine (20 mL), dried over MgSO$_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes:EtOAc 2:1 to 1:1] yielded anthraquinone 35a (28 mg, 50 µmol, 69% yield) as a purple solid. 35a: R$_f$=0.58 (silica gel, hexanes:EtOAc 1:1); [α]$_D^{25}$=+2600° (c=0.002, EtOAc); IR (film) v$_{max}$=3376, 3240, 2955, 2876, 1625, 1580, 1481, 1353, 1322, 1258, 1232 cm$^{-1}$; $^1$H NMR (600 MHz, CD$_3$CN): δ=13.11 (s, 1H), 9.94 (d, J=3.8 Hz, 1H), 8.39 (s, 1H), 8.01 (d, J=8.6 Hz, 1H), 7.35 (d, J=2.0 Hz, 1H), 6.99 (dd, J=8.6, 2.0 Hz, 1H), 5.93 (d, J=10.0 Hz, 1H), 5.86 (d, J=10.0 Hz, 1H), 5.16 (br, 2H), 5.10 (d, J=4.8 Hz, 1H), 4.92 (d, J=4.0 Hz, 1H), 4.54 (q, J=6.3 Hz, 1H), 4.40 (d, J=4.9 Hz, 1H), 1.38 (d, J=6.3 Hz, 3H), 0.98 (t, J=8.0 Hz, 9H), 0.66 (q, J=7.9 Hz, 6H) ppm; $^{13}$C NMR (150 MHz, CD$_3$CN): δ=189.3, 183.8, 156.4, 154.1, 144.0, 136.1, 135.4, 130.2, 129.7, 125.4, 124.9, 123.7, 120.3, 114.8, 112.6, 109.9, 100.3, 100.1, 91.3, 88.3, 77.3, 66.8, 65.0, 64.8, 44.3, 22.6, 7.3, 5.6 ppm; HRMS (ESI-TOF): calcd for C$_{32}$H$_{33}$N$_2$O$_6$Si$^+$ [M+H$^+$]: 569.2102, found 569.2104.

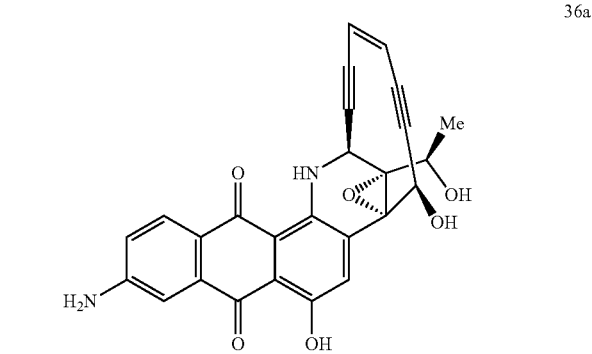 [SMILES: C[C@@H](O)[C@@]12O[C@]13c1cc(O)c4c(c1N[C@H]2C#C/C=C\C#C[C@H]3O)C(=O)c1ccc(N)cc1C4=O]

8-Amino-uncialamycin (36a)

To a solution of anthraquinone 35a (28 mg, 50 µmol, 1.0 equiv) in degassed THF (7.5 mL) at room temperature was added a solution of 1:1 3HF.Et$_3$N:THF (2.5 mL). The reaction flask was wrapped with aluminium foil, and the reaction mixture was stirred at room temperature for 1.5 h, then partitioned between EtOAc (25 mL) and saturated aq.

NaHCO$_3$ (25 mL). The organic layer was washed with brine (25 mL), dried over Na$_2$SO$_4$, and concentrated to ca. 1 mL in volume. Flash column chromatography [deactivated silica gel (see General Methods), hexanes:EtOAc 1:1 to 1:3] yielded 8-amino-uncialamycin (36a) (22 mg, 48 µmol, 98% yield) as a purple solid. 36a: R$_f$=0.24 (silica gel, hexanes: EtOAc 1:1); [α]$_D^{25}$=+870° (c=0.02, EtOAc); IR (film) ν$_{max}$=3375, 3239, 2934, 1626, 1581, 1480, 1357, 1326, 1258, 1233 cm$^{-1}$; $^1$H NMR (400 MHz, CD$_3$CN): δ=13.10 (s, 1H), 9.96 (d, J=4.0 Hz, 1H), 8.41 (s, 1H), 8.00 (d, J=8.6 Hz, 1H), 7.34 (d, J=2.4 Hz, 1H), 6.98 (dd, J=8.6, 2.4 Hz, 1H), 5.95 (dd, J=10.0, 0.6 Hz, 1H), 5.88 (dt, J=10.0, 1.2 Hz, 1H), 5.24 (d, J=5.0 Hz, 1H), 5.17 (br, 2H), 4.86 (dd, J=4.3, 1.6 Hz, 1H), 4.50 (d, J=4.9 Hz, 1H), 4.37 (dq, J=5.0, 6.5 Hz, 1H), 3.26 (d, J=4.9 Hz, 1H), 1.38 (d, J=6.5 Hz, 3H) ppm; $^{13}$C NMR (150 MHz, CD$_3$CN): δ=189.3, 183.9, 156.4, 154.1, 143.8, 136.0, 135.4, 130.2, 129.7, 125.3, 124.5, 123.9, 120.3, 114.8, 112.7, 109.9, 100.4, 99.5, 91.2, 88.8, 76.9, 66.0, 65.5, 64.8, 44.2, 21.2 ppm; HRMS (ESI-TOF): calcd for C$_{26}$H$_{19}$N$_2$O$_6^+$ [M+H$^+$]: 455.1238, found 455.1239.

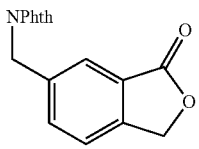

Phthalide 40a

To a suspension of dimethylbenzoic acid (7.5 g, 49.9 mmol, 1.0 equiv), and anhydrous K$_2$CO$_3$ (10.3 g, 74.8 mmol, 1.5 equiv, dried under high vacuum at 110° C. for 16 h prior to use) in DMF (50 mL), MeI (7.79 g, 3.42 mL, 54.9 mmol, 1.1 equiv) was added dropwise over 10 min under vigorous stirring at room temperature. Upon completion of addition, the reaction mixture was stirred for additional 5 h at room temperature, then poured into H$_2$O (100 mL) and extracted with EtOAc (3×100 mL). The combined organic layers were washed with water (3×50 mL) and brine (2×50 mL), dried over MgSO$_4$ and concentrated to yield crude product 37a as a colorless oil. Ester 37a and N-bromosuccinimide (19.1 g, 100 mmol, 2.1 equiv) were dissolved in CCl$_4$ (50 mL), the reaction mixture was heated to 80° C. and benzoyl peroxide (121 mg, 0.5 mmol, 0.01 equiv) was added in one portion. Heating continued for 8 h and the reaction mixture was cooled to ambient temperature, and then stored at 0° C. for 12 h. The reaction mixture was then filtered, and the precipitates were rinsed with CCl$_4$ (0-5° C.). The combined filtrates were then washed with saturated aq. NaHCO$_3$ (25 mL) and brine (25 mL), dried over MgSO$_4$, and concentrated to yield crude product 38a as a yellowish solid. Neat dibromoester 38a was heated to 150° C. in a slight vacuum for 10 h. The reaction mixture was cooled to ambient temperature and a light brown solid was obtained as crude product 39a. Bromophthalide 39a was dissolved in DMF (50 mL), anhydrous K$_2$CO$_3$ (10.3 g, 74.8 mmol, 1.5 equiv, dried under high vacuum at 110° C. for 16 h prior to use) and n-Bu$_4$NI (1.8 g, 5.0 mmol, 0.1 equiv) were added sequentially, followed by phthalimide (8.0 g, 54.9 mmol, 1.1 equiv) in one portion. The reaction mixture was stirred at 40° C. for 4 h, then poured into H$_2$O (100 mL) and extracted with EtOAc (3×100 mL). The combined organic layers were washed with water (3×50 mL) and brine (2×50 mL), dried over MgSO$_4$ and concentrated. Flash column chromatography (silica gel, CH$_2$Cl$_2$:EtOAc 10:1 to 8:1) gave phthalide 40a as a yellowish solid (10.8 g, 36.9 mmol, 74% yield). 40a: R$_f$=0.31 (silica gel, CH$_2$Cl$_2$:EtOAc 8:1); $^1$H NMR (600 MHz, CDCl$_3$): δ=7.93 (s, 1H), 7.87 (dd, J=5.4, 3.1 Hz, 2H), 7.76 (d, J=7.9 Hz, 1H), 7.75 (dd, J=5.5, 3.0 Hz, 2H), 7.47 (d, J=7.8 Hz, 1H), 5.29 (s, 2H), 4.96 (s, 2H) ppm; HRMS (ESI-TOF): calcd for C$_{17}$H$_{12}$NO$_4^+$ [M+H$^+$]: 294.0761, found 294.0765.

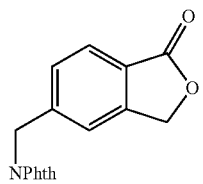

Phthalide 40b

Prepared according to the general procedure described above for the preparation of 40a, from 2,4-dimethylbenzoic acid (1.52 g, 10.1 mmol, 1.0 equiv) to yield phthalide 40b as a yellowish solid (2.08 g, 7.09 mmol, 70% yield). 40b: R$_f$=0.31 (silica gel, CH$_2$Cl$_2$:EtOAc 8:1); $^1$H NMR (400 MHz, CDCl$_3$): δ=7.86 (dd, J=5.4, 3.1 Hz, 2H), 7.85 (d, J=8.0 Hz, 1H), 7.74 (dd, J=5.5, 3.0 Hz, 2H), 7.57 (d, J=7.6 Hz, 1H), 7.51 (s, 1H), 5.44 (s, 2H), 4.87 (s, 2H) ppm; HRMS (ESI-TOF): calcd for C$_{17}$H$_{12}$NO$_4^+$ [M+H$^+$]: 294.0761, found 294.0760.

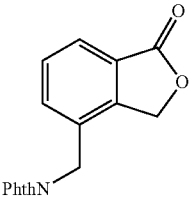

Phthalide 40c

Prepared according to the general procedure described above for the preparation of 40a, from 2,3-dimethylbenzoic acid (2.00 g, 13.3 mmol, 1.0 equiv) to yield phthalide 40c as a yellowish solid (2.15 g, 7.33 mmol, 55% yield). 40c: R$_f$=0.31 (silica gel, CH$_2$Cl$_2$:EtOAc 8:1); $^1$H NMR (400 MHz, CDCl$_3$): δ=7.86 (d, J=7.6, 1H), 7.85 (dd, J=5.4, 3.1 Hz, 2H), 7.80 (d, J=7.6 Hz, 1H), 7.75 (dd, J=5.5, 3.0 Hz, 2H), 7.51 (t, J=7.6 Hz, 1H), 5.54 (s, 2H), 4.85 (s, 2H) ppm; HRMS (ESI-TOF): calcd for C$_{17}$H$_{12}$NO$_{4+}$[M+H$^+$]: 294.0761, found 294.0763.

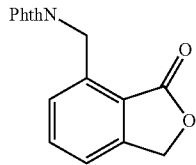

Phthalide 40d

Prepared according to the general procedure described above for the preparation of 40a, from 2,6-dimethylbenzoic acid (2.02 g, 13.5 mmol, 1.0 equiv) to yield phthalide 40d as a yellowish solid (2.53 g, 8.63 mmol, 64% yield). 40d: $R_f$=0.31 (silica gel, $CH_2Cl_2$:EtOAc 8:1); $^1H$ NMR (500 MHz, $CDCl_3$): δ=7.91 (dd, J=5.4, 3.1 Hz, 2H), 7.77 (dd, J=5.5, 3.0 Hz, 2H), 7.56 (t, J=7.7 Hz, 1H), 7.37 (dd, J=7.7, 0.8 Hz, 1H), 7.18 (dd, J=7.7, 0.8 Hz, 1H), 5.48 (s, 2H), 5.33 (s, 2H) ppm; HRMS (ESI-TOF): calcd for $C_{17}H_{12}NO_4^+$ [M+H$^+$]: 294.0761, found 294.0765.

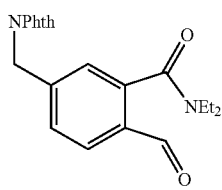

Formylbenzamide 43a

To a stirred suspension of phthalide 40a (10.8 g, 36.9 mmol, 1.0 equiv) in $CCl_4$/benzene (140 mL, 1:1) at ambient temperature, was added N-bromosuccinimide (7.85 g, 44.3 mmol, 1.2 equiv) in one portion. The reaction mixture was heated to reflux, and azobisisobutyronitrile (1.21 g, 7.37 mmol, 0.2 equiv) was then added in one portion. The reaction mixture was vigorously stirred at reflux for another 2 h, then cooled to ambient temperature, and stored at 0° C. for 8 h. The reaction mixture was filtered, and the precipitates were rinsed with $CCl_4$ (0-5° C.). The combined filtrates were then washed with saturated aq. $NaHCO_3$ (25 mL) and brine (25 mL), dried over $Mg_2SO_4$, and concentrated to yield crude 41a as a yellow foam, which was suspended in $H_2O$/THF (140 mL, 1:1). The suspension was stirred at 85° C. for 5 h and cooled to ambient temperature. The reaction mixture was extracted with EtOAc (5×50 mL), and the combined organic layers were dried over $MgSO_4$ and concentrated to yield crude 42a as a yellow hygroscopic solid, which was dried over $P_2O_5$ for a further 8 h. The crude acid 42a was suspended in $SOCl_2$ (40 mL) and the reaction mixture heated at reflux for 2 h. The reaction mixture was concentrated under $N_2$ and the residue was coevaporated with toluene (2×25 mL) to remove all traces of $SOCl_2$. The crude product was dissolved in $CH_2Cl_2$ (35 mL) and the reaction mixture was cooled to 0° C. A solution of diethylamine (5.0 g, 7 mL, 67.7 mmol, 1.8 equiv) in $CH_2Cl_2$ (7 mL) was added dropwise, ice bath was removed and the reaction mixture was stirred at ambient temperature for 2 h. The reaction was quenched with 1N HCl (70 mL), and the reaction mixture was extracted with $CH_2Cl_2$ (2×50 mL). The combined organic layers were washed with brine (50 mL), dried over $MgSO_4$ and concentrated. Flash column chromatography (silica gel, hexanes:EtOAc 3:1 to 2:1) yielded formylbenzamide 43a as a yellowish solid (6.05 g, 16.6 mmol, 45% yield). 43a: $R_f$=0.31 (silica gel, hexanes:EtOAc 2:1); $^1H$ NMR (400 MHz, $CDCl_3$): δ=9.99 (s, 1H), 7.88 (d, J=8.0 Hz, 1H), 7.85 (dd, J=5.4, 3.1 Hz, 2H), 7.73 (dd, J=5.5, 3.0 Hz, 2H), 7.57 (dd, J=8.0, 1.4 Hz, 1H), 7.38 (d, J=1.4 Hz, 1H), 4.89 (s, 2H), 3.58 (q, J=7.1 Hz, 2H), 3.07 (q, J=7.1 Hz, 2H), 1.28 (t, J=7.1 Hz, 3H), 1.00 (t, J=7.1 Hz, 3H) ppm; $^{13}C$ NMR (100 MHz, $CDCl_3$): δ=189.9, 168.2, 167.7, 142.6, 140.0, 134.2, 132.0, 131.8, 130.3, 129.1, 126.7, 123.5, 43.0, 41.0, 39.1, 13.7, 12.6 ppm; HRMS (ESI-TOF): calcd for $C_{21}H_{21}N_2O_4^+$ [M+H$^+$]: 365.1496, found 365.1496.

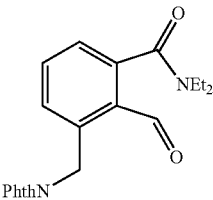

Formylbenzamide 43c

Prepared according to the general procedure described above for the preparation of 43a, from phthalide 40c (2.11 g, 7.21 mmol, 1.0 equiv) to yield formylbenzamide 43c as a yellowish solid (1.05 g, 2.88 mmol, 40% yield). 43c: $R_f$=0.31 (silica gel, hexanes:EtOAc 2:1); $^1H$ NMR (400 MHz, $CDCl_3$): δ=10.36 (s, 1H), 7.91 (dd, J=5.4, 3.1 Hz, 2H), 7.76 (dd, J=5.5, 3.0 Hz, 2H), 7.51 (t, J=7.6 Hz, 1H), 7.27 (d, J=7.6 Hz, 1H), 7.25 (dd, J=7.6, 1.0 Hz, 1H), 5.32 (s, 2H), 3.61 (q, J=7.2 Hz, 2H), 3.14 (q, J=7.2, 2H), 1.30 (t, J=7.2 Hz, 3H), 1.06 (t, J=7.2 Hz, 3H) ppm; HRMS (ESI-TOF): calcd for $C_{21}H_{21}N_2O_4^+$ [M+H$^+$]: 365.1496, found 365.1496.

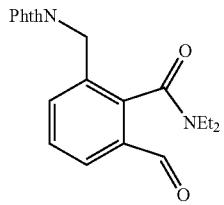

Formylbenzamide 43d

Prepared according to the general procedure described above for the preparation of 43a, from phthalide 40d (2.49 g, 8.49 mmol, 1.0 equiv) to yield formylbenzamide 43d as a yellowish solid (1.30 g, 3.57 mmol, 42% yield). 43d: $R_f$=0.31 (silica gel, hexanes:EtOAc 2:1); H NMR (500 MHz, $CDCl_3$): δ=10.04 (s, 1H), 7.89 (dd, J=5.4, 3.1 Hz, 2H), 7.86 (dd, J=7.5, 1.4 Hz, 1H), 7.76 (dd, J=5.5, 3.0 Hz, 2H), 7.49 (dt, J=7.7, 1.4 Hz, 1H), 7.46 (t, J=7.6 Hz, 1H), 5.09 (d, J=16 Hz, 1H), 4.68 (d, J=16 Hz, 1H), 3.58 (q, J=7.1 Hz, 2H), 3.07 (q, J=7.1 Hz, 2H), 1.28 (t, J=7.1 Hz, 3H), 1.00 (t, J=7.1 Hz, 3H) ppm; $^{13}C$ NMR (100 MHz, $CDCl_3$): δ=189.9, 168.2, 167.7, 142.6, 140.0, 134.2, 132.0, 131.8, 130.3, 129.1, 126.7, 123.5, 43.0, 41.0, 39.1, 13.7, 12.6 ppm; HRMS (ESI-TOF): calcd for $C_{21}H_{21}N_2O_4^+$ [M+H$^+$]: 365.1496, found 365.1496.

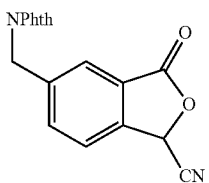

Cyanophthalide 44a

To a stirred solution of formyl-benzamide 43a (1.17 g, 3.22 mmol, 1.0 equiv) in CH$_2$Cl$_2$ (6 mL) at 0° C., was added TMSCN (640 mg, 0.81 mL, 6.44 mmol, 2.0 equiv), and a solution of KCN (5.2 mg, 0.08 mmol, 0.025 equiv) and 18-crown-6 (16 mg, 0.06 mmol, 0.02 equiv) in THF (0.6 mL). The reaction mixture was stirred at the same temperature in a sealed flask for 1.5 h, and for 30 min at ambient temperature. The reaction mixture was then concentrated under N$_2$ and the residue was coevaporated with toluene (2×25 mL) to remove all traces of TMSCN. The resulting brown oil was dissolved in AcOH (3 mL) and stirred for 48 h at room temperature until TLC showed full conversion (hexanes:EtOAc 3:2). The reaction was quenched by careful addition of 1N NaOH (10 mL), and the resulting mixture was partitioned between EtOAc (20 mL) and 1N NaOH (10 mL). The aqueous layer was extracted with EtOAc (3×20 mL), and the combined organic layers were washed with H$_2$O (20 mL) and brine (20 mL), dried over MgSO$_4$ and concentrated. Flash column chromatography (silica gel, hexanes:EtOAc 2:1 to 3:2) gave a yellowish solid, which was recrystallized from EtOAc to yield cyanophthalide 44a as a white solid (902 mg, 2.83 mmol, 88% yield). 44a: R$_f$=0.31 (silica gel, hexanes:EtOAc 3:2); $^1$H NMR (400 MHz, CDCl$_3$): δ=7.99 (s, 1H), 7.91 (d, J=8.0 Hz, 1H), 7.86 (dd, J=5.4, 3.1 Hz, 2H), 7.74 (dd, J=5.5, 3.0 Hz, 2H), 7.67 (d, J=8.0 Hz, 1H), 6.06 (s, 1H), 4.98 (s, 2H) ppm; $^{13}$C NMR (100 MHz, CDCl$_3$): δ=167.7, 167.0, 141.2, 140.6, 136.0, 134.4, 131.7, 126.2, 125.0, 123.6, 123.1, 113.6, 65.5, 40.7 ppm; HRMS (ESI-TOF): calcd for C$_{18}$H$_{11}$N$_2$O$_4$$^+$ [M+H$^+$]: 319.0713, found 319.0715.

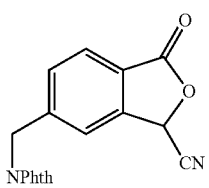

Cyanophthalide 44b

Prepared according to the general procedure described above for the preparation of 44a, from formylbenzamide 43b (605 mg, 1.66 mmol, 1.0 equiv) to yield cyanophthalide 44b as a white solid (450 mg, 1.41 mmol, 85% yield). 44b: R$_f$=0.31 (silica gel, hexanes:EtOAc 3:2); $^1$H NMR (600 MHz, CDCl$_3$): δ=7.94 (d, J=7.9 Hz, 1H), 7.89 (dd, J=5.4, 3.1 Hz, 2H), 7.77 (d, J=7.9 Hz, 1H), 7.76 (dd, J=5.5, 3.1 Hz, 2H), 7.75 (s, 1H), 6.04 (s, 1H), 4.99 (dd, J=15.0, 25.4 Hz, 2H) ppm; $^{13}$C NMR (100 MHz, CDCl$_3$): δ=167.7, 166.9, 144.8, 142.4, 134.5, 132.0, 131.8, 127.0, 124.0, 123.7, 122.8, 113.6, 65.5, 41.1 ppm; HRMS (ESI-TOF): calcd for C$_{18}$H$_{11}$N$_2$O$_4$$^+$ [M+H$^+$]: 319.0713, found 319.0715.

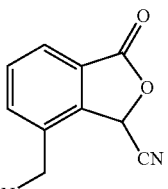

Cyanophthalide 44c

Prepared according to the general procedure described above for the preparation of 44a, from formylbenzamide 43c (992 mg, 2.72 mmol, 1.0 equiv) to yield cyanophthalide 44c as a white solid (650 mg, 2.04 mmol, 75% yield). 44a: R$_f$=0.30 (silica gel, hexanes:EtOAc 3:2); $^1$H NMR (500 MHz, CD$_3$CN): δ=7.88 (d, J=7.7, 1H), 7.87 (dd, J=5.4, 3.1 Hz, 2H), 7.86 (d, J=7.7 Hz, 1H), 7.81 (dd, J=5.5, 3.0 Hz, 2H), 7.70 (t, J=7.7 Hz, 1H), 6.48 (s, 1H), 4.98 (dd, J=15.6, 27.8 Hz, 2H) ppm; $^{13}$C NMR (100 MHz, CDCl$_3$): δ=169.0, 168.7, 141.4, 137.1, 135.4, 133.1, 132.9, 132.7, 126.5, 126.0, 124.2, 115.1, 66.7, 38.0 ppm; HRMS (ESI-TOF): calcd for C$_{18}$H$_{11}$N$_2$O$_4$$^+$ [M+H$^+$]: 319.0713, found 319.0715.

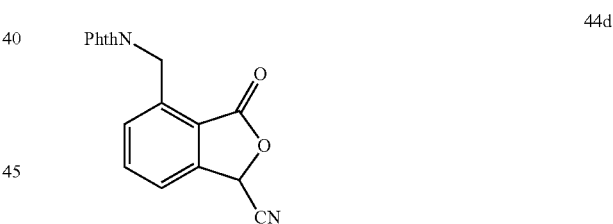

Cyanophthalide 44d

Prepared according to the general procedure described above for the preparation of 44a, from formylbenzamide 43d (1.24 g, 3.41 mmol, 1.0 equiv) to yield cyanophthalide 44d as a white solid (902 mg, 2.83 mmol, 83% yield). 44d: R$_f$=0.30 (silica gel, hexanes:EtOAc 3:2); $^1$H NMR (600 MHz, CDCl$_3$): δ=7.91 (dd, J=5.4, 3.1 Hz, 2H), 7.78 (dd, J=5.5, 3.0 Hz, 2H), 7.72 (t, J=7.7 Hz, 1H), 7.60 (d, J=7.7 Hz, 1H), 7.39 (d, J=7.7 Hz, 1H), 6.10 (s, 1H), 5.43 (dd, J=18.1, 25.7 Hz, 2H) ppm; $^{13}$C NMR (100 MHz, CDCl$_3$): δ=167.8, 167.0, 142.4, 138.4, 135.8, 134.4, 131.9, 129.1, 123.7, 123.6, 121.7, 113.7, 65.5, 36.5 ppm; HRMS (ESI-TOF): calcd for C$_{18}$H$_{11}$N$_2$O$_4$$^+$ [M+H$^+$]: 319.0713, found 319.0715.

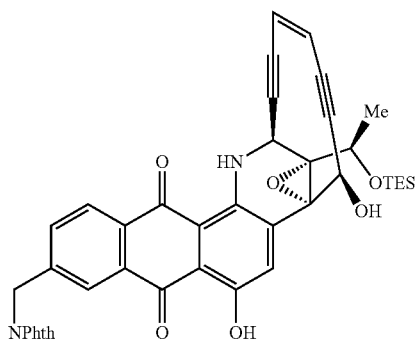

Anthraquinone 46aa

To a solution of cyanophthalide 44a (91 mg, 0.27 mmol, 2.0 equiv) in THF (1.2 mL) at −78° C. was added LiHMDS (1.0 M in THF, 0.43 mL, 0.43 mmol, 3.0 equiv). The resulting mixture was stirred at −78° C. for 20 min, and a pre-cooled solution of quinone aminal 22a (78 mg, 0.14 mmol, 1.0 equiv) in THF (1.4 mL) at −78° C. was added via cannula. After stirring for 5 min at −78° C., the reaction mixture was warmed to ambient temperature and stirred for another 1.5 h during which time the reaction mixture turned dark red and TLC showed full consumption of 22a (8% EtOAc in CH$_2$Cl$_2$). The reaction mixture was then quenched by the addition of pH 6.8 buffer (30 mL) and extracted with EtOAc (3×30 mL). The combined organic extracts were washed with brine (30 mL), dried over MgSO$_4$, and filtered through a short plug of Celite® (washed with EtOAc prior to use). The solids were rinsed with EtOAc, and the combined filtrates were concentrated to yield crude alloc-anthraquinone 45aa as a dark red solid, which was dissolved in degassed THF (2.0 mL) under Ar and cooled to 0° C. To this solution was added Pd(PPh$_3$)$_4$ (32 mg, 10.4 μmol, 0.16 equiv), followed by dropwise addition of morpholine (32 mg, 32 μL, 0.34 mmol, 2.4 equiv). The reaction flask was wrapped with aluminium foil, and the resulting mixture was allowed to stir at 0° C. for 2 h during which time the reaction mixture turned dark purple. The cooling bath was removed and the reaction mixture was stirred at ambient temperature for 20 min, and then quenched by the addition of pH 6.8 buffer (30 mL) and extracted with EtOAc (3×30 mL). The combined organic extracts were washed with H$_2$O (30 mL) and brine (30 mL), dried over MgSO$_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes:EtOAc 2:1 to 1:1] yielded anthraquinone 46aa as a purple solid (92 mg, 0.13 mmol, 90% yield). 46aa: R$_f$=0.58 (silica gel, hexanes:EtOAc 1:1); [α]$_D^{25}$=+2600° (c=0.002, EtOAc); $^1$H NMR (600 MHz, CD$_3$CN): δ=13.11 (s, 1H), 9.97 (d, J=4.0 Hz, 1H), 8.46 (s, 1H), 8.23 (d, J=8.0 Hz, 1H), 8.20 (s, 1H), 7.87 (d, J=1.9 Hz, 2H), 7.81 (d, J=2.2 Hz, 1H), 7.80 (d, J=1.9 Hz, 2H), 5.94 (d, J=10.0 Hz, 1H), 5.87 (d, J=9.8 Hz, 1H), 5.10 (s, 1H), 4.97 (s, 2H), 4.97 (s, 1H), 4.55 (q, J=5.8 Hz, 1H), 4.45 (d, J=3.7 Hz, 1H), 1.38 (d, J=5.8 Hz, 3H), 0.98 (t, J=7.6 Hz, 9H), 0.66 (q, J=7.6 Hz, 6H) ppm; $^{13}$C NMR (150 MHz, CD$_3$CN): δ=188.2, 183.8, 169.0, 156.7, 144.8, 143.5, 136.3, 135.4, 135.1, 134.8, 133.8, 133.0, 130.9, 128.3, 126.1, 124.9, 124.1, 123.8, 114.2, 112.2, 100.2, 99.7, 91.3, 88.4, 77.4, 66.7, 64.9, 64.7, 44.3, 41.8, 22.6, 7.3, 5.6 ppm; HRMS (ESI-TOF): calcd for C$_{41}$H$_{36}$N$_2$O$_8$Si$^+$ [M+H$^+$]: 712.2241, found 712.2243.

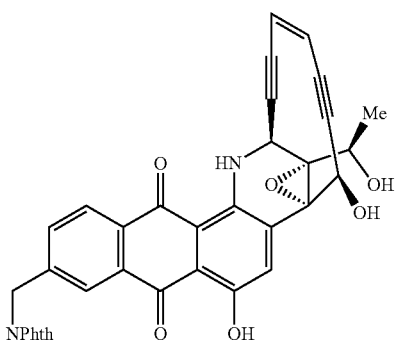

8-Phthalimidomethyl-uncialamycin (47aa)

To a stirred solution of anthraquinone 46aa (92 mg, 0.13 mmol, 1.0 equiv) in degassed THF (15 mL) at room temperature was added a solution of 1:1 3HF.Et$_3$N:THF (5.0 mL). The reaction flask was wrapped with aluminium foil, and the reaction mixture was stirred at room temperature for 1.5 h, then partitioned between EtOAc (50 mL) and saturated aq. NaHCO$_3$ (50 mL). The aqueous layer was extracted with EtOAc (2×25 mL), and the combined organic extracts were washed with brine (25 mL), dried over Na$_2$SO$_4$, and concentrated to ca. 1 mL in volume. Flash column chromatography (deactivated silica gel, hexanes:EtOAc 1:1 to 1:2) yielded phthalimidomethyl-uncialamycin (47aa) as a purple solid (76 mg, 0.13 mmol, 98% yield). 47aa: R$_f$=0.24 [deactivated silica gel (see General Methods), hexanes:EtOAc 1:1]; [α]$_D^{25}$=+26000° (c=0.005, EtOAc) [This value (probably too high), was obtained at the dilution at which the polarimeter exhibited a rotation read-out; at higher concentration the instrument did not provide a read-out due to the insolubility of the compound]; $^1$H NMR (600 MHz, CD$_3$CN): δ=13.10 (s, 1H), 9.99 (d, J=4.1 Hz, 1H), 8.48 (s, 1H), 8.23 (d, J=8.1 Hz, 1H), 8.21 (s, 1H), 7.87 (dd, J=5.4, 3.1 Hz, 2H), 7.82 (d, J=2.2 Hz, 1H), 7.81 (dd, J=5.5, 3.0 Hz, 2H), 5.96 (d, J=9.9 Hz, 1H), 5.88 (d, J=9.9 Hz, 1H), 5.24 (d, J=4.9 Hz, 1H), 5.49 (s, 2H), 4.91 (dd, J=4.4, 1.4 Hz, 1H), 4.44 (d, J=4.9 Hz, 1H), 4.38 (dq, J=5.0, 6.5 Hz, 1H), 3.27 (d, J=4.9 Hz, 1H), 1.38 (d, J=6.5 Hz, 3H) ppm; $^{13}$C NMR (150 MHz, CD$_3$CN): δ=188.2, 183.9, 169.0, 156.7, 144.7, 143.6, 136.2, 135.4, 135.1, 134.8, 133.8, 133.0, 130.9, 128.4, 126.1, 124.5, 124.1, 124.1, 114.3, 112.3, 100.3, 99.1, 91.3, 88.8, 77.0, 65.8, 65.3, 64.7, 44.2, 41.8, 21.2 ppm; HRMS (ESI-TOF): calcd for C$_{35}$H$_{23}$N$_2$O$_8$[M+H$^+$]: 599.1449, found 599.1447.

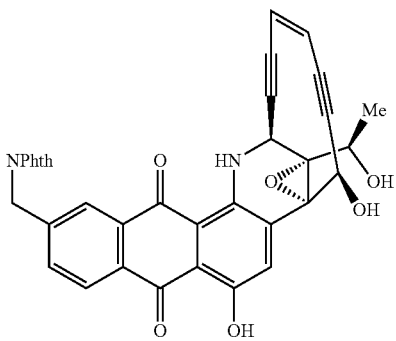

7-Phthalimidomethyl-uncialamycin (47ba)

Prepared according to the general procedure described above for the preparation of 47aa, from cyanophthalide 44b (23 mg, 73 µmol, 3.0 equiv) and quinone aminal 22a (13 mg, 24 µmol, 1.0 equiv) through the intermediate 46ba to yield 7-phthalimido-methyl-uncialamycin (47ba) (11 mg, 18 µmol, 76% yield) as a purple solid. 47ba: $R_f$=0.24 (silica gel, hexanes:EtOAc 1:1); $[\alpha]_D^{25}$=+28000° (c=0.005, EtOAc) [This value (probably too high), was obtained at the dilution at which the polarimeter exhibited a rotation read-out; at higher concentration the instrument did not provide a read-out due to the insolubility of the compound]; $^1$H NMR (600 MHz, CD$_3$CN): δ=13.13 (s, 1H), 9.96 (d, J=4.1 Hz, 1H), 8.49 (s, 1H), 8.20 (s, 1H), 8.19 (d, J=8.1 Hz, 1H), 7.87 (dd, J=5.4, 3.1 Hz, 2H), 7.81 (dd, J=5.5, 3.0 Hz, 2H), 7.77 (d, J=8.1 Hz, 1H), 5.96 (d, J=10.0 Hz, 1H), 5.87 (d, J=10.0 Hz, 1H), 5.24 (d, J=4.5 Hz, 1H), 4.98 (s, 2H), 4.90 (dd, J=4.4, 1.5 Hz, 1H), 4.56 (d, J=4.9 Hz, 1H), 4.38 (dq, J=5.0, 6.5 Hz, 1H), 3.32 (d, J=5.0 Hz, 1H), 1.38 (d, J=6.5 Hz, 3H) ppm; $^{13}$C NMR (150 MHz, CD$_3$CN): δ=188.1, 183.8, 169.0, 156.7, 144.8, 144.7, 136.1, 136.0, 135.4, 133.5, 133.0, 132.9, 131.0, 127.7, 126.8, 124.5, 124.1, 124.1, 114.2, 112.4, 100.4, 99.1, 91.3, 88.8, 77.0, 65.9, 65.3, 64.7, 44.3, 41.9, 21.2 ppm; HRMS (ESI-TOF): calcd for $C_{35}H_{23}N_2O_8^+$ [M+H$^{+}$]: 599.1449, found 599.1449.

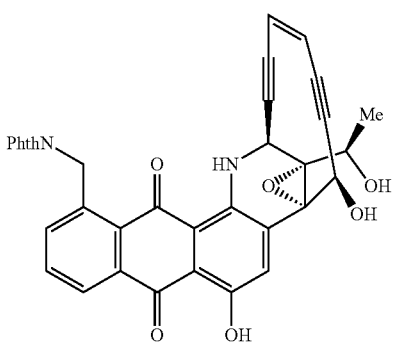

6-Phthalimidomethyl-uncialamycin (47ca)

Prepared according to the general procedure described above for the preparation of 47aa, from cyanophthalide 44c (59 mg, 0.18 mmol, 3.0 equiv) and quinone aminal 22a (33 mg, 61 µmol, 1.0 equiv) through the intermediate 46ca to yield 6-phthalimido-methyl-uncialamycin (47ca) (1 mg, 2 µmol, 3% yield) as a purple solid. 47ca: $R_f$=0.23 (silica gel, hexanes:EtOAc 1:1); $[\alpha]_D^{25}$=+28000° (c=0.005, EtOAc) [This value (probably too high), was obtained at the dilution at which the polarimeter exhibited a rotation read-out; at higher concentration the instrument did not provide a read-out due to the insolubility of the compound]; $^1$H NMR (600 MHz, CD$_3$CN): δ=13.07 (s, 1H), 9.92 (d, J=4.1 Hz, 1H), 8.52 (s, 1H), 8.31 (d, J=7.7 Hz, 1H), 7.92 (dd, J=5.4, 3.1 Hz, 2H), 7.85 (dd, J=5.5, 3.0 Hz, 2H), 7.69 (t, J=7.9 Hz, 1H), 7.57 (d, J=7.9 Hz, 1H), 5.98 (d, J=9.5 Hz, 1H), 5.91 (d, J=9.7 Hz, 1H), 5.51 (d, J=2.9 Hz, 2H), 5.26 (d, J=4.8 Hz, 1H), 4.93 (dd, J=4.2, 1.5 Hz, 1H), 4.58 (d, J=5.1 Hz, 1H), 4.39 (dq, J=5.0, 6.5 Hz, 1H), 3.33 (d, J=4.9 Hz, 1H), 1.40 (d, J=6.5 Hz, 3H) ppm; HRMS (ESI-TOF): calcd for $C_{35}H_{23}N_2O_8^+$ [M+H$^{+}$]: 599.1449, found 599.1444.

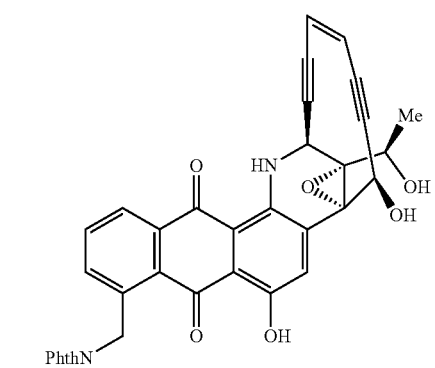

9-Phthalimidomethyl-uncialamycin (47da)

Prepared according to the general procedure described above for the preparation of 47aa, from cyanophthalide 44d (59 mg, 0.18 mmol, 3.0 equiv) and quinone aminal 22a (33 mg, 61 µmol, 1.0 equiv) through the intermediate 46da to yield 9-phthalimido-methyl-uncialamycin (47da) (26 mg, 43 µmol, 71% yield) as a purple solid. 47da: $R_f$=0.25 (silica gel, hexanes:EtOAc 1:1); $[\alpha]_D^{25}$=+30000° (c=0.005, EtOAc) [This value (probably too high), was obtained at the dilution at which the polarimeter exhibited a rotation read-out; at higher concentration the instrument did not provide a read-out due to the insolubility of the compound]; $^1$H NMR (600 MHz, CD$_3$CN): δ=13.19 (s, 1H), 9.95 (d, J=4.0 Hz, 1H), 8.53 (s, 1H), 8.32 (d, J=7.9 Hz, 1H), 7.92 (dd, J=5.4, 3.1 Hz, 2H), 7.86 (dd, J=5.5, 3.0 Hz, 2H), 7.73 (t, J=7.8 Hz, 1H), 7.52 (d, J=7.8 Hz, 1H), 5.98 (d, J=10.0 Hz, 1H), 5.90 (d, J=10.0 Hz, 1H), 5.49 (s, 2H), 5.24 (d, J=5.0 Hz, 1H), 4.93 (dd, J=4.4, 1.4 Hz, 1H), 4.58 (d, J=5.0 Hz, 1H), 4.39 (dq, J=5.0, 6.5 Hz, 1H), 3.33 (d, J=5.0 Hz, 1H), 1.39 (d, J=6.5 Hz, 3H) ppm; $^{13}$C NMR (150 MHz, CD$_3$CN): δ=190.9, 184.0, 169.4, 156.6, 144.3, 140.2, 137.7, 135.7, 135.4, 135.1, 133.2, 131.6, 131.2, 130.7, 127.5, 124.5, 124.1, 124.1, 115.1, 112.1, 100.4, 99.1, 91.2, 88.8, 77.1, 65.9, 65.3, 64.7, 44.3, 42.1, 21.2 ppm; HRMS (ESI-TOF): calcd for $C_{35}H_{23}N_2O_8^+$ [M+H$^{+}$]: 599.1449, found 599.1445.

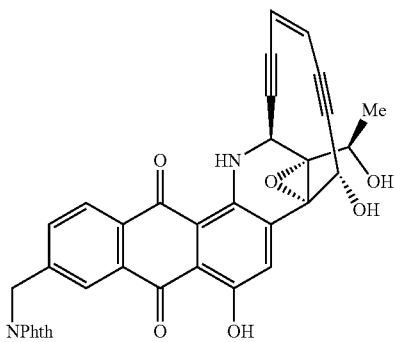

8-Phthalimidomethyl-17-epi-uncialamycin (47ab)

Prepared according to the general procedure described above for the preparation of 47aa, from cyanophthalide 44a (47 mg, 0.15 mmol, 3.0 equiv) and quinone aminal 22b (26 mg, 48 μmol, 1.0 equiv) through the intermediate 46ab to yield 8-phthalimidomethyl-17-epi-uncialamycin (47ab) (21 mg, 35 μmol, 73% yield) as a purple solid. 47ab: $R_f$=0.30 (silica gel, hexanes:EtOAc 1:1); $[\alpha]_D^{25}$=+26000° (c=0.005, EtOAc) [This value (probably too high), was obtained at the dilution at which the polarimeter exhibited a rotation read-out; at higher concentration the instrument did not provide a read-out due to the insolubility of the compound]; IR (film) $\nu_{max}$=3424, 2918, 1770, 1716, 1625, 1597, 1493, 1394, 1329, 1248, 1207 cm$^{-1}$; $^1$H NMR (400 MHz, CD$_3$CN): δ=13.13 (s, 1H), 10.04 (d, J=3.9 Hz, 1H), 8.25 (d, J=8.1 Hz, 1H), 8.21 (d, J=1.2 Hz, 1H), 7.88 (dd, J=5.4, 3.2 Hz, 2H), 7.83 (d, J=1.0 Hz, 1H), 7.81 (dd, J=5.4, 3.2 Hz, 2H), 7.62 (s, 1H), 5.93 (AB system, 2H), 5.86 (d, J=4.2 Hz, 1H), 5.11 (dq, J=5.0, 6.5 Hz, 1H), 4.98 (s, 2H), 4.87 (d, J=4.2 Hz, 1H), 4.11 (d, J=4.4 Hz, 1H), 3.13 (d, J=4.6 Hz, 1H), 1.34 (d, J=6.5 Hz, 3H) ppm; $^{13}$C NMR (150 MHz, CD$_3$CN): δ=188.2, 184.0, 169.0, 156.9, 143.8, 143.7, 137.0, 135.4, 135.1, 134.8, 133.8, 133.0, 128.4, 126.6, 126.6, 126.1, 124.1, 123.9, 114.6, 112.2, 100.5, 99.9, 90.4, 88.8, 76.7, 65.6, 65.3, 60.4, 43.8, 41.7, 20.3 ppm; HRMS (ESI-TOF): calcd for C$_{35}$H$_{23}$N$_2$O$_8$$^+$[M+H$^+$]: 599.1449, found 599.1444.

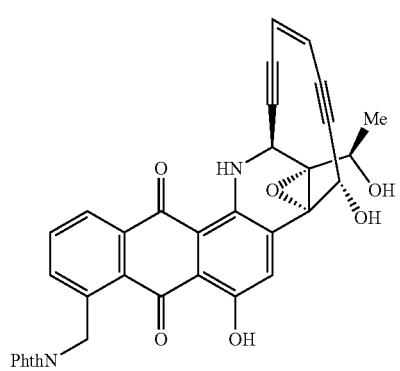

9-Phthalimidomethyl-17-epi-uncialamycin (47db)

Prepared according to the general procedure described above for the preparation of 47aa, from cyanophthalide 44d (23 mg, 73 μmol, 3.0 equiv) and quinone aminal 22b (13 mg, 24 μmol, 1.0 equiv) through intermediate 46db to yield 9-phthalimidomethyl-17-epi-uncialamycin (47db) (10 mg, 17 μmol, 70% yield) as a purple solid. 47db: $R_f$=0.30 (silica gel, hexanes:EtOAc 1:1); $^1$H NMR (500 MHz, CD$_3$CN): δ=13.22 (s, 1H), 10.00 (d, J=4.0 Hz, 1H), 8.32 (dd, J=7.9, 1.2 Hz, 1H), 7.92 (dd, J=5.4, 3.2 Hz, 2H), 7.85 (dd, J=5.4, 3.2 Hz, 2H), 7.72 (t, J=7.9 Hz, 1H), 7.65 (s, 1H), 7.52 (dd, J=7.9, 1.2 Hz, 1H), 5.95 (AB system, 2H), 5.88 (d, J=4.8 Hz, 1H), 5.48 (s, 2H), 5.12 (dq, J=5.0, 6.5 Hz, 1H), 4.89 (dd, J=4.5, 1.3 Hz, 1H), 4.28 (d, J=4.9 Hz, 1H), 3.21 (d, J=4.9 Hz, 1H), 1.35 (d, J=6.5 Hz, 3H) ppm; HRMS (ESI-TOF): calcd for C$_{35}$H$_{23}$N$_2$O$_8$$^+$ [M+H$^+$]: 599.1449, found 599.1444.

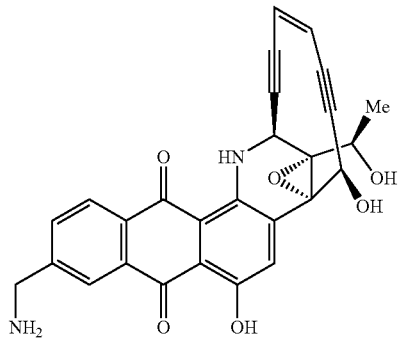

8-Aminomethyl-uncialamycin (48aa)

To a solution of 8-phthalimidomethyl-uncialamycin (47aa) (3.6 mg, 5 μmol, 1.0 equiv) in degassed THF (1.0 mL) at 0° C. was added aq. MeNH$_2$ (40%, 1.0 mL) drop-wise. The reaction flask was wrapped with aluminium foil, and the reaction mixture was stirred at 10° C. for 18 h, then cooled to 0° C. and diluted with degassed THF (10 mL), concentrated at 5° C. under N$_2$ to ca. 1 mL in volume, and diluted with cold degassed THF (0° C., 10 mL). Repeat the same operations 5 times to yield crude 8-aminomethyl-uncialamycin (48aa) as a purple solid, which was immediately used for the next step (CAUTION: 48aa was extremely unstable, both acid- and base-sensitive, slowly decomposed at −78° C., use fresh for best yields). 48aa: R$_f$=0.10 (silica gel, MeOH:EtOAc 1:1); HRMS (ESI-TOF): calcd for C$_{27}$H$_{21}$N$_2$O$_6$$^+$ [M+H$^+$]: 469.1394, found 469.1397.

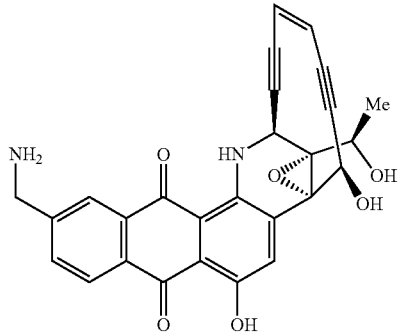

7-Aminomethyl-uncialamycin (48ba)

Prepared according to the general procedure described above for the preparation of 48aa, from 7-phthalimidomethyl-uncialamycin (47ba) (1.5 mg, 2 μmol, 1.0 equiv) to yield crude 7-aminomethyl-uncialamycin (48ba) as a purple solid, which was immediately used for the next step (CAUTION: 48ba was extremely unstable, both acid- and base-sensitive, slowly decomposed at −78° C., use fresh for best yields). 48ba: $R_f$=0.10 (silica gel, MeOH:EtOAc 1:1); HRMS (ESI-TOF): calcd for $C_{27}H_{21}N_2O_6^+$ [M+H]$^+$: 469.1394, found 469.1396.

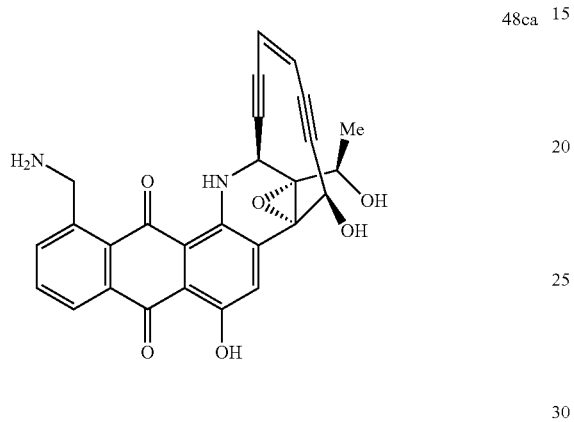

6-Aminomethyl-uncialamycin (48ca)

Prepared according to the general procedure described above for the preparation of 48aa, from 6-phthalimidomethyl-uncialamycin (47ca) (1.0 mg, 1 μmol, 1.0 equiv) to yield crude 6-aminomethyl-uncialamycin (48ca) as a purple solid, which was immediately used for the next step (CAUTION: 48ca was extremely unstable, both acid- and base-sensitive, slowly decomposed at −78° C., use fresh for best yields). 48ca: $R_f$=0.10 (silica gel, MeOH:EtOAc 1:1); HRMS (ESI-TOF): calcd for $C_{27}H_{21}N_2O_6^+$ [M+H]$^+$: 469.1394, found 469.1390.

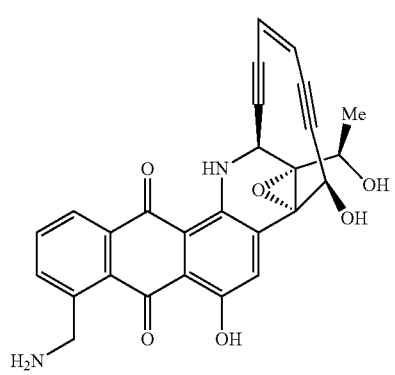

9-Aminomethyl-uncialamycin (48da)

Prepared according to the general procedure described above for the preparation of 48aa, from 9-phthalimidomethyl-uncialamycin (47da) (3.0 mg, 4 μmol, 1.0 equiv) to yield crude 9-aminomethyl-uncialamycin (48da) as a purple solid, which was immediately used for the next step (CAUTION: 48da was extremely unstable, both acid- and base-sensitive, slowly decomposed at −78° C., use fresh for best yields). 48da: $R_f$=0.10 (silica gel, MeOH:EtOAc 1:1); HRMS (ESI-TOF): calcd for $C_{27}H_{21}N_2O_6^+$ [M+H]$^+$: 469.1394, found 469.1399.

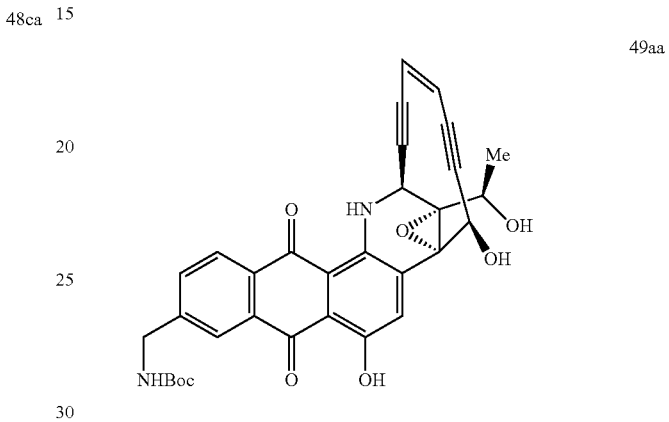

8-tert-Butylcarbamoylmethyl-uncialamycin (49aa)

Crude 8-aminomethyl-uncialamycin (48aa) [prepared according to the general procedure described above from 8-phthalimidomethyl-uncialamycin (47aa) (3.6 mg, 5 μmol, 1.0 equiv)] was suspended in degassed THF (1.0 mL) at 0° C., and saturated aq. NaHCO$_3$ (1.0 mL) was added in one portion, followed by Boc$_2$O (1.3 mg, 6 μmol, 1.2 equiv). The reaction flask was wrapped with aluminium foil, and the reaction mixture was stirred at 0° C. for 1.5 h, then partitioned between EtOAc (5 mL) and pH 6.8 buffer (5 mL). The aqueous layer was extracted with EtOAc (2×25 mL), and the combined organic extracts were washed with brine (5 mL), dried over Na$_2$SO$_4$, and concentrated to ca. 1 mL in volume. Flash column chromatography [deactivated silica gel (see General Methods), hexanes:EtOAc 1:1 to 1:2] yielded 8-tert-butylcarbamoylmethyl-uncialamycin (49aa) (2.7 mg, 4.5 μmol, 95% yield) as a purple solid. 49aa: $R_f$=0.27 (silica gel, hexanes:EtOAc 1:1); $[\alpha]_D^{25}$=+2300° (c=0.002, EtOAc); $^1$H NMR (600 MHz, CD$_3$CN): δ=13.17 (s, 1H), 10.00 (d, J=4.4 Hz, 1H), 8.50 (s, 1H), 8.25 (d, J=8.1 Hz, 1H), 8.15 (s, 1H), 7.75 (dd, J=8.0, 1.8 Hz, 1H), 6.03 (br, 1H), 5.97 (d, J=9.9 Hz, 1H), 5.89 (dt, J=9.9, 1.3 Hz, 1H), 5.24 (d, J=4.4 Hz, 1H), 4.92 (dd, J=4.4, 1.7 Hz, 2H), 4.65 (d, J=5.0 Hz, 1H), 4.39 (d, J=5.7, 1H), 4.38 (dq, J=5.0, 6.5 Hz, 1H), 3.37

(d, J=4.8 Hz, 1H), 1.43 (s, 9H), 1.38 (d, J=6.5 Hz, 3H) ppm; $^{13}$C NMR (150 MHz, CD$_3$CN): δ=188.5, 184.1, 156.6, 147.3, 144.6, 136.1, 134.6, 134.0, 133.7, 128.1, 125.0, 124.5, 124.1, 114.4, 112.4, 100.4, 99.1, 91.2, 88.8, 79.8, 77.0, 65.8, 65.3, 64.7, 44.3, 44.2, 28.5, 21.2 ppm; HRMS (ESI-TOF): calcd for C$_{32}$H$_{29}$N$_2$O$_8^+$ [M+H$^+$]: 569.1918, found 569.1918.

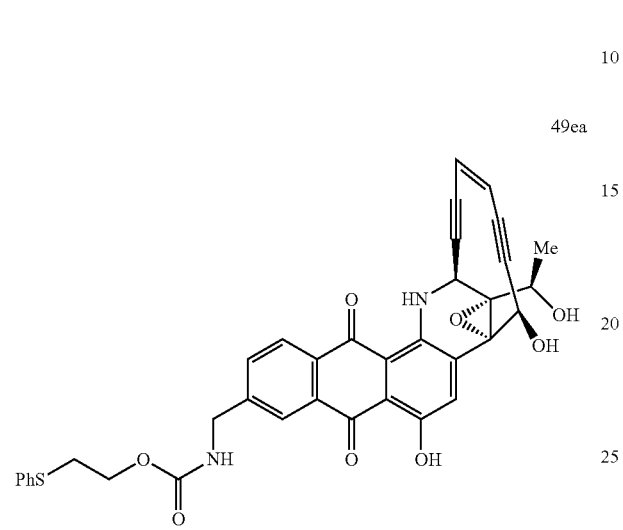

Sulfide 49ea

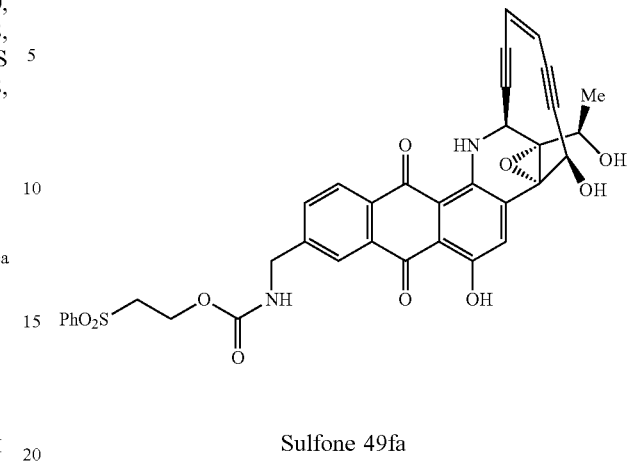

Sulfone 49fa

Crude 8-aminomethyl-uncialamycin (48aa) [prepared according to the general procedure described above from 8-phthalimidomethyl-uncialamycin (47aa, 16 mg, 27 μmol, 1.0 equiv)] was suspended in degassed THF (1.0 mL) at 0° C., and saturated aq. NaHCO$_3$ (1.0 mL) was added in one portion, followed by dropwise addition of a solution of 2-(phenylthio)ethyl chloroformate (14 mg, 66 μmol, 2.5 equiv) in degassed THF (0.5 mL). The reaction flask was wrapped with aluminium foil, and the reaction mixture was stirred at 0° C. for 5 h, then partitioned between EtOAc (5 mL) and pH 6.8 buffer (5 mL). The aqueous layer was extracted with EtOAc (2×25 mL), and the combined organic extracts were washed with brine (5 mL), dried over Na$_2$SO$_4$, and concentrated to ca. 1 mL in volume. Flash column chromatography [deactivated silica gel (see General Methods), hexanes:EtOAc 1:1 to 1:2] to yield sulfide 49ea (9.5 mg, 14 μmol, 55% yield) as a purple solid. 49ea: R$_f$=0.23 (silica gel, hexanes:EtOAc 1:1); $^1$H NMR (600 MHz, CD$_3$CN): δ=13.20 (s, 1H), 10.01 (d, J=4.1 Hz, 1H), 8.50 (s, 1H), 8.23 (d, J=8.0 Hz, 1H), 8.16 (s, 1H), 7.73 (dd, J=8.0, 1.8 Hz, 1H), 6.00 (br, 1H), 5.98 (d, J=10.0 Hz, 1H), 5.89 (dt, J=10.0, 1.3 Hz, 1H), 5.24 (d, J=4.4 Hz, 1H), 4.94 (dd, J=4.4, 1.7 Hz, 2H), 4.65 (d, J=5.0 Hz, 1H), 4.4-4.2 (m, 2H), 4.39 (d, J=5.0, 1H), 4.38 (dq, J=5.0, 6.5 Hz, 1H), 3.35 (d, J=4.8 Hz, 1H), 3.2-3.0 (m, 2H), 1.38 (d, J=6.5 Hz, 3H) ppm; $^{13}$C NMR (150 MHz, CD$_3$CN): δ=188.6, 184.2, 154.4, 147.3, 144.6, 136.1, 135.1, 134.6, 134.0, 133.8, 129.1, 128.6, 128.1, 125.3 125.1, 124.5, 124.1, 114.3, 112.4, 100.3, 99.1, 91.2, 88.8, 77.1, 65.8, 65.3, 64.7, 64.6, 44.3, 44.2, 32.4, 21.2 ppm; HRMS (ESI-TOF): calcd for C$_{36}$H$_{29}$N$_2$O$_8$S$^+$ [M+H$^+$]: 649.1639 found 649.1638.

To a stirred solution of sulfide 49ea (6.5 mg, 10 μmol, 1.0 equiv) in CH$_2$Cl$_2$ (0.5 mL) was added freshly prepared dimethyldi-oxirane (2.0 mL, ~0.1 M in acetone, 0.2 mmol, 20 equiv) at −78° C., the reaction mixture was wrapped in aluminium foil, and allowed to warm to 0° C. After stirring at 0° C. for 20 min, Me$_2$S (84 mg, 0.1 mL, 1.4 mmol, 135 equiv) was added in one portion, and stirring was continued for 20 min at the same temperature. The reaction mixture was then diluted with EtOAc (25 mL), washed with H$_2$O (5 mL) and brine (5 mL), dried over Na$_2$SO$_4$, and concentrated to ca. 1 mL in volume. Flash column chromatography [deactivated silica gel (see General Methods), hexanes:EtOAc 1:1 to 1:3] yielded sulfone 49fa (2.7 mg, 4.5 μmol, 55% yield) as a purple solid. 49fa: R$_f$=0.23 [deactivated silica gel (see General Methods), hexanes:EtOAc 1:3 then EtOAc:MeOH 50:1]; $^1$H NMR (600 MHz, CD$_3$CN): δ=13.19 (s, 1H), 9.99 (d, J=4.1 Hz, 1H), 8.51 (s, 1H), 8.24 (d, J=8.0 Hz, 1H), 8.18 (s, 1H), 7.73 (dd, J=8.0, 1.8 Hz, 1H), 6.05 (br, 1H), 5.97 (d, J=10.0 Hz, 1H), 5.88 (dt, J=10.0, 1.3 Hz, 1H), 5.26 (d, J=4.4 Hz, 1H), 4.97 (dd, J=4.4, 1.7 Hz, 2H), 4.66 (d, J=5.0 Hz, 1H), 4.6-4.3 (m, 2H), 4.39 (d, J=5.1, 1H), 4.38 (dq, J=5.0, 6.5 Hz, 1H), 3.50 (br, 2H), 3.35 (d, J=4.9 Hz, 1H), 1.38 (d, J=6.5 Hz, 3H) ppm; $^{13}$C NMR (150 MHz, CD$_3$CN): δ=188.5, 184.1, 153.7, 147.3, 144.6, 139.1, 136.1, 134.6, 134.1, 134.0, 133.7, 129.5, 128.1, 128.0, 125.0, 124.5, 124.1, 114.4, 112.4, 100.4, 99.1, 91.2, 88.8, 77.0, 65.8, 65.3, 64.7, 59.4, 55.2, 44.3, 44.2, 21.2 ppm; HRMS (ESI-TOF): calcd for C$_{36}$H$_{29}$N$_2$O$_{10}$S$^+$ [M+H$^+$]: 681.1537, found 681.1532.

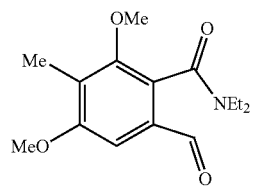

Formylbenzamide 52

To a stirred solution of methyl 2,4-dihydroxy-3-methylbenzoate (0.93 g, 5.10 mmol) in DMF (10 mL) was added anhydrous K$_2$CO$_3$ (5.64 g, 40.8 mmol, 8.0 equiv, dried under high vacuum at 110° C. for 16 h prior to use) and methyl iodide (925 µL, 2.90 g, 20.4 mmol, 4.0 equiv) at ambient temperature under N₂. After being stirred at 50° C. for 9 h, the reaction mixture was filtered through a short pad of Celite®. The filtrate was diluted with EtOAc (25 mL) and acidified with 3N HCl (20 mL). The organic layer was separated, and the aqueous layer was extracted with EtOAc (3×25 mL). The combined organic layers were washed with saturated aq. NaHCO₃ (25 mL), and brine (3×25 mL), dried over MgSO₄, and concentrated to afford methyl ether 50 (1.05 g, 5.01 mmol, 98% yield) as a colorless oil. Trimethylaluminum (2.0 M solution in hexanes, 5.0 mL, 10.0 mmol, 2.0 equiv) was added to an ice-cooled solution of diethylamine (2.0 mL, 1.46 g, 20.0 mmol, 4.0 equiv) in benzene (3.0 mL). After 10 min, the cooling bath was removed and the reaction flask was allowed to warm to ambient temperature. A solution of methyl ether 50 (vide supra) in 2.0 mL benzene was added dropwise to the reaction mixture over 5 min. The reaction mixture was then heated at reflux in an oil bath at 120° C. (CAUTION: gas evolution). After 7 h, the heating bath was removed and the reaction flask was allowed to cool to ambient temperature. The reaction mixture was poured carefully into a mixture of ice water (25 mL) and conc. HCl (0.5 mL). The layers were separated, and the aqueous layer was extracted with EtOAc (3×25 L). The combined organic layers were washed with H₂O (25 mL), and brine (25 mL), dried over MgSO₄, and concentrated. Flash column chromatography (silica gel, hexanes:EtOAc 3:1 to 1:1) gave benzamide 51 as a yellowish oil (2.14 g, 8.5 mmol, 85% yield). To a stirred solution of benzamide 51 in THF (60 mL) at −78° C., was added N,N,N',N'-tetramethylethylenediamine (2.54 mL, 1.98 g, 17.0 mmol, 2.0 equiv), followed by dropwise addition of tert-BuLi (1.7 M solution in pentane, 10.0 mL, 17.0 mmol, 2.0 equiv) at −78° C. After 50 min, DMF (7.85 mL, 102 mmol, 12 equiv) was added, and after further 50 min, the cooling bath was removed and the mixture was allowed to warm to ambient temperature over 2 h. The reaction mixture was diluted with H₂O (25 mL), and after 20 min of stirring, the diluted solution was partially concentrated to remove the volatile organic solvents. To the aqueous residue was added EtOAc (50 mL), and the two layers were separated. The aqueous layer was extracted with EtOAc (50 mL). The combined organic layers were washed with H₂O (25 mL) and brine (3×25 mL), dried over MgSO₄, and concentrated. Flash column chromatography (silica gel, hexanes:EtOAc 2:1 to 1:1) gave formylbenzamide 52 as a pale yellow solid (2.37 g, 8.5 mmol, 99% yield). 52: $R_f$=0.31 (silica gel, hexanes:EtOAc 1:1); $^1$H NMR (500 MHz, CDCl₃): δ=9.93 (s, 1H), 7.20 (s, 1H), 3.90 (s, 3H), 3.80 (s, 3H), 3.73 (dq, J=7.1, 13.7 Hz, 1H), 3.52 (dq, J=7.1, 13.7 Hz, 1H), 3.03 (ddq, J=7.2, 14.4, 14.4, Hz, 2H), 2.21 (s, 3H), 1.29 (t, J=7.1 Hz, 3H), 1.00 (t, J=7.2 Hz, 3H) ppm; $^{13}$C NMR (125 MHz, CDCl₃): δ=189.9, 166.2, 159.0, 155.1, 131.3, 128.1, 120.2, 104.3, 112.3, 62.0, 55.9, 43.2, 39.2, 13.8, 12.7, 9.7 ppm; HRMS (ESI-TOF): calcd for $C_{15}H_{22}NO_4^+$ [M+H⁺]: 280.1543, found 280.1540.

Cyanophthalide 55

To a stirred solution of formylbenzamide 52 (2.37 g, 8.5 mmol, 1.0 equiv.) in CCl₄ (8 mL) was added N-bromosuccinimide (1.95 g, 10.2 mmol, 1.2 equiv) at ambient temperature under N₂, the reaction mixture was heated to 80° C. and benzoyl peroxide (121 mg, 0.5 mmol, 0.06 equiv) was added in one portion. Heating continued for 2 h and the reaction mixture was allowed to cool to ambient temperature, washed with saturated aq. NaHCO₃ (25 mL) and brine (25 mL), dried over MgSO₄ and concentrated to give crude benzylbromide 53 as a light brown solid. Benzylbromide 53 was then dissolved in DMF (7.5 mL), K₂CO₃ (1.75 g, 12.8 mmol, 1.5 equiv) and n-Bu₄NI (0.31 g, 0.85 mmol, 0.1 equiv) were added sequentially, followed by phthalimide (1.4 g, 9.4 mmol, 1.1 equiv) in one portion. The reaction mixture was stirred at 40° C. for 2 h, then poured into H₂O (25 mL) and extracted with EtOAc (3×25 mL). The combined organic layers were washed with water (3×25 mL) and brine (2×25 mL), dried over MgSO₄ and concentrated. Flash column chromatography (silica gel, hexanes:EtOAc 2:1 to 1:2) gave phthalimide 54 as a yellowish solid (2.16 g, 5.1 mmol, 60% yield for 2 steps). To a stirred solution of phthalimide 54 in CH₂Cl₂ (10 mL) at 0° C., was added TMSCN (1.01 g, 1.28 mL, 10.2 mmol, 2.0 equiv), and a solution of KCN (8.2 mg, 0.13 mmol, 0.025 equiv) and 18-crown-6 (25 mg, 0.09 mmol, 0.02 equiv) in THF (1.0 mL). The reaction mixture was stirred at the same temperature in a sealed flask for 1.5 h, and for 30 min at ambient temperature. The reaction mixture was then concentrated under N₂ and the residue was coevaporated with toluene (2×25 mL) to remove all traces of TMSCN. The resulting brown oil was dissolved in AcOH (5 mL) and stirred for 80 h at room temperature until TLC showed full conversion (hexames:EtOAc 1:1). The reaction was quenched by careful addition of 1N NaOH (15 mL), and the resulting mixture was partitioned between EtOAc (30 mL) and 1N NaOH (15 mL). The aqueous layer was extracted with EtOAc (3×30 mL), and the combined organic layers were washed with H₂O (30 mL) and brine (30 mL), dried over MgSO₄ and concentrated. Flash column chromatography (silica gel, hexanes:EtOAc 3:2 to 1:1) gave a yellowish solid, which was recrystallized from EtOAc to yield cyanophthalide 55 as a yellowish solid. (1.36 g, 3.6 mmol, 70% yield). 52: $R_f$=0.35 (silica gel, hexanes:EtOAc 1:1); $^1$H NMR (500 MHz, CDCl₃): δ=7.81 (dd, J=5.5, 3.0 Hz, 2H), 7.71 (dd, J=5.5, 3.0 Hz, 2H), 6.81 (s, 1H), 5.93 (s, 1H), 4.97 (s, 2H), 4.23 (s, 3H), 3.94 (s, 3H) ppm; $^{13}$C NMR (100 MHz, CDCl₃): δ=167.7, 165.3, 165.0, 159.4, 145.4, 134.0, 131.9, 123.2, 119.7, 114.0, 107.7, 99.4, 64.9, 63.2, 56.8, 31.4 ppm; HRMS (ESI-TOF): calcd for $C_{20}H_{15}N_2O_6^+$ [M+H⁺]: 379.0925, found 379.0926.

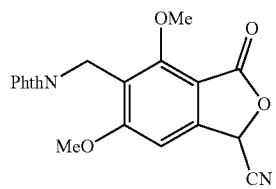

55

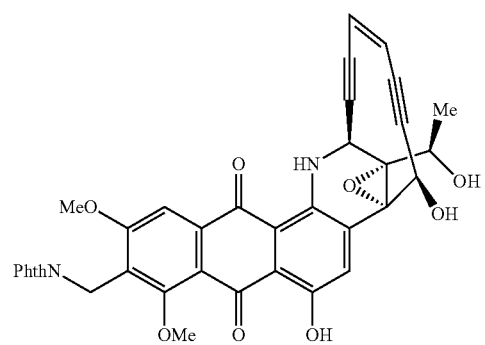

58a

8-Phthalimidomethyl-7,9-dimethoxy-uncialamycin (58a)

To a stirred solution of cyanophthalide 55 (72 mg, 0.19 mmol, 3.0 equiv) in THF (0.8 mL) at −78° C. was added LiHMDS (1.0 M in THF, 0.25 mL, 0.25 mmol, 4.0 equiv). The resulting mixture was stirred at −78° C. for 20 min, and a pre-cooled solution of quinone aminal 22a (34 mg, 63 μmol, 1.0 equiv) in THF (0.8 mL) at −78° C. was added via cannula. After stirring for 5 min at −78° C., the reaction mixture was allowed to warm to ambient temperature and stirred for another 90 min during which time the reaction mixture turned dark red. The reaction mixture was then quenched with pH 6.8 buffer (30 mL) and extracted with EtOAc (3×30 mL). The combined organic extracts were washed with brine (30 mL), dried over $MgSO_4$, and filtered through a short plug of Celite® (washed with EtOAc prior to use). The solids were rinsed with EtOAc, and the combined filtrates were concentrated to yield crude alloc-anthraquinone 56a as a dark red solid, which was dissolved in degassed THF (1.5 mL) under Ar and cooled to 0° C. To this solution was added $Pd(PPh_3)_4$ (4 mg, 1.3 μmol, 0.2 equiv), followed by dropwise addition of morpholine (7 mg, 7 μL, 76 μmol, 1.2 equiv), the reaction flask was wrapped with aluminium foil, and the resulting mixture was allowed to stir at 0° C. for 2 h during which time it turned purple. The cooling bath was removed and the reaction mixture was stirred at ambient temperature for 20 min, and then quenched by the addition of pH 6.8 buffer (10 mL) and extracted with EtOAc (3×10 mL). The combined organic extracts were washed with $H_2O$ (10 mL) and brine (10 mL), dried over $MgSO_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes:EtOAc 1:1 to 1:2] yielded crude anthraquinone 57a as a purple solid. To a solution of anthraquinone 57a in degassed THF (1.5 mL) at room temperature was added a solution of 1:1 $3HF.Et_3N$:THF (0.5 mL). The reaction flask was wrapped with aluminium foil, and the reaction mixture was stirred at room temperature for 1.5 h, then partitioned between EtOAc (10 mL) and saturated aq. $NaHCO_3$ (10 mL). The organic layer was washed with brine (10 mL), dried over $Na_2SO_4$, and concentrated to ca. 1 mL in volume. Flash column chromatography [deactivated silica gel (see General Methods), hexanes:EtOAc 1:1 to 1:3] yielded 8-phthalimidomethyl-7,9-dimethoxy-uncialamycin (58a) (5 mg, 7.6 μmol, 12% yield) as a purple solid. 58a: $R_f$=0.42 (silica gel, hexanes:EtOAc 1:2); $^1$H NMR (600 MHz, $CD_3CN$): δ=13.58 (s, 1H), 9.88 (d, J=4.2 Hz, 1H), 8.47 (s, 1H), 7.80 (dd, J=5.4, 3.1 Hz, 2H), 7.77 (dd, J=5.5, 3.0 Hz, 2H), 7.67 (s, 1H), 5.96 (d, J=10.0 Hz, 1H), 5.88 (d, J=9.9 Hz, 1H), 5.23 (d, J=4.9 Hz, 1H), 4.97 (s, 2H), 4.91 (dd, J=4.3, 1.4 Hz, 1H), 4.54 (d, J=5.0 Hz, 1H), 4.37 (dq, J=5.0, 6.5 Hz, 1H), 3.93 (s, 3H), 3.92 (s, 3H), 3.30 (d, J=4.9 Hz, 1H), 1.38 (d, J=6.3 Hz, 3H) ppm; $^{13}$C NMR (150 MHz, $CD_3CN$): δ=187.1, 183.4, 168.7, 164.3, 162.2, 156.3, 144.3, 139.0, 135.1, 134.6, 133.0, 131.5, 130.7, 125.2, 124.5, 124.1, 123.8, 119.6, 114.9, 112.3, 100.4, 99.1, 91.2, 88.8, 77.0, 65.9, 65.3, 64.8, 62.7, 57.2, 56.0, 44.3, 21.2 ppm; HRMS (ESI-TOF): calcd for $C_{37}H_{27}N_2O_{10}^+$ [M+H$^+$]: 659.1660, found 659.1664.

8-Phthalimidomethyl-7,9-dimethoxy-17-epi-uncialamycin (58b)

Prepared according to the general procedure described above for the preparation of 58a, from cyanophthalide 55 (30 mg, 78 μmol, 3.0 equiv) and quinone aminal 22b (14 mg, 26 μmol, 1.0 equiv) through intermediate 57b to yield 8-phthalimidomethyl-7,9-dimethoxy-17-epi-uncialamycin (58b) (2 mg, 44 μmol, 12% yield) as a purple solid. 58b: $R_f$=0.52 (silica gel, hexanes:EtOAc 1:2); $^1$H NMR (500 MHz, $CD_3CN$): δ=13.63 (s, 1H), 9.93 (d, J=4.0 Hz, 1H), 7.80 (m, 2H), 7.77 (m, 2H), 7.67 (s, 1H), 7.59 (s, 1H), 5.93 (AB system, 2H), 5.85 (d, J=4.9 Hz, 1H), 5.10 (dq, J=5.0, 6.5 Hz, 1H), 4.97 (s, 2H), 4.87 (dd, J=4.6, 1.4 Hz, 1H), 4.27 (d, J=5.0 Hz, 1H), 3.19 (d, J=4.8 Hz, 1H), 1.34 (d, J=6.5 Hz, 3H) ppm; HRMS (ESI-TOF): calcd for $C_{37}H_{27}N_2O_{10}^+$ [M+H$^+$]: 659.1660, found 659.1663.

Formylbenzamide 60

To a stirred solution of 6,7-dimethyl-2-naphthoic acid (2.46 g, 12.3 mmol) was suspended in $SOCl_2$ (15 mL) and the reaction mixture was heated at reflux for 2 h. The reaction mixture was then cooled to ambient temperature and concentrated under $N_2$ and the residue was coevaporated with toluene (2×25 mL) to remove all traces of $SOCl_2$. The crude product was dissolved in $CH_2Cl_2$ (2 mL) and the reaction mixture was cooled to 0° C. A solution of diethylamine (1.62 g, 2.29 mL, 22.1 mmol, 1.8 equiv) in $CH_2Cl_2$ (2 mL) was added dropwise. Upon completion of addition, the ice bath was removed and the reaction mixture was stirred at ambient temperature for 2 h. The reaction was quenched with 1N HCl (25 mL), and the aqueous layer was extracted with $CH_2Cl_2$ (2×20 mL). The combined organic layers were washed with brine (20 mL), dried over $MgSO_4$ and concentrated to afford benzamide 59 (3.11 g, 12.2 mmol, 99% yield) as a yellow solid. To a stirred solution of benzamide 59 in THF (75 mL) at −78° C., was added N,N,N',N'-tetramethylethylenediamine (3.64 mL, 2.83 g, 24.4 mmol, 2.0 equiv), followed by dropwise addition of tert-BuLi (1.7 M solution in pentane, 14.3 mL, 24.4 mmol, 2.0 equiv) at −78° C. After 50 min, DMF (11.24 mL, 146 mmol, 12 equiv) was added, and after further 50 min of stirring, the cooling bath was removed and the reaction flask was allowed to warm to ambient temperature. After 2 h, the reaction mixture was diluted with $H_2O$ (25 mL). After 20 min of further stirring, the diluted solution was partially concentrated to remove the volatile organic solvents. To the resulting aqueous residue was added EtOAc (50 mL), and the two layers were separated. The aqueous layer was extracted with EtOAc (50 mL), and the combined organic layers were washed with $H_2O$ (25 mL) and brine (3×25 mL), dried over $MgSO_4$, and concentrated. Flash column chromatography (silica gel, hexanes:EtOAc 2:1 to 1:1) gave formylbenzamide 60 as a pale yellow solid (1.07 g, 3.78 mmol, 31% yield). 52: $R_f$=0.31 (silica gel, hexanes:EtOAc 1:1); $^1$H NMR (500 MHz, $CDCl_3$): S=10.13 (s, 1H), 8.65 (s, 1H), 8.56 (s, 1H), 7.41 (s, 1H), 7.20 (s, 1H), 3.83 (dq, J=7.1, 13.7 Hz, 1H), 3.55 (dq, J=7.1, 13.7 Hz, 1H), 3.03 (ddq, J=7.2, 14.4, 14.4, Hz, 2H), 2.21 (s, 3H), 2.20 (s, 3H), 1.25 (t, J=7.1 Hz, 3H), 0.98 (t, J=7.2 Hz, 3H) ppm; $^{13}$C NMR (125 MHz, $CDCl_3$): δ=190.0, 160.2, 138.8, 138.4, 133.1, 132.9, 132.3, 132.1, 132.0, 128.9, 128.6, 128.5, 120.2, 43.2, 39.2, 13.8, 12.7, 9.7 ppm; HRMS (ESI-TOF): calcd for $C_{18}H_{22}NO_2^+$ [M+H$^+$]: 284.1645, found 284.1640.

35 µmol, 0.025 equiv) and 18-crown-6 (6.8 mg, 25 µmol, 0.02 equiv) in THF (0.3 mL). The reaction mixture was stirred at the same temperature in a sealed flask for 1.5 h, and for 30 min at ambient temperature. The reaction mixture was then concentrated under $N_2$ and the residue was coevaporated with toluene (2×10 mL) to remove all traces of TMSCN. The resulting brown oil was dissolved in AcOH (1.5 mL) and stirred for 80 h at room temperature until TLC showed full conversion (hexanes:EtOAc 1:1). The reaction was quenched by careful addition of 1N NaOH (5 mL), and the resulting mixture was partitioned between EtOAc (10 mL) and 1N NaOH (5 mL). The aqueous layer was extracted with EtOAc (3×10 mL), and the combined organic layers were washed with $H_2O$ (10 mL) and brine (10 mL), dried over $MgSO_4$ and concentrated. Flash column chromatography (silica gel, $CH_2Cl_2$:EtOAc 30:1 to 20:1) gave a mixture of cyanophthalide 63a/63b as a yellowish solid. (ca. 1:1 by $^1$H NMR, 375 mg, 0.98 mmol, 70% yield). 63a: $R_f$=0.35 (silica gel, hexanes:EtOAc 1:1); 63b: $R_f$=0.33 (silica gel, hexanes:EtOAc 1:1); $^1$H NMR (500 MHz, $CDCl_3$): δ=8.41 (s, 1H), 8.37 (s, 1H), 7.81 (m, 4H), 7.71 (m, 4H), 7.61 (s, 1H), 7.59 (s, 1H), 7.56 (s, 1H), 7.55 (s, 1H), 7.49 (s, 1H), 7.47 (s, 1H), 6.04 (b, 2H), 5.17 (s, 2H), 5.15 (s, 2H), 2.27 (s, 3H), 2.24 (s, 3H) ppm; HRMS (ESI-TOF): calcd for $C_{23}H_{15}N_2O_4^+$ [M+H$^+$]: 383.1026, found 383.1026.

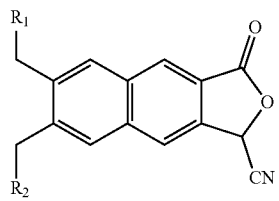

$R_1$ = PhthN, $R_2$ = H 63a
$R_1$ = H, $R_2$ = PhthN 63b

Cyanophthalide 63a/63b

To a stirred solution of formylbenzamide 60 (1.07 g, 3.78 mmol, 1.0 equiv.) in $CCl_4$ (4 mL) was added N-bromosuccinimide (866 mg, 4.53 mmol, 1.2 equiv) at ambient temperature under $N_2$, the reaction mixture was heated to 80° C. and benzoyl peroxide (54 mg, 0.222 mmol, 0.06 equiv) was added in one portion. Heating continued for 2 h and the reaction mixture was cooled to ambient temperature, washed with saturated aq. $NaHCO_3$ (10 mL) and brine (10 mL), dried over $MgSO_4$ and concentrated to give crude mixture of benzylbromide 61a/61b (ca. 1:1 by $^1$H NMR) as a light brown solid. Benzylbromide 61a/61b (ca. 1:1 by $^1$H NMR) was then dissolved in DMF (3.5 mL), $K_2CO_3$ (777 mg, 5.69 mmol, 1.5 equiv) and n-$Bu_4$NI (138 mg, 0.378 mmol, 0.1 equiv) were added sequentially, followed by phthalimide (622 mg, 4.18 mmol, 1.1 equiv) in one portion. The reaction mixture was stirred at 40° C. for 2 h, then poured into $H_2O$ (10 mL) and extracted with EtOAc (3×10 mL). The combined organic layers were washed with water (3×10 mL) and brine (2×10 mL), dried over $MgSO_4$ and concentrated. Flash column chromatography (silica gel, hexanes:EtOAc 2:1 to 1:2) gave a mixture of phthalimide 62a/62b as a yellowish solid (ca. 1:1 by $^1$H NMR, 599 mg, 1.40 mmol, 37% yield for 2 steps). To a stirred solution of phthalimide 62a/62b in $CH_2Cl_2$ (3 mL) at 0° C., was added TMSCN (277 mg, 0.35 mL, 2.80 mmol, 2.0 equiv), and a solution of KCN (2.2 mg,

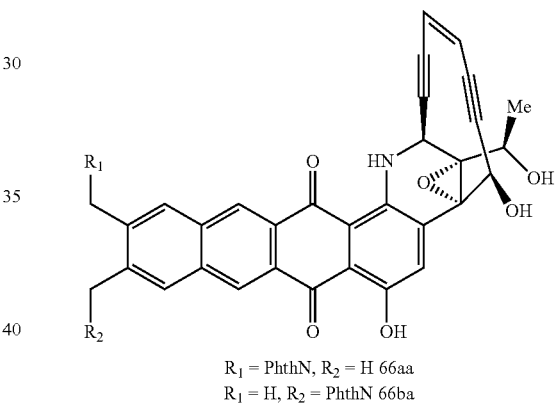

$R_1$ = PhthN, $R_2$ = H 66aa
$R_1$ = H, $R_2$ = PhthN 66ba

Phthalimidomethylbenzo-uncialamycin 66aa/66ba

To a solution of cyanophthalide 63a/63b (ca. 1:1 by $^1$H NMR, 73 mg, 0.19 mmol, 3.0 equiv) in THF (0.8 mL) at −78° C. was added LiHMDS (1.0 M in THF, 0.25 mL, 0.25 mmol, 4.0 equiv). The resulting mixture was stirred at −78° C. for 20 min, and a pre-cooled solution of quinone aminal 22a (34 mg, 63 µmol, 1.0 equiv) in THF (0.8 mL) at −78° C. was added via cannula. After stirring for 5 min at −78° C., the reaction mixture was warmed to ambient temperature and stirred for another 90 min during which time the reaction mixture turned dark red. The reaction mixture was then quenched by the addition of pH 6.8 buffer (30 mL) and extracted with EtOAc (3×30 mL). The combined organic extracts were washed with brine (30 mL), dried over $MgSO_4$, and filtered through a short plug of Celite® (washed with EtOAc prior to use). The solids were rinsed with EtOAc, and the combined filtrates were concentrated to yield crude mixture of alloc-anthraquinone 64aa/64ba (ca. 1:1 by $^1$H NMR) as a dark red solid, which was dissolved in degassed THF (1.5 mL) under Ar and cooled to 0° C. To this solution was added Pd(PPh$_3$)$_4$ (4 mg, 1.3 µmol, 0.2 equiv), followed by dropwise addition of morpholine (7 mg, 7 µL, 76 µmol, 1.2 equiv), the reaction flask was wrapped with aluminium foil, and the resulting mixture was allowed to stir at 0° C. for 2 h during which time it turned purple. The cooling bath was removed and the reaction mixture was stirred at ambient temperature for 20 min, and then quenched by the addition of pH 6.8 buffer (10 mL) and extracted with EtOAc (3×10 mL). The combined organic extracts were washed with H$_2$O (10 mL) and brine (10 mL), dried over MgSO$_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes:EtOAc 1:1 to 1:2] yielded crude mixture of anthraquinone 65aa/66ba (ca. 1:1 by $^1$H NMR) as a purple solid. To a solution of anthraquinone 65aa/66ba in degassed THF (1.5 mL) at room temperature was added a solution of 1:1 3HF.Et$_3$N:THF (0.5 mL). The reaction flask was wrapped with aluminium foil, and the reaction mixture was stirred at room temperature for 1.5 h, then partitioned between EtOAc (10 mL) and saturated aq. NaHCO$_3$ (10 mL). The organic layer was washed with brine (10 mL), dried over Na$_2$SO$_4$, and concentrated to ca. 1 mL in volume. Flash column chromatography [deactivated silica gel (see General Methods), hexanes:EtOAc 1:1 to 1:3] yielded a 1:1 mixture of phthalimido-methylbenzo-uncialamycin 66aa/66ba (ca. 1:1 by $^1$H NMR, 12 mg, 17.7 µmol, 28% yield) as a purple solid. 66aa/66ba: R$_f$=0.42 (silica gel, hexanes:EtOAc 1:2); $^1$H NMR (600 MHz, CD$_3$CN): δ=13.49 (s, 2H), 9.91 (d, J=4.1 Hz, 1H), 9.88 (d, J=4.2 Hz, 1H), 8.47 (s, 1H), 8.31 (s, 1H), 7.80 (m, 4H), 7.76 (m, 4H), 7.67 (s, 1H), 7.65 (s, 1H), 7.43 (s, 1H), 7.41 (s, 1H), 5.96 (d, J=10.0 Hz, 2H), 5.89 (d, J=9.9 Hz, 2H), 5.25 (d, J=5.0 Hz, 1H), 5.23 (d, J=4.9 Hz, 1H), 5.11 (s, 2H), 5.07 (s, 2H), 4.91 (dd, J=4.4, 1.4 Hz, 1H), 4.89 (dd, J=4.5, 1.4 Hz, 1H), 4.53 (d, J=5.0 Hz, 1H), 4.51 (d, J=5.0 Hz, 1H), 4.37 (dq, J=5.0, 6.5 Hz, 1H), 4.35 (dq, J=5.0, 6.5 Hz, 1H), 3.30 (d, J=4.9 Hz, 1H), 2.11 (s, 3H), 2.09 (s, 3H), 1.38 (d, J=6.5 Hz, 3H), 1.38 (d, J=6.5 Hz, 3H) ppm; HRMS (ESI-TOF): calcd for C$_{40}$H$_{27}$N$_2$O$_8^+$ [M+H$^+$]: 663.1762, found 663.1764.

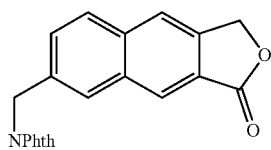

Phthalide 72

To a stirred solution of 2,7-dihydroxyl-2-naphthoic acid (7.50 g, 36.7 mmol, 1.0 equiv) in MeOH (50 mL), was added conc. H$_2$SO$_4$ (1.0 mL) in one portion at room temperature, and the reaction mixture was heated at reflux for 12 h. Upon cooling, the ester 67, which separated as needles, was collected on a filter. The filtrate was concentrated to obtain a second crop of crystals. The two crops were combined, dissolved in ether, and washed with 5% aq.NaHCO$_3$ and H$_2$O. The organic layer was dried over MgSO$_4$, concentrated to dryness and the crude product was recrystallized from methanol to yield ester 67 as a white solid (7.85 g, 36.0 mmol, 98% yield). A solution of N-phenyltrifluoromethanesulphonimide (39.8 g, 111 mmol, 3.0 equiv) in CH$_2$Cl$_2$ (125 mL) was added dropwise to a solution of ester 67 (7.85 g, 36.0 mmol, 1.0 equiv), N-diisopropylethylamine (25.9 mL, 148 mmol, 4.1 equiv), and DMAP (452 mg, 3.7 mmol, 0.10 equiv) in CH$_2$Cl$_2$ (100 mL) at 0° C. Upon completion of addition, the ice-bath was removed and the reaction mixture was stirred for additional 1.5 h at room temperature, then quenched with saturated aq. NaHCO$_3$ (10 mL), and diluted with H$_2$O (40 mL). The aqueous layer was extracted with CH$_2$Cl$_2$ (3×30 mL), and the combined organic layers were dried over MgSO$_4$ and concentrated. Flash column chromatography [deactivated silica gel (see General Methods), hexanes:EtOAc 10:1] yielded bis-triflate 68 as a white solid (14.72 g, 30.5 mmol, 85% yield). Trimethylboroxine (11.26 g, 89.8 mmol, 3.0 equiv) was added to a mixture of triflate 68 (14.72 g, 30.5 mmol, 1.0 equiv), Pd(PPh$_3$)$_4$ (3.46 g, 3.0 mmol, 0.1 equiv) and K$_2$CO$_3$ (24.80 g, 179.4 mmol, 6.0 equiv) in degassed dioxane (150 mL), and the reaction mixture was stirred at 95° C. for 1 h. H$_2$O (25 mL) was added, and the mixture was stirred for a further 4 h at 95° C. The cooled reaction mixture was filtered through a short plug of Celite®, and concentrated. Flash column chromatography (silica gel, hexanes:EtOAc 10:1 to 5:1) yielded methyl 2-naphthoate 69 as a white solid (5.29 g, 24.7 mmol, 81% yield). Ester 69 (5.29 g, 24.7 mmol, 1.0 equiv) and N-bromosuccinimide (19.1 g, 100 mmol, 4.0 equiv) were dissolved in CCl$_4$ (50 mL), the reaction mixture was heated to 80° C. and benzoyl peroxide (121 mg, 0.5 mmol, 0.02 equiv) was added in one portion. Heating continued for 8 h and the reaction mixture was cooled to ambient temperature, and then stored at 0° C. for 12 h. The reaction mixture was then filtered, and the precipitates were rinsed with CCl$_4$ (0-5° C.). The combined filtrates were then washed with saturated aq. NaHCO$_3$ (25 mL) and brine (25 mL), dried over MgSO$_4$, and concentrated to yield crude product 70 as a yellowish solid. Neat dibromoester 70 was heated to 150° C. in a slight vacuum for 10 h. The reaction mixture cooling to ambient temperature gave crude product 71 as a light brown solid. Crude bromophthalide 71 was dissolved in DMF (50 mL), anhydrous K$_2$CO$_3$ (10.3 g, 74.8 mmol, 3.0 equiv, dried under high vacuum at 110° C. for 16 h prior to use) and n-Bu$_4$NI (1.8 g, 5.0 mmol, 0.2 equiv) were added sequentially, followed by phthalimide (8.0 g, 54.9 mmol, 2.2 equiv) in one portion. The reaction mixture was stirred at 40° C. for 4 h, then poured into H$_2$O (100 mL) and extracted with EtOAc (3×100 mL). The combined organic layers were washed with water (3×50 mL) and brine (2×50 mL), dried over MgSO$_4$ and concentrated. Flash column chromatography (silica gel, CH$_2$Cl$_2$:EtOAc 10:1 to 8:1) gave phthalide 72 as a yellowish solid (4.94 g, 14.4 mmol, 39% yield). 72: R$_f$=0.31 (silica gel, CH$_2$Cl$_2$:EtOAc 8:1); $^1$H NMR (600 MHz, CDCl$_3$): δ=8.48 (s, 1H), 8.03 (d, J=8.0 Hz, 1H), 7.88 (s, 1H), 7.87 (dd, J=5.4, 3.1 Hz, 2H), 7.75 (dd, J=5.5, 3.0 Hz, 2H), 7.64 (s, 1H), 7.47 (d, J=7.8 Hz, 1H), 5.45 (s, 2H), 4.99 (s, 2H) ppm; HRMS (ESI-TOF): calcd for C$_{21}$H$_{14}$NO$_4^+$ [M+H$^+$]: 344.0917, found 344.0915.

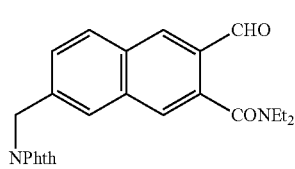

Formylbenzamide 75

To a stirred suspension of phthalide 72 (4.94 g, 14.4 mmol, 1.0 equiv) in $CCl_4$/benzene (50 mL, 1:1) at ambient temperature, was added N-bromosuccinimide (3.06 g, 17.3 mmol, 1.2 equiv) in one portion. The reaction mixture was heated to reflux, and azobisisobutyronitrile (0.47 g, 2.87 mmol, 0.2 equiv) was then added in one portion. The reaction mixture was vigorously stirred at reflux for another 2 h, then cooled to ambient temperature, and stored at 0° C. for 8 h. The reaction mixture was filtered, and the precipitates were rinsed with $CCl_4$ (0-5° C.). The combined filtrates were then washed with saturated aq. $NaHCO_3$ (10 mL) and brine (10 mL), dried over $Mg_2SO_4$, and concentrated to yield crude 73 as a yellow foam, which was suspended in $H_2O$/THF (50 mL, 1:1). The suspension was stirred at 85° C. for 5 h and then allowed to cool to ambient temperature. The reaction mixture was extracted with EtOAc (5×20 mL) and the combined organic layers were dried over $MgSO_4$ and concentrated to yield crude 74 as a yellow hygroscopic solid, which was dried over $P_2O_5$ for 8 h. The crude acid 74 was suspended in $SOCl_2$ (15 mL) and the reaction mixture was heated at reflux for 2 h. The reaction mixture was concentrated under $N_2$ and the last traces of volatiles (e.g. $SOCl_2$) were removed azeotropically with toluene (2×10 mL). The crude product was dissolved in $CH_2Cl_2$ (15 mL) and the solution was cooled to 0° C. A solution of diethylamine (1.91 g, 2.68 mL, 26.0 mmol, 1.8 equiv) in $CH_2Cl_2$ (3.0 mL) was added dropwise, the ice bath was removed and the reaction mixture was stirred at ambient temperature for 2 h. The reaction was quenched with 1N aq. HCl (27 mL), and the resulting reaction mixture was extracted with $CH_2Cl_2$ (2×20 mL). The combined organic layers were washed with brine (20 mL), dried over $MgSO_4$ and concentrated. Flash column chromatography (silica gel, hexanes:EtOAc 3:1 to 2:1) yielded formylbenzamide 75 as a yellowish solid (2.57 g, 6.19 mmol, 43% yield). 75: $R_f$=0.31 (silica gel, hexanes:EtOAc 2:1); $^1H$ NMR (600 MHz, $CDCl_3$): δ=10.13 (s, 1H), 8.61 (s, 1H), 8.50 (s, 1H), 8.00 (d, J=7.9 Hz, 1H), 7.81 (dd, J=5.4, 3.1 Hz, 2H), 7.71 (dd, J=5.5, 3.0 Hz, 2H), 7.64 (s, 1H), 7.21 (d, J=7.8 Hz, 1H), 3.81 (dq, J=7.1, 13.7 Hz, 1H), 3.51 (dq, J=7.1, 13.7 Hz, 1H), 3.01 (ddq, J=7.2, 14.4, 14.4, Hz, 2H), 1.21 (t, J=7.1 Hz, 3H), 0.99 (t, J=7.2 Hz, 3H) ppm; HRMS (ESI-TOF): calcd for $C_{25}H_{23}N_2O_4^+$ [M+H$^+$]: 415.1652, found 415.1658.

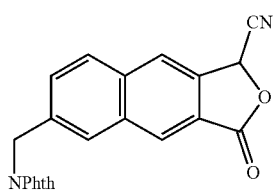

Cyanophthalide 76

To a stirred solution of formyl-benzamide 75 (1.33 g, 3.20 mmol, 1.0 equiv) in $CH_2Cl_2$ (6 mL) at 0° C., was added TMSCN (640 mg, 0.81 mL, 6.44 mmol, 2.0 equiv), and a solution of KCN (5.2 mg, 0.08 mmol, 0.025 equiv) and 18-crown-6 (16 mg, 0.06 mmol, 0.02 equiv) in THF (0.6 mL). The reaction mixture was stirred at the same temperature in a sealed flask for 1.5 h, and for additional 30 min at ambient temperature. The reaction mixture was concentrated under $N_2$ and the residue was then azeotropically dried with toluene (2×25 mL) to remove all traces of TMSCN. The resulting brown oil was dissolved in AcOH (3 mL) and stirred for 48 h at room temperature until TLC showed full conversion (hexames:EtOAc 3:2). The reaction was quenched by careful addition of 1N aq. NaOH (10 mL), and the resulting mixture was extracted with EtOAc (20 mL). The aqueous layer was extracted with EtOAc (3×20 mL), and the combined organic layers were washed with $H_2O$ (20 mL) and brine (20 mL), dried over $MgSO_4$ and concentrated. Flash column chromatography (silica gel, hexanes:EtOAc 2:1 to 3:2) gave a yellowish solid, which was recrystallized from EtOAc to yield cyanophthalide 76 (825 mg, 2.24 mmol, 70% yield). 76: $R_f$=0.33 (silica gel, hexanes:EtOAc 3:2); $^1H$ NMR (400 MHz, $CDCl_3$): δ=8.53 (s, 1H), 7.99 (d, J=8.0 Hz, 1H), 7.86 (dd, J=5.4, 3.1 Hz, 2H), 7.74 (dd, J=5.5, 3.0 Hz, 2H), 7.64 (s, 1H), 7.53 (s, 1H), 7.35 (d, J=8.0 Hz, 1H), 6.01 (s, 1H), 4.99 (s, 2H) ppm; HRMS (ESI-TOF): calcd for $C_{22}H_{13}N_2O_4^+$ [M+H$^+$]: 369.0870, found 369.0872.

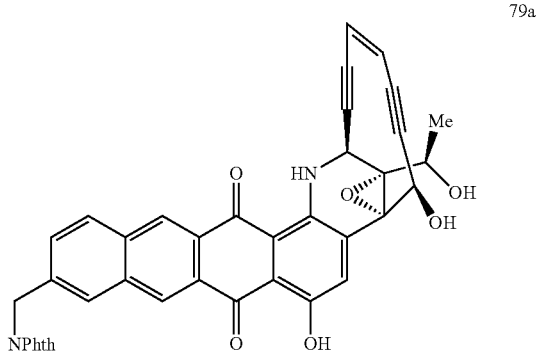

Phthalimidomethyl-benzo-uncialamycin 79a

To a solution of cyanophthalide 76 (70 mg, 0.19 mmol, 3.0 equiv) in THF (0.8 mL) at −78° C. was added LiHMDS (1.0 M in THF, 0.25 mL, 0.25 mmol, 4.0 equiv). The resulting mixture was stirred at −78° C. for 20 min, and a pre-cooled solution of quinone aminal 22a (see last disclosure, 34 mg, 63 μmol, 1.0 equiv) in THF (0.8 mL) at −78° C. was added via cannula. After stirring for 5 min at −78° C., the reaction mixture was allowed to warm to ambient temperature and stirred for another 110 min during which time the reaction mixture turned dark red. The resulting mixture was quenched by addition of pH 6.8 phosphate buffer (30 mL) and extracted with EtOAc (3×30 mL). The combined organic extracts were washed with brine (30 mL), dried over $MgSO_4$, and filtered through a short plug of Celite® (washed with EtOAc prior to use). The solids were rinsed with EtOAc, and the combined filtrates were concentrated to yield crude mixture of alloc-naphthacenequinone 77a as a dark red solid. Without purification, this product (77a) was dissolved in degassed THF (1.5 mL) under Ar and cooled to 0° C. To this stirred solution was added Pd(PPh$_3$)$_4$ (4 mg, 1.3 Vμmol, 0.2 equiv) followed by dropwise addition of morpholine (7 mg, 7 μL, 76 Vμmol, 1.2 equiv). The reaction flask was wrapped with aluminium foil, and the resulting mixture was allowed to stir at 0° C. for 2 h during which time it turned dark blue. The cooling bath was removed and the reaction mixture was stirred at ambient temperature for 20 min, quenched by addition of pH 6.8 phosphate buffer (10 mL), and extracted with EtOAc (3×10 mL). The combined organic extracts were washed with H$_2$O (10 mL) and brine (10 mL), dried over MgSO$_4$, and filtered through a short plug of Celite® (washed with EtOAc prior to use). The obtained solids were rinsed with EtOAc, and the combined filtrates were concentrated to ca. 1 mL in volume. Flash column chromatography [deactivated silica gel (see General Methods), hexanes:EtOAc 1:1 to 1:2] yielded crude mixture of naphthacenequinone 78a as a dark purple solid. To a solution of naphthacenequinone 78a in degassed THF (1.5 mL) at room temperature was added a solution of 1:1 3HF.Et$_3$N:THF (0.5 mL). The reaction flask was wrapped with aluminium foil, and the reaction mixture was stirred at room temperature for 2 h, then partitioned between EtOAc (10 mL) and saturated aq. NaHCO$_3$ (10 mL). The organic layer was washed with brine (10 mL), dried over Na$_2$SO$_4$, and concentrated to ca. 1 mL in volume. Flash column chromatography [deactivated silica gel (see General Methods), hexanes:EtOAc 1:1 to 1:3] yielded a 1:1 mixture of phthalimidomethyl-benzo-uncialamycin 79a (27 mg, 42.2 Vμmol, 67% yield) as a dark purple solid. 79a: R$_f$=0.42 (silica gel, hexanes:EtOAc 1:2); $^1$H NMR (600 MHz, CD$_3$CN): δ=13.49 (s, 1H), 9.89 (d, J=4.2 Hz, 1H), 8.47 (s, 1H), 8.31 (s, 1H), 7.91 (d, J=8.0 Hz, 1H), 7.80 (m, 2H), 7.76 (m, 2H), 7.44 (s, 1H), 7.21 (d, J=8.0 Hz, 1H), 5.96 (d, J=10.0 Hz, 1H), 5.89 (d, J=9.9 Hz, 1H), 5.24 (d, J=5.0 Hz, 1H), 5.10 (s, 2H), 4.90 (dd, J=4.4, 1.4 Hz, 1H), 4.52 (d, J=5.0 Hz, 1H), 4.37 (dq, J=5.0, 6.5 Hz, 1H), 3.30 (d, J=4.9 Hz, 1H), 1.38 (d, J=6.5 Hz, 3H) ppm; HRMS (ESI-TOF): calcd for C$_{39}$H$_{25}$N$_2$O$_8$ [M+H$^+$]: 649.1605, found 649.1604.

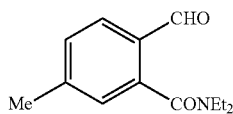

Formylbenzamide 81

A solution of 2-bromo-5-methylbenzoic acid (156 mg, 0.73 mmol, 1.0 equiv) in SOCl$_2$ (5 mL) was stirred at reflux for 2 h. The reaction mixture was concentrated under N$_2$ and the residue was coevaporated with toluene (2×5 mL) to remove all traces of SOCl$_2$. The crude product was dissolved in CH$_2$Cl$_2$ (5 mL) and the reaction mixture was cooled to 0° C. A solution of diethylamine (97 mg, 0.14 mL, 1.31 mmol, 1.8 equiv) in CH$_2$Cl$_2$ (0.2 mL) was added dropwise, the ice bath was removed and the reaction mixture was stirred at ambient temperature for 2 h. The reaction was quenched with 1N aq. HCl (1.5 mL), and the resulting mixture was extracted with CH$_2$Cl$_2$ (2×5 mL). The combined organic layers were washed with brine (5 mL), dried over MgSO$_4$ and concentrated. Flash column chromatography (silica gel, hexanes:EtOAc 3:1 to 2:1) yielded benzamide 80 as a yellowish solid (194 mg, 0.72 mmol, 98% yield). To a stirred solution of i-PrMgBr (0.85 mL, 1.0 M in THF, 0.85 mmol, 1.2 equiv) in THF (1.0 mL) at 0° C. was added n-BuLi (0.68 mL, 2.50 M in hexanes, 1.70 mmol, 2.4 equiv). The resulting yellow solution was cooled to −78° C. and a solution of bromide 80 (234 mg, 0.72 mmol, 1.0 equiv) in THF (1.0 mL) was added dropwise. After stirring for 1 h at −78° C., DMF (0.23 mL, 2.88 mmol, 4.0 equiv) was added. After stirring for 3 h at −78° C., saturated aq. NH$_4$Cl (5 mL) was added and the resulting mixture was allowed to reach ambient temperature. The mixture was extracted with EtOAc (10 mL), the organic layer was dried over MgSO$_4$, concentrated, and purified by column chromatography (silica gel, hexanes:EtOAc=1:1) to provide aldehyde 81 (156 mg, 0.71 mmol, 99% yield) as a white powder. 81: R$_f$=0.42 (silica gel, hexanes:EtOAc 1:2); $^1$H NMR (500 MHz, CDCl$_3$): δ=10.01 (s, 1H), 7.77 (s, 1H), 7.45 (d, J=7.7 Hz, 1H), 7.28 (d, J=7.7 Hz, 1H), 3.42 (m, 2H), 3.13 (m, 2H), 2.46 (s, 3H), 1.32 (t, J=7.1 Hz, 3H), 1.08 (t, J=7.2 Hz, 3H) ppm; HRMS (ESI-TOF): calcd for C$_{15}$H$_{22}$NO$_4^+$ [M+H$^{+}$]: 280.1543, found 280.1540.

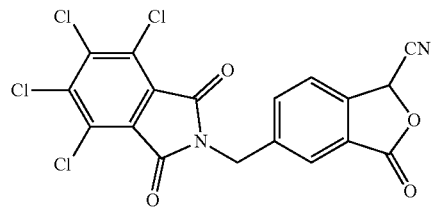

Cyanophthalide 84

To a stirred solution of formylbenzamide 81 (156 mg, 0.71 mmol, 1.0 equiv.) in CCl$_4$ (0.7 mL) was added N-bromosuccinimide (163 mg, 0.85 mmol, 1.2 equiv) at ambient temperature under N$_2$, the reaction mixture was heated to 80° C., and benzoyl peroxide (10 mg, 0.04 mmol, 0.06 equiv) was added in one portion. Heating was continued for 2 h at the same temperature and then the reaction mixture was allowed to cool to ambient temperature, washed with saturated aq. NaHCO$_3$ (2 mL) and brine (2 mL), dried over MgSO$_4$, and concentrated to give crude benzyl-bromide 82 as a light brown solid. Benzylbromide 82 was dissolved in DMF (0.6 mL), and to the stirred solution were added sequentially K$_2$CO$_3$ (146 mg, 1.07 mmol, 1.5 equiv), n-Bu$_4$NI (26 mg, 0.07 mmol, 0.1 equiv), and 2,3,4,5-tetrachlorophthalimide (224 mg, 0.79 mmol, 1.1 equiv, in one portion). The reaction mixture was heated to 70° C., and stirred at that temperature for 2 h, then poured into H$_2$O (2 mL) and extracted with EtOAc (3×2 mL). The combined organic layers were washed with water (3×2 mL) and brine (2×2 mL), dried over MgSO$_4$, and concentrated. Flash column chromatography (silica gel, hexanes:EtOAc 2:1 to 1:2) gave tetrachlorophthalimide 83 as a yellowish solid (214 mg, 0.43 mmol, 60% yield for 2 steps). To a stirred solution of tetrachloro-phthalimide 83 in CH$_2$Cl$_2$ (0.8 mL) at 0° C., was added TMSCN (84 mg, 0.11 mL, 0.85 mmol, 2.0 equiv), and a solution of KCN (1 mg, 0.02 mmol, 0.025 equiv) and 18-crown-6 (2 mg, 0.01 mmol, 0.02 equiv) in THF (0.1 mL). The reaction mixture was stirred at the same temperature in a sealed flask for 1.5 h, and for 30 min at ambient temperature. The resulting mixture was concentrated under N$_2$, and the residue was dried with azeotropical removal of all traces of TMSCN with toluene (2×2 mL). The resulting brown oil was dissolved in AcOH (0.5 mL) and stirred for 48 h at room temperature until TLC showed full conversion (hexames:EtOAc 1:1). The reaction was quenched by careful addition of 1N aq. NaOH (1.5 mL), and the resulting mixture was partitioned between EtOAc (3 mL) and H$_2$O (1.5 mL). The aqueous layer was extracted with EtOAc (3×3 mL), and the combined organic layers were washed with H$_2$O (3 mL) and brine (3 mL), dried over MgSO$_4$ and concentrated. Flash column chromatography (silica gel, hexanes:EtOAc 3:2 to 1:1) gave a yellowish solid, which was recrystallized from EtOAc to yield cyanophthalide 84 as a yellowish solid (136 mg, 0.30 mmol, 70% yield). 84: $R_f$=0.35 (silica gel, hexanes:EtOAc 1:1); $^1$H NMR (500 MHz, CDCl$_3$): δ=6.81 (s, 1H), 5.93 (s, 1H), 4.97 (s, 2H), 4.23 (s, 3H), 3.94 (s, 3H) ppm; HRMS (ESI-TOF): calcd for $C_{18}H_7Cl_4N_2O_4^+$ [M+H$^+$]: 454.9154, found 454.9156.

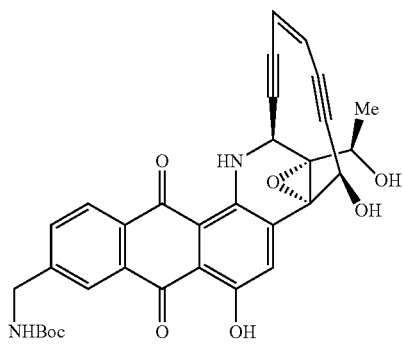

8-tert-Butylcarbamoylmethyl-uncialamycin (49aa)

To a stirred solution of cyanophthalide 84 (36 mg, 80 µmol, 3.0 equiv) in THF (0.35 mL) at −78° C. was added LiHMDS (1.0 M in THF, 0.11 mL, 0.11 mmol, 4.0 equiv). The resulting mixture was stirred at −78° C. for 20 min, and a pre-cooled solution of quinone aminal 22a (see previous disclosure, 15 mg, 28 µmol, 1.0 equiv) in THF (0.35 mL) at −78° C. was added via cannula. After stirring for 5 min at −78° C., the reaction mixture was allowed to warm to ambient temperature and stirred for another 90 min, during which time the reaction mixture turned dark red. The resulting mixture was then quenched with pH 6.8 buffer (15 mL) and extracted with EtOAc (3×15 mL). The combined organic extracts were washed with brine (15 mL), dried over MgSO$_4$, and filtered through a short plug of Celite® (washed with EtOAc prior to use). The solids were rinsed with EtOAc, and the combined filtrates were concentrated to yield crude alloc-uncialamycin derivative 85a as a dark red solid, which was dissolved in degassed THF (1.0 mL) under Ar and cooled to 0° C. To this solution was added Pd(PPh$_3$)$_4$ (2 mg, 0.7 µmol, 0.2 equiv), followed by dropwise addition of ethylenediamine (5 mg, 6 µL, 84 µmol, 3.0 equiv), the reaction flask was wrapped with aluminium foil, and the resulting mixture was allowed to stir at 0° C. for 2 h, during which time it turned purple. H$_2$O (0.5 mL) was then added and the resulting mixture was stirred at 50° C. for 2 h, diluted with pH 7.2 phosphate buffer (10 mL) and extracted with EtOAc (5×10 mL). The combined organic extracts were washed with H$_2$O (10 mL) and brine (10 mL), dried over MgSO$_4$, and filtered. The filtrates were concentrated to ca. 1 mL in volume to yield a crude solution of 8-aminomethyl-uncialamycin (48aa), to which with stirring at 0° C. were sequentially added degassed THF (1.0 mL), saturated aq. NaHCO$_3$ (1.0 mL, in one portion), and Boc$_2$O (7 mg, 34 µmol, 1.2 equiv). The reaction flask was wrapped with aluminium foil, and the reaction mixture was stirred at 0° C. for 1.5 h, and then partitioned between EtOAc (5 mL) and pH 6.8 phosphate buffer (5 mL). The aqueous layer was extracted with EtOAc (2×25 mL), and the combined organic extracts were washed with brine (5 mL), dried over Na$_2$SO$_4$, and concentrated to ca. 1 mL in volume. Flash column chromatography [deactivated silica gel (see General Methods), hexanes:EtOAc 1:1 to 1:2] yielded 8-tert-butylcarbamoylmethyl-uncialamycin (49aa) (5.0 mg, 8.3 µmol, 30% yield for 3 steps) as a purple solid. 49aa: $R_f$=0.27 (silica gel, hexanes:EtOAc 1:1); [α]$_D^{25}$=+2300° (c=0.002, EtOAc); $^1$H NMR (600 MHz, CD$_3$CN): δ=13.17 (s, 1H), 10.00 (d, J=4.4 Hz, 1H), 8.50 (s, 1H), 8.25 (d, J=8.1 Hz, 1H), 8.15 (s, 1H), 7.75 (dd, J=8.0, 1.8 Hz, 1H), 6.03 (br, 1H), 5.97 (d, J=9.9 Hz, 1H), 5.89 (dt, J=9.9, 1.3 Hz, 1H), 5.24 (d, J=4.4 Hz, 1H), 4.92 (dd, J=4.4, 1.7 Hz, 2H), 4.65 (d, J=5.0 Hz, 1H), 4.39 (d, J=5.7, 1H), 4.38 (dq, J=5.0, 6.5 Hz, 1H), 3.37 (d, J=4.8 Hz, 1H), 1.43 (s, 9H), 1.38 (d, J=6.5 Hz, 3H) ppm; $^{13}$C NMR (150 MHz, CD$_3$CN): δ=188.5, 184.1, 156.6, 147.3, 144.6, 136.1, 134.6, 134.0, 133.7, 128.1, 125.0, 124.5, 124.1, 114.4, 112.4, 100.4, 99.1, 91.2, 88.8, 79.8, 77.0, 65.8, 65.3, 64.7, 44.3, 44.2, 28.5, 21.2 ppm; HRMS (ESI-TOF): calcd for $C_{32}H_{29}N_2O_8^+$ [M+H$^+$]: 569.1918, found 569.1918.

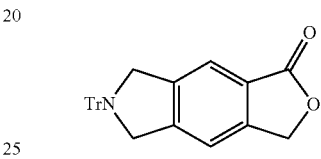

Isoindoline 89

To a suspension of trimethylbenzoic acid (15.0 g, 91.4 mmol, 1.0 equiv), and anhydrous K$_2$CO$_3$ (18.8 g, 137 mmol, 1.5 equiv) in DMF (100 mL), MeI (14.3 g, 6.27 mL, 100 mmol, 1.1 equiv) was added dropwise over 3 min under vigorous stirring at room temperature. Upon completion of addition, the reaction mixture was stirred for additional 5 h at room temperature, then poured into H$_2$O (200 mL) and extracted with Et$_2$O (3×200 mL). The combined organic layers were washed with water (3×100 mL) and brine (2×100 mL), dried over MgSO$_4$ and concentrated to yield crude product 86 as a colorless oil. Ester 86 and N-bromosuccinimide (52.0 g, 292 mmol, 3.2 equiv) were dissolved in CCl$_4$ (200 mL), the reaction mixture was heated to 80° C. and benzoyl peroxide (242 mg, 1.0 mmol, 0.02 equiv) was added in one portion. Heating continued for 8 h and the reaction mixture was cooled to ambient temperature, and then stored at 0° C. for 3 h. The reaction mixture was then filtered through a short plug of Celite®, and the precipitates were rinsed with CCl$_4$ (0-5° C.). The combined filtrates were then washed with saturated aq. NaHCO$_3$ (25 mL) and brine (25 mL), dried over MgSO$_4$, and concentrated to yield crude product 87 as a white solid. Neat tribromoester 87 was heated to 150° C. in a slight vacuum for 10 h. The reaction mixture was cooled to ambient temperature and a dark brown solid was obtained as crude product 88. Dibromophthalide 88 was dissolved in DMF (100 mL), i-Pr$_2$NEt (29.5 g, 39.7 mL, 228 mmol, 2.5 equiv) was added in one portion, followed by tritylamine (23.7 g, 91.4 mmol, 1.0 equiv). The reaction mixture was stirred at 60° C. for 4 h, then poured into H$_2$O (300 mL) and vigorously stirred for 15 min. The precipitates were filtered and rinsed with H$_2$O, and dried under vacuum to yield isoindoline 89 as a white solid. The combined filtrates were extracted with EtOAc (3×100 mL), and the combined organic layers were washed with water (3×50 mL) and brine (2×50 mL), dried over MgSO$_4$ and concentrated. Flash column chromatography (silica gel, CH$_2$Cl$_2$:EtOAc 50:1 to 20:1) gave a second portion of isoindoline 89 as a white solid (20.6 g, 49.3 mmol, 54% yield). 89: $R_f$=0.47 (silica gel, $CH_2Cl_2$:EtOAc 20:1); IR (film) $v_{max}$=3708, 3681, 2973, 2939, 2923, 2866, 2844, 2826, 1762, 1709, 1614, 1428, 1394, 1350, 1301, 1150, 1126, 1053, 1032, 1008 $cm^{-1}$; $^1H$ NMR (600 MHz, $CDCl_3$): S=7.59 (m, 6H), 7.30 (m, 11H), 5.21 (s, 2H), 3.99 (d, J=7.6 Hz, 4H) ppm; $^{13}C$ NMR (150 MHz, $CDCl_3$): S=171.0, 145.7, 142.1, 130.1, 129.4, 128.5, 128.0, 127.7, 126.5, 126.4, 119.0, 115.6, 75.1, 69.4, 52.2, 51.6 ppm; HRMS (ESI-TOF): calcd for $C_{29}H_{24}NO_2^+$ [M+H$^+$]: 418.1802, found 418.1807.

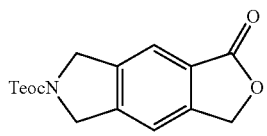

Isoindoline 90

To a stirred solution of isoindoline 89 (15.4 g, 36.9 mmol, 1.0 equiv) in $CH_2Cl_2$ (50 mL) at ambient temperature, was added TFA (50.5 g, 33.9 mL, 443 mmol, 12 equiv) dropwise at 0° C. The reaction mixture was allowed to stir at ambient temperature for 45 min, and then concentrated under $N_2$ and the residue was coevaporated with toluene (2×25 mL) to remove all traces of TFA. The resulting brown oil was dissolved in THF (50 mL), and saturated aq. $NaHCO_3$ (20 mL) was added in one portion, followed by a solution of TeocCl in THF (1.0 M, 50 mL, 50 mmol, 1.4 equiv) at 0° C. The reaction mixture was vigorously stirred at ambient temperature for another 12 h, then concentrated to ca. 25 mL, diluted with $CH_2Cl_2$ (50 mL) and quenched with saturated aq. $NaHCO_3$ (20 mL). The aqueous phase was extracted with $CH_2Cl_2$ (2×50 mL), and the combined organic phases were then washed with $H_2O$ (25 mL) and brine (25 mL), dried over $Mg_2SO_4$, and concentrated. Flash column chromatography (silica gel, hexanes:EtOAc 3:1 to 2:1) yielded isoindoline 90 as a yellowish solid (10.0 g, 31.3 mmol, 85% yield). 90: $R_f$=0.31 (silica gel, hexanes:EtOAc 2:1); $^1H$ NMR (400 MHz, $CDCl_3$): δ=9.99 (s, 1H), 7.88 (d, J=8.0 Hz, 1H), 7.85 (dd, J=5.4, 3.1 Hz, 2H), 7.73 (dd, J=5.5, 3.0 Hz, 2H), 7.57 (dd, J=8.0, 1.4 Hz, 1H), 7.38 (d, J=1.4 Hz, 1H), 4.89 (s, 2H), 3.58 (q, J=7.1 Hz, 2H), 3.07 (q, J=7.1 Hz, 2H), 1.28 (t, J=7.1 Hz, 3H), 1.00 (t, J=7.1 Hz, 3H) ppm; $^{13}C$ NMR (100 MHz, $CDCl_3$): δ=189.9, 168.2, 167.7, 142.6, 140.0, 134.2, 132.0, 131.8, 130.3, 129.1, 126.7, 123.5, 43.0, 41.0, 39.1, 13.7, 12.6 ppm; HRMS (ESI-TOF): calcd for $C_{16}H_{22}NO_4Si^+$ [M+H$^+$]: 320.1313, found 320.1318.

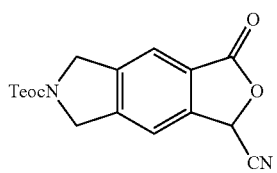

Cyanophthalide 93

To a stirred solution of isoindoline 90 (1.60 g, 5.0 mmol, 1.0 equiv) in aq. MeOH (85%, 20 mL) was added powdered KOH (420 mg, 7.5 mmol, 1.5 equiv) in one portion, and the mixture was stirred at ambient temperature for 12 h. The reaction mixture was concentrated under vacuum to remove MeOH, and the residue was diluted with $H_2O$ (10 mL). The mixture was then neutralized (pH=4) by addition of aq. $KHSO_4$ (1.0 M). The precipitates thus formed were collected by filtration and rinsed with $H_2O$ (3×5 mL) to give hydroxyacid 91 as a brownish solid. Hydroxyacid 91 was added to a stirred suspension of PCC (1.61 g, 7.5 mmol, 1.5 equiv) in $CH_2Cl_2$ (20 mL) at ambient temperature. The reaction mixture was stirred for 3 h at ambient temperature, diluted with $Et_2O$ (50 mL), and passed through a short plug of Celite®. The residual solids were washed with $Et_2O$ (3×15 mL), and the combined filtrates were concentrated to give the crude hydroxyphthalide 92 as a dark red solid. Hydroxyphthalide 92 was suspended in acetone cyanohydrin (0.7 mL, 7.5 mmol, 1.5 equiv), and i-$Pr_2NEt$ (13 μL, 75 μmol, 0.015 equiv) was added in one portion at 0° C. The reaction mixture was stirred at the same temperature in a sealed flask for 1.5 h, and for 30 min at ambient temperature. The reaction mixture was then concentrated under $N_2$ and the residue was coevaporated with toluene (2×25 mL) to remove all traces of acetone cyanohydrin. The resulting brown oil was dissolved in $CH_2Cl_2$ (25 mL) and DCC (1.20 g, 6.0 mmol, 1.2 equiv) was added in one portion at 0° C. The reaction mixture was stirred for 8 h at room temperature until TLC showed full conversion (hexanes:EtOAc 3:2). The reaction was filtered to remove the urea byproduct and the filtrate was concentrated. Flash column chromatography (silica gel, hexanes:EtOAc 2:1 to 3:2) gave a yellowish solid, which was recrystallized from EtOAc to yield cyanophthalide 93 as a white solid (826 mg, 2.4 mmol, 48% yield). 93: $R_f$=0.31 (silica gel, hexanes:EtOAc 3:2); $^1H$ NMR (400 MHz, $CDCl_3$): δ=7.99 (s, 1H), 7.91 (d, J=8.0 Hz, 1H), 7.86 (dd, J=5.4, 3.1 Hz, 2H), 7.74 (dd, J=5.5, 3.0 Hz, 2H), 7.67 (d, J=8.0 Hz, 1H), 6.06 (s, 1H), 4.98 (s, 2H) ppm; $^{13}C$ NMR (100 MHz, $CDCl_3$): δ=167.7, 167.0, 141.2, 140.6, 136.0, 134.4, 131.7, 126.2, 125.0, 123.6, 123.1, 113.6, 65.5, 40.7 ppm; HRMS (ESI-TOF): calcd for $C_{17}H_{21}N_2O_4Si^+$ [M+H$^+$]: 345.1265, found 345.1271.

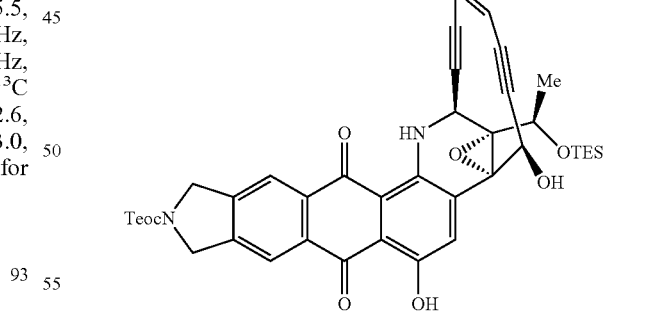

Anthraquinone 94a

To a solution of cyanophthalide 93 (93 mg, 0.27 mmol, 2.0 equiv) in THF (1.2 mL) at −78° C. was added LiHMDS (1.0 M in THF, 0.43 mL, 0.43 mmol, 3.0 equiv). The resulting mixture was stirred at −78° C. for 20 min, and a pre-cooled solution of quinone aminal 22a (78 mg, 0.14 mmol, 1.0 equiv) in THF (1.4 mL) at −78° C. was added via cannula. After stirring for 5 min at −78° C., the reaction mixture was warmed to ambient temperature and stirred for another 1.5 h during which time the reaction mixture turned dark red and TLC showed full consumption of 22a (8% EtOAc in CH$_2$Cl$_2$). The reaction mixture was then quenched by the addition of pH 6.8 buffer (30 mL) and extracted with EtOAc (3×30 mL). The combined organic extracts were washed with brine (30 mL), dried over MgSO$_4$, and filtered through a short plug of Celite® (washed with EtOAc prior to use). The solids were rinsed with EtOAc, and the combined filtrates were concentrated to yield crude alloc-anthraquinone 94a as a dark red solid, which was dissolved in degassed THF (2.0 mL) under Ar and cooled to 0° C. To this solution was added Pd(PPh$_3$)$_4$ (32 mg, 10.4 µmol, 0.16 equiv), followed by dropwise addition of morpholine (32 mg, 32 µL, 0.34 mmol, 2.4 equiv). The reaction flask was wrapped with aluminium foil, and the resulting mixture was allowed to stir at 0° C. for 2 h during which time the reaction mixture turned dark purple. The cooling bath was removed and the reaction mixture was stirred at ambient temperature for 20 min, and then quenched by the addition of pH 6.8 buffer (30 mL) and extracted with EtOAc (3×30 mL). The combined organic extracts were washed with H$_2$O (30 mL) and brine (30 mL), dried over MgSO$_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes:EtOAc 2:1 to 1:1] yielded anthraquinone 95a as a purple solid (93 mg, 0.13 mmol, 90% yield). 95a: R$_f$=0.58 (silica gel, hexanes:EtOAc 1:1); [α]$_D^{25}$=+2600° (c=0.002, EtOAc); $^1$H NMR (600 MHz, CD$_3$CN): δ=13.11 (s, 1H), 9.97 (d, J=4.0 Hz, 1H), 8.46 (s, 1H), 8.23 (d, J=8.0 Hz, 1H), 8.20 (s, 1H), 7.87 (d, J=1.9 Hz, 2H), 7.81 (d, J=2.2 Hz, 1H), 7.80 (d, J=1.9 Hz, 2H), 5.94 (d, J=10.0 Hz, 1H), 5.87 (d, J=9.8 Hz, 1H), 5.10 (s, 1H), 4.97 (s, 2H), 4.97 (s, 1H), 4.55 (q, J=5.8 Hz, 1H), 4.45 (d, J=3.7 Hz, 1H), 1.38 (d, J=5.8 Hz, 3H), 0.98 (t, J=7.6 Hz, 9H), 0.66 (q, J=7.6 Hz, 6H) ppm; $^{13}$C NMR (150 MHz, CD$_3$CN): δ=188.2, 183.8, 169.0, 156.7, 144.8, 143.5, 136.3, 135.4, 135.1, 134.8, 133.8, 133.0, 130.9, 128.3, 126.1, 124.9, 124.1, 123.8, 114.2, 112.2, 100.2, 99.7, 91.3, 88.4, 77.4, 66.7, 64.9, 64.7, 44.3, 41.8, 22.6, 7.3, 5.6 ppm; HRMS (ESI-TOF): calcd for C$_{40}$H$_{47}$N$_2$O$_8$Si$_2^+$ [M+H$^+$]: 739.2865, found 739.2871.

and the reaction mixture was stirred at room temperature for 1.5 h, then partitioned between EtOAc (50 mL) and saturated aq. NaHCO$_3$ (50 mL). The aqueous layer was extracted with EtOAc (2×25 mL), and the combined organic extracts were washed with brine (25 mL), dried over Na$_2$SO$_4$, and concentrated to ca. 1 mL in volume. Flash column chromatography (deactivated silica gel, hexanes:EtOAc 1:1 to 1:2) yielded isoindoline-uncialamycin 96 as a purple solid (76 mg, 0.13 mmol, 98% yield). 96: R$_f$=0.24 [deactivated silica gel (see General Methods), hexanes:EtOAc 1:1]; [α]$_D^{25}$=+1600° (c=0.005, EtOAc); $^1$H NMR (600 MHz, CD$_3$CN): δ=13.10 (s, 1H), 9.99 (d, J=4.1 Hz, 1H), 8.48 (s, 1H), 8.23 (d, J=8.1 Hz, 1H), 8.21 (s, 1H), 7.87 (dd, J=5.4, 3.1 Hz, 2H), 7.82 (d, J=2.2 Hz, 1H), 7.81 (dd, J=5.5, 3.0 Hz, 2H), 5.96 (d, J=9.9 Hz, 1H), 5.88 (d, J=9.9 Hz, 1H), 5.24 (d, J=4.9 Hz, 1H), 5.49 (s, 2H), 4.91 (dd, J=4.4, 1.4 Hz, 1H), 4.44 (d, J=4.9 Hz, 1H), 4.38 (dq, J=5.0, 6.5 Hz, 1H), 3.27 (d, J=4.9 Hz, 1H), 1.38 (d, J=6.5 Hz, 3H) ppm; $^{13}$C NMR (150 MHz, CD$_3$CN): δ=188.2, 183.9, 169.0, 156.7, 144.7, 143.6, 136.2, 135.4, 135.1, 134.8, 133.8, 133.0, 130.9, 128.4, 126.1, 124.5, 124.1, 124.1, 114.3, 112.3, 100.3, 99.1, 91.3, 88.8, 77.0, 65.8, 65.3, 64.7, 44.2, 41.8, 21.2 ppm; HRMS (ESI-TOF): calcd for C$_{34}$H$_{33}$N$_2$O$_8$Si$^+$ [M+H$^+$]: 625.2001, found 625.2006.

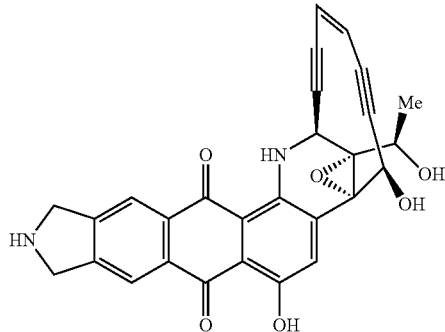

Isoindoline-uncialamycin 97

To a solution of isoindoline-uncialamycin 96 (3.6 mg, 5 µmol, 1.0 equiv) in degassed THF (1.0 mL) at 0° C. was added TBAF/HOAc (1/1, 1.0 M, 0.1 mL) dropwise. The reaction flask was wrapped with aluminium foil, and the reaction mixture was stirred at ambient temperature for 6 h, then quenched by H$_2$O (1.0 mL), cooled to 0° C. and diluted with degassed THF (10 mL), the organic phase was separated and concentrated at 5° C. under N$_2$ to ca. 1 mL in volume, and diluted with cold degassed THF (0° C., 10 mL). Repeat the same operations 5 times to yield crude isoindoline-uncialamycin 97 as a purple solid, which was immediately used for the next step (CAUTION: 97 was extremely unstable, both acid- and base-sensitive, slowly decomposed at −78° C., use fresh for best yields). 97: R$_f$=0.10 (silica gel, MeOH:EtOAc 1:1); HRMS (ESI-TOF): calcd for C$_{28}$H$_{21}$N$_2$O$_6^+$ [M+H$^+$]: 481.1394, found 481.1397.

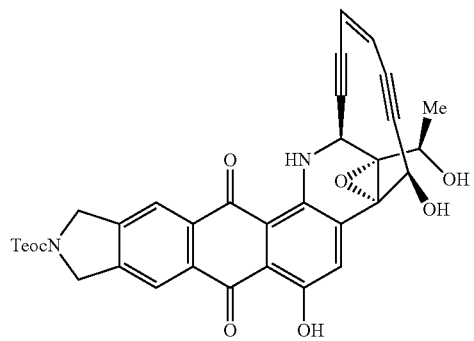

Isoindoline-uncialamycin 96

To a stirred solution of anthraquinone 95a (93 mg, 0.13 mmol, 1.0 equiv) in degassed THF (15 mL) at room temperature was added a solution of 1:1 3HF.Et$_3$N:THF (5.0 mL). The reaction flask was wrapped with aluminium foil,

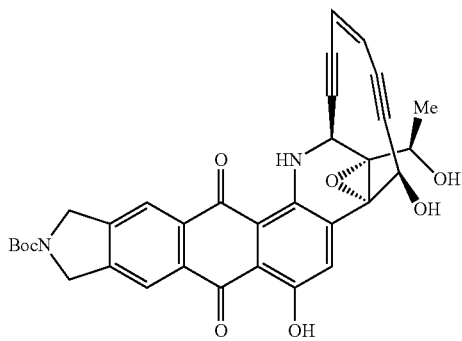

tert-Butylcarbamoyl-isoindoline-uncialamycin 98

Crude isoindoline-uncialamycin 97 [prepared according to the procedure described above from 8-phthalimidomethyl-uncialamycin 47aa (3.6 mg, 5 μmol, 1.0 equiv)] was suspended in degassed THF (1.0 mL) at 0° C., and saturated aq. NaHCO$_3$ (1.0 mL) was added in one portion, followed by Boc$_2$O (1.3 mg, 6 μmol, 1.2 equiv). The reaction flask was wrapped with aluminium foil, and the reaction mixture was stirred at 0° C. for 1.5 h, then partitioned between EtOAc (5 mL) and pH 6.8 buffer (5 mL). The aqueous layer was extracted with EtOAc (2×25 mL), and the combined organic extracts were washed with brine (5 mL), dried over Na$_2$SO$_4$, and concentrated to ca. 1 mL in volume. Flash column chromatography [deactivated silica gel (see General Methods), hexanes:EtOAc 1:1 to 1:2] yielded 8-tert-butylcarbamoylmethyl-isoindoline-uncialamycin 98 (2.7 mg, 4.5 μmol, 95% yield) as a purple solid. 98: R$_f$=0.27 (silica gel, hexanes:EtOAc 1:1); [α]$_D^{25}$=+23000 (c=0.002, EtOAc); $^1$H NMR (600 MHz, CD$_3$CN): δ=13.17 (s, 1H), 10.00 (d, J=4.4 Hz, 1H), 8.50 (s, 1H), 8.25 (d, J=8.1 Hz, 1H), 8.15 (s, 1H), 7.75 (dd, J=8.0, 1.8 Hz, 1H), 6.03 (br, 1H), 5.97 (d, J=9.9 Hz, 1H), 5.89 (dt, J=9.9, 1.3 Hz, 1H), 5.24 (d, J=4.4 Hz, 1H), 4.92 (dd, J=4.4, 1.7 Hz, 2H), 4.65 (d, J=5.0 Hz, 1H), 4.39 (d, J=5.7, 1H), 4.38 (dq, J=5.0, 6.5 Hz, 1H), 3.37 (d, J=4.8 Hz, 1H), 1.43 (s, 9H), 1.38 (d, J=6.5 Hz, 3H) ppm; $^{13}$C NMR (150 MHz, CD$_3$CN): δ=188.5, 184.1, 156.6, 147.3, 144.6, 136.1, 134.6, 134.0, 133.7, 128.1, 125.0, 124.5, 124.1, 114.4, 112.4, 100.4, 99.1, 91.2, 88.8, 79.8, 77.0, 65.8, 65.3, 64.7, 44.3, 44.2, 28.5, 21.2 ppm; HRMS (ESI-TOF): calcd for C$_{33}$H$_{29}$N$_2$O$_8^+$ [M+H]$^+$: 581.1918, found 581.1918.

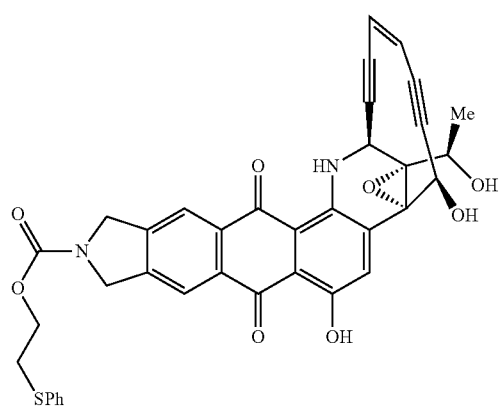

Sulfide 99

Crude 8-aminomethyl-uncialamycin 97 [prepared according to the general procedure described above from 8-phthalimidomethyl-uncialamycin (96, 16 mg, 27 μmol, 1.0 equiv)] was suspended in degassed THF (1.0 mL) at 0° C., and saturated aq. NaHCO$_3$ (1.0 mL) was added in one portion, followed by dropwise addition of a solution of 2-(phenylthio)ethyl chloroformate (14 mg, 66 μmol, 2.5 equiv) in degassed THF (0.5 mL). The reaction flask was wrapped with aluminium foil, and the reaction mixture was stirred at 0° C. for 5 h, then partitioned between EtOAc (5 mL) and pH 6.8 buffer (5 mL). The aqueous layer was extracted with EtOAc (2×25 mL), and the combined organic extracts were washed with brine (5 mL), dried over Na$_2$SO$_4$, and concentrated to ca. 1 mL in volume. Flash column chromatography [deactivated silica gel (see General Methods), hexanes:EtOAc 1:1 to 1:2] to yield sulfide 99 (9.5 mg, 14 μmol, 55% yield) as a purple solid. 99: R$_f$=0.23 (silica gel, hexanes:EtOAc 1:1); $^1$H NMR (600 MHz, CD$_3$CN): δ=13.20 (s, 1H), 10.01 (d, J=4.1 Hz, 1H), 8.50 (s, 1H), 8.23 (d, J=8.0 Hz, 1H), 8.16 (s, 1H), 7.73 (dd, J=8.0, 1.8 Hz, 1H), 6.00 (br, 1H), 5.98 (d, J=10.0 Hz, 1H), 5.89 (dt, J=10.0, 1.3 Hz, 1H), 5.24 (d, J=4.4 Hz, 1H), 4.94 (dd, J=4.4, 1.7 Hz, 2H), 4.65 (d, J=5.0 Hz, 1H), 4.4-4.2 (m, 2H), 4.39 (d, J=5.0, 1H), 4.38 (dq, J=5.0, 6.5 Hz, 1H), 3.35 (d, J=4.8 Hz, 1H), 3.2-3.0 (m, 2H), 1.38 (d, J=6.5 Hz, 3H) ppm; $^{13}$C NMR (150 MHz, CD$_3$CN): δ=188.6, 184.2, 154.4, 147.3, 144.6, 136.1, 135.1, 134.6, 134.0, 133.8, 129.1, 128.6, 128.1, 125.3 125.1, 124.5, 124.1, 114.3, 112.4, 100.3, 99.1, 91.2, 88.8, 77.1, 65.8, 65.3, 64.7, 64.6, 44.3, 44.2, 32.4, 21.2 ppm; HRMS (ESI-TOF): calcd for C$_{37}$H$_{29}$N$_2$O$_8$S$^+$ [M+H]$^+$: 661.1639 found 661.1638.

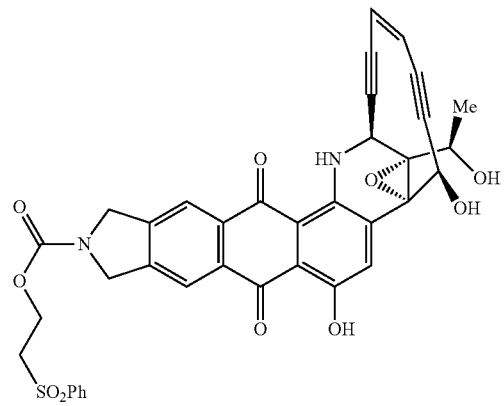

Sulfone 100

To a stirred solution of sulfide 99 (6.5 mg, 10 μmol, 1.0 equiv) in CH$_2$Cl$_2$ (0.5 mL) was added freshly prepared dimethyldioxirane (2.0 mL, ~0.1 M in acetone, 0.2 mmol, 20 equiv) at −78° C., the reaction mixture was wrapped in aluminium foil, and allowed to warm to 0° C. After stirring at 0° C. for 20 min, Me$_2$S (84 mg, 0.1 mL, 1.4 mmol, 135 equiv) was added in one portion, and stirring was continued for 20 min at the same temperature. The reaction mixture was then diluted with EtOAc (25 mL), washed with H$_2$O (5 mL) and brine (5 mL), dried over Na$_2$SO$_4$, and concentrated to ca. 1 mL in volume. Flash column chromatography [deactivated silica gel (see General Methods), hexanes:

EtOAc 1:1 to 1:3] yielded sulfone 100 (2.7 mg, 4.5 μmol, 55% yield) as a purple solid. 100: $R_f$=0.23 [deactivated silica gel (see General Methods), hexanes:EtOAc 1:3 then EtOAc: MeOH 50:1]; $^1$H NMR (600 MHz, CD$_3$CN): δ=13.19 (s, 1H), 9.99 (d, J=4.1 Hz, 1H), 8.51 (s, 1H), 8.24 (d, J=8.0 Hz, 1H), 8.18 (s, 1H), 7.73 (dd, J=8.0, 1.8 Hz, 1H), 6.05 (br, 1H), 5.97 (d, J=10.0 Hz, 1H), 5.88 (dt, J=10.0, 1.3 Hz, 1H), 5.26 (d, J=4.4 Hz, 1H), 4.97 (dd, J=4.4, 1.7 Hz, 2H), 4.66 (d, J=5.0 Hz, 1H), 4.6-4.3 (m, 2H), 4.39 (d, J=5.1, 1H), 4.38 (dq, J=5.0, 6.5 Hz, 1H), 3.50 (br, 2H), 3.35 (d, J=4.9 Hz, 1H), 1.38 (d, J=6.5 Hz, 3H) ppm; $^{13}$C NMR (150 MHz, CD$_3$CN): S=188.5, 184.1, 153.7, 147.3, 144.6, 139.1, 136.1, 134.6, 134.1, 134.0, 133.7, 129.5, 128.1, 128.0, 125.0, 124.5, 124.1, 114.4, 112.4, 100.4, 99.1, 91.2, 88.8, 77.0, 65.8, 65.3, 64.7, 59.4, 55.2, 44.3, 44.2, 21.2 ppm; HRMS (ESI-TOF): calcd for C$_{37}$H$_{29}$N$_2$O$_{10}$S$^+$ [M+H$^+$]: 693.1537, found 693.1532.

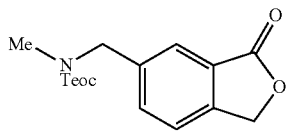

Phthalide 101

To a solution of 6-bromomethylphthalide (11.3 g, 49.9 mmol, 1.0 equiv) in DMF (50 mL), anhydrous Cs$_2$CO$_3$ (24.3 g, 74.8 mmol, 1.5 equiv) and n-Bu$_4$NI (1.8 g, 5.0 mmol, 0.1 equiv) were added sequentially, followed by N-methyl-2-(trimethylsilyl)ethylcarbamate (9.6 g, 54.9 mmol, 1.1 equiv) in one portion. The reaction mixture was stirred at 60° C. for 2 h, then poured into H$_2$O (300 mL) and vigorously stirred for 15 min. The precipitates were filtered and rinsed with H$_2$O, and dried under vacuum to yield phthalide 101 as a white solid. The combined filtrates were extracted with EtOAc (3×100 mL), and the combined organic layers were washed with water (3×50 mL) and brine (2×50 mL), dried over MgSO$_4$ and concentrated. Flash column chromatography (silica gel, CH$_2$Cl$_2$:EtOAc 10:1 to 8:1) gave a second portion of phthalide 101 as a white solid (13.0 g, 40.4 mmol, 81% yield). 101: $R_f$=0.31 (silica gel, CH$_2$Cl$_2$:EtOAc 8:1); IR (film) $v_{max}$=3708, 3681, 2973, 2939, 2923, 2866, 2844, 2826, 1762, 1709, 1614, 1428, 1394, 1350, 1301, 1150, 1126, 1053, 1032, 1008 cm$^{-1}$; $^1$H NMR (600 MHz, CDCl$_3$): δ=7.93 (s, 1H), 7.87 (dd, J=5.4, 3.1 Hz, 2H), 7.76 (d, J=7.9 Hz, 1H), 7.75 (dd, J=5.5, 3.0 Hz, 2H), 7.47 (d, J=7.8 Hz, 1H), 5.29 (s, 2H), 4.96 (s, 2H) ppm; $^{13}$C NMR (150 MHz, CDCl$_3$): δ=170.6, 167.8, 146.0, 137.9, 134.4, 134.2, 131.9, 126.4, 125.3, 123.6, 122.5, 69.5, 40.9 ppm; HRMS (ESI-TOF): calcd for C$_{16}$H$_{24}$NO$_4$Si$^+$ [M+H$^+$]:322.1469, found 322.1465.

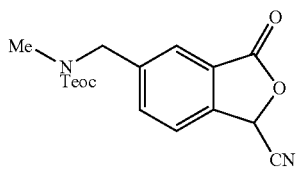

Cyanophthalide 104

To a stirred solution of phthalide 101 (1.61 g, 5.0 mmol, 1.0 equiv) in aq. MeOH (85%, 20 mL) was added powdered KOH (420 mg, 7.5 mmol, 1.5 equiv) in one portion, and the mixture was stirred at ambient temperature for 12 h. The reaction mixture was concentrated under vacuum to remove MeOH, and the residue was diluted with H$_2$O (10 mL). The mixture was then neutralized (pH=4) by addition of aq. KHSO$_4$ (1.0 M). The precipitates thus formed were collected by filtration and rinsed with H$_2$O (3×5 mL) to give hydroxyacid 102 as a brownish solid. Hydroxyacid 102 was added to a stirred suspension of PCC (1.61 g, 7.5 mmol, 1.5 equiv) in CH$_2$Cl$_2$ (20 mL) at ambient temperature. The reaction mixture was stirred for 3 h at ambient temperature, diluted with Et$_2$O (50 mL), and passed through a short plug of Celite®. The residual solids were washed with Et$_2$O (3×15 mL), and the combined filtrates were concentrated to give the crude hydroxyphthalide 103 as a dark red solid. Hydroxyphthalide 103 was suspended in acetone cyanohydrin (0.7 mL, 7.5 mmol, 1.5 equiv), and i-Pr$_2$NEt (13 μL, 75 μmol, 0.015 equiv) was added in one portion at 0° C. The reaction mixture was stirred at the same temperature in a sealed flask for 1.5 h, and for 30 min at ambient temperature. The reaction mixture was then concentrated under N$_2$ and the residue was coevaporated with toluene (2×25 mL) to remove all traces of acetone cyanohydrin. The resulting brown oil was dissolved in CH$_2$Cl$_2$ (25 mL) and DCC (1.20 g, 6.0 mmol, 1.2 equiv) was added in one portion at 0° C. The reaction mixture was stirred for 8 h at room temperature until TLC showed full conversion (hexames:EtOAc 3:2). The reaction was filtered to remove the urea byproduct and the filtrate was concentrated. Flash column chromatography (silica gel, hexanes:EtOAc 2:1 to 3:2) gave a yellowish solid, which was recrystallized from EtOAc to yield cyanophthalide 104 as a white solid (917 mg, 2.65 mmol, 53% yield). 104: $R_f$=0.31 (silica gel, hexanes:EtOAc 3:2); $^1$H NMR (400 MHz, CDCl$_3$): δ=7.99 (s, 1H), 7.91 (d, J=8.0 Hz, 1H), 7.86 (dd, J=5.4, 3.1 Hz, 2H), 7.74 (dd, J=5.5, 3.0 Hz, 2H), 7.67 (d, J=8.0 Hz, 1H), 6.06 (s, 1H), 4.98 (s, 2H) ppm; $^{13}$C NMR (100 MHz, CDCl$_3$): δ=167.7, 167.0, 141.2, 140.6, 136.0, 134.4, 131.7, 126.2, 125.0, 123.6, 123.1, 113.6, 65.5, 40.7 ppm; HRMS (ESI-TOF): calcd for C$_{17}$H$_{23}$N$_2$O$_4$Si$^+$ [M+H$^+$]: 347.1422, found 347.1425.

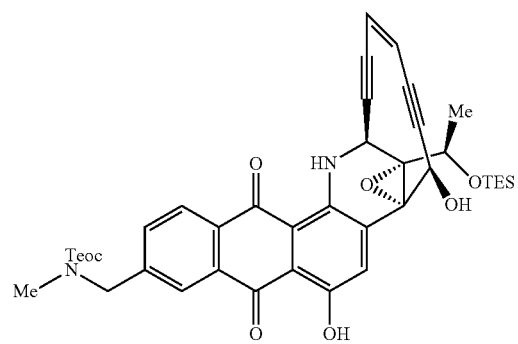

Anthraquinone 106a

To a solution of cyanophthalide 104 (10 mg, 29 μmol, 2.0 equiv) in THF (0.12 mL) at −78° C. was added LiHMDS (1.0 M in THF, 43 µL, 43 µmol, 3.0 equiv). The resulting mixture was stirred at −78° C. for 20 min, and a pre-cooled solution of quinone aminal 22a (8 mg, 14 µmol, 1.0 equiv) in THF (0.14 mL) at −78° C. was added via cannula. After stirring for 5 min at −78° C., the reaction mixture was warmed to ambient temperature and stirred for another 1.5 h during which time the reaction mixture turned dark red and TLC showed full consumption of 22a (8% EtOAc in CH$_2$Cl$_2$). The reaction mixture was then quenched by the addition of pH 6.8 buffer (3 mL) and extracted with EtOAc (3×3 mL). The combined organic extracts were washed with brine (3 mL), dried over MgSO$_4$, and filtered through a short plug of Celite® (washed with EtOAc prior to use). The solids were rinsed with EtOAc, and the combined filtrates were concentrated to yield crude alloc-anthraquinone 28a as a dark red solid, which was dissolved in degassed THF (0.2 mL) under Ar and cooled to 0° C. To this solution was added Pd(PPh$_3$)$_4$ (3 mg, 1.0 µmol, 0.16 equiv), followed by dropwise addition of morpholine (3 mg, 3 µL, 30 µmol, 2.4 equiv). The reaction flask was wrapped with aluminium foil, and the resulting mixture was allowed to stir at 0° C. for 2 h during which time the reaction mixture turned dark purple. The cooling bath was removed and the reaction mixture was stirred at ambient temperature for 20 min, and then quenched by the addition of pH 6.8 buffer (3 mL) and extracted with EtOAc (3×3 mL). The combined organic extracts were washed with H$_2$O (3 mL) and brine (3 mL), dried over MgSO$_4$, and filtered through a short plug of Celite® (washed with EtOAc prior to use). The solids were rinsed with EtOAc, and the combined filtrates were concentrated to ca. 1 mL in volume. Flash column chromatography [deactivated silica gel (see General Methods), hexanes: EtOAc 2:1 to 1:1] yielded anthraquinone 106a as a purple solid (8 mg, 11 µmol, 80% yield). 106a: R$_f$=0.58 (silica gel, hexanes:EtOAc 1:1); [α]$_D^{25}$=+2600° (c=0.002, EtOAc); $^1$H NMR (600 MHz, CD$_3$CN): δ=13.11 (s, 1H), 9.97 (d, J=4.0 Hz, 1H), 8.46 (s, 1H), 8.23 (d, J=8.0 Hz, 1H), 8.20 (s, 1H), 7.87 (d, J=1.9 Hz, 2H), 7.81 (d, J=2.2 Hz, 1H), 7.80 (d, J=1.9 Hz, 2H), 5.94 (d, J=10.0 Hz, 1H), 5.87 (d, J=9.8 Hz, 1H), 5.10 (s, 1H), 4.97 (s, 2H), 4.97 (s, 1H), 4.55 (q, J=5.8 Hz, 1H), 4.45 (d, J=3.7 Hz, 1H), 1.38 (d, J=5.8 Hz, 3H), 0.98 (t, J=7.6 Hz, 9H), 0.66 (q, J=7.6 Hz, 6H) ppm; $^{13}$C NMR (150 MHz, CD$_3$CN): δ=188.2, 183.8, 169.0, 156.7, 144.8, 143.5, 136.3, 135.4, 135.1, 134.8, 133.8, 133.0, 130.9, 128.3, 126.1, 124.9, 124.1, 123.8, 114.2, 112.2, 100.2, 99.7, 91.3, 88.4, 77.4, 66.7, 64.9, 64.7, 44.3, 41.8, 22.6, 7.3, 5.6 ppm; HRMS (ESI-TOF): calcd for C$_{40}$H$_{49}$N$_2$O$_8$Si$_2^+$ [M+H$^+$]: 741.3022, found 741.3023.

107

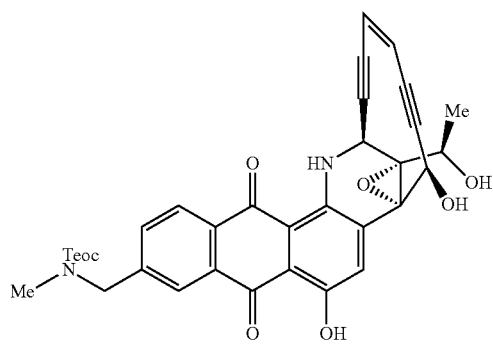

N-methyl-8-[2-(trimethylsilyl)ethyl]carbamoylmethyl-uncialamycin 107

To a stirred solution of anthraquinone 106a (7 mg, 10 µmol, 1.0 equiv) in degassed THF (1.5 mL) at room temperature was added a solution of 1:1 3HF.Et$_3$N:THF (0.5 mL). The reaction flask was wrapped with aluminium foil, and the reaction mixture was stirred at room temperature for 1.5 h, then partitioned between EtOAc (5.0 mL) and saturated aq. NaHCO$_3$ (5.0 mL). The aqueous layer was extracted with EtOAc (2×2.5 mL), and the combined organic extracts were washed with brine (2.5 mL), dried over Na$_2$SO$_4$, and concentrated to ca. 1 mL in volume. Flash column chromatography (deactivated silica gel, hexanes: EtOAc 1:1 to 1:2) yielded uncialamycin analog 107 as a purple solid (7 mg, 10 µmol, 99% yield). 107: R$_f$=0.24 [deactivated silica gel (see General Methods), hexanes: EtOAc 1:1]; [α]$_D^{25}$=+1600° (c=0.005, EtOAc); $^1$H NMR (600 MHz, CD$_3$CN): δ=13.10 (s, 1H), 9.99 (d, J=4.1 Hz, 1H), 8.48 (s, 1H), 8.23 (d, J=8.1 Hz, 1H), 8.21 (s, 1H), 7.87 (dd, J=5.4, 3.1 Hz, 2H), 7.82 (d, J=2.2 Hz, 1H), 7.81 (dd, J=5.5, 3.0 Hz, 2H), 5.96 (d, J=9.9 Hz, 1H), 5.88 (d, J=9.9 Hz, 1H), 5.24 (d, J=4.9 Hz, 1H), 5.49 (s, 2H), 4.91 (dd, J=4.4, 1.4 Hz, 1H), 4.44 (d, J=4.9 Hz, 1H), 4.38 (dq, J=5.0, 6.5 Hz, 1H), 3.27 (d, J=4.9 Hz, 1H), 1.38 (d, J=6.5 Hz, 3H) ppm; $^{13}$C NMR (150 MHz, CD$_3$CN): δ=188.2, 183.9, 169.0, 156.7, 144.7, 143.6, 136.2, 135.4, 135.1, 134.8, 133.8, 133.0, 130.9, 128.4, 126.1, 124.5, 124.1, 124.1, 114.3, 112.3, 100.3, 99.1, 91.3, 88.8, 77.0, 65.8, 65.3, 64.7, 44.2, 41.8, 21.2 ppm; HRMS (ESI-TOF): calcd for C$_{34}$H$_{35}$N$_2$O$_8$Si$^+$ [M+H$^+$]: 627.2157, found 627.2157.

108

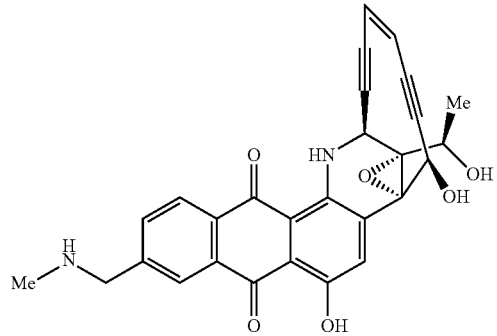

N-methyl-8-aminomethyl-uncialamycin 108

To a solution of uncialamycin analog 107 (3.6 mg, 5 µmol, 1.0 equiv) in degassed THF (1.0 mL) at 0° C. was added TBAF/HOAc (1/1, 1.0 M, 0.1 mL) dropwise. The reaction flask was wrapped with aluminium foil, and the reaction mixture was stirred at ambient temperature for 6 h, then quenched by H$_2$O (1.0 mL), cooled to 0° C. and diluted with degassed THF (10 mL), the organic phase was separated and concentrated at 5° C. under N$_2$ to ca. 1 mL in volume, and diluted with cold degassed THF (0° C., 10 mL). Repeat the same operations 5 times to yield crude N-methyl-8-aminomethyl-uncialamycin 108 as a purple solid, which was immediately used for the next step (CAUTION: 108 was extremely unstable, both acid- and base-sensitive, slowly decomposed at −78° C., use fresh for best yields). 108: $R_f$=0.10 (silica gel, MeOH:EtOAc 1:1); HRMS (ESI-TOF): calcd for $C_{28}H_{23}N_2O_6^+$ [M+H$^+$]: 483.1551, found 483.1557.

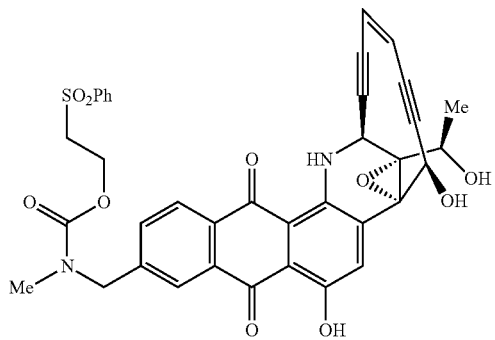

Sulfone 110

To a stirred solution of sulfide 109 (4 mg, 5.5 µmol, 1.0 equiv) in CH$_2$Cl$_2$ (0.3 mL) was added freshly prepared dimethyldioxirane (1.0 mL, ~0.1 M in acetone, 0.1 mmol, 18 equiv) at −78° C., the reaction mixture was wrapped in aluminium foil, and allowed to warm to 0° C. After stirring at 0° C. for 20 min, Me$_2$S (42 mg, 50 µL, 0.7 mmol, 135 equiv) was added in one portion, and stirring was continued for 20 min at the same temperature. The reaction mixture was then diluted with EtOAc (12 mL), washed with H$_2$O (3 mL) and brine (3 mL), dried over Na$_2$SO$_4$, and concentrated to ca. 1 mL in volume. Flash column chromatography [deactivated silica gel (see General Methods), hexanes:EtOAc 1:1 to 1:3] yielded sulfone 110 (20 mg, 3.4 µmol, 62% yield) as a purple solid. 110: $R_f$=0.23 [deactivated silica gel (see General Methods), hexanes:EtOAc 1:3 then EtOAc:MeOH 50:1]; $^1$H NMR (600 MHz, CD$_3$CN): δ=13.19 (s, 1H), 9.99 (d, J=4.1 Hz, 1H), 8.51 (s, 1H), 8.24 (d, J=8.0 Hz, 1H), 8.18 (s, 1H), 7.73 (dd, J=8.0, 1.8 Hz, 1H), 6.05 (br, 1H), 5.97 (d, J=10.0 Hz, 1H), 5.88 (dt, J=10.0, 1.3 Hz, 1H), 5.26 (d, J=4.4 Hz, 1H), 4.97 (dd, J=4.4, 1.7 Hz, 2H), 4.66 (d, J=5.0 Hz, 1H), 4.6-4.3 (m, 2H), 4.39 (d, J=5.1, 1H), 4.38 (dq, J=5.0, 6.5 Hz, 1H), 3.50 (br, 2H), 3.35 (d, J=4.9 Hz, 1H), 1.38 (d, J=6.5 Hz, 3H) ppm; $^{13}$C NMR (150 MHz, CD$_3$CN): S=188.5, 184.1, 153.7, 147.3, 144.6, 139.1, 136.1, 134.6, 134.1, 134.0, 133.7, 129.5, 128.1, 128.0, 125.0, 124.5, 124.1, 114.4, 112.4, 100.4, 99.1, 91.2, 88.8, 77.0, 65.8, 65.3, 64.7, 59.4, 55.2, 44.3, 44.2, 21.2 ppm; HRMS (ESI-TOF): calcd for $C_{37}H_{31}N_2O_{10}S^+$ [M+H$^+$]: 695.1694, found 695.1692.

Example 4—Biological Activity of Uncialamycin Derivatives

The compounds of the present disclosure have been shown to be cytotoxic in a variety of different cancer cell lines. The cytotoxicities are comparable to the cytotoxicity of the compounds when the compound has been conjugated to an antibody (i.e. as in an ADC) demonstrating that the compounds are cytotoxins independent the antibody. This observation supports the idea that the compounds' cytotoxicity is not attributable to an antibody-related effector function such as antibody-dependent cell-mediated cytotoxicity (ADCC).

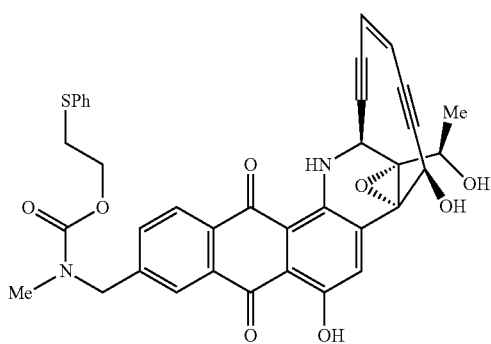

Sulfide 109

Crude N-methyl-8-aminomethyl-uncialamycin 108 [prepared according to the general procedure described above from uncialamycin analog 107 (6 mg, 9 µmol, 1.0 equiv)] was suspended in degassed THF (0.3 mL) at 0° C., and saturated aq. NaHCO$_3$ (0.3 mL) was added in one portion, followed by dropwise addition of a solution of 2-(phenylthio)ethyl chloroformate (5 mg, 22 µmol, 2.5 equiv) in degassed THF (0.2 mL). The reaction flask was wrapped with aluminium foil, and the reaction mixture was stirred at 0° C. for 5 h, then partitioned between EtOAc (2 mL) and pH 6.8 buffer (2 mL). The aqueous layer was extracted with EtOAc (2×8 mL), and the combined organic extracts were washed with brine (2 mL), dried over Na$_2$SO$_4$, and concentrated to ca. 1 mL in volume. Flash column chromatography [deactivated silica gel (see General Methods), hexanes:EtOAc 1:1 to 1:2] to yield sulfide 109 (4 mg, 5.5 µmol, 61% yield) as a purple solid. 109: $R_f$=0.23 (silica gel, hexanes:EtOAc 1:1); $^1$H NMR (600 MHz, CD$_3$CN): δ=13.20 (s, 1H), 10.01 (d, J=4.1 Hz, 1H), 8.50 (s, 1H), 8.23 (d, J=8.0 Hz, 1H), 8.16 (s, 1H), 7.73 (dd, J=8.0, 1.8 Hz, 1H), 6.00 (br, 1H), 5.98 (d, J=10.0 Hz, 1H), 5.89 (dt, J=10.0, 1.3 Hz, 1H), 5.24 (d, J=4.4 Hz, 1H), 4.94 (dd, J=4.4, 1.7 Hz, 2H), 4.65 (d, J=5.0 Hz, 1H), 4.4-4.2 (m, 2H), 4.39 (d, J=5.0, 1H), 4.38 (dq, J=5.0, 6.5 Hz, 1H), 3.35 (d, J=4.8 Hz, 1H), 3.2-3.0 (m, 2H), 1.38 (d, J=6.5 Hz, 3H) ppm; $^{13}$C NMR (150 MHz, CD$_3$CN): δ=188.6, 184.2, 154.4, 147.3, 144.6, 136.1, 135.1, 134.6, 134.0, 133.8, 129.1, 128.6, 128.1, 125.3 125.1, 124.5, 124.1, 114.3, 112.4, 100.3, 99.1, 91.2, 88.8, 77.1, 65.8, 65.3, 64.7, 64.6, 44.3, 44.2, 32.4, 21.2 ppm; HRMS (ESI-TOF): calcd for $C_{37}H_{31}N_2O_8S^+$ [M+H$^+$]: 663.1796 found 663.1798.

An ATP luminescence assay was used, the procedure being as follows: Cells were seeded at $1 \times 10^3$ cells/well in 96-well plates for 3 h for ATP CellTiter$^{Glo}$™ assays, respectively. Serial dilutions (1:3) of compounds were added to the wells. Plates were allowed to incubate for 72 h. A CellTiter$^{Glo}$™ cell viability kit from Promega was used to measure ATP content of cells treated with compounds following manufacturer's instruction. A decrease in the ATP content is a measure of decrease in cellular viability. The $EC_{50}$ value—the concentration at which an agent reduces cell viability by 50% of the maximum effect—was determined using PRISM™ software, version 5.0 (GraphPad Software, La Jolla, Calif., USA).

The results from the assays are presented in Table 1. The compounds were tested against ADR, a multi-drug resistant breast cancer cell line as well as the H226, N87, and OVCAR3 cell lines.

TABLE 1

Biological Activity of the Compounds of the Present Disclosure Against Cancer Cell Lines

| Compound | Cell Line & $EC_{50}$ (nM) | | | |
|---|---|---|---|---|
| | ADR* | H226 | N87 | OVCAR3 |
| 116 | 3.3 | 4.2 | 8.7 | 16 |
| 26a (Comparative) | 0.39 | 1.8 | 1.8 | 4.7 |
| 36a (Comparative**) | 0.67 | 2.4 | 2.7 | 7.4 |
| 48aa | 0.020 | 0.028 | 0.011 | 0.320 |

TABLE 1-continued

Biological Activity of the Compounds of the Present Disclosure Against Cancer Cell Lines

| Compound | Cell Line & EC$_{50}$ (nM) | | | |
|---|---|---|---|---|
| | ADR* | H226 | N87 | OVCAR3 |
| 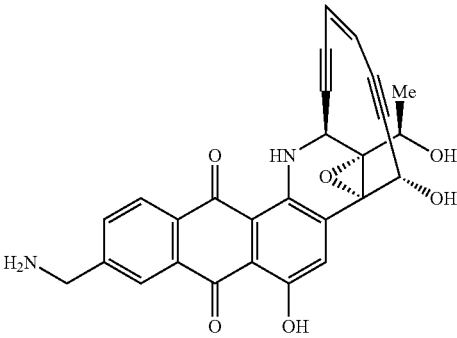 48ab | 0.054 | 0.051 | 0.023 | 0.280 |
| 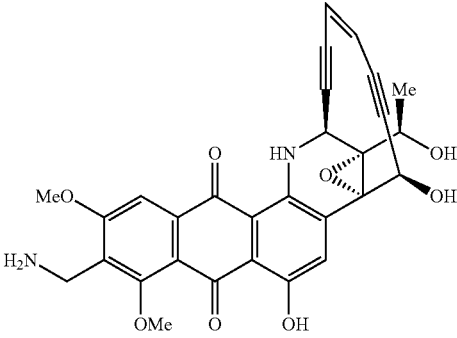 [SMILES: COc1cc2c(c(OC)c1CN)C(=O)c1c(O)cc3c(c1C2=O)N[C@H]1C#C/C=C\C#C[C@@H](O)[C@@]32O[C@@]12[C@@H](C)O] | 0.340 | 0.077 | 0.15 | 0.40 |
| 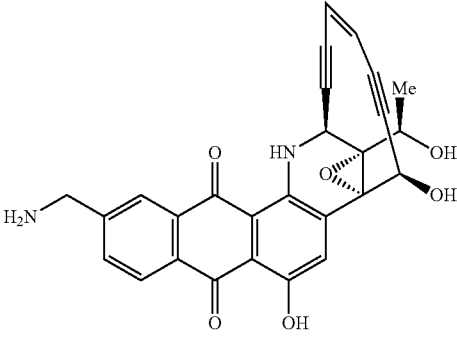 48ba | 0.029 | 0.012 | 0.010 | 0.066 |

*Multidrug resistant breast cancer cell line

**U.S. Pat. No. 8,709,431

Under certain conditions, some of the compounds of the present disclosure are unstable, but sufficient quantities for performing the biological assays were obtained by removing the phthalimide group from the phthalimide-protected precursor with methanamine (as described in Example 5) and isolating the compound as its formate salt.

Example 5—Conjugation of Uncialamycin to a Linker for Attachment to an Antibody

To prepare an ADC, it is necessary to provide a linker covalently connecting the antibody and the cytotoxic analog of uncialamycin. Once the ADC has reached the site of intended action, the linker desirably is cleavable to release the cytotoxin.

One of the compounds of this disclosure, 8-aminomethyluncialamycin (48aa), is a potent cytotoxin but is unstable and difficult to derivatize with the linker needed to prepare an antibody-drug conjugate.

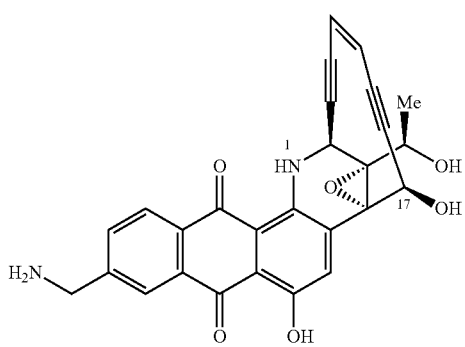

Thus, to make a derivative of 48aa suitable for conjugation, such as 116 in Scheme 22 below, an alternative approach was utilized. In this approach, instead of derivatizing 48aa itself, a protected precursor compound 77a, which has Alloc and TES protecting groups on N1 and the hydroxyl group of C17 was utilized. When the phthalimide protecting group of compound 77a is removed, resulting 111 is much more stable than 48aa and amenable to chemistry to attach a linker thereto. Without being bound by theory, the instability of 48aa is due to its free methylamino group but that in 111, the Alloc and TES groups negate the destabilizing effect of the methylamino group. While the conjugation of the linker is shown with 48aa, it is contemplated that any of the compounds of the present disclosure can be similarly derivatized.

Scheme 22

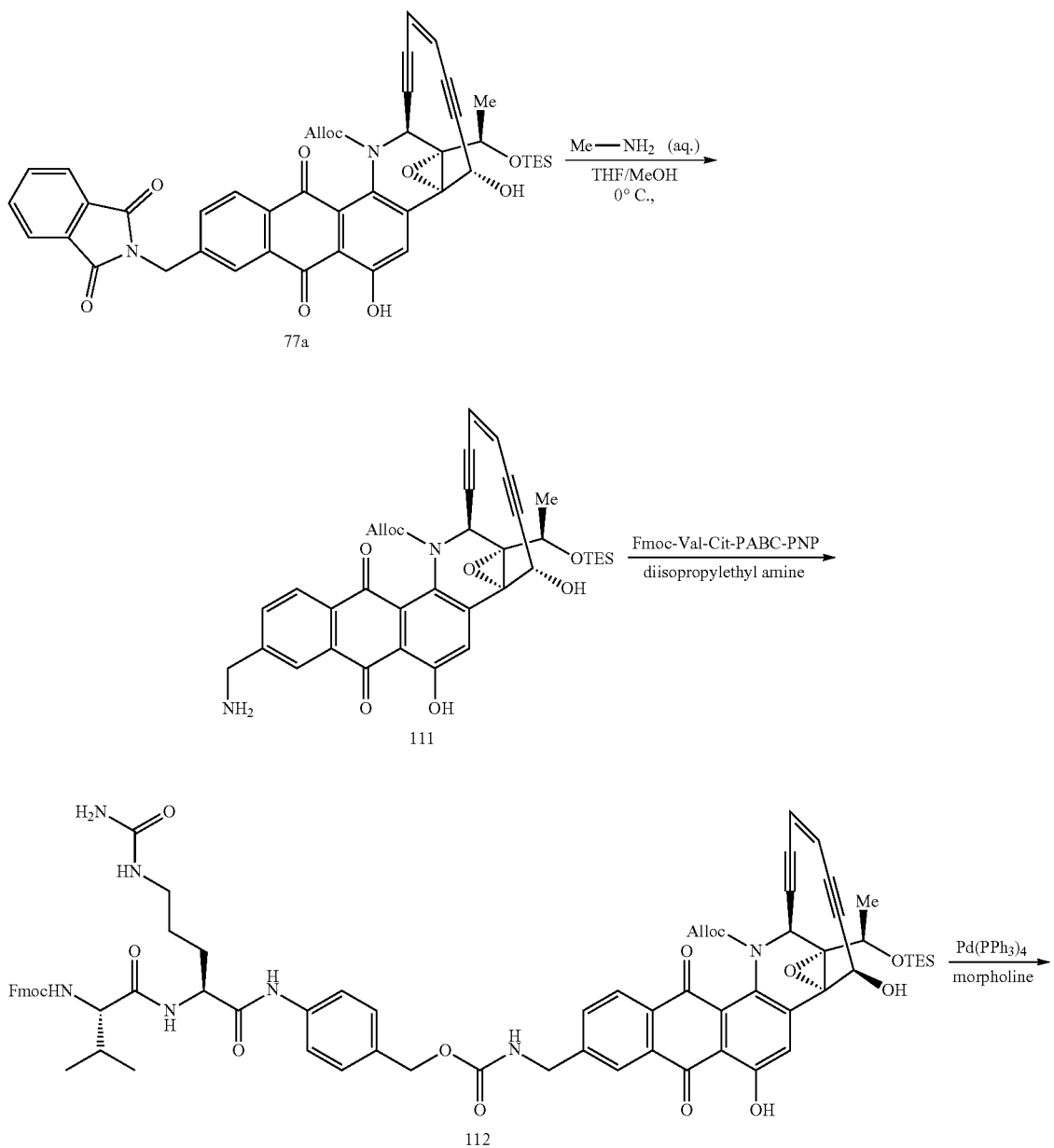

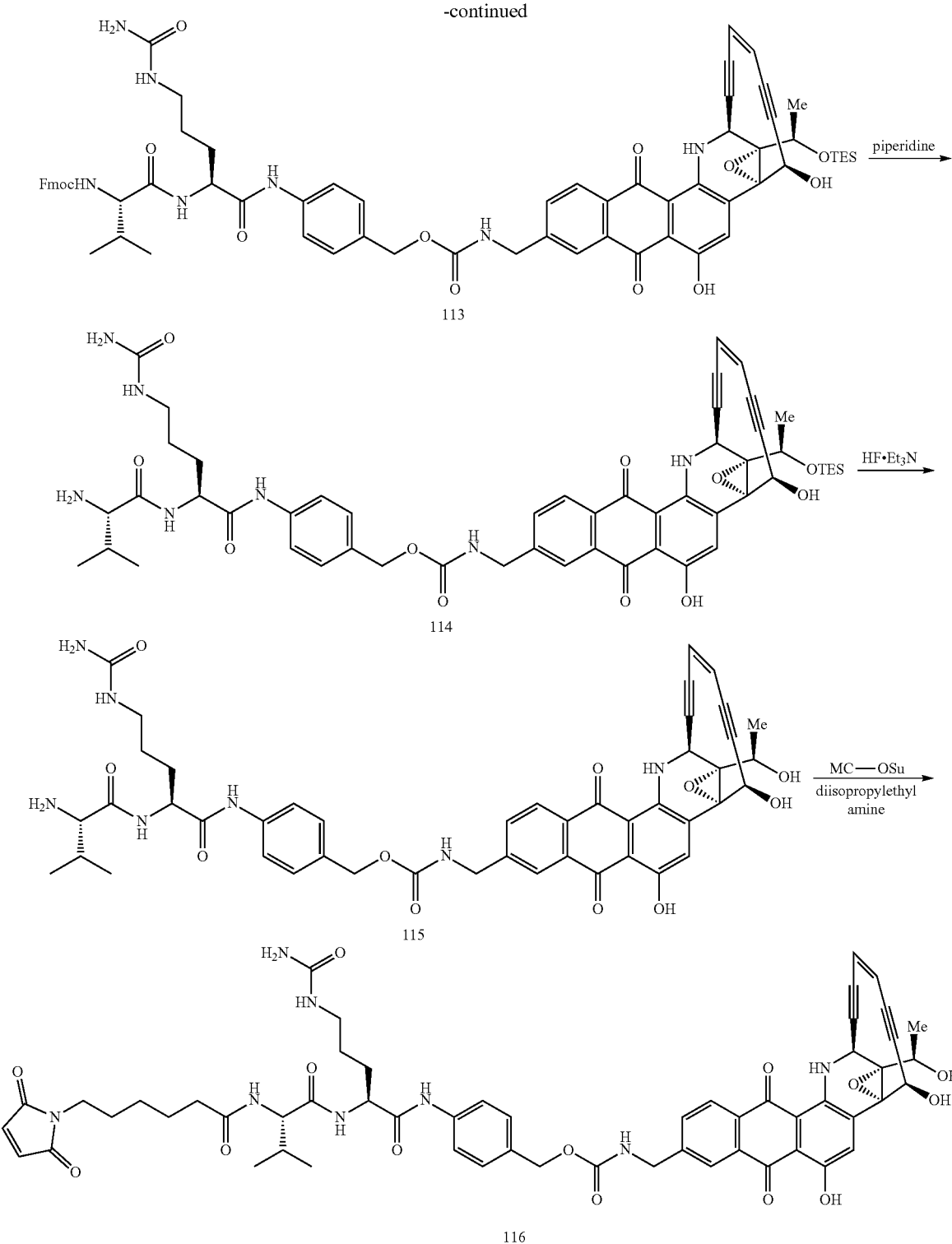

Compound 77a (48.3 mg, 0.061 mmol) was dissolved in MeOH (5 mL) and THF (1 mL) was added to solublize it. The solution was cooled to 0° C. and 40% aq. methanamine (500 μL, 6.06 mmol) was added slowly down the side of flask during which the color became darker. The mixture was left inside a 0° C. freezer overnight. LCMS showed approximately 75% conversion to compound 111 ([M+H]: 667.3). The reaction mixture was warmed to room temperature (RT) and stirred for 4 h, after which conversion was greater than 94%. The reaction was diluted with EtOAc (10 mL) and washed with saturated aqueous NaHCO₃ (10 mL) and brine (10 mL). The organic layer was dried over Na$_2$SO$_4$, filtered, concentrated, subjected to high vacuum for 30 min and taken to the next step without further purification.

To a solution of compound 111 (0.041 g, 0.061 mmol) in DMF (1 mL), Hunig's base (0.032 mL, 0.183 mmol) and (9H-fluoren-9-yl)methyl ((S)-3-methyl-1-(((S)-1-((4-((((4-nitrophenoxy)carbonyl)oxy)methyl)phenyl)amino)-1-oxo-5-ureido-pentan-2-yl)amino)-1-oxobutan-2-yl)carbamate (0.056 g, 0.073 mmol) was added at RT. After 3 h, LCMS analysis showed 85% conversion to compound 112 ([M+H]: 1295.6). The crude reaction mixture was used in the next step without further purification.

Compound 112 was dissolved in THF (1 mL) and the mixture was cooled to 0° C. To this solution, Pd(PPh$_3$)$_4$ (7.05 mg, 6.10 µmol) was added followed by morpholine (0.013 mL, 0.146 mmol). The color changed from brown to purple within 5 sec. The reaction was stirred at 0° C. for 2 h, after which LCMS showed the disappearance of starting material and the appearance of desired product 113 ([M+H]: 1210.5). The reaction mixture was diluted with EtOAc (10 mL) and washed with pH 6.8 phosphate buffer (10 mL). The aqueous layer was extracted with EtOAc (3×10 mL) and the combined organic layers were dried over Na$_2$SO$_4$, filtered, and concentrated. The crude product was purified using a COMBIFLASH® liquid chromatography system (40 g silica gel) with 0-20% MeOH in CH$_2$Cl$_2$ gradient to give compound 4 as a purple solid. $^1$H NMR (400 MHz, DMSO-d$_6$) δ 13.17 (s, 1H), 10.07 (s, 1H), 10.00 (d, J=4.4 Hz, 1H), 8.52 (s, 1H), 8.21 (d, J=8 Hz, 1H), 8.13-8.10 (m, 2H), 8.01 (t, J=5.6 Hz, 1H), 7.89 (d, J=7.2 Hz, 2H), 7.81 (d, J=7.2 Hz, 1H), 7.74 (t, J=7.6 Hz, 2H, 7.60 (d, J=8.4 Hz, 2H), 7.44-7.39 (m, 3H), 7.32 (t, J=7.2 Hz, 3H), 6.71 (d, J=5.2 Hz, 1H), 6.10-5.96 (m, 3H), 5.40 (s, 2H), 5.11 (dd, J=4.8, 1.2 Hz, 1H), 5.05-5.01 (m, 2H), 4.51 (dd, J=12.8, 6.4 Hz, 1H), 4.41-4.40 (m, 3H), 4.31-4.23 (m, 3H), 3.93 (t, J=8.8 Hz, 1H), 3.03-2.93 (m, 2H), 2.00-1.99 (m, 1H), 1.69-1.58 (m, 2H), 1.35 (d, J=6.4 Hz, 6H), 0.97-0.85 (m, 15H), 0.62 (q, J=8.0 Hz, 6H).

To a solution of compound 113 (0.074 g, 0.061 mmol) in DMF (3 mL), piperidine (50 µL, 0.506 mmol) was added. The reaction mixture was stirred at RT for 1 h. LCMS showed the formation of compound 114 ([M+H]: 988.4). The reaction mixture was cooled to 0° C. and triethylamine (85 µL, 0.610 mmol) was added, followed by triethylamine trihydrofluoride (99 µL, 0.610 mmol). After 5 min, the cold bath was removed and the reaction mixture was stirred for 1 h. LCMS showed the formation of compound 115 ([M+H]: 874.4). The reaction mixture was diluted with EtOAc (50 mL) and washed with brine (50 mL). The organic layer was dried over Na$_2$SO$_4$, filtered, and concentrated.

The crude compound 115 was dissolved in NMP (3 mL) and Hunig's base (0.032 mL, 0.183 mmol) was added, followed by 2,5-dioxopyrrolidin-1-yl 6-(2,5-dioxo-2,5-di-hydro-1H-pyrrol-1-yl)hexanoate (22.57 mg, 0.073 mmol). After 2 h, LCMS showed the formation of product 116 ([M+H]: 1067.5). Another 1.2 equiv. of 6-maleimidocaproic acid N-hydroxysuccinimide ester (MC-OSu) and 3 equiv. of Hunig's base (0.032 mL, 0.183 mmol) were added. The reaction flask was covered with aluminum foil and kept at 0° C. overnight. LCMS showed the completion of reaction. The reaction was diluted with 2 mL DMSO and purified on a Waters Delta Prep 4000™ machine with an X Bridge prep C18 column (30×250 mm, 5 mm OBD) using 5-95% water/acetonitrile (0.05% formic acid) gradient over 40 min. A fraction collected at 20.2 min was found to contain the desired product. It was lyophilized to provide 6.3 mg (8.42% overall yield from 77a) of 116 as a purple solid. $^1$H NMR (400 MHz, DMSO-D$_6$) δ 13.11 (s, 1H), 9.93 (s, 2H), 8.45 (s, 1H), 8.42 (s, 1H), 8.22-8.13 (m, 2H), 8.08 (d, J=7.6 Hz, 1H), 8.00 (t, J=6.0 Hz, 1H), 7.80 (d, J=8.4 Hz, 2H), 7.60 (d, J=8.4 Hz, 2H), 7.30 (d, J=8.4 Hz, 2H), 6.99 (s, 2H), 6.67 (d, J=4.4 Hz, 2H), 6.07-5.96 (m, 3H), 5.40 (bs, 3H), 5.14 (d, J=3.6 Hz, 1H), 5.06 (dd, J=4.8, 1.6 Hz, 1H), 5.00 (s, 2H), 4.40-4.31 (m, 4H), 4.17 (dd, J=8.4, 6.8 Hz, 1H), 3.07-2.91 (m, 2H), 2.20-2.09 (m, 2H), 1.99-193 (m, 2H), 1.70-1.45 (m, 5H), 1.31-1.14 (m, 7H), 0.85 (d, J=6.8 Hz, 3H), 0.77 (d, J=6.8 Hz, 3H).

Example 6—Conjugation of Compound to Antibody

The following general procedure was used to prepare antibody-drug conjugates (ADCs) of 116, having a structure as shown below where Ab denotes an antibody and the repeating unit m is repeated 1, 2, 3, 4, 5, 6, 7, 8, 9, or 10. In some particular non-limiting examples, m is 1, 2, 3, or 4.

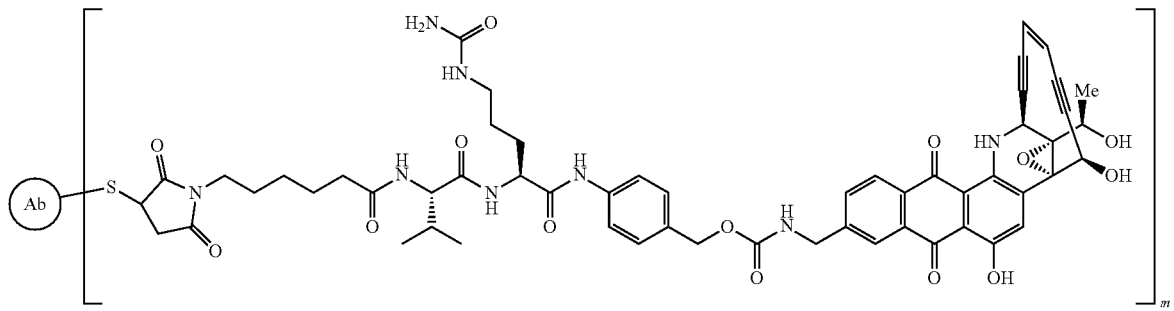

116 ADC with Antibody Ab

This procedure is based on introduction of free thiol groups into an antibody by reaction of lysine ε-amino groups with 2-iminothiolane, followed by reaction with a maleimide-containing drug-linker moiety such as, but not limited to 116. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

In some embodiments, a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug (cytotoxin)-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols.

The sample is then filtered via a 0.2 μfilter The material is buffer exchanged via TFF VivaFlow 50 Sartorius 30 MWCO PES membrane into 10 mg/mL glycine, 20 mg/mL sorbitol, 5% acetonitrile pH 5.0 (5×TFF buffer exchange volume), to remove any unreacted drug. The final formulation is carried out by TFF into 20 mg/mL sorbitol, 10 mg/mL glycine, pH 5.0.

Employing the above general technique, three ADCs of 116 were prepared, as shown in Table 2.

TABLE 2

Non-limiting Examples of Antibody-Drug Conjugates of the Present Disclosure

| ADC | Antibody | DAR |
|---|---|---|
| I | Anti-Mesothelin (6A4) | 2 |
| II | Anti-Glypican 3 (4A6) | 1.4 |
| III | Anti-CD70 (2H5) | 1.8 |

The anti-mesothelin antibody in ADC I was 6A4, whose complimentary determining regions (CDRs) and other features are disclosed in Terrett et al., U.S. Pat. No. 8,268,970 B2 (2012), the disclosure of which is incorporated herein by reference. The anti-glypican 3 antibody in ADC II was 4A6, whose CDRs and other features are disclosed in Terrett et al., U.S. Pat. No. 8,680,247 (2014), the disclosure of which is incorporated herein by reference. The anti-CD70 antibody in ADC III was 2H5, whose CDRs and other features are disclosed in Terret et al., U.S. Pat. No. 8,124,738 (2012), the disclosure of which is incorporated herein by reference.

Example 7—Biological Activity of the Antibody-Drug Conjugates

The following procedure was used for $^3$H-thymidine incorporation proliferation assays to measure the in vitro activity of the ADCs prepared against various cancer cells lines.

Cells were seeded at $1.25 \times 10^4$ cells/well in 96-well plates for 3 h for $^3$H thymidine assays, respectively. Serial dilutions (1:3) of the conjugate were added to the wells. Plates were allowed to incubate for 72 h. The plates were pulsed with 1.0 μCi of $^3$H-thymidine per well for the last 24 h of the total incubation period, harvested, and read on a Top Count Scintillation Counter (Packard Instruments, Meriden, Conn.). A decrease in the extent of $^3$H-thymidine incorporation is a measure of decrease in cellular proliferation. The $EC_{50}$ value—the concentration at which an agent inhibits or reduces cell proliferation by 50% of the maximum inhibition—was determined using PRISM™ software, version 5.0 (GraphPad Software, La Jolla, Calif., USA).

The activity of ADC I, which is a conjugate of an anti-mesothelin antibody, was tested against H226 (lung), N87 (gastric), and OVCAR3 (ovarian) cancer cells, all of which express mesothelin, with ADC II serving as a comparative ADC. Results are shown in Table 3. The activities of the comparative ADC II against these cell lines were noticeably lower.

TABLE 3

ADC Activity against Mesothelin Expressing Cancer Cells

| Cancer Cell | ADC | $EC_{50}$ (nM) |
|---|---|---|
| H226 | I | 0.011 |
| H226 | III | 0.47 |
| N87 | I | 0.10 |
| N87 | II | 1.3 |
| OVCAR3 | I | 0.51 |
| OVCAR3 | II | 2.1 |

The activity of ADC II, which is an ADC of an anti-glypican 3 antibody, was tested against Hep3B and HepG2 liver cancer cells, which express glypican-3. ADC I was also tested for comparative purposes. The results are provided in Table 4. The potency of ADC II was noticeably greater than that of comparative ADC I against these cell lines.

TABLE 4

ADC Activity against Glypican-3 Expressing Cancer Cells

| Cancer Cell | ADC | $EC_{50}$ (nM) |
|---|---|---|
| Hep3B | II | 0.0080 |
| Hep3B | I | 0.50 |
| HepG2 | II | 0.041 |
| HepG2 | I | 0.97 |

The activity of ADC III, which is an ADC of an anti-CD70 antibody, was tested against 786-0 cells, which are renal cancer cells expressing CD70. ADC I was also tested for comparative purposes. Results are provided in Table 5. Again, the comparative ADC was much less potent than the ADC designed to target the specific cell line.

TABLE 5

ADC Activity against CD70 Expressing Cancer Cells

| Cancer Cell | ADC | $EC_{50}$ (nM) |
|---|---|---|
| 786-O | III | 0.011 |
| 786-O | I | 0.60 |

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference:

U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 6,232,287
U.S. Pat. No. 6,528,481
U.S. Pat. No. 6,984,720
U.S. Pat. No. 7,335,748
U.S. Pat. No. 7,387,776
U.S. Pat. No. 7,452,964
U.S. Pat. No. 7,671,010
U.S. Pat. No. 7,781,565
U.S. Pat. No. 7,875,278
U.S. Pat. No. 8,008,449
U.S. Pat. No. 8,097,703
U.S. Pat. No. 8,124,738
U.S. Pat. No. 8,268,970
U.S. Pat. No. 8,450,278
U.S. Pat. No. 8,507,445
U.S. Pat. No. 8,680,247
U.S. Pat. No. 8,709,431
U.S. Patent Publication 2004/0005647
U.S. Patent Publication 2006/0234299
U.S. Patent Publication 2006/0223114
U.S. Patent Publication 2006/0058510
U.S. Patent Publication 2006/0088908
U.S. Patent Publication 2009/0074660
U.S. Patent Publication 2009/0253899
U.S. Patent Publication 2009/0297438
U.S. Patent Publication 2010/0034826
U.S. Patent Publication 2010/0143368
U.S. Patent Publication 2010/0150950
U.S. Patent Publication 2010/0092484
U.S. Patent Publication 2010/0209432
U.S. Patent Publication 2010/0285564
U.S. Patent Publication 2010/0317547
U.S. Patent Publication 2010/0093024
U.S. Patent Publication 2013/0209494
WO 2005/051976
WO 2006/056464
WO 2008/030612
WO 2010/087994
WO 2013/122823
Agard et al., *J. Amer. Chem. Soc.* 2004, 126, 15046-15047
Austin-Ward et al., 1998
Barclay et al. (eds.), *The Leucocyte Antigen Facts Book*, 1993, Academic Press.
Best, *Biochemistry* 2009, 48, 6571-6584
Bukowski et al., 1998
Burkly et al. *Cytokine* 40:1-16 (2007).
Campbell, et al., *Cancer Research*, 51(19):5329-5338, 1991.
Chen, J. S., *PhD Thesis*, 2008.
Christodoulides et al., 1998
Cumber et al. (1992)
Davidson et al., 1998
Goerke et al., *Biotechnol. Bioeng.* 2009, 102 (2), 400-416.
Green et al., 1999
*Handbook of Pharmaceutical Salts: Properties, and Use* (2002)
Hanibuchi et al., 1998
Harvey et al., 2004
Hellstrand et al., 1998
Hui, et al., 1998
Jeger et al., *Angew. Chem. Int. Ed.* 2010, 49, 9995-9997.
Ju et al., 2000
Kohl et al., 2003
Levary et al., *PLoS One* 2011, 6(4), e18342
Liu et al., *Mol. Cancer Ther.*, 2:1341-1350, 2003.
*March's Advanced Organic Chemistry: Reactions, Mechanisms, and Structure* (2007)
Mitchell et al., 1990
Mitchell et al., 1993
Montalbetti and Falque, *Tetrahedron*, 61:10827-10852, 2005.
Morton et al., 1992
Nechushtan et al., 1997
Nicolaou, et al., *Angew. Chem. Int. Ed.* 2007, 46, 4704.
Nicolaou, et al., *Angew. Chem. Int. Ed.* 2008, 47, 185.
Onda et al., *Cancer Res.*, 64:1419-1424, 2004.
Pack et al. (1992)
Pietras et al., 1998
*Practical Process Research & Development* (2000)
Proft, *Biotechnol. Lett.* 2010, 32, 1-10.
Qin et al., 1998
Ravindranath et al., 1991
Remington's Pharmaceutical Sciences, 15th Edition, chapter 33, in particular pages 624-652
Remington's Pharmaceutical Sciences, 15th Edition, pages 1035-1038 and 1570-1580
Rosenberg et al., 1988; 1989
Skerra, 2001.
Thompson (ed.), 1994, The Cytokine Handbook, Academic Press, San Diego
Weitman, et al., *Cancer Research*, 52(12):3396-3401, 1992.
Winkles, *Nat Rev Drug Discov* 7:411-425 (2008).
Winthrop et al., *Clin. Cancer Res.*, 9:3845s-3853s, 2003.
Zhou et al., *Mol Cancer Ther.* 10(7):1276-88, 2011.

The invention claimed is:
1. A compound of the formula:

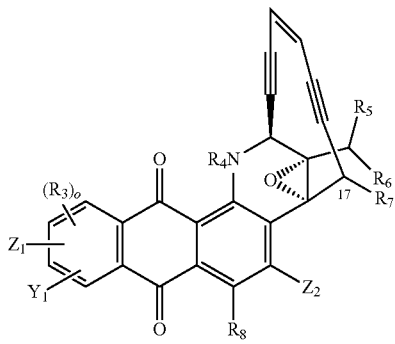
(I)

wherein:

Y$_1$ is —(CH$_2$)$_m$NR$_1$R$_2$;

wherein:

m is 1, 2, 3, 4, 5, or 6; and

R$_1$ and R$_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group; or R$_1$ and R$_2$ are taken together and are divalent amine protecting group, alkanediyl$_{(C1-12)}$, alkylaminodiyl$_{(C1-8)}$; alkoxydiyl$_{(C1-8)}$; or a substituted version of either of these groups; or Z$_1$ is absent or hydrogen;

Z$_2$ is hydrogen;

o is 1, 2, or 3;

R$_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups;

R$_4$ is hydrogen, alkyl$_{(C1-12)}$, a monovalent amine protecting group, or substituted alkyl$_{(C1-12)}$;

R$_5$, R$_6$, and R$_7$ are each independently hydrogen, hydroxy, amino, mercapto, —OX$_1$, —NX$_2$X$_3$, or —SX$_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups;

wherein:

X$_1$ is a hydroxy protecting group;

X$_2$ and X$_3$ are independently selected from hydrogen, a monovalent amine protecting group, or when X$_2$ and X$_3$ are taken together form a divalent amine protecting group; and X$_4$ is a thiol protecting group;

R$_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or a pharmaceutically acceptable salt thereof.

2. The compound of claim 1, further defined as:

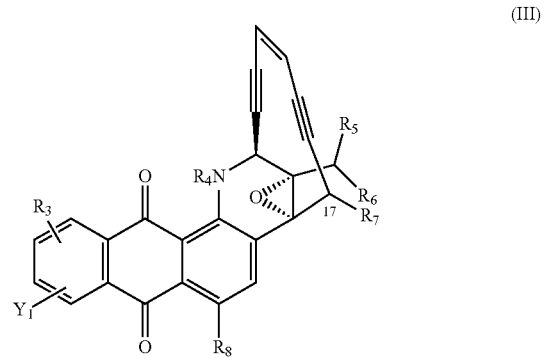
(III)

wherein:

Y$_1$ is —CH$_2$NR$_1$R$_2$ wherein:

R$_1$ and R$_2$ are each independently selected from hydrogen, hydroxy, alkyl$_{(C1-12)}$, alkenyl$_{(C\leq12)}$, alkynyl$_{(C\leq12)}$, aryl$_{(C\leq12)}$, aralkyl$_{(C\leq12)}$, acyl$_{(C\leq12)}$, or a substituted version of any of these groups;

R$_1$ and R$_2$ are taken together and are a divalent protecting group, alkanediyl$_{(1-12)}$, alkoxydiyl$_{(C1-8)}$; or a substituted version of either of these groups;

R$_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups;

R$_4$ is hydrogen, alkyl$_{(C1-12)}$, a monovalent amine protecting group, or substituted alkyl$_{(C1-12)}$;

R$_5$, R$_6$, and R$_7$ are each independently hydrogen, hydroxy, amino, mercapto, —OX$_1$, —NX$_2$X$_3$, or —SX$_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups;

wherein:

X$_1$ is a hydroxy protecting group;

X$_2$ and X$_3$ are independently selected from hydrogen, a monovalent amine protecting group, or when X$_2$ and X$_3$ are taken together form a divalent amine protecting group; and X$_4$ is a thiol protecting group;

R$_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or a pharmaceutically acceptable salt thereof.

3. The compound of claim 1, wherein the formula is further defined as:

(V)

wherein:

$Y_1$ is —$(CH_2)_m NR_1R_2$;

wherein:

m is 1, 2, 3, 4, 5, or 6; and $R_1$ and $R_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group;

$R_1$ and $R_2$ are taken together and are a divalent protecting group, alkanediyl$_{(C\leq12)}$, alkylaminodiyl$_{(C\leq8)}$; alkoxydiyl$_{(C\leq8)}$; or a substituted version of either of these groups; or $Z_1$ is absent or hydrogen;

$R_3$ is hydrogen, hydroxy, halo, amino, cyano, nitro, phosphate, or mercapto, or alkyl$_{(C1-12)}$, alkenyl$_{(C2-12)}$, alkynyl$_{(C2-12)}$, aryl$_{(C6-12)}$, aralkyl$_{(C7-12)}$, heteroaryl$_{(C1-12)}$, heterocycloalkyl$_{(C2-12)}$, acyl$_{(C1-12)}$, alkoxy$_{(C1-12)}$, acyloxy$_{(C1-12)}$, alkylamino$_{(C1-12)}$, dialkylamino$_{(C2-12)}$, amido$_{(C1-12)}$, or a substituted version of any of these groups;

o is 1, 2, or 3;

$R_4$ is hydrogen, alkyl$_{(C1-12)}$, a monovalent amine protecting group, or substituted alkyl$_{(C1-12)}$;

$R_5$, $R_6$, and $R_7$ are each independently hydrogen, hydroxy, amino, mercapto, —$OX_1$, —$NX_2X_3$, or —$SX_4$; or alkyl$_{(C1-12)}$, alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups;

wherein:

$X_1$ is a hydroxy protecting group;

$X_2$ and $X_3$ are independently selected from hydrogen, a monovalent amine protecting group, or when $X_2$ and $X_3$ are taken together form a divalent amine protecting group; and $X_4$ is a thiol protecting group; and $R_8$ is hydroxy, amino, or mercapto; or alkoxy$_{(C1-12)}$, acyloxy$_{(C1-12)}$, alkylamino$_{(C1-12)}$, dialkylamino$_{(C2-12)}$, alkylthio$_{(C1-12)}$, amido$_{(C1-12)}$, or a substituted version of any of these groups; or a pharmaceutically acceptable salt thereof.

4. The compound of claim 1, wherein the formula is further defined as:

(VI)

wherein:

$R_1$ and $R_2$ are each independently selected from hydrogen, hydroxy, alkyl$_{(C1-12)}$, substituted alkyl$_{(C1-12)}$, alkenyl$_{(C2-12)}$, substituted alkenyl$_{(C2-12)}$, alkynyl$_{(C2-12)}$, substituted alkynyl$_{(C2-12)}$, aryl$_{(C6-12)}$, substituted aryl$_{(C6-12)}$, aralkyl$_{(C7-12)}$, substituted aralkyl$_{(C7-12)}$, heteroaryl$_{(C1-12)}$, substituted heteroaryl$_{(C1-12)}$, heterocycloalkyl$_{(C2-12)}$, substituted heterocycloalkyl$_{(C2-12)}$, acyl$_{(C1-12)}$, substituted acyl$_{(C1-12)}$, acyloxy$_{(C1-12)}$, substituted acyloxy$_{(C1-12)}$, alkylamino$_{(C1-12)}$, substituted alkylamino$_{(C1-12)}$; a monovalent amine protecting group;

$R_3$ is hydrogen, hydroxy, halo, alkoxy$_{(C1-12)}$ or substituted alkoxy$_{(C1-12)}$;

o is 1, 2, or 3;

$R_4$ is hydrogen, a monovalent amine protecting group, alkyl$_{(C1-12)}$, or substituted alkyl$_{(C1-12)}$;

$R_5$, $R_6$, and $R_7$ are each independently hydrogen, hydroxy; or alkyl$_{(C1-12)}$ or substituted alkyl$_{(C1-12)}$;

wherein:

$X_1$ is a hydroxy protecting group; and $R_8$ is hydroxy, amino, or mercapto; or a pharmaceutically acceptable salt thereof.

5. The compound of claim 1, wherein the formula is further defined as:

(VII)

wherein:

R₁ and R₂ are each independently selected from hydrogen, hydroxy, alkyl$_{(C1-12)}$, substituted alkyl$_{(C1-12)}$, aryl$_{(6-12)}$, substituted aryl$_{(C6-12)}$, aralkyl$_{(C7-12)}$, substituted aralkyl$_{(C7-12)}$, acyl$_{(C1-12)}$, substituted acyl$_{(C1-12)}$, a monovalent amine protecting group, or R₁ and R₂ are taken together and form a divalent amine protecting group, or alkyl$_{(C1-12)}$, aryl$_{(C6-12)}$, aralkyl$_{(C7-12)}$, acyl$_{(C1-12)}$, or a substituted version of any of these groups;

R₃ is hydrogen, hydroxy, halo, alkoxy$_{(C1-12)}$ or substituted alkoxy$_{(C1-12)}$; and o is 1, 2, or 3; or a pharmaceutically acceptable salt thereof.

6. The compound of claim 1, wherein the formula is further defined as:

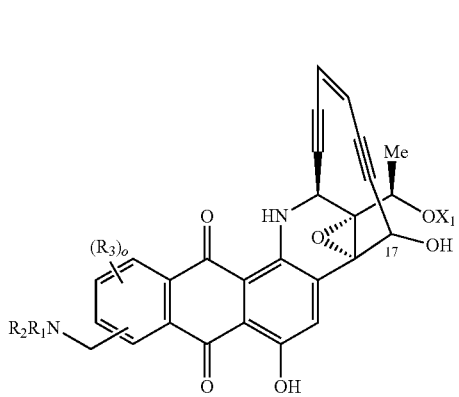

(VII)

wherein:

X₁ is a hydroxy protecting group;

R₁ and R₂ are each independently selected from hydrogen, alkyl$_{(C1-12)}$, or substituted alkyl$_{(C1-12)}$; and R₃ is hydrogen, alkoxy$_{(C1-12)}$, or substituted alkoxy$_{(C1-12)}$; and o is 2;

or a pharmaceutically acceptable salt thereof.

7. The compound of claim 1, wherein Z₁ is hydrogen.

8. The compound of claim 1, wherein m is 1, 2, or 3.

9. The compound of claim 1, wherein R₁ or R₂ is hydrogen, alkyl$_{(C1-12)}$ substituted alkyl$_{(C1-12)}$, or a monovalent amine protecting group, or R₁ is taken together with R₂ and is a divalent amine protecting group.

10. The compound of claim 1, wherein R₃ is hydrogen, alkoxy$_{(C1-12)}$, or R₄ is hydrogen or a monovalent amine protecting group.

11. The compound of claim 1, wherein R₅ is alkyl$_{(C1-12)}$ or R₆, R₇, or R₈ is hydroxy.

12. The compound of claim 1, wherein the compound is further defined as:

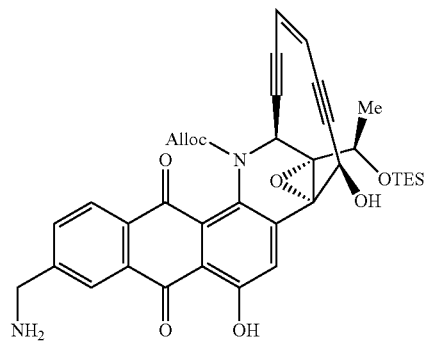

or a pharmaceutically acceptable salt thereof.

13. The compound of claim 1, wherein the compound is further defined as:

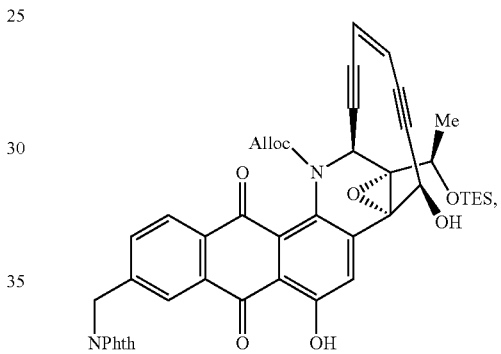

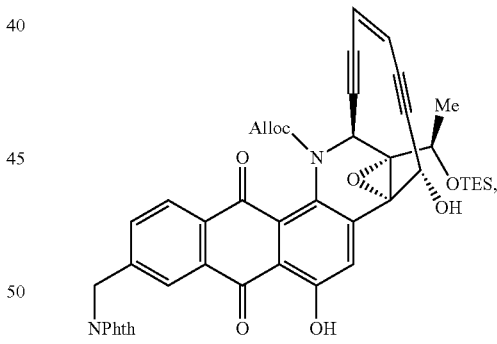

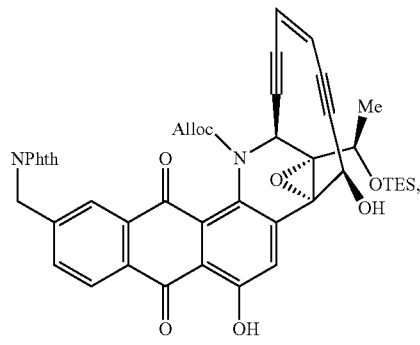

193
-continued
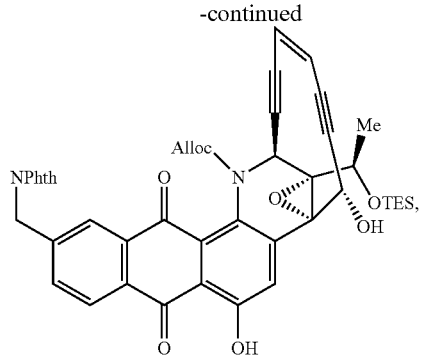
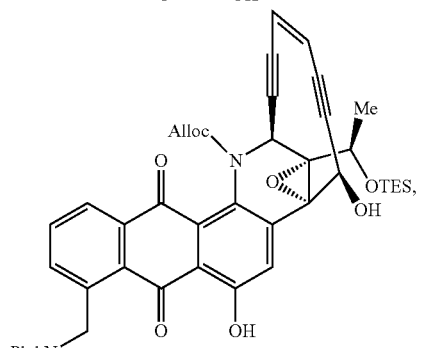
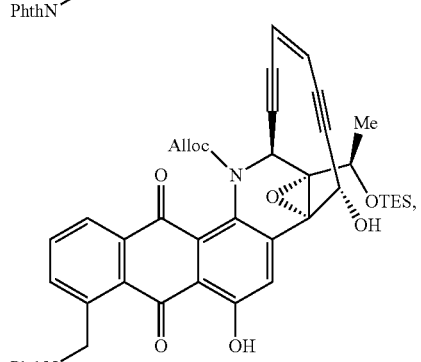
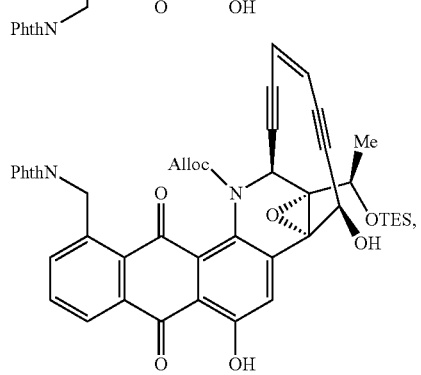
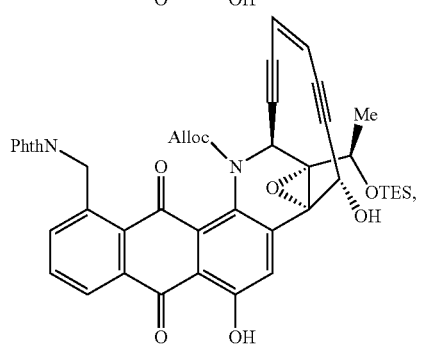
194
-continued
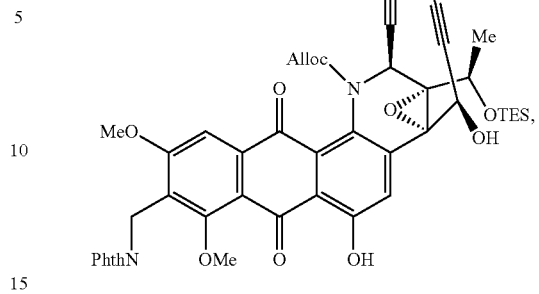
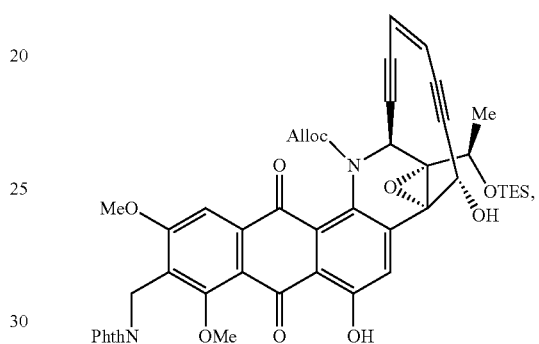
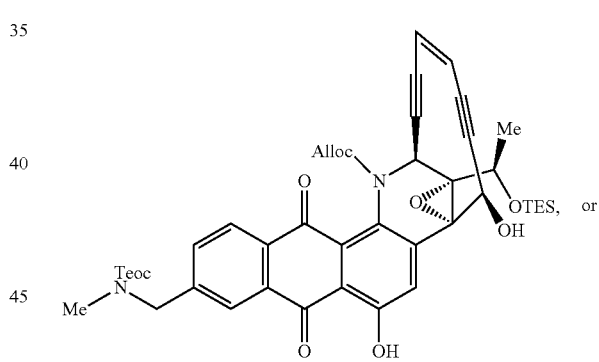
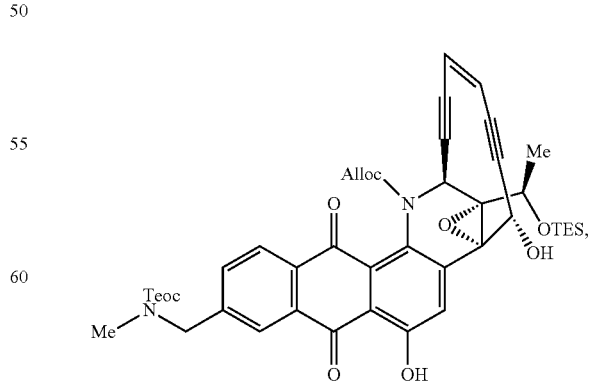
or a pharmaceutically acceptable salt thereof.

14. The compound of claim 1, further defined as:
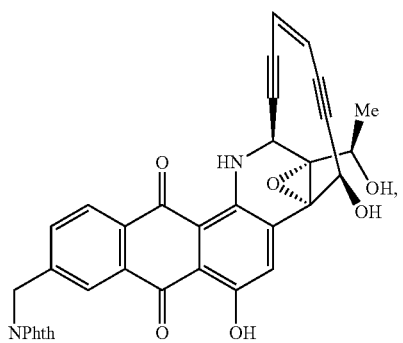
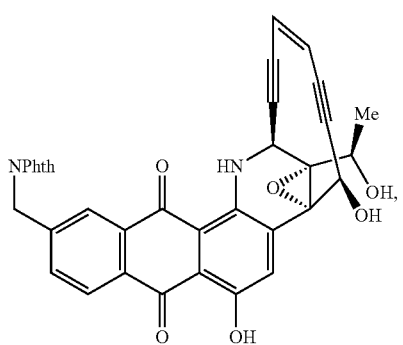
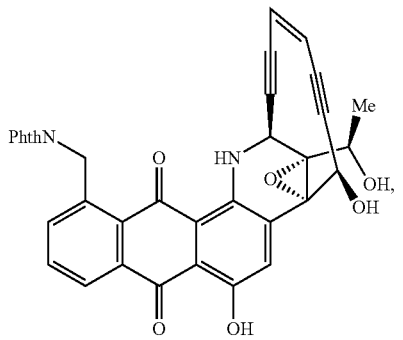
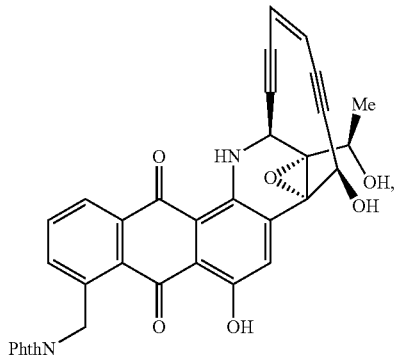
-continued
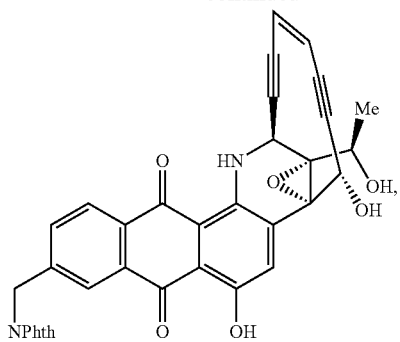
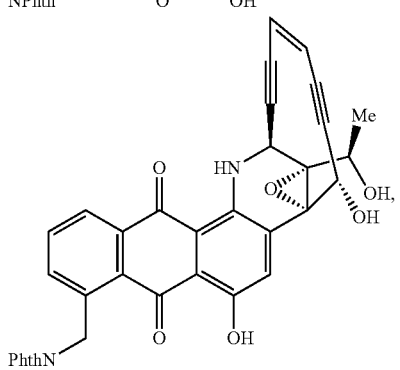
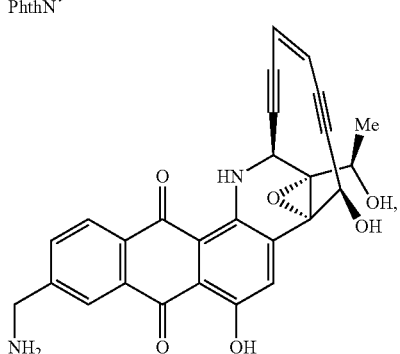
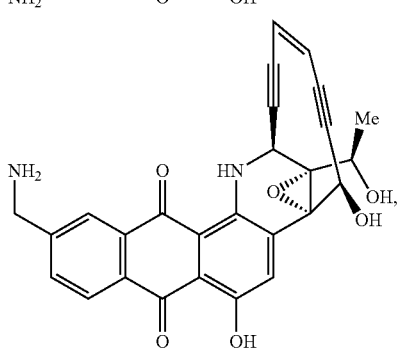
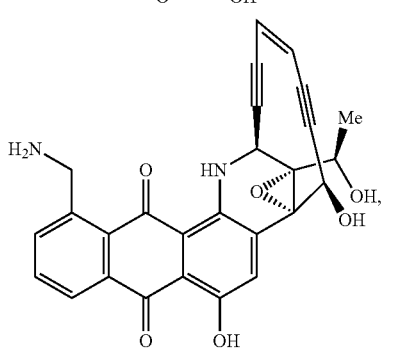

197
-continued
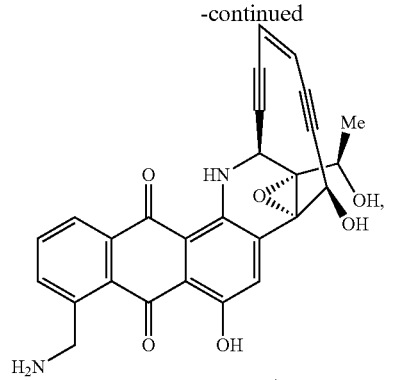
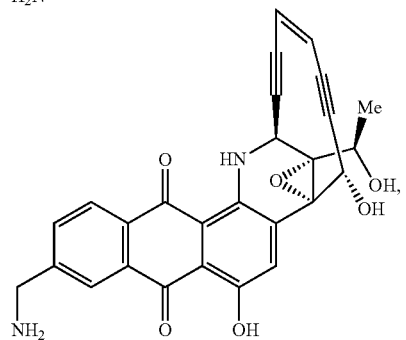
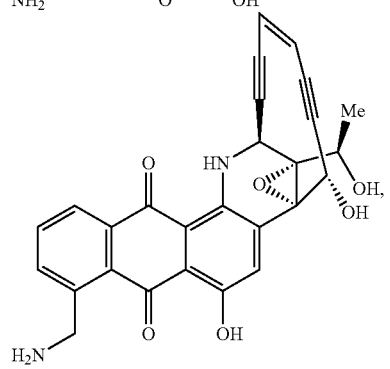
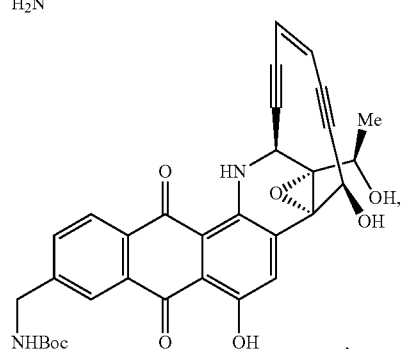
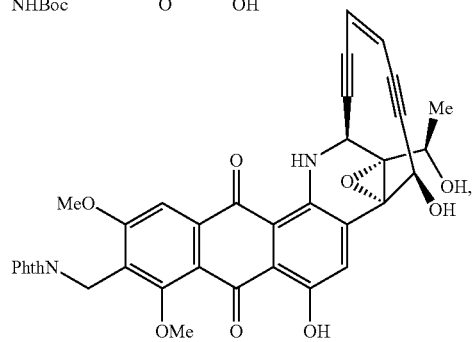
198
-continued
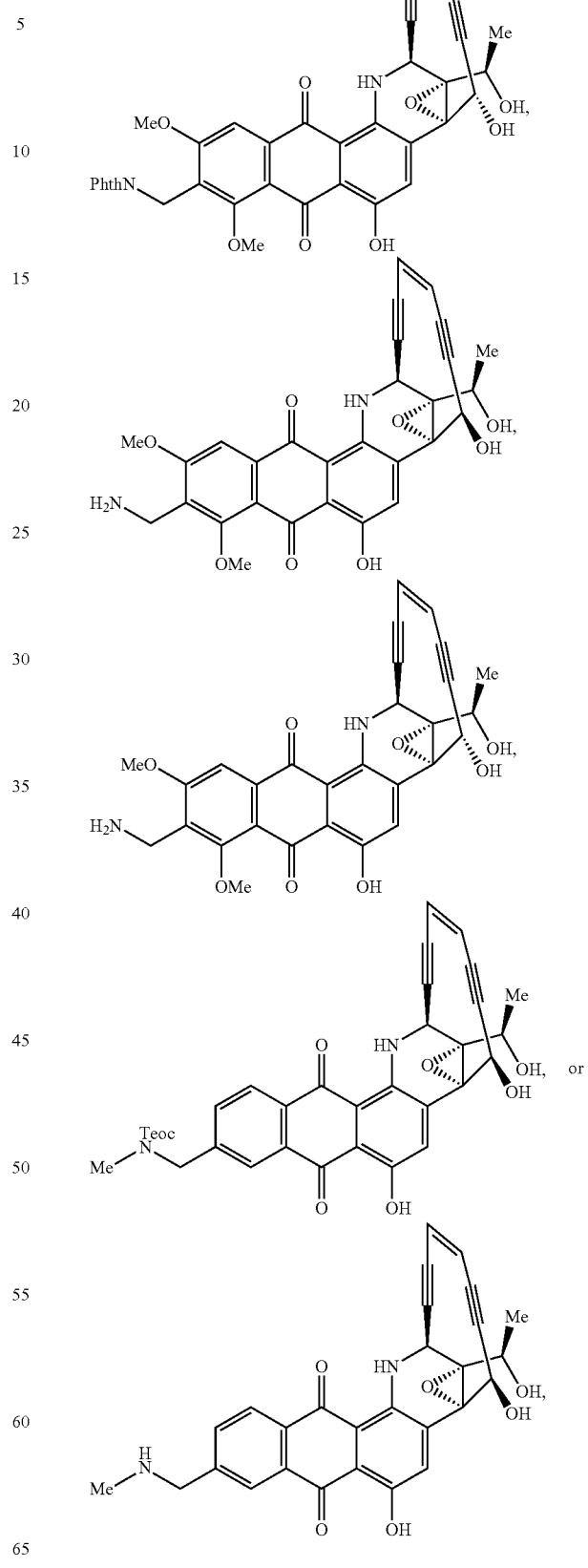
or a pharmaceutically acceptable salt thereof.

15. A pharmaceutical composition comprising a compound of claim 1 and an excipient.

16. A conjugate of the formula:

$$(A_5\text{-}L)_r\text{-}A_6 \qquad (XVII)$$

wherein:
- $A_5$ is a compound of claim 1;
- L is a linker;
- r is 1, 2, 3, 4, 5, 6, 7, 8, 9, 10, 11, or 12; and
- $A_6$ is a cell targeting moiety.

17. The conjugate of claim 16, wherein L comprises a polypeptide cleavable by an intracellular enzyme or a self-immolating group.

18. The conjugate of claim 16, wherein $A_6$ is an antibody whose antigen is a tumor associated antigen.

19. The conjugate of claim 16, further comprising a structure of the formula:

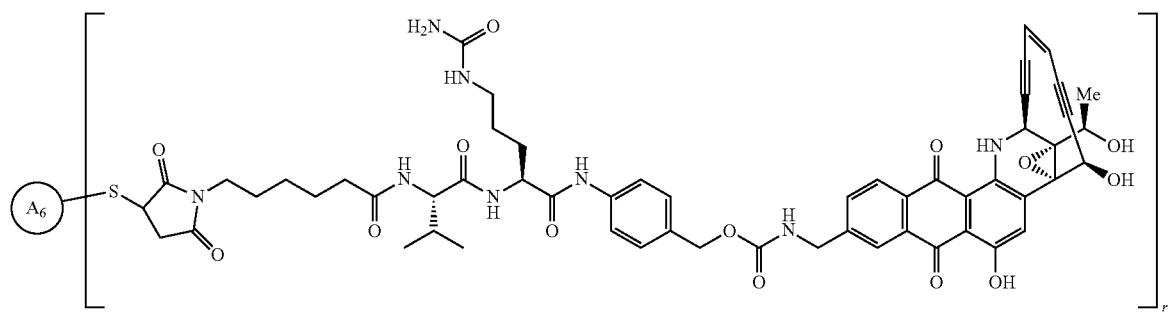

wherein:
$A_6$ is an antibody and r is 1, 2, 3, or 4.

20. The conjugate of claim 19, wherein the antibody is an anti-mesothelin, anti-glypican-3, or anti-CD70 antibody.

* * * * *

UNITED STATES PATENT AND TRADEMARK OFFICE
CERTIFICATE OF CORRECTION

PATENT NO. : 10,889,590 B2  
APPLICATION NO. : 16/357109  
DATED : January 12, 2021  
INVENTOR(S) : Kyriacos C. Nicolaou et al.

Page 1 of 1

It is certified that error appears in the above-identified patent and that said Letters Patent is hereby corrected as shown below:

On the Title Page

Item (56) third reference in section, delete "Uncialamycim" and insert -- Uncialamycin -- therefor.

In the Claims

Claim 2, Column 188, Line 36, delete "alkanediyl$_{(1\text{-}12)}$" and insert -- alkanediyl$_{(C1\text{-}12)}$ -- therefor.

Claim 2, Column 188, Line 38, after "groups;" insert -- or --.

Claim 5, Column 191, Line 4, delete "aryl$_{(6\text{-}12)}$," and insert -- aryl$_{(C6\text{-}12)}$, -- therefor.

Claim 9, Column 191, Line 59, after "alkyl$_{(C1\text{-}12)}$" and before "substituted alkyl$_{(C1\text{-}12)}$" insert -- , --.

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*